US012270044B2

(12) United States Patent
Gill et al.

(10) Patent No.: US 12,270,044 B2
(45) Date of Patent: *Apr. 8, 2025

(54) CRISPR SYSTEMS WITH ENGINEERED DUAL GUIDE NUCLEIC ACIDS

(71) Applicants: Celyntra Therapeutics SA, Mont-Saint-Guibert (BE); DANMARKS TEKNISKE UNIVERSITET, KGS Lyngby (DK)

(72) Inventors: Ryan T. Gill, Denver, CO (US); Tanya Warnecke, Boulder, CO (US); Andrea Barghetti, Copenhagen (DK); Line Dahl Poulsen, Ballerup (DK)

(73) Assignees: Celyntra Therapeutics SA, Mont-Saint-Guibert (BE); DANMARKS TEKNISKE UNIVERSITET, KGS Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/190,063

(22) Filed: Mar. 24, 2023

(65) Prior Publication Data
US 2023/0407342 A1 Dec. 21, 2023

Related U.S. Application Data

(63) Continuation of application No. 17/963,889, filed on Oct. 11, 2022, which is a continuation of application No. 17/506,572, filed on Oct. 20, 2021, which is a continuation of application No. PCT/US2020/054050, filed on Oct. 2, 2020.

(60) Provisional application No. 62/910,055, filed on Oct. 3, 2019.

(51) Int. Cl.
C12N 9/22 (2006.01)
C12N 15/11 (2006.01)
C12N 15/70 (2006.01)
C12N 15/85 (2006.01)
C12N 15/90 (2006.01)

(52) U.S. Cl.
CPC ............ C12N 15/907 (2013.01); C12N 9/22 (2013.01); C12N 15/11 (2013.01); C12N 15/70 (2013.01); C12N 15/85 (2013.01); C12N 2310/20 (2017.05); C12N 2800/22 (2013.01)

(58) Field of Classification Search
None
See application file for complete search history.

(56) References Cited

U.S. PATENT DOCUMENTS

| 7,446,190 | B2 | 11/2008 | Sadelain et al. |
| 8,399,645 | B2 | 3/2013 | Campana et al. |
| 8,697,359 | B1 | 4/2014 | Zhang |
| 8,906,682 | B2 | 12/2014 | June et al. |
| 9,181,527 | B2 | 11/2015 | Sentman |
| 9,266,960 | B2 | 2/2016 | Morgan et al. |
| 9,272,002 | B2 | 3/2016 | Powell, Jr. et al. |
| 9,580,727 | B1 * | 2/2017 | Donohoue ............ C12N 15/111 |
| 9,790,490 | B2 * | 10/2017 | Zhang ................... C12N 15/82 |
| 9,890,396 | B2 | 2/2018 | Chatterjee et al. |
| 9,896,696 | B2 | 2/2018 | Begemann et al. |
| 9,982,278 | B2 | 5/2018 | Gill et al. |
| 9,982,279 | B1 | 5/2018 | Gill et al. |
| 10,011,849 | B1 * | 7/2018 | Gill ........................ C12N 15/111 |
| 10,113,167 | B2 | 10/2018 | Doudna et al. |
| 10,113,179 | B2 | 10/2018 | Begemann et al. |
| 2009/0222937 | A1 | 9/2009 | Arnould et al. |
| 2009/0271881 | A1 | 10/2009 | Arnould et al. |
| 2010/0229252 | A1 | 9/2010 | Perez-Michaut |
| 2010/0311124 | A1 | 12/2010 | Liu et al. |
| 2011/0016540 | A1 | 1/2011 | Weinstein et al. |
| 2011/0023139 | A1 | 1/2011 | Weinstein et al. |
| 2011/0023144 | A1 | 1/2011 | Weinstein et al. |
| 2011/0023145 | A1 | 1/2011 | Weinstein et al. |
| 2011/0023146 | A1 | 1/2011 | Weinstein et al. |
| 2011/0023153 | A1 | 1/2011 | Weinstein et al. |
| 2011/0091441 | A1 | 4/2011 | Gouble et al. |
| 2011/0158957 | A1 | 6/2011 | Bonini et al. |
| 2011/0182867 | A1 | 7/2011 | Orkin et al. |
| 2011/0225664 | A1 | 9/2011 | Smith |
| 2012/0159653 | A1 | 6/2012 | Weinstein et al. |
| 2012/0328580 | A1 | 12/2012 | Edge et al. |
| 2013/0145487 | A1 | 6/2013 | Cedrone |
| 2013/0202678 | A1 | 8/2013 | Yu et al. |

(Continued)

FOREIGN PATENT DOCUMENTS

| WO | 2013126794 A1 | 8/2013 |
| WO | 2013142034 A1 | 9/2013 |

(Continued)

OTHER PUBLICATIONS

European Patent Office, International Search Report and Written Opinion for PCT/US20/54050 mailed Dec. 3, 2021, 13 pages.
Abun, Kornel et al., "Accurate analysis of genuine CRISPR editing events with ampliCan", Published by Cold Spring Harbor Laboratory Press, 2019 pp. 843-847.
Swarts, Daan C et al: 11 Cas9 versus Cas12a/Cpf1: Structure-function comparisons and implications for genome editing, Wiley Interdisciplinary Reviews: Rna, vol. 9, No. 5, May 22, 2018 (May 22, 2018), 19 pages.
Zetsche, Bernd, et al., "Cpf1 is a Single RNA-Guided Endonuclease of a Class 2 CRISPR-Cas System", CellPress, Oct. 22, 2015, pp. 759-771.

(Continued)

Primary Examiner — Neil P Hammell
Assistant Examiner — Khaleda B Hasan
(74) Attorney, Agent, or Firm — N.V. Nederlandsch Octrooibureau

(57) ABSTRACT

The present invention relates to an engineered Clustered Regularly Interspaced Short Palindromic Repeats (CRISPR) system comprising engineered dual guide nucleic acids (e.g., RNAs) capable of activating a CRISPR-Associated (Cas) nuclease, such as a type V-A Cas nuclease. Also provided are methods of targeting, editing, and/or modifying a nucleic acid using the engineered CRISPR system, and compositions and cells comprising the engineered CRISPR system.

27 Claims, 20 Drawing Sheets

Specification includes a Sequence Listing.

(56) References Cited

U.S. PATENT DOCUMENTS

| | | |
|---|---|---|
| 2015/0344912 A1 | 12/2015 | Kim et al. |
| 2016/0200824 A1 | 7/2016 | Chmielewski et al. |
| 2016/0289675 A1 | 10/2016 | Ryan et al. |
| 2016/0311917 A1 | 10/2016 | Beatty et al. |
| 2016/0362472 A1 | 12/2016 | Bitter et al. |
| 2017/0107539 A1 | 4/2017 | Yu et al. |
| 2017/0355985 A1 | 12/2017 | Dellinger et al. |
| 2018/0003696 A1 | 1/2018 | Sharei et al. |
| 2018/0044700 A1 | 2/2018 | Doudna et al. |
| 2018/0119140 A1 | 5/2018 | Porteus et al. |
| 2018/0282763 A1 | 10/2018 | Cigan et al. |
| 2018/0363009 A1 | 12/2018 | Doudna et al. |
| 2018/0371498 A1 | 12/2018 | Gill et al. |

FOREIGN PATENT DOCUMENTS

| | | |
|---|---|---|
| WO | 2013176772 A1 | 11/2013 |
| WO | 2013163628 A3 | 1/2014 |
| WO | 2015048577 A2 | 4/2015 |
| WO | 2015070083 A1 | 5/2015 |
| WO | 2015089354 A1 | 6/2015 |
| WO | 2015120180 A1 | 8/2015 |
| WO | 2015134812 A1 | 9/2015 |
| WO | 2015138510 A1 | 9/2015 |
| WO | 2015148670 A1 | 10/2015 |
| WO | 2015148860 A1 | 10/2015 |
| WO | 2015148863 A3 | 10/2015 |
| WO | 2015153780 A1 | 10/2015 |
| WO | 2015153789 A1 | 10/2015 |
| WO | 2015153791 A1 | 10/2015 |
| WO | 2016120220 A1 | 8/2016 |
| WO | 2015188141 A2 | 10/2016 |
| WO | 2016164356 A1 | 10/2016 |
| WO | 2017017184 A1 | 2/2017 |
| WO | 2017040945 A1 | 3/2017 |
| WO | 2017053729 A1 | 3/2017 |
| WO | 2017/106569 A1 | 6/2017 |

* cited by examiner

COMBINATIONS 3 AND 6
Secondary structure.
ΔG = -8.3 kcal/mol

COMBINATIONS 3 AND 4
Secondary structure.
ΔG = -8.0 kcal/mol

COMBINATIONS 9 AND 10
Secondary structure:
ΔG = -14.1 kcal/mol

COMBINATIONS 7 AND 8
Secondary structure:
ΔG = -11.0 kcal/mol

COMBINATIONS 13 AND 14
Secondary structure:
ΔG = -10.9 kcal/mol

COMBINATIONS 11 AND 12
Secondary structure:
ΔG = -7.9 kcal/mol

COMBINATIONS 15 AND 16
Secondary structure:
ΔG = -13.7 kcal/mol

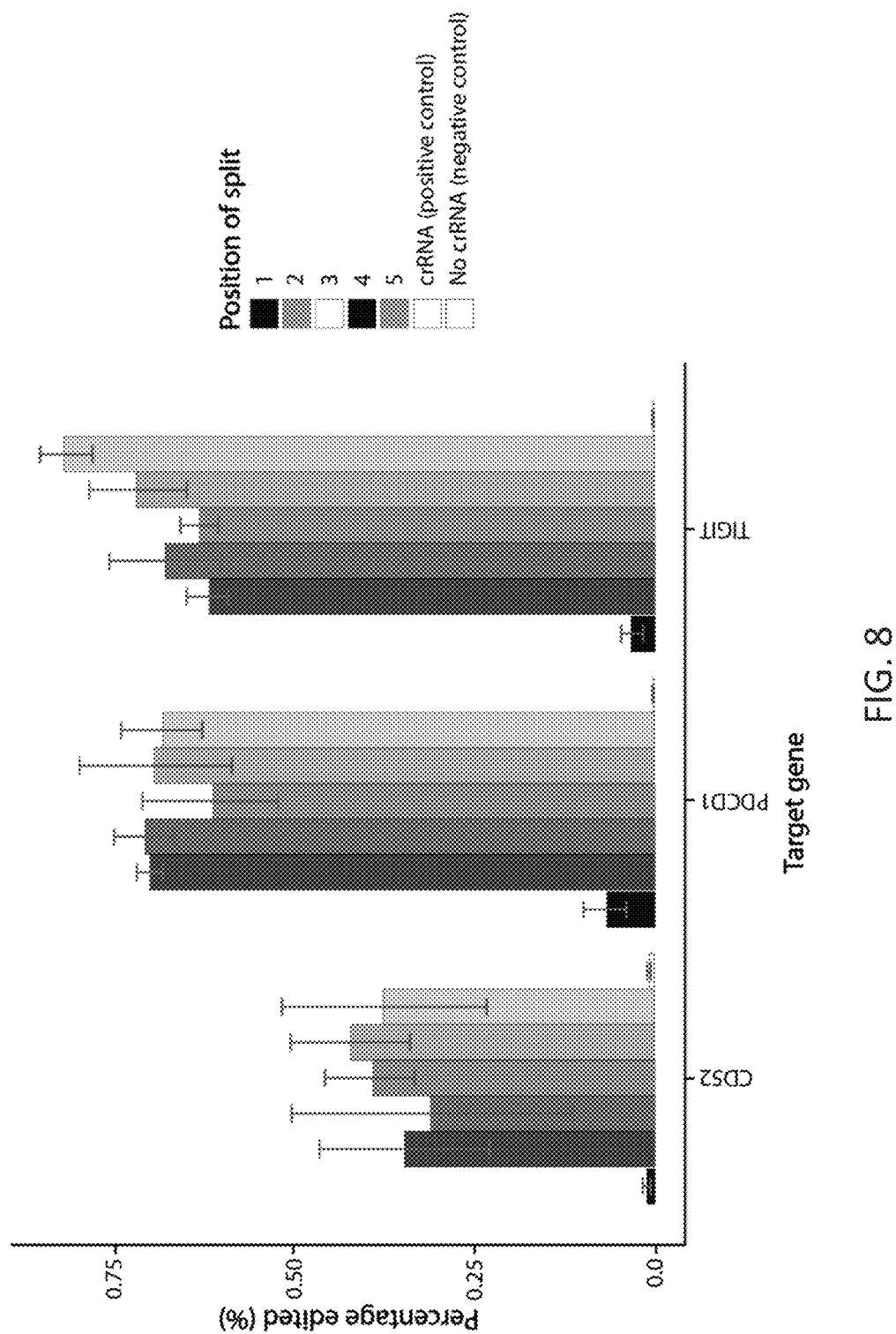

CRISPR SYSTEMS WITH ENGINEERED DUAL GUIDE NUCLEIC ACIDS

RELATED APPLICATIONS

This application is a continuation of U.S. patent application Ser. No. 17/963,889 filed Oct. 11, 2022, which is a continuation of U.S. patent application Ser. No. 17/506,572, filed Oct. 20, 2021, which claims the benefit of and priority to International Application No. PCT/US2020/054050, filed on Oct. 2, 2020, which claims priority to U.S. Provisional Patent Application No. 62/910,055, filed on Oct. 3, 2019, the disclosure of which is hereby incorporated by reference in its entirety for all purposes.

SEQUENCE LISTING

The instant application contains a Sequence Listing which has been submitted electronically in XML text format encoded as XML and is hereby incorporated by reference in its entirety. Said .XML file was created on Apr. 24, 2023, is named ARTN-009 CON3-T1_SL.xml and is 304,536 bytes in size. The sequence listing contained in this .XML file is part of the specification and is hereby incorporated by reference herein in its entirety.

FIELD OF THE INVENTION

The present invention relates to an engineered Clustered Regularly Interspaced Short Palindromic Repeats (CRISPR) system comprising engineered dual guide nucleic acids (e.g., RNAs) capable of activating a CRISPR-Associated (Cas) nuclease, methods of targeting, editing, and/or modifying a nucleic acid using the engineered CRISPR system, and compositions and cells comprising the engineered CRISPR system.

BACKGROUND OF THE INVENTION

Recent advances have been made in precise genome targeting technologies. For example, specific loci in genomic DNA can be targeted, edited, or otherwise modified by designer meganucleases, zinc finger nucleases, or transcription activator-like effectors (TALEs). Furthermore, the CRISPR-Cas systems of bacterial and archaeal adaptive immunity have been adapted for precise targeting of genomic DNA in eukaryotic cells. Compared to the earlier generations of genome editing tools, the CRISPR-Cas systems are easy to set up, scalable, and amenable to targeting multiple positions within the eukaryotic genome, thereby providing a major resource for new applications in genome engineering.

Two distinct classes of CRISPR-Cas systems have been identified. Class 1 CRISPR-Cas systems utilize multi-protein effector complexes, whereas class 2 CRISPR-Cas systems utilize single-protein effectors (see, Makarova et al. (2017) CELL, 168:328). Among the three types of class 2 CRISPR-Cas systems, type II and type V systems typically target DNA and type VI systems typically target RNA (id.). Naturally occurring type II effector complexes consist of Cas9, CRISPR RNA (crRNA), and trans-activating CRISPR RNA (tracrRNA), but the crRNA and tracrRNA can be fused as a single guide RNA in an engineered system for simplicity (see, Wang et al. (2016) ANNU. REV. BIOCHEM., 85:227). Certain naturally occurring type V systems, such as type V-A, type V-C, and type V-D systems, do not require tracrRNA and use crRNA alone as the guide for cleavage of target DNA (see, Zetsche et al. (2015) CELL, 163:759; Makarova et al. (2017) CELL, 168:328).

The CRISPR-Cas systems have been engineered for various purposes, such as genomic DNA cleavage, base editing, epigenome editing, and genomic imaging (see, e.g., Wang et al. (2016) ANNU. REV. BIOCHEM., 85:227 and Rees et al. (2018) NAT. REV. GENET., 19:770). Although significant developments have been made, there still remains a need for new and useful CRISPR-Cas systems as powerful precise genome targeting tools.

SUMMARY OF THE INVENTION

The invention is based, in part, upon the design of a dual guide CRISPR-Cas system in which a targeter nucleic acid and a modulator nucleic acid, when hybridized to form a complex, can activate a Cas nuclease that, in a naturally occurring system, is activated by a single crRNA in the absence of a tracrRNA. The engineered dual guide CRISPR-Cas system described herein can be used to target, edit, or modify a target nucleic acid such as genomic DNA.

Type V-A, type V-C, and type V-D CRISPR-Cas systems naturally include a Cas nuclease and a single guide RNA (i.e., crRNA). By splitting the single guide RNA into two different nucleic acids, the engineered system describe herein provides better flexibility and tunability. For example, the efficiency of nucleic acid cleavage can be increased or decreased by adjusting the hybridization length and/or affinity of the targeter nucleic acid and the modulator nucleic acid. Furthermore, given the length limitation of nucleic acids that can be synthesized with high yield and accuracy, the use of dual guide nucleic acids allows incorporation of more polynucleotide elements that can improve editing efficacy and/or specificity.

In particular, the dual guide system can be engineered as a tunable system to decrease off-target editing, and thus can be used to edit a nucleic acid with high specificity. The system can be employed in a number of applications, for example, editing cells such as mammalian cells for use in therapy. The decrease in off-target editing is particularly desirable when creating genetically engineered proliferating cells, such as stem cells, progenitor cells, and immune memory cells, to be administered to a subject in need of the therapy. High specificity can be accomplished using the dual guide systems described herein, which optionally further include, for example, one or more chemical modifications to the targeter nucleic acid and/or modulator nucleic acid, an editing enhancer sequence, and/or a donor template-recruiting sequence.

Accordingly, in one aspect, the present invention provides an engineered, non-naturally occurring system comprising:
  (a) a targeter nucleic acid comprising:
    (i) a spacer sequence designed to hybridize with a target nucleotide sequence; and
    (ii) a targeter stem sequence; and
  (b) a modulator nucleic acid comprising a modulator stem sequence complementary to the targeter stem sequence, wherein the targeter nucleic acid and the modulator nucleic acid are separate nucleic acids, and
  wherein a complex comprising the targeter nucleic acid and the modulator nucleic acid is capable of activating a CRISPR Associated (Cas) nuclease that, in a naturally occurring system, is activated by a single crRNA in the absence of a tracrRNA.

In certain embodiments, the Cas nuclease is a type V-A Cas nuclease.

In certain embodiments, the targeter stem sequence and the modulator stem sequence are each 4-10 nucleotides in length. In certain embodiments, the targeter stem sequence and the modulator stem sequence are each 5 nucleotides in length. In certain embodiments, the targeter stem sequence and the modulator stem sequence are hybridized through Watson-Crick base pairing.

In certain embodiments, the spacer sequence is about 20 nucleotides in length. In certain embodiments, the spacer sequence is 18 nucleotides in length or shorter. In certain embodiments, the spacer sequence is 17 nucleotides in length or shorter.

In certain embodiments, the targeter nucleic acid comprises, from 5' to 3', the targeter stem sequence, the spacer sequence, and an optional additional nucleotide sequence.

In certain embodiments, the targeter nucleic acid comprises a ribonucleic acid (RNA). In certain embodiments, the targeter nucleic acid comprises a modified RNA. In certain embodiments, the targeter nucleic acid comprises a combination of RNA and DNA. In certain embodiments, the targeter nucleic acid comprises a chemical modification. In certain embodiments, the chemical modification is present in one or more nucleotides at the 3' end of the targeter nucleic acid. In certain embodiments, the chemical modification is selected from the group consisting of 2'-O-methyl, 2'-fluoro, 2'-O-methoxyethyl, phosphorothioate, phosphorodithioate, pseudouridine, and any combinations thereof.

In certain embodiments, the modulator nucleic acid further comprises an additional nucleotide sequence. In certain embodiments, the additional nucleotide sequence is positioned 5' to the modulator stem sequence. In certain embodiments, the additional nucleotide sequence is 4-50 nucleotides in length. In certain embodiments, the additional nucleotide sequence comprises a donor template-recruiting sequence capable of hybridizing with a donor template. In certain embodiments, the engineered, non-naturally occurring system further comprises the donor template. In certain embodiments, the modulator nucleic acid comprises one or more nucleotides 3' to the modulator stem sequence.

In certain embodiments, the modulator nucleic acid comprises an RNA. In certain embodiments, the modulator nucleic acid comprises a modified RNA. In certain embodiments, the modulator nucleic acid comprises a combination of RNA and DNA. In certain embodiments, the modulator nucleic acid comprises a chemical modification. In certain embodiments, the chemical modification is present in one or more nucleotides at the 5' end of the modulator nucleic acid. In certain embodiments, the chemical modification is selected from the group consisting of 2'-O-methyl, 2'-fluoro, 2'-O-methoxyethyl, phosphorothioate, phosphorodithioate, pseudouridine, and any combinations thereof.

In certain embodiments, the targeter nucleic acid and the modulator nucleic acid are not covalently linked.

In certain embodiments, the Cas nuclease comprises an amino acid sequence at least 80% identical to SEQ ID NO: 1. In certain embodiments, the Cas nuclease is Cpf1. In certain embodiments, the engineered, non-naturally occurring system further comprises the Cas nuclease. In certain embodiments, the targeter nucleic acid, the modulator nucleic acid, and the Cas nuclease are present in a ribonucleoprotein (RNP) complex.

In another aspect, the present invention provides a eukaryotic cell comprising an engineered, non-naturally occurring system disclosed herein.

In another aspect, the present invention provides a composition (e.g., pharmaceutical composition) comprising an engineered, non-naturally occurring system or a eukaryotic cell disclosed herein.

In another aspect, the present invention provides a method of cleaving a target DNA having a target nucleotide sequence, the method comprising contacting the target DNA with an engineered, non-naturally occurring system disclosed herein, thereby resulting in cleavage of the target DNA.

In certain embodiments, the contacting occurs in vitro.

In certain embodiments, the contacting occurs in a cell ex vivo. In certain embodiments, the target DNA is genomic DNA of the cell. In certain embodiments, the system is delivered into the cell as a pre-formed RNP complex. In certain embodiments, the pre-formed RNP complex is delivered into the cell by electroporation.

In another aspect, the present invention provides a method of editing the genome of a eukaryotic cell, the method comprising delivering an engineered, non-naturally occurring system disclosed herein into the eukaryotic cell, thereby resulting in editing of the genome of the eukaryotic cell.

In certain embodiments, the system is delivered into the cell as a pre-formed RNP complex. In certain embodiments, the system is delivered into the cell by electroporation.

In certain embodiments of the method involving a eukaryotic cell, the cell is an immune cell. In certain embodiments, the immune cell is a T lymphocyte.

BRIEF DESCRIPTION OF THE DRAWINGS

In FIGS. 4A-4F, RNA #1 is a single guide RNA (SEQ ID NO: 150). RNAs #2 (SEQ ID NO: 42), #4 (SEQ ID NO: 15), #6 (SEQ ID NO: 53), #8 (SEQ ID NO: 55), and #10 (SEQ ID NO: 57) represent modulator RNAs, and RNAs #3, #5 (SEQ ID NO: 145), #7, #9, and #11 represent targeter RNAs. In FIGS. 4G-4H, RNAs #12 (SEQ ID NO: 148) and #14 (SEQ ID NO: 149)

are single guide RNAs containing hairpin sequences. RNA #13 (SEQ ID NO: 60) is a modulator RNA corresponding to RNA #12 (SEQ ID NO: 148), and RNA #15 (SEQ ID NO: 159) is a targeter RNA corresponding to RNA #14 (SEQ ID NO: 149). FIG. 4I is a set of photographs showing gel electrophoresis results from an in vitro cleavage experiment using MAD7 complexed with combinations of targeter and modulator RNAs.

FIG. 5A depicts SEQ ID NO: 150. FIG. 5B depicts SEQ ID NO: 151). FIG. 5C depicts SEQ ID NO: 45. FIG. 5D depicts SEQ ID NO: 66. FIG. 5E depicts SEQ ID NO: 70. FIG. 5F depicts SEQ ID NO: 72. FIG. 5G depicts SEQ ID NO: 68. FIG. 5H depicts SEQ ID NO: 72. FIG. 5I depicts SEQ ID NO: 76. Where a crRNA is split into a combination of a modulator RNA and a targeter RNA, thick crosses (within the loop regions, corresponding to combinations 3, 5, 7, 9, 11, 13, and 15) and thin crosses (within the stem regions, corresponding to combinations 4, 6, 8, 10, 12, 14, and 16) indicate the sites where the crRNAs are split. The Gibbs free energy change (ΔG) during the secondary structure formation of the corresponding crRNA, as predicted by the RNAfold program, is noted for each construct or combination.

FIG. 8 is a bar graph showing the percentage of genome copies edited in the CD52, PDCD1, or TIGIT genes of Jurkat cells after delivery of dual guide CRISPR systems with the crRNA split at different sites (1, 2, 3, 4, or 5 nucleotides with regards to the 5'end of the loop).

DETAILED DESCRIPTION OF THE INVENTION

Figure 1A:
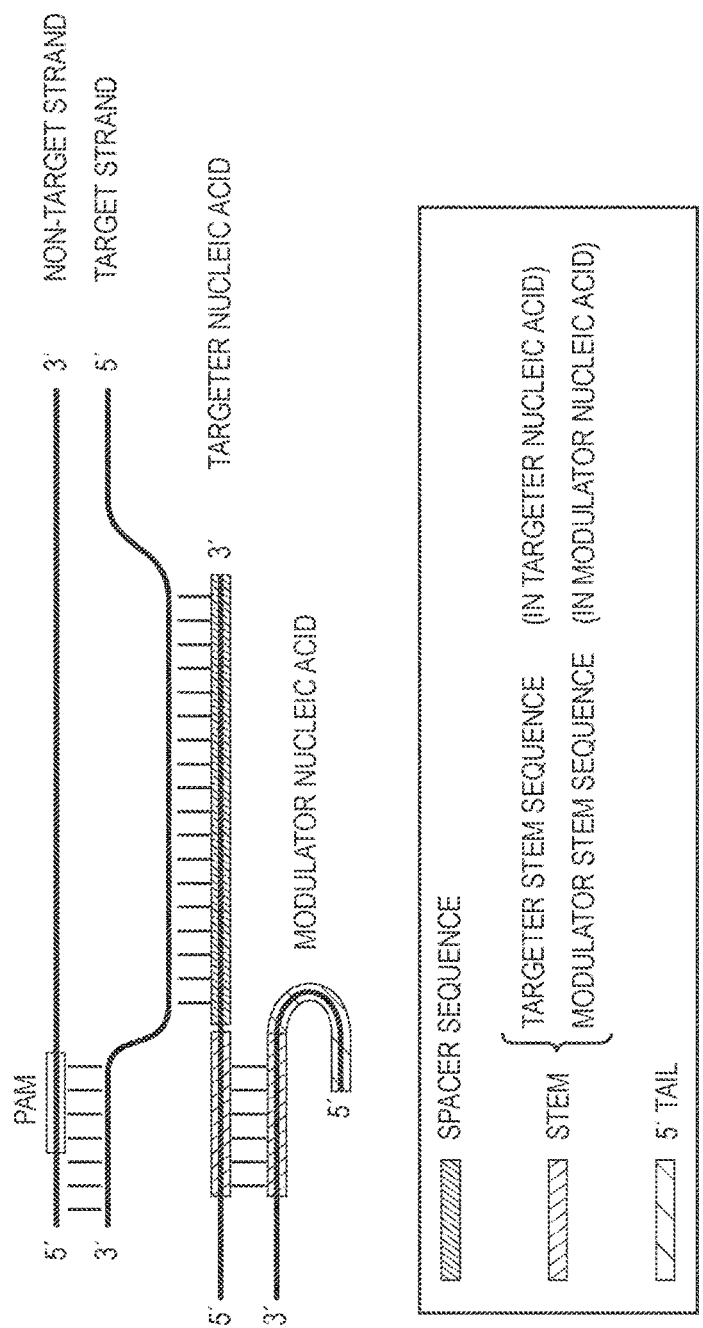
FIG. 1A is a schematic representation showing the structure of an exemplary dual guide type V-A CRISPR-Cas system.
Figure 1B:
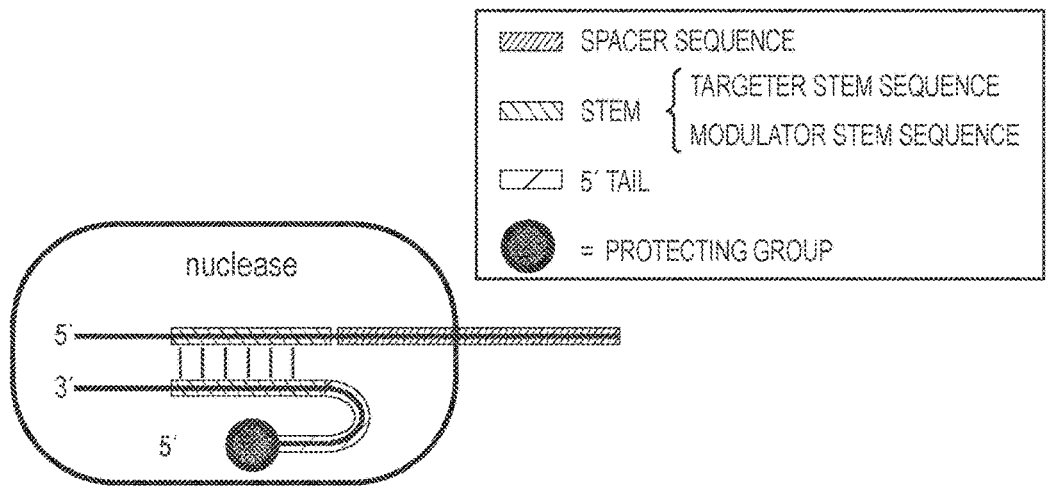
FIGS. 1B-1D are a series of schematic representation showing incorporation of a protecting group (e.g., a protective nucleotide sequence or a chemical modification) (FIG. 1B), a donor template-recruiting sequence (FIG. 1C), and an editing enhancer (FIG. 1D) into the dual guide type V-A CRISPR-Cas system.
Figure 1C:
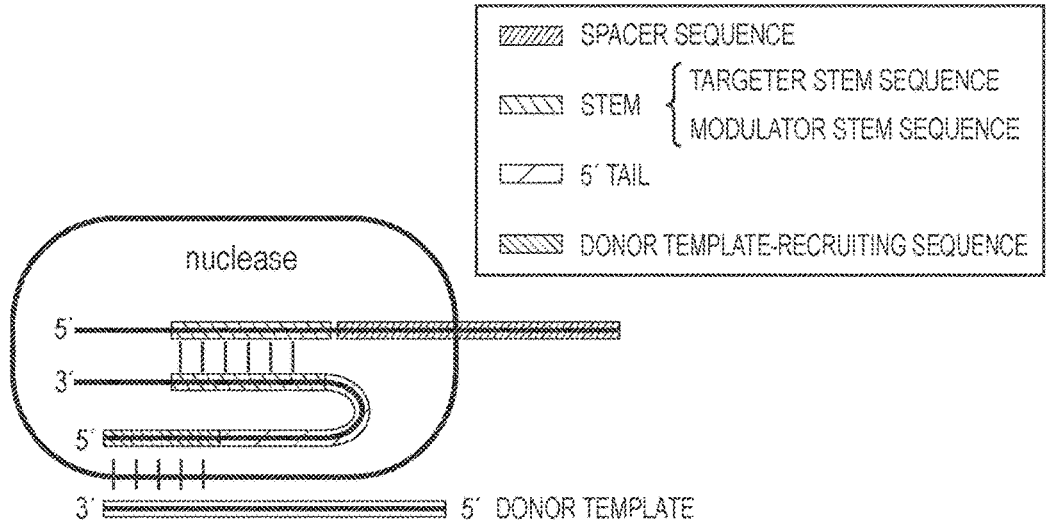

The invention is based, in part, upon the design of a dual guide CRISPR-Cas system in which a targeter nucleic acid and a modulator nucleic acid, when hybridized to form a complex, can activate a Cas nuclease that, in a naturally occurring system, is activated by a single crRNA in the absence of a tracrRNA. The engineered dual guide CRISPR-Cas system described herein can be used to target, edit, or modify a target nucleic acid such as genomic DNA.

Type V-A, type V-C, and type V-D CRISPR-Cas systems naturally include a Cas nuclease and a single guide RNA (i.e., crRNA). By splitting the single guide RNA into two different nucleic acids, the engineered system describe herein provides better flexibility and tunability. For example, the efficiency of nucleic acid cleavage can be increased or decreased by adjusting the hybridization length and/or affinity of the targeter nucleic acid and the modulator nucleic acid. Furthermore, given the length limitation of nucleic acids that can be synthesized with high yield and accuracy, the use of dual guide nucleic acids allows incorporation of more polynucleotide elements that can improve editing efficacy and/or specificity.

In particular, the dual guide system can be engineered as a tunable system to decrease off-target editing, and thus can be used to edit a nucleic acid with high specificity. The system can be employed in a number of applications, for example, editing cells such as mammalian cells for use in therapy. The decrease in off-target editing is particularly desirable when creating genetically engineered proliferating cells, such as stem cells, progenitor cells, and immune memory cells, to be administered to a subject in need of the therapy. High specificity can be accomplished using the dual guide systems described herein, which optionally further include, for example, one or more chemical modifications to the targeter nucleic acid and/or modulator nucleic acid, an editing enhancer sequence, and/or a donor template-recruiting sequence.

The features and uses of the dual guide CRISPR-Cas system are discussed in the following sections.

I. Engineered, Non-Naturally Occurring Dual Guide CRISPR-Cas Systems

The engineered, non-naturally occurring system of the present invention comprises:
 (a) a targeter nucleic acid comprising:
  (i) a spacer sequence designed to hybridize with a target nucleotide sequence; and
  (ii) a targeter stem sequence; and
 (b) a modulator nucleic acid comprising a modulator stem sequence complementary to the targeter stem sequence, wherein the targeter nucleic acid and the modulator nucleic acid are separate nucleic acids, and wherein a complex comprising the targeter nucleic acid and the modulator nucleic acid is capable of activating a Cas nuclease that, in a naturally occurring system, is activated by a single crRNA in the absence of a tracrRNA.

Type V-A, type V-C, and type V-D CRISPR-Cas systems are distinctive subtypes of CRISPR-Cas systems under the classification described in Makarova et al. (2017) CELL, 168:328. Naturally occurring CRISPR-Cas systems of these subtypes lack a tracrRNA and rely on a single crRNA to guide the CRISPR-Cas complex to the target DNA. Naturally occurring type V-A Cas proteins comprise a RuvC-like nuclease domain but lack an HNH endonuclease domain, and recognize a 5' T-rich protospacer adjacent motif (PAM), the 5' orientation determined using the non-target strand (i.e., the strand not hybridized with the spacer sequence) as the coordinate. Naturally occurring type V-A CRISPR-Cas systems cleave a double-stranded DNA to generate a staggered double-stranded break rather than a blunt end. The cleavage site is distant from the PAM site (e.g., separated by at least 10, 11, 12, 13, 14, or 15 nucleotides from the PAM on the non-target strand and/or separated by at least 15, 16, 17, 18, or 19 nucleotides from the sequence complementary to PAM on the target strand).

Accordingly, in another aspect, the instant disclosure provides an engineered, non-naturally occurring system comprising:
 (a) a targeter nucleic acid comprising:
  (i) a spacer sequence designed to hybridize with a target nucleotide sequence; and
  (ii) a targeter stem sequence; and
 (b) a modulator nucleic acid comprising a modulator stem sequence complementary to the targeter stem sequence, wherein the targeter nucleic acid and the modulator nucleic acid are separate nucleic acids, and wherein a complex comprising the targeter nucleic acid and the modulator nucleic acid is capable of activating a type V-A, type V-C, or type V-D Cas nuclease. In certain embodiments, the Cas nuclease is a type V-A Cas nuclease.

Cas Proteins

The terms "CRISPR-Associated protein," "Cas protein," and "Cas," as used interchangeably herein, refer to a naturally occurring Cas protein or an engineered Cas protein. Non-limiting examples of Cas protein engineering includes but are not limited to mutations and modifications of the Cas protein that alter the activity of the Cas, alter the PAM specificity, broaden the range of recognized PAMs, and/or reduce the ability to modify one or more off-target loci as compared to a corresponding unmodified Cas. In certain embodiments, the altered activity of the engineered Cas comprises altered ability (e.g., specificity or kinetics) to bind the naturally occurring or engineered dual guide nucleic acids, altered ability (e.g., specificity or kinetics) to bind the target nucleotide sequence, altered processivity of nucleic acid scanning, and/or altered effector (e.g., nuclease) activity. A Cas protein having the nuclease activity is referred to as a "CRISPR-Associated nuclease" or "Cas nuclease," as used interchangeably herein.

In certain embodiments, the Cas nuclease that a complex comprising the targeter nucleic acid and the modulator nucleic acid is capable of activating is a type V-A, type V-C, or type V-D Cas nuclease. In certain embodiments, the Cas nuclease is a type V-A nuclease.

In certain embodiments, the type V-A Cas nucleases comprises Cpf1. Cpf1 proteins are known in the art and are described in U.S. Pat. Nos. 9,790,490 and 10,113,179. Cpf1 orthologs can be found in various bacterial and archaeal genomes. For example, in certain embodiments, the Cpf1 protein is derived from *Francisella novicida* U112 (Fn), *Acidaminococcus* sp. BV3L6 (As), *Lachnospiraceae bacterium* ND2006 (Lb), *Lachnospiraceae bacterium* MA2020 (Lb2), *Candidatus methanoplasma termitum* (CMt), *Moraxella bovoculi* 237 (Mb), *Porphyromonas creviorica-nis* (Pc), *Prevotella disiens* (Pd), *Francisella tularensis* 1, *Francisella tularensis* subsp. *novicida*, *Prevotella albensis*, *Lachnospiraceae bacterium* MC2017 1, *Butyrivibrio pro-teoclasticus*, *Peregrinibacteria bacterium* GW2011_GWA2_33_10, *Parcubacteria bacterium* GW2011_GWC2_44_17, *Smithella* sp. SCADC, *Eubacte-rium eligens*, *Leptospira inadai*, *Porphyromonas macacae*, *Prevotella bryantii*, *Proteocatella sphenisci*, *Anaerovibrio* sp. RM50, *Moraxella caprae*, *Lachnospiraceae bacterium* COE1, or *Eubacterium coprostanoligenes*.

In certain embodiments, the type V-A Cas nuclease comprises AsCpf1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 3. In certain embodiments, the type V-A Cas protein comprises the amino acid sequence set forth in SEQ ID NO: 3.

AsCpf1
(SEQ ID NO: 3)
MTQFEGFTNLYQVSKTLRFELIPQGKTLKHIQEQGFIEEDKARNDHYKEL

KPIIDRIYKTYADQCLQLVQLDWENLSAAIDSYRKEKTEETRNALIEEQA

TYRNAIHDYFIGRTDNLTDAINKRHAEIYKGLFKAELFNGKVLKQLGTVT

TTEHENALLRSFDKFTTYFSGFYENRKNVFSAEDISTAIPHRIVQDNFPK

FKENCHIFTRLITAVPSLREHFENVKKAIGIFVSTSIEEVFSFPFYNQLL

TQTQIDLYNQLLGGISREAGTEKIKGLNEVLNLAIQKNDETAHIIASLPH

RFIPLFKQILSDRNTLSFILEEFKSDEEVIQSFCKYKTLLRNENVLETAE

ALFNELNSIDLTHIFISHKKLETISSALCDHWDTLRNALYERRISELTGK

ITKSAKEKVQRSLKHEDINLQEIISAAGKELSEAFKQKTSEILSHAHAAL

DQPLPTTLKKQEEKEILKSQLDSLLGLYHLLDWFAVDESNEVDPEFSARL

TGIKLEMEPSLSFYNKARNYATKKPYSVEKFKLNFQMPTLASGWDVNKEK

NNGAILFVKNGLYYLGIMPKQKGRYKALSFEPTEKTSEGFDKMYYDYFPD

AAKMIPKCSTQLKAVTAHFQTHTTPILLSNNFIEPLEITKEIYDLNNPEK

EPKKFQTAYAKKTGDQKGYREALCKWIDFTRDFLSKYTKTTSIDLSSLRP

SSQYKDLGEYYAELNPLLYHISFQRIAEKEIMDAVETGKLYLFQIYNKDF

AKGHHGKPNLHTLYWTGLFSPENLAKTSIKLNGQAELFYRPKSRMKRMAH

RLGEKMLNKKLKDQKTPIPDTLYQELYDYVNHRLSHDLSDEARALLPNVI

TKEVSHEIIKDRRFTSDKFFFHVPITLNYQAANSPSKFNQRVNAYLKEHP

ETPIIGIDRGERNLIYITVIDSTGKILEQRSLNTIQQFDYQKKLDNREKE

RVAARQAWSVVGTIKDLKQGYLSQVIHEIVDLMIHYQAVVVLENLNFGFK

SKRTGIAEKAVYQQFEKMLIDKLNCLVLKDYPAEKVGGVLNPYQLTDQFT

SFAKMGTQSGFLFYVPAPYTSKIDPLTGFVDPFVWKTIKNHESRKHFLEG

FDFLHYDVKTGDFILHFKMNRNLSFQRGLPGFMPAWDIVFEKNETQFDAK

GTPFIAGKRIVPVIENHRFTGRYRDLYPANELIALLEEKGIVFRDGSNIL

PKLLENDDSHAIDTMVALIRSVLQMRNSNAATGEDYINSPVRDLNGVCFD

SRFQNPEWPMDADANGAYHIALKGQLLLNHLKESKDLKLQNGISNQDWLA

YIQELRN

In certain embodiments, the type V-A Cas nuclease comprises LbCpf1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 4. In certain embodiments, the type V-A Cas protein comprises the amino acid sequence set forth in SEQ ID NO: 4.

LbCpf1
(SEQ ID NO: 4)
MSKLEKFTNCYSLSKTLRFKAIPVGKTQENIDNKRLLVEDEKRAEDYKGV

KKLLDRYYLSFINDVLHSIKLKNLNNYISLFRKKTRTEKENKELENLEIN

LRKEIAKAFKGNEGYKSLFKKDIIETILPEFLDDKDEIALVNSFNGFTTA

FTGFFDNRENMFSEEAKSTSIAFRCINENLTRYISNMDIFEKVDAIFDKH

EVQEIKEKILNSDYDVEDFFEGEFFNFVLTQEGIDVYNAIIGGFVTESGE

KIKGLNEYINLYNQKTKQKLPKFKPLYKQVLSDRESLSFYGEGYTSDEEV

LEVFRNTLNKNSEIFSSIKKLEKLFKNFDEYSSAGIFVKNGPAISTISKD

IFGEWNVIRDKWNAEYDDIHLKKKAVVTEKYEDDRRKSFKKIGSFSLEQL

-continued
QEYADADLSVVEKLKEIIQKVDEIYKVYGSSEKLFDADFVLEKSLKKND

AVVAIMKDLLDSVKSFENYIKAFFGEGKETNRDESFYGDFVLAYDILLKV

DHIYDAIRNYVTQKPYSKDKFKLYFQNPQFMGGWDKDKETDYRATILRYG

SKYYLAIMDKKYAKCLQKIDKDDVNGNYEKINYKLLPGPNKMLPKVFFSK

KWMAYYNPSEDIQKIYKNGTFKKGDMFNLNDCHKLIDFFKDSISRYPKWS

NAYDFNFSETEKYKDIAGFYREVEEQGYKVSFESASKKEVDKLVEEGKLY

MFQIYNKDFSDKSHGTPNLHTMYFKLLFDENNHGQIRLSGGAELFMRRAS

LKKEELVVHPANSPIANKNPDNPKKTTTLSYDVYKDKRFSEDQYELHIPI

AINKCPKNIFKINTEVRVLLKHDDNPYVIGIDRGERNLLYIVVVDGKGNI

VEQYSLNEIINNFNGIRIKTDYHSLLDKKEKERFEARQNWTSIENIKELK

AGYISQVVHKICELVEKYDAVIALEDLNSGFKNSRVKVEKQVYQKFEKML

IDKLNYMVDKKSNPCATGGALKGYQITNKFESFKSMSTQNGFIFYIPAWL

TSKIDPSTGFVNLLKTKYTSIADSKKFISSFDRIMYVPEEDLFEFALDYK

NFSRTDADYIKKWKLYSYGNRIRIFRNPKKNNVFDWEEVCLTSAYKELFN

KYGINYQQGDIRALLCEQSDKAFYSSFMALMSLMLQMRNSITGRTDVDFL

ISPVKNSDGIFYDSRNYEAQENAILPKNADANGAYNIARKVLWAIGQFKK

AEDEKLDKVKIAISNKEWLEYAQTSVKH

In certain embodiments, the type V-A Cas nuclease comprises FnCpf1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 5. In certain embodiments, the type V-A Cas protein comprises the amino acid sequence set forth in SEQ ID NO: 5.

FnCpf1
(SEQ ID NO: 5)
MSIYQEFVNKYSLSKTLRFELIPQGKTLENIKARGLILDDEKRAKDYKKA

KQIIDKYHQFFIEEILSSVCISEDLLQNYSDVYFKLKKSDDDNLQKDFKS

AKDTIKKQISEYIKDSEKFKNLFNQNLIDAKKGQESDLILWLKQSKDNGI

ELFKANSDITDIDEALEIIKSFKGWTTYFKGFHENRKNVYSSNDIPTSII

YRIVDDNLPKFLENKAKYESLKDKAPEAINYEQIKKDLAEELTFDIDYKT

SEVNQRVFSLDEVFEIANFNNYLNQSGITKFNTIIGGKFVNGENTKRKGI

NEYINLYSQQINDKTLKKYKMSVLFKQILSDTESKSFVIDKLEDDSDVVT

TMQSFYEQIAAFKTVEEKSIKETLSLLFDDLKAQKLDLSKIYFKNDKSLT

DLSQQVFDDYSVIGTAVLEYITQQIAPKNLDNPSKKEQELIAKKTEKAKY

LSLETIKLALEEFNKHRDIDKQCRFEEILANFAAIPMIFDEIAQNKDNLA

QISIKYQNQGKKDLLQASAEDDVKAIKDLLDQTNNLLHKLKIFHISQSED

KANILDKDEHFYLVFEECYFELANIVPLYNKIRNYITQKPYSDEKFKLNF

ENSTLANGWDKNKEPDNTAILFIKDDKYYLGVMNKKNNKIFDDKAIKENK

GEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSI

-continued
DEFYREVENQGYKLTFENISESYIDSVVNQGKLYLFQIYNKDFSAYSKGR

PNLHTLYWKALFDERNLQDVVYKLNGEAELFYRKQSIPKKITHPAKEAIA

NKNKDNPKKESVFEYDLIKDKRFTEDKFFFHCPITINFKSSGANKENDEI

NLLLKEKANDVHILSIDRGERHLAYYTLVDGKGNIIKQDTFNIIGNDRMK

TNYHDKLAAIEKDRDSARKDWKKINNIKEMKEGYLSQVVHEIAKLVIEYN

AIVVFEDLNFGFKRGRFKVEKQVYQKLEKMLIEKLNYLVFKDNEFDKTGG

VLRAYQLTAPFETFKKMGKQTGIIYYVPAGFTSKICPVTGFVNQLYPKYE

SVSKSQEFFSKFDKICYNLDKGYFEFSFDYKNFGDKAAKGKWTIASFGSR

LINFRNSDKNHNWDTREVYPTKELEKLLKDYSIEYGHGECIKAAICGESD

KKFFAKLTSVLNTILQMRNSKTGTELDYLISPVADVNGNFFDSRQAPKNM

PQDADANGAYHIGLKGLMLLGRIKNNQEGKKLNLVIKNEEYFEFVQNRNN

In certain embodiments, the type V-A Cas nuclease comprises *Prevotella bryantii* Cpf1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 6. In certain embodiments, the type V-A Cas protein comprises the amino acid sequence set forth in SEQ ID NO: 6.

*Prevotella bryantii* Cpf1
(SEQ ID NO: 6)
MQINNLKIIYMKFTDFTGLYSLSKTLRFELKPIGKTLENIKKAGLLEQDQ

HRADSYKKVKKIIDEYHKAFIEKSLSNFELKYQSEDKLDSLEEYLMYYSM

KRIEKTEKDKFAKIQDNLRKQIADHLKGDESYKTIFSKDLIRKNLPDFVK

SDEERTLIKEFKDFTTYFKGFYENRENMYSAEDKSTAISHRIIHENLPKF

VDNINAFSKIILIPELREKLNQIYQDFEEYLNVESIDEIFHLDYFSMVMT

QKQIEVYNAIIGGKSTNDKKIQGLNEYINLYNQHKDCKLPKLKLLFKQI

LSDRIAISWLPDNFKDDQEALDSIDTCYKNLLNDGNVLGEGNLKLLLENI

DTYNLKGIFIRNDLQLTDISQKMYASWNVIQDAVILDLKKQVSRKKKESA

EDYNDRLKKLYTSQESFSIQYLNDCLRAYGKTENIQDYFAKLGAVNNEHE

QTINLFAQVRNAYTSVQAILTTPYPENANLAQDKETVALIKNLLDSLKRL

QRFIKPLLGKGDESDKDERFYGDFTPLWETLNQITPLYNMVRNYMTRKPY

SQEKIKLNFENSTLLGGWDLNKEHDNTAIILRKNGLYYLAIMKKSANKIF

DKDKLDNSGDCYEKMVYKLLPGANKMLPKVFFSKSRIDEFKPSENIIENY

KKGTHKKGANFNLADCHNLIDFFKSSISKHEDWSKFNFHFSDTSSYEDLS

DFYREVEQQGYSISFCDVSVEYINKMVEKGDLYLFQIYNKDFSEFSKGTP

NMHTLYWNSLFSKENLNNIIYKLNGQAEIFFRKKSLNYKRPTHPAHQAIK

NKNKCNEKKESIFDYDLVKDKRYTVDKFQFHVPITMNFKSTGNTNINQQV

IDYLRTEDDTHIIGIDRGERHLLYLVVIDSHGKIVEQFTLNEIVNEYGGN

IYRTNYHDLLDTREQNREKARESWQTIENIKELKEGYISQVIHKITDLMQ

KYHAVVVLEDLNMGFMRGRQKVEKQVYQKFEEMLINKLNYLVNKKADQNS

AGGLLHAYQLTSKFESFQKLGKQSGFLFYIPAWNTSKIDPVTGFVNLFDT

-continued

RYESIDKAKAFFGKFDSIRYNADKDWFEFAFDYNNFTTKAEGTRTNWTIC

TYGSRIRTFRNQAKNSQWDNEEIDLTKAYKAFFAKHGINIYDNIKEAIAM

ETEKSFFEDLLHLLKLTLQMRNSITGTTTDYLISPVHDSKGNFYDSRICD

NSLPANADANGAYNIARKGLMLIQQIKDSTSSNRFKFSPITNKDWLIFAQ

EKPYLND

In certain embodiments, the type V-A Cas nuclease comprises *Proteocatella sphenisci* Cpf1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 7. In certain embodiments, the type V-A Cas protein comprises the amino acid sequence set forth in SEQ ID NO: 7.

*Proteocatella sphenisci* Cpf1
(SEQ ID NO: 7)
MENFKNLYPINKTLRFELRPYGKTLENFKKSGLLEKDAFKANSRRSMQAI

IDEKFKETIEERLKYTEFSECDLGNMTSKDKKITDKAATNLKKQVILSFD

DEIFNNYLKPDKNIDALFKNDPSNPVISTFKGFTTYFVNFFEIRKHIFKG

ESSGSMAYRIIDENLTTYLNNIEKIKKLPEELKSQLEGIDQIDKLNNYNE

FITQSGITHYNEIIGGISKSENVKIQGINEGINLYCQKNKVKLPRLTPLY

KMILSDRVSNSFVLDTIENDTELIEMISDLINKTEISQDVIMSDIQNIFI

KYKQLGNLPGISYSSIVNAICSDYDNNFGDGKRKKSYENDRKKHLETNVY

SINYISELLTDTDVSSNIKMRYKELEQNYQVCKENFNATNWMNIKNIKQS

EKTNLIKDLLDILKSIQRFYDLFDIVDEDKNPSAEFYTWLSKNAEKLDFE

FNSVYNKSRNYLTRKQYSDKKIKLNFDSPTLAKGWDANKEIDNSTIIMRK

FNNDRGDYDYFLGIWNKSTPANEKIIPLEDNGLFEKMQYKLYPDPSKMLP

KQFLSKIWKAKHPTTPEFDKKYKEGRHKKGPDFEKEFLHELIDCFKHGLV

NHDEKYQDVFGFNLRNTEDYNSYTEFLEDVERCNYNLSFNKIADTSNLIN

DGKLYVFQIWSKDFSIDSKGTKNLNTIYFESLFSEENMIEKMFKLSGEAE

IFYRPASLNYCEDIIKKGHHHAELKDKFDYPIIKDKRYSQDKFFFHVPMV

INYKSEKLNSKSLNNRTNENLGQFTHIIGIDRGERHLIYLTVVDVSTGEI

VEQKHLDEIINTDTKGVEHKTHYLNKLEEKSKTRDNERKSWEAIETIKEL

KEGYISHVINEIQKLQEKYNALIVMENLNYGFKNSRIKVEKQVYQKFETA

LIKKFNYIIDKKDPETYIHGYQLTNPITTLDKIGNQSGIVLYIPAWNTSK

IDPVTGFVNLLYADDLKYKNQEQAKSFIQKIDNIYFENGEFKFDIDFSKW

NNRYSISKTKWTLTSYGTRIQTFRNPQKNNKWDSAEYDLTEEFKLILNID

GTLKSQDVETYKKFMSLFKLMLQLRNSVTGTDIDYMISPVTDKTGTHFDS

RENIKNLPADADANGAYNIARKGIMAIENIMNGISDPLKISNEDYLKYIQ

NQQE

In certain embodiments, the type V-A Cas nuclease comprises Anaerovibrio sp. RM50 Cpf1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 8. In certain embodiments, the type V-A Cas protein comprises the amino acid sequence set forth in SEQ ID NO: 8.

*Anaerovibrio* sp. RM50 Cpf1
(SEQ ID NO: 8)
MVAFIDEFVGQYPVSKTLRFEARPVPETKKWLESDQCSVLFNDQKRNEYY

GVLKELLDDYYRAYIEDALTSFTLDKALLENAYDLYCNRDTNAFSSCCEK

LRKDLVKAFGNLKDYLLGSDQLKDLVKLKAKVDAPAGKGKKKIEVDSRLI

NWLNNNAKYSAEDREKYIKAIESFEGFVTYLTNYKQARENMFSSEDKSTA

IAFRVIDQNMVTYFGNIRIYEKIKAKYPELYSALKGFEKFFSPTAYSEIL

SQSKIDEYNYQCIGRPIDDADFKGVNSLINEYRQKNGIKARELPVMSMLY

KQILSDRDNSFMSEVINRNEEAIECAKNGYKVSYALFNELLQLYKKIFTE

DNYGNIYVKTQPLTELSQALFGDWSILRNALDNGKYDKDIINLAELEKYF

SEYCKVLDADDAAKIQDKFNLKDYFIQKNALDATLPDLDKITQYKPHLDA

MLQAIRKYKLFSMYNGRKKMDVPENGIDFSNEFNAIYDKLSEFSILYDRI

RNFATKKPYSDEKMKLSFNMPTMLAGWDYNNETANGCFLFIKDGKYFLGV

ADSKSKNIFDFKKNPHLLDKYSSKDIYYKVKYKQVSGSAKMLPKVVFAGS

NEKIFGHLISKRILEIREKKLYTAAAGDRKAVAEWIDFMKSAIAIHPEWN

EYFKFKFKNTAEYDNANKFYEDIDKQTYSLEKVEIPTEYIDEMVSQHKLY

LFQLYTKDFSDKKKKKGTDNLHTMYWHGVFSDENLKAVTEGTQPIIKLNG

EAEMFMRNPSIEFQVTHEHNKPIANKNPLNTKKESVFNYDLIKDKRYTER

KFYFHCPITLNFRADKPIKYNEKINRFVENNPDVCIIGIDRGERHLLYYT

VINQTGDILEQGSLNKISGSYTNDKGEKVNKETDYHDLLDRKEKGKHVAQ

QAWETIENIKELKAGYLSQVVYKLTQLMLQYNAVIVLENLNVGFKRGRTK

VEKQVYQKFEKAMIDKLNYLVFKDRGYEMNGSYAKGLQLTDKFESFDKIG

KQTGCIYYVIPSYTSHIDPKTGFVNLLNAKLRYENITKAQDTIRKFDSIS

YNAKADYFEFAFDYRSFGVDMARNEWVVCTCGDLRWEYSAKTRETKAYSV

TDRLKELFKAHGIDYVGGENLVSHITEVADKHELSTLLFYLRLVLKMRYT

VSGTENENDFILSPVEYAPGKFFDSREATSTEPMNADANGAYHIALKGLM

TIRGIEDGKLHNYGKGGENAAWFKFMQNQEYKNNG

In certain embodiments, the type V-A Cas nuclease comprises *Moraxella caprae* Cpf1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 9. In certain embodiments, the type V-A Cas protein comprises the amino acid sequence set forth in SEQ ID NO: 9.

*Moraxella caprae* Cpf1

(SEQ ID NO: 9)
MLFQDFTHLYPLSKTMRFELKPIGKTLEHIHAKNFLSQDETMADMYQKVK
AILDDYHRDFIADMMGEVKLTKLAEFYDVYLKFRKNPKDDGLQKQLKDLQ
AVLRKEIVKPIGNGGKYKAGYDRLFGAKLFKDGKELGDLAKFVIAQEGES
SPKLAHLAHFEKFSTYFTGFHDNRKNMYSDEDKHTAITYRLIHENLPRFI
DNLQILATIKQKHSALYDQIINELTASGLDVSLASHLDGYHKLLTQEGIT
AYNTLLGGISGEAGSRKIQGINELINSHHNQHCHKSERIAKLRPLHKQIL
SDGMGVSFLPSKFADDSEMCQAVNEFYRHYADVFAKVQSLFDGFDDHQKD
GIYVEHKNLNELSKQAFGDFALLGRVLDGYYVDVVNPEFNERFAKAKTDN
AKAKLTKEKDKFIKGVHSLASLEQAIEHYTARHDDESVQAGKLGQYFKHG
LAGVDNPIQKIHNNHSTIKGFLERERPAGERALPKIKSGKNPEMTQLRQL
KELLDNALNVAHFAKLLTTKTTLDNQDGNFYGEFGALYDELAKIPTLYNK
VRDYLSQKPFSTEKYKLNFGNPTLLNGWDLNKEKDNFGIILQKDGCYYLA
LLDKAHKKVFDNAPNTGKNVYQKMIYKLLPGPNKMLPKVFFAKSNLDYYN
PSAELLDKYAQGTHKKGNNFNLKDCHALIDFFKAGINKHPEWQHFGFKFS
PTSSYQDLSDFYREVEPQGYQVKFVDINADYINELVEQGQLYLFQIYNKD
FSPKAHGKPNLHTLYFKALFSKDNLANPIYKLNGEAQIFYRKASLDMNET
TIHRAGEVLENKNPDNPKKRQFVYDIIKDKRYTQDKFMLHVPITMNFGVQ
GMTIKEFNKKVNQSIQQYDEVNVIGIDRGERHLLYLTVINSKGEILEQRS
LNDITTASANGTQMTTPYHKILDKREIERLNARVGWGEIETIKELKSGYL
SHVVHQISQLMLKYNAIVVLEDLNFGFKRGRFKVEKQIYQNFENALIKKL
NHLVLKDEADDEIGSYKNALQLTNNFTDLKSIGKQTGFLFYVPAWNTSKI
DPETGFVDLLKPRYENIAQSQAFFGKFDKICYNADKDYFEFHIDYAKFTD
KAKNSRQIWKICSHGDKRYVYDKTANQNKGATKGINVNDELKSLFARHHI
NDKQPNLVMDICQNNDKEFHKSLIYLLKTLLALRYSNASSDEDFILSPVA
NDEGMFFNSALADDTQPQNADANGAYHIALKGLWVLEQIKNSDDLNKVKL
AIDNQTWLNFAQNR

In certain embodiments, the type V-A Cas nuclease comprises *Lachnospiraceae bacterium* COE1 Cpf1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 10. In certain embodiments, the type V-A Cas protein comprises the amino acid sequence set forth in SEQ ID NO: 10.

*Lachnospiraceae bacterium* COE1 Cpf1

(SEQ ID NO: 10)
MHENNGKIADNFIGIYPVSKTLRFELKPVGKTQEYIEKHGILDEDLKRAG
DYKSVKKIIDAYHKYFIDEALNGIQLDGLKNYYELYEKKRDNNEEKEFQK
IQMSLRKQIVKRFSEHPQYKYLFKKELIKNVLPEFTKDNAEEQTLVKSFQ
EFTTYFEGFHQNRKNMYSDEEKSTAIAYRVVHQNLPKYIDNMRIFSMILN
TDIRSDLTELFNNLKTKMDITIVEEYFAIDGENKVVNQKGIDVYNTILGA
FSTDDNTKIKGLNEYINLYNQKNKAKLPKLKPLFKQILSDRDKISFIPEQ
FDSDTEVLEAVDMFYNRLLQFVIENEGQITISKLLTNFSAYDLNKIYVKN
DTTISAISNDLFDDWSYISKAVRENYDSENVDKNKRAAAYEEKKEKALSK
IKMYSIEELNFFVKKYSCNECHIEGYFERRILEILDKMRYAYESCKILHD
KGLINNISLCQDRQAISELKDFLDSIKEVQWLLKPLMIGQEQADKEEAFY
TELLRIWEELEPITLLYNKVRNYVTKKPYTLEKVKLNFYKSTLLDGWDKN
KEKDNLGIILLKDGQYYLGIMNRRNNKIADDAPLAKTDNVYRKMEYKLLT
KVSANLPRIFLKDKYNPSEEMLEKYEKGTHLKGENFCIDDCRELIDFFKK
GIKQYEDWGQFDFKFSDTESYDDISAFYKEVEHQGYKITFRDIDETYIDS
LVNEGKLYLFQIYNKDFSPYSKGTKNLHTLYWEMLFSQQNLQNIVYKLNG
NAEIFYRKASINQKDVVVHKADLPIKNKDPQNSKKESMFDYDIIKDKRFT
CDKYQFHVPITMNFKALGENHFNRKVNRLIHDAENMHIIGIDRGERNLIY
LCMIDMKGNIVKQISLNEIISYDKNKLEHKRNYHQLLKTREDENKSARQS
WQTIHTIKELKEGYLSQVIHVITDLMVEYNAIVVLEDLNFGFKQGRQKFE
RQVYQKFEKMLIDKLNYLVDKSKGMDEDGGLLHAYQLTDEFKSFKQLGKQ
SGFLYYIPAWNTSKLDPTTGFVNLFYTKYESVEKSKEFINNFTSILYNQE
REYFEFLFDYSAFTSKAEGSRLKWTVCSKGERVETYRNPKKNNEWDTQKI
DLTFELKKLFNDYSISLLDGDLREQMGKIKDKADFYKKFMKLFALIVQMRN
SDEREDKLISPVLNKYGAFFETGKNERMPLDADANGAYNIARKGLWIIEK
IKNTDVEQLDKVKLTISNKEWLQYAQEHIL

In certain embodiments, the type V-A Cas nuclease comprises *Eubacterium* coprostanoligenes Cpf1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 11. In certain embodiments, the type V-A Cas protein comprises the amino acid sequence set forth in SEQ ID NO: 11.

*Eubacterium coprostanoligenes* Cpf1

(SEQ ID NO: 11)
MDFFKNDMYFLCINGIIVISKLFAYLFLMYKRGVVMIKDNFVNVYSLSKT
IRMALIPWGKTEDNFYKKFLLEEDEERAKNYIKVKGYMDEYHKNFIESAL
NSVVLNGVDEYCELYFKQNKSDSEVKKIESLEASMRKQISKAMKEYTVDG
VKIYPLLSKKEFIRELLPEFLTQDEEIETLEQFNDFSTYFQGFWENRKNI
YTDEEKSTGVPYRCINDNLPKFLDNVKSFEKVILALPQKAVDELNANFNG
VYNVDVQDVFSVDYFNFVLSQSGIEKYNNIIGGYSNSDASKVQGLNEKIN
LYNQQIAKSDKSKKLPLLKPLYKQILSDRSSLSFIPEKFKDDNEVLNSIN
VLYDNIAESLEKANDLMSDIANYNTDNIFISSGVAVTDISKKVFGDWSLI
RNNWNDEYESTHKKGKNEEKFYEKEDKEFKKIKSFSVSELQRLANSDLSI
VDYLVDESASLYADIKTAYNNAKDLLSNEYSHSKRLSKNDDAIELIKSFL
DSIKNYEAFLKPLCGTGKEESKDNAFYGAFLECFEEIRQVDAVYNKVRNH

ITQKPYSNDKIKLNFQNPQFLAGWDKNKERAYRSVLLRNGEKYYLAIMEK

GKSKLFEDFPEDESSPFEKIDYKLLPEPSKMLPKVFFATSNKDLFNPSDE

ILNIRATGSFKKGDSFNLDDCHKFIDFYKASIENHPDWSKFDFDFSETND

YEDISKFFKEVSDQGYSIGYRKISESYLEEMVDNGSLYMFQLYNKDFSEN

RKSKGTPNLHTLYFKMLFDERNLEDVVYKLSGGAEMFYRKPSIDKNEMIV

HPKNQPIDNKNPNNVKKTSTFEYDIVKDMRYTKPQFQLHLPIVLNFKANS

KGYINDDVRNVLKNSEDTYVIGIDRGERNLVYACVVDGNGKLVEQVPLNV

IEADNGYKTDYHKLLNDREEKRNEARKSWKTIGNIKELKEGYISQVVHKI

CQLVVKYDAVIAMEDLNSGFVNSRKKVEKQVYQKFERMLTQKLNYLVDKK

LDPNEMGGLLNAYQLTNEATKVRNGRQDGIIFYIPAWLTSKIDPTTGFVN

LLKPKYNSVSASKEFFSKFDEIRYNEKENYFEFSFNYDNFPKCNADFKRE

WTVCTYGDRIRTFRDPENNNKFNSEVVVLNDEFKNLFVEFDIDYTDNLKE

QILAMDEKSFYKKLMGLLSLTLQMRNSISKNVDVDYLISPVKNSNGEFYD

SRNYDITSSLPCDADSNGAYNIARKGLWAINQIKQADDETKANISIKNSE

WLQYAQNCDEV

In certain embodiments, the type V-A Cas nuclease is not Cpf1. In certain embodiments, the type V-A Cas nuclease is not AsCpf1.

In certain embodiments, the type V-A Cas nuclease comprises MAD1, MAD2, MAD3, MAD4, MAD5, MAD6, MAD7, MAD8, MAD9, MAD10, MAD11, MAD12, MAD13, MAD14, MAD15, MAD16, MAD17, MAD18, MAD19, or MAD20, or variants thereof. MAD1-MAD20 are known in the art and are described in U.S. Pat. No. 9,982,279.

In certain embodiments, the type V-A Cas nuclease comprises MAD7 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 1. In certain embodiments, the type V-A Cas protein comprises the amino acid sequence set forth in SEQ ID NO: 1.

MAD7
(SEQ ID NO: 1)
MNNGTNNFQNFIGISSLQKTLRNALIPTETTQQFIVKNGIIKEDELRGEN

RQILKDIMDDYYRGFISETLSSIDDIDWTSLFEKMEIQLKNGDNKDTLIK

EQTEYRKAIHKKFANDDRFKNMFSAKLISDILPEFVIHNNNYSASEKEEK

TQVIKLFSRFATSFKDYFKNRANCFSADDISSSSCHRIVNDNAEIFFSNA

LVYRRIVKSLSNDDINKISGDMKDSLKEMSLEEIYSYEKYGEFITQEGIS

FYNDICGKVNSFMNLYCQKNKENKNLYKLQKLHKQILCIADTSYEVPYKF

ESDEEVYQSVNGFLDNISSKHIVERLRKIGDNYNGYNLDKIYIVSKFYES

VSQKTYRDWETINTALEIHYNNILPGNGKSKADKVKKAVKNDLQKSITEI

NELVSNYKLCSDDNIKAETYIHEISHILNNFEAQELKYNPEIHLVESELK

ASELKNVLDVIMNAFHWCSVFMTEELVDKDNNFYAELEEIYDEIYPVISL

YNLVRNYVTQKPYSTKKIKLNFGIPTLADGWSKSKEYSNNAIILMRDNLY

YLGIFNAKNKPDKKIIEGNTSENKGDYKKMIYNLLPGPNKMIPKVFLSSK

TGVETYKPSAYILEGYKQNKHIKSSKDFDITFCHDLIDYFKNCIAIHPEW

KNFGFDFSDTSTYEDISGFYREVELQGYKIDWTYISEKDIDLLQEKGQLY

LFQIYNKDFSKKSTGNDNLHTMYLKNLFSEENLKDIVLKLNGEAEIFFRK

SSIKNPIIHKKGSILVNRTYEAEEKDQFGNIQIVRKNIPENIYQELYKYF

NDKSDKELSDEAAKLKNVVGHHEAATNIVKDYRYTYDKYFLHMPITINFK

ANKTGFINDRILQYIAKEKDLHVIGIDRGERNLIYVSVIDTCGNIVEQKS

FNIVNGYDYQIKLKQQEGARQIARKEWKEIGKIKEIKEGYLSLVIHEISK

MVIKYNAIIAMEDLSYGFKKGRFKVERQVYQKFETMLINKLNYLVFKDIS

ITENGGLLKGYQLTYIPDKLKNVGHQCGCIFYVPAAYTSKIDPTTGFVNI

FKFKDLTVDAKREFIKKFDSIRYDSEKNLFCFTFDYNNFITQNTVMSKSS

WSVYTYGVRIKRRFVNGRFSNESDTIDITKDMEKTLEMTDINWRDGHDLR

QDIIDYEIVQHIFEIFRLTVQMRNSLSELEDRDYDRLISPVLNENNIFYD

SAKAGDALPKDADANGAYCIALKGLYEIKQITENWKEDGKFSRDKLKISN

KDWFDFIQNKRYL

In certain embodiments, the type V-A Cas nuclease comprises MAD2 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 2. In certain embodiments, the type V-A Cas protein comprises the amino acid sequence set forth in SEQ ID NO: 2.

MAD2
(SEQ ID NO: 2)
MSSLTKFTNKYSKQLTIKNELIPVGKTLENIKENGLIDGDEQLNENYQKA

KIIVDDFLRDFINKALNNTQIGNWRELADALNKEDEDNIEKLQDKIRGII

VSKFETFDLFSSYSIKKDEKIIDDDNDVEEEELDLGKKTSSFKYIFKKNL

FKLVLPSYLKTTNQDKLKIISSFDNFSTYFRGFFENRKNIFTKKPISTSI

AYRIVHDNFPKFLDNIRCFNVWQTECPQLIVKADNYLKSKNVIAKDKSLA

NYFTVGAYDYFLSQNGIDFYNNIIGGLPAFAGHEKIQGLNEFINQECQKD

SELKSKLKNRHAFKMAVLFKQILSDREKSFVIDEFESDAQVIDAVKNFYA

EQCKDNNVIFNLLNLIKNIAFLSDDELDGIFIEGKYLSSVSQKLYSDWSK

LRNDIEDSANSKQGNKELAKKIKTNKGDVEKAISKYEFSLSELNSIVHDN

TKFSDLLSCTLHKVASEKLVKVNEGDWPKHLKNNEEKQKIKEPLDALLEI

YNTLLIFNCKSFNKNGNFYVDYDRCINELSSVVYLYNKTRNYCTKKPYNT

DKFKLNFNSPQLGEGFSKSKENDCLTLLFKKDDNYYVGIIRKGAKINFDD

TQAIADNTDNCIFKMNYFLLKDAKKFIPKCSIQLKEVKAHFKKSEDDYIL

SDKEKFASPLVIKKSTFLLATAHVKGKKGNIKKFQKEYSKENPTEYRNSL

NEWIAFCKEFLKTYKAATIFDITTLKKAEEYADIVEFYKDVDNLCYKLEF

CPIKTSFIENLIDNGDLYLFRINNKDFSSKSTGTKNLHTLYLQAIFDERN

LNNPTIMLNGGAELFYRKESIEQKNRITHKAGSILVNKVCKDGTSLDDKI

-continued

RNEIYQYENKFIDTLSDEAKKVLPNVIKKEATHDITKDKRFTSDKFFFHC

PLTINYKEGDTKQFNNEVLSFLRGNPDINIIGIDRGERNLIYVTVINQKG

EILDSVSFNTVTNKSSKIEQTVDYEEKLAVREKERIEAKRSWDSISKIAT

LKEGYLSAIVHEICLLMIKHNAIVVLENLNAGFKRIRGGLSEKSVYQKFE

KMLINKLNYFVSKKESDWNKPSGLLNGLQLSDQFESFEKLGIQSGFIFYV

PAAYTSKIDPTTGFANVLNLSKVRNVDAIKSFFSNFNEISYSKKEALFKF

SFDLDSLSKKGFSSFVKFSKSKWNVYTFGERIIKPKNKQGYREDKRINLT

FEMKKLLNEYKVSFDLENNLIPNLTSANLKDTFWKELFFIFKTTLQLRNS

VTNGKEDVLISPVKNAKGEFFVSGTHNKTLPQDCDANGAYHIALKGLMIL

ERNNLVREEKDTKKIMAISNVDWFEYVQKRRGVL

In certain embodiments, the type V-A Cas nucleases comprises Csm1. Csm1 proteins are known in the art and are described in U.S. Pat. No. 9,896,696. Csm1 orthologs can be found in various bacterial and archaeal genomes. For example, in certain embodiments, the Csm1 protein is derived from *Smithella* sp. SCADC (Sm), *Sulfuricurvum* sp. (Ss), or *Microgenomates* (*Roizmanbacteria*) *bacterium* (Mb).

In certain embodiments, the type V-A Cas nuclease comprises SmCsm1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 12. In certain embodiments, the type V-A Cas protein comprises the amino acid sequence set forth in SEQ ID NO: 12.

*Smithella* sp. SCADC Csm1
(SEQ ID NO: 12)
MEKYKITKTIRFKLLPDKIQDISRQVAVLQNSTNAEKKNNLLRLVQRGQE

LPKLLNEYIRYSDNHKLKSNVTVHFRWLRLFTKDLFYNWKKDNTEKKIKI

SDVVYLSHVFEAFLKEWESTIERVNADCNKPEESKTRDAEIALSIRKLGI

KHQLPFIKGFVDNSNDKNSEDTKSKLTALLSEFEAVLKICEQNYLPSQSS

GIAIAKASFNYYTINKKQKDFEAEIVALKKQLHARYGNKKYDQLLRELNL

IPLKELPLKELPLIEFYSEIKKRKSTKKSEFLEAVSNGLVFDDLKSKFPL

FQTESNKYDEYLKLSNKITQKSTAKSLLSKDSPEAQKLQTEITKLKKNRG

EYFKKAFGKYVQLCELYKEIAGKRGKLKGQIKGIENERIDSQRLQYWALV

LEDNLKHSLILIPKEKTNELYRKVWGAKDDGASSSSSSTLYYFESMTYRA

LRKLCFGINGNTFLPEIQKELPQYNQKEFGEFCFHKSNDDKEIDEPKLIS

FYQSVLKTDFVKNTLALPQSVFNEVAIQSFETRQDFQIALEKCCYAKKQI

ISESLKKEILENYNTQIFKITSLDLQRSEQKNLKGHTRIWNRFWTKQNEE

INYNLRLNPEIAIVWRKAKKTRIEKYGERSVLYEPEKRNRYLHEQYTLCT

TVTDNALNNEITFAFEDTKKKGTEIVKYNEKINQTLKKEFNKNQLWFYGI

DAGEIELATLALMNKDKEPQLFTVYELKKLDFFKHGYIYNKERELVIREK

PYKAIQNLSYFLNEELYEKTFRDGKFNETYNELFKEKHVSAIDLTTAKVI

NGKIILNGDMITFLNLRILHAQRKIYEELIENPHAELKEKDYKLYFEIEG

KDKDIYISRLDFEYIKPYQEISNYLFAYFASQQINEAREEEQINQTKRAL

AGNMIGVIYYLYQKYRGIISIEDLKQTKVESDRNKFEGNIERPLEWALYR

KFQQEGYVPPISELIKLRELEKFPLKDVKQPKYENIQQFGIIKFVSPEET

STTCPKCLRRFKDYDKNKQEGFCKCQCGFDTRNDLKGFEGLNDPDKVAAF

NIAKRGFEDLQKYK

In certain embodiments, the type V-A Cas nuclease comprises SsCsm1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 13. In certain embodiments, the type V-A Cas protein comprises the amino acid sequence set forth in SEQ ID NO: 13.

*Sulfuricurvum* sp. Csm1
(SEQ ID NO: 13)
MLHAFTNQYQLSKTLRFGATLKEDEKKCKSHEELKGFVDISYENMKSSAT

IAESLNENELVKKCERCYSEIVKFHNAWEKIYYRTDQIAVYKDFYRQLSR

KARFDAGKQNSQLITLASLCGMYQGAKLSRYITNYWKDNITRQKSFLKDF

SQQLHQYTRALEKSDKAHTKPNLINFNKTFMVLANLVNEIVIPLSNGAIS

FPNISKLEDGEESHLIEFALNDYSQLSELIGELKDAIATNGGYTPFAKVT

LNHYTAEQKPHVFKNDIDAKIRELKLIGLVETLKGKSSEQIEEYFSNLDK

FSTYNDRNQSVIVRTQCFKYKPIPPFLVKHQLAKYISEPNGWDEDAVAKVL

DAVGAIRSPAHDYANNQEGFDLNHYPIKVAFDYAWEQLANSLYTTVTFPQ

EMCEKYLNSIYGCEVSKEPVFKFYADLLYIRKNLAVLEHKNNLPSNQEEF

ICKINNTFENIVLPYKISQFETYKKDILAWINDGHDHKKYTDAKQQLGFI

RGGLKGRIKAEEVSQKDKYGKIKSYYENPYTKLTNEFKQISSTYGKTFAE

LRDKFKEKNEITKITHFGIIIEDKNRDRYLLASELKHEQINHVSTILNKL

DKSSEFITYQVKSLTSKTLIKLIKNHTTKKGAISPYADFHTSKTGFNKNE

IEKNWDNYKREQVLVEYVKDCLTDSTMAKNQNWAEFGWNFEKCNSYEDIE

HEIDQKSYLLQSDTISKQSIASLVEGGCLLLPIINQDITSKERKDKNQFS

KDWNHIFEGSKEFRLHPEFAVSYRTPIEGYPVQKRYGRLQFVCAFNAHIV

PQNGEFINLKKQIENFNDEDVQKRNVTEFNKKVNHALSDKEYVVIGIDRG

LKQLATLCVLDKRGKILGDFEIYKKEFVRAEKRSESHWEHTQAETRHILD

LSNLRVETTIEGKKVLVDQSLTLVKKNRDTPDEEATEENKQKIKLKQLSY

IRKLQHKMQTNEQDVLDLINNEPSDEEFKKRIEGLISSFGEGQKYADLPI

NTMREMISDLQGVIARGNNQTEKNKIIELDAADNLKQGIVANMIGIVNYI

FAKYSYKAYISLEDLSRAYGGAKSGYDGRYLPSTSQDEDVDFKEQQNQML

AGLGTYQFFEMQLLKKLQKIQSDNTVLRFVPAFRSADNYRNILRLEETKY

KSKPFGVVHFIDPKFTSKKCPVCSKTNVYRDKDDILVCKECGFRSDSQLK

ERENNIHYIHNGDDNGAYHIALKSVENLIQMK

In certain embodiments, the type V-A Cas nuclease comprises MbCsm1 or a variant thereof. In certain embodiments, the type V-A Cas protein comprises an amino acid sequence at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence set forth in SEQ ID NO: 14. In certain embodiments, the type V-A Cas protein comprises the amino acid sequence set forth in SEQ ID NO: 14.

*Microgenomates (Roizmanbacteria) bacterium* Csm1
(SEQ ID NO: 14)
MEIQELKNLYEVKKTVRFELKPSKKKIFEGGDVIKLQKDFEKVQKFFLDI

FVYKNEHTKLEFKKKREIKYTWLRTNTKNEFYNWRGKSDTGKNYALNKIG

FLAEEILRWLNEWQELTKSLKDLTQREEHKQERKSDIAFVLRNFLKRQNL

PFIKDFFNAVIDIQGKQGKESDDKIRKFREEIKEIEKNLNACSREYLPTQ

SNGVLLYKASFSYYTLNKTPKEYEDLKKEKESELSSVLLKEIYRRKRFNR

TTNQKDTLFECTSDWLVKIKLGKDIYEWTLDEAYQKMKIWKANQKSNFIE

AVAGDKLTHQNFRKQFPLFDASDEDFETFYRLTKALDKNPENAKKIAQKR

GKFFNAPNETVQTKNYHELCELYKRIAVKRGKIIAEIKGIENEEVQSQLL

THWAVIAEERDKKFIVLIPRKNGGKLENHKNAHAFLQEKDRKEPNDIKVY

HFKSLTLRSLEKLCFKEAKNTFAPEIKKETNPKIWFPTYKQEWNSTPERL

IKFYKQVLQSNYAQTYLDLVDFGNLNTFLETHFTTLEEFESDLEKTCYTK

VPVYFAKKELETFADEFEAEVFEITTRSISTESKRKENAHAEIWRDFWSR

ENEEENHITRLNPEVSVLYRDEIKEKSNTSRKNRKSNANNRFSDPRFTLA

TTITLNADKKKSNLAFKTVEDINIHIDNFNKKFSKNFSGEWVYGIDRGLK

ELATLNVVKFSDVKNVFGVSQPKEFAKIPIYKLRDEKAILKDENGLSLKN

AKGEARKVIDNISDVLEEGKEPDSTLFEKREVSSIDLTRAKLIKGHIISN

GDQKTYLKLKETSAKRRIFELFSTAKIDKSSQFHVRKTIELSGTKIYWLC

EWQRQDSWRTEKVSLRNTLKGYLQNLDLKNRFENIETIEKINHLRDAITA

NMVGILSHLQNKLEMQGVIALENLDTVREQSNKKMIDEHFEQSNEHVSRR

LEWALYCKFANTGEVPPQIKESIFLRDEFKVCQIGILNFIDVKGTSSNCP

NCDQESRKTGSHFICNFQNNCIFSSKENRNLLEQNLHNSDDVAAFNIAKR

GLEIVKV

More type V-A Cas nucleases and their corresponding naturally occurring CRISPR-Cas systems can be identified by computational and experimental methods known in the art, e.g., as described in U.S. Pat. No. 9,790,490 and Shmakov et al. (2015) MOL. CELL, 60:385. Exemplary computational methods include analysis of putative Cas proteins by homology modeling, structural BLAST, PSI-BLAST, or HHPred, and analysis of putative CRISPR loci by identification of CRISPR arrays. Exemplary experimental methods include in vitro cleavage assays and in-cell nuclease assays (e.g., the Surveyor assay) as described in Zetsche et al. (2015) CELL, 163:759.

In certain embodiments, the Cas nuclease directs cleavage of one or both strands at the target locus, such as the target strand (i.e., the strand having the target nucleotide sequence that hybridizes with a single guide nucleic acid or dual guide nucleic acids) and/or the non-target strand. In certain embodiments, the Cas nuclease directs cleavage of one or both strands within about 1, 2, 3, 4, 5, 6, 7, 8, 9, 10, 15, 20, 25, 50, 100, 200, 500, or more nucleotides from the first or last nucleotide of the target nucleotide sequence or its complementary sequence. In certain embodiments, the cleavage is staggered, i.e. generating sticky ends. In certain embodiments, the cleavage generates a staggered cut with a 5' overhang. In certain embodiments, the cleavage generates a staggered cut with a 5' overhang of 1 to 5 nucleotides, e.g., of 4 or 5 nucleotides. In certain embodiments, the cleavage site is distant from the PAM, e.g., the cleavage occurs after the 18th nucleotide on the non-target strand and after the 23rd nucleotide on the target strand.

In certain embodiments, the engineered, non-naturally occurring system of the present invention further comprises the Cas nuclease that a complex comprising the targeter nucleic acid and the modulator nucleic acid is capable of activating. In other embodiments, the engineered, non-naturally occurring system of the present invention further comprises a Cas protein that is related to the Cas nuclease that a complex comprising the targeter nucleic acid and the modulator nucleic acid is capable of activating. For example, in certain embodiments, the Cas protein comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to the Cas nuclease. In certain embodiments, the Cas protein comprises a nuclease-inactive mutant of the Cas nuclease. In certain embodiments, the Cas protein further comprises an effector domain.

In certain embodiments, the Cas protein lacks substantially all DNA cleavage activity. Such a Cas protein can be generated by introducing one or more mutations to an active Cas nuclease (e.g., a naturally occurring Cas nuclease). A mutated Cas protein is considered to lack substantially all DNA cleavage activity when the DNA cleavage activity of the protein has no more than about 25%, 10%, 5%, 1%, 0.1%, 0.01%, or less of the DNA cleavage activity of the corresponding non-mutated form, for example, nil or negligible as compared with the non-mutated form. Thus, the Cas protein may comprise one or more mutations (e.g., a mutation in the RuvC domain of a type V-A Cas protein) and be used as a generic DNA binding protein with or without fusion to an effector domain. Exemplary mutations include D908A, E993A, and D1263A with reference to the amino acid positions in AsCpf1; D832A, E925A, and D1180A with reference to the amino acid positions in LbCpf1; and D917A, E1006A, and D1255A with reference to the amino acid position numbering of the FnCpf1. More mutations can be designed and generated according to the crystal structure described in Yamano et al. (2016) CELL, 165:949.

It is understood that the Cas protein, rather than losing nuclease activity to cleave all DNA, may lose the ability to cleave only the target strand or only the non-target strand of a double-stranded DNA, thereby being functional as a nickase (see, Gao et al. (2016) CELL RES., 26:901). Accordingly, in certain embodiments, the Cas nuclease is a Cas nickase. In certain embodiments, the Cas nuclease has the activity to cleave the non-target strand but lacks substantially the activity to cleave the target strand, e.g., by a mutation in the Nuc domain. In certain embodiments, the Cas nuclease has the cleavage activity to cleave the target strand but lacks substantially the activity to cleave the non-target strand.

In other embodiments, the Cas nuclease has the activity to cleave a double-stranded DNA and result in a double-strand break.

Cas proteins that lack substantially all DNA cleavage activity or have the ability to cleave only one strand may also be identified from naturally occurring systems. For example, certain naturally occurring CRISPR-Cas systems may retain the ability to bind the target nucleotide sequence but lose entire or partial DNA cleavage activity in eukaryotic (e.g., mammalian or human) cells. Such type V-A proteins are disclosed, for example, in Kim et al. (2017) ACS SYNTH. BIOL. 6 (7): 1273-82 and Zhang et al. (2017) CELL DISCOV. 3:17018.

The activity of the Cas protein (e.g., Cas nuclease) can be altered, thereby creating an engineered Cas protein. In certain embodiments, the altered activity of the engineered Cas protein comprises increased targeting efficiency and/or decreased off-target binding. While not wishing to be bound by theory, it is hypothesized that off-target binding can be recognized by the Cas protein, for example, by the presence of one or more mismatches between the spacer sequence and the target nucleotide sequence, which may affect the stability and/or conformation of the CRISPR-Cas complex. In certain embodiments, the altered activity comprises modified binding, e.g., increased binding to the target locus (e.g., the target strand or the non-target strand) and/or decreased binding to off-target loci. In certain embodiments, the altered activity comprises altered charge in a region of the protein that associates with a single guide nucleic acid or dual guide nucleic acids. In certain embodiments, the altered activity of the engineered Cas protein comprises altered charge in a region of the protein that associates with the target strand and/or the non-target strand. In certain embodiments, the altered activity of the engineered Cas protein comprises altered charge in a region of the protein that associates with an off-target locus. The altered charge can include decreased positive charge, decreased negative charge, increased positive charge, and increased negative charge. For example, decreased negative charge and increased positive charge may generally strengthen the binding to the nucleic acid(s) whereas decreased positive charge and increased negative charge may weaken the binding to the nucleic acid(s). In certain embodiments, the altered activity comprises increased or decreased steric hindrance between the protein and a single guide nucleic acid or dual guide nucleic acids. In certain embodiments, the altered activity comprises increased or decreased steric hindrance between the protein and the target strand and/or the non-target strand. In certain embodiments, the altered activity comprises increased or decreased steric hindrance between the protein and an off-target locus. In certain embodiments, the modification or mutation comprises a substitution of Lys, His, Arg, Glu, Asp, Ser, Gly, or Thr. In certain embodiments, the modification or mutation comprises a substitution with Gly, Ala, Ile, Glu, or Asp. In certain embodiments, the modification or mutation comprises an amino acid substitution in the groove between the WED and RuvC domain of the Cas protein (e.g., a type V-A Cas protein).

In certain embodiments, the altered activity of the engineered Cas protein comprises increased nuclease activity to cleave the target locus. In certain embodiments, the altered activity of the engineered Cas protein comprises decreased nuclease activity to cleave an off-target locus. In certain embodiments, the altered activity of the engineered Cas protein comprises altered helicase kinetics. In certain embodiments, the engineered Cas protein comprises a modification that alters formation of the CRISPR complex.

In certain embodiments, a protospacer adjacent motif (PAM) or PAM-like motif directs binding of the Cas protein complex to the target locus. Many Cas proteins have PAM specificity. The precise sequence and length requirements for the PAM differ depending on the Cas protein used. PAM sequences are typically 2-5 base pairs in length and are adjacent to (but located on a different strand of target DNA from) the target nucleotide sequence. PAM sequences can be identified using a method known in the art, such as testing cleavage, targeting, or modification of oligonucleotides having the target nucleotide sequence and different PAM sequences.

Exemplary PAM sequences are provided in Table 1. In one embodiment, the Cas protein is MAD7 and the PAM is TTTN, wherein N is A, C, G, or T. In one embodiment, the Cas protein is MAD7 and the PAM is CTTN, wherein N is A, C, G, or T. In another embodiment, the Cas protein is AsCpf1 and the PAM is TTTN, wherein N is A, C, G, or T. In another embodiment, the Cas protein is FnCpf1 and the PAM is 5' TTN, wherein N is A, C, G, or T. PAM sequences for certain other type V-A Cas proteins are disclosed in Zetsche et al. (2015) CELL, 163:759 and U.S. Pat. No. 9,982,279. Further, engineering of the PAM Interacting (PI) domain of a Cas protein may allow programing of PAM specificity, improve target site recognition fidelity, and increase the versatility of the engineered, non-naturally occurring system. Exemplary approaches to alter the PAM specificity of Cpf1 is described in Gao et al. (2017) NAT. BIOTECHNOL., 35:789.

In certain embodiments, the engineered Cas protein comprises a modification that alters the Cas protein specificity in concert with modification to targeting range. Cas mutants can be designed to have increased target specificity as well as accommodating modifications in PAM recognition, for example by choosing mutations that alter PAM specificity (e.g., in the PI domain) and combining those mutations with groove mutations that increase (or if desired, decrease) specificity for the on-target locus versus off-target loci. The Cas modifications described herein can be used to counter loss of specificity resulting from alteration of PAM recognition, enhance gain of specificity resulting from alteration of PAM recognition, counter gain of specificity resulting from alteration of PAM recognition, or enhance loss of specificity resulting from alteration of PAM recognition.

In certain embodiments, the engineered Cas protein comprises one or more nuclear localization signal (NLS) motifs. In certain embodiments, the engineered Cas protein comprises at least 2 (e.g., at least 3, at least 4, at least 5, at least 6, at least 7, at least 8, at least 9, or at least 10) NLS motifs. Non-limiting examples of NLS motifs include: the NLS of SV40 large T-antigen, having the amino acid sequence of PKKKRKV (SEQ ID NO: 23); the NLS from nucleoplasmin, e.g., the nucleoplasmin bipartite NLS having the amino acid sequence of KRPAATKKAGQAKKKK (SEQ ID NO: 24); the c-myc NLS, having the amino acid sequence of PAAKRVKLD (SEQ ID NO: 25) or RQRRNELKRSP (SEQ ID NO: 26); the hRNPA1 M9 NLS, having the amino acid sequence of NQSSNFGPMKGGNFG-GRSSGPYGGGGQYFAKPRNQGGY (SEQ ID NO: 27); the importin-a IBB domain NLS, having the amino acid sequence of RMRIZFKNKGKDTAELRRRRVEVS-VELRKAKKDEQILKRRNV (SEQ ID NO: 28); the myoma T protein NLS, having the amino acid sequence of VSRKRPRP (SEQ ID NO: 29) or PPKKARED (SEQ ID NO: 30); the human p53 NLS, having the amino acid sequence of PQPKKKPL (SEQ ID NO: 31); the mouse c-abl IV NLS, having the amino acid sequence of SALIKKKKK-MAP (SEQ ID NO: 32); the influenza virus NS1 NLS, having the amino acid sequence of DRLRR (SEQ ID NO: 33) or PKQKKRK (SEQ ID NO: 34); the hepatitis virus 8 antigen NLS, having the amino acid sequence of RKLKK-KIKKL (SEQ ID NO: 35); the mouse Mx1 protein NLS, having the amino acid sequence of REKKKFLKRR (SEQ ID NO: 36); the human poly(ADP-ribose) polymerase NLS, having the amino acid sequence of KRKGDEVDGVDE-VAKKKSKK (SEQ ID NO: 37); the human glucocorticoid receptor NLS, having the amino acid sequence of RKCLQAGMNLEARKTKK (SEQ ID NO: 38), and synthetic NLS motifs such as PAAKKKKLD (SEQ ID NO: 39).

In general, the one or more NLS motifs are of sufficient strength to drive accumulation of the Cas protein in a detectable amount in the nucleus of a eukaryotic cell. The strength of nuclear localization activity may derive from the number of NLS motif(s) in the Cas protein, the particular NLS motif(s) used, the position(s) of the NLS motif(s), or a combination of these factors. In certain embodiments, the engineered Cas protein comprises at least 1 (e.g., at least 2, at least 3, at least 4, at least 5, at least 6, at least 7, at least 8, at least 9, or at least 10) NLS motif(s) at or near the N-terminus (e.g., within about 1, 2, 3, 4, 5, 10, 15, 20, 25, 30, 40, 50, or more amino acids along the polypeptide chain from the N-terminus). In certain embodiments, the engineered Cas protein comprises at least 1 (e.g., at least 2, at least 3, at least 4, at least 5, at least 6, at least 7, at least 8, at least 9, or at least 10) NLS motif(s) at or near the C-terminus (e.g., within about 1, 2, 3, 4, 5, 10, 15, 20, 25, 30, 40, 50, or more amino acids along the polypeptide chain from the C-terminus). In certain embodiments, the engineered Cas protein comprises at least 1 (e.g., at least 2, at least 3, at least 4, at least 5, at least 6, at least 7, at least 8, at least 9, or at least 10) NLS motif(s) at or near the C-terminus and at least 1 (e.g., at least 2, at least 3, at least 4, at least 5, at least 6, at least 7, at least 8, at least 9, or at least 10) NLS motif(s) at or near the N-terminus. In certain embodiments, the engineered Cas protein comprises one, two, or three NLS motifs at or near the C-terminus. In certain embodiments, the engineered Cas protein comprises one NLS motif at or near the N-terminus and one, two, or three NLS motifs at or near the C-terminus. In certain embodiments, the engineered Cas protein comprises a nucleoplasmin NLS at or near the C-terminus.

Detection of accumulation in the nucleus may be performed by any suitable technique. For example, a detectable marker may be fused to the nucleic acid-targeting protein, such that location within a cell may be visualized. Cell nuclei may also be isolated from cells, the contents of which may then be analyzed by any suitable process for detecting the protein, such as immunohistochemistry, Western blot, or enzyme activity assay. Accumulation in the nucleus may also be determined indirectly, such as by an assay that detects the effect of the nuclear import of a Cas protein complex (e.g., assay for DNA cleavage or mutation at the target locus, or assay for altered gene expression activity) as compared to a control not exposed to the Cas protein or exposed to a Cas protein lacking one or more of the NLS motifs.

The Cas protein in the invention may comprise a chimeric Cas protein, e.g., a Cas protein having enhanced function by being a chimera. Chimeric Cas proteins may be new Cas proteins containing fragments from more than one naturally occurring Cas proteins or variants thereof. For example, fragments of multiple type V-A Cas homologs (e.g., orthologs) may be fused to form a chimeric Cas protein. In certain embodiments, the chimeric Cas protein comprises fragments of Cpf1 orthologs from multiple species and/or strains.

In certain embodiments, the Cas protein comprises one or more effector domains. The one or more effector domains may be located at or near the N-terminus of the Cas protein and/or at or near the C-terminus of the Cas protein. In certain embodiments, an effector domain comprised in the Cas protein is a transcriptional activation domain (e.g., VP64), a transcriptional repression domain (e.g., a KRAB domain or an SID domain), an exogenous nuclease domain (e.g., FokI), a deaminase domain (e.g., cytidine deaminase or adenine deaminase), or a reverse transcriptase domain (e.g., a high fidelity reverse transcriptase domain). Other activities of effector domains include but are not limited to methylase activity, demethylase activity, transcription release factor activity, translational initiation activity, translational activation activity, translational repression activity, histone modification (e.g., acetylation or demethylation) activity, single-stranded RNA cleavage activity, double-strand RNA cleavage activity, single-strand DNA cleavage activity, double-strand DNA cleavage activity, and nucleic acid binding activity.

In certain embodiments, the Cas protein comprises one or more protein domains that enhance homology-directed repair (HDR) and/or inhibit non-homologous end joining (NHEJ). Exemplary protein domains having such functions are described in Jayavaradhan et al. (2019) NAT. COMMUN. 10 (1): 2866 and Janssen et al. (2019) MOL. THER. NUCLEIC ACIDS 16:141-54. In certain embodiments, the Cas protein comprises a dominant negative version of p53-binding protein 1 (53BP1), for example, a fragment of 53BP1 comprising a minimum focus forming region (e.g., amino acids 1231-1644 of human 53BP1). In certain embodiments, the Cas protein comprises a motif that is targeted by APC-Cdh1, such as amino acids 1-110 of human Geminin, thereby resulting in degradation of the fusion protein during the HDR non-permissive G1 phase of the cell cycle.

In certain embodiments, the Cas protein comprises an inducible or controllable domain. Non-limiting examples of inducers or controllers include light, hormones, and small molecule drugs. In certain embodiments, the Cas protein comprises a light inducible or controllable domain. In certain embodiments, the Cas protein comprises a chemically inducible or controllable domain.

In certain embodiments, the Cas protein comprises a tag protein or peptide for ease of tracking or purification. Non-limiting examples of tag proteins and peptides include fluorescent proteins (e.g., green fluorescent protein (GFP), YFP, RFP, CFP, mCherry, tdTomato), HIS tags (e.g., 6×His tag (SEQ ID NO: 143)), hemagglutinin (HA) tag, FLAG tag, and Myc tag.

In certain embodiments, the Cas protein is conjugated to a non-protein moiety, such as a fluorophore useful for genomic imaging. In certain embodiments, the Cas protein is covalently conjugated to the non-protein moiety. The terms "CRISPR-Associated protein," "Cas protein," "Cas," "CRISPR-Associated nuclease," and "Cas nuclease" are used herein to include such conjugates despite the presence of one or more non-protein moieties.

Targeter and Modulator Nucleic Acids

The engineered, non-naturally occurring system of the present invention comprises a targeter nucleic acid and a modulator nucleic acid that, when hybridized to form a complex, are capable of activating a Cas nuclease disclosed herein. In certain embodiments, the Cas nuclease is activated by a single crRNA in the absence of a tracrRNA in a naturally occurring system. In certain embodiments, the Cas nuclease is a type V-A, type V-C, or type V-D nuclease.

The term "targeter nucleic acid," as used herein, refers to a nucleic acid comprising (i) a spacer sequence designed to hybridize with a target nucleotide sequence; and (ii) a targeter stem sequence capable of hybridizing with an additional nucleic acid to form a complex, wherein the complex is capable of activating a Cas nuclease (e.g., a type V-A Cas nuclease) under suitable conditions, and wherein the targeter nucleic acid alone, in the absence of the additional nucleic acid, is not capable of activating the Cas nuclease under the same conditions.

The term "modulator nucleic acid," as used herein in connection with a given targeter nucleic acid and its corresponding Cas nuclease, refers to a nucleic acid capable of hybridizing with the targeter nucleic acid to form a complex, wherein the complex, but not the modulator nucleic acid alone, is capable of activating the type Cas nuclease under suitable conditions.

The term "suitable conditions," as used in the definitions of "targeter nucleic acid" and "modulator nucleic acid," refers to the conditions under which a naturally occurring CRISPR-Cas system is operative, such as in a prokaryotic cell, in a eukaryotic (e.g., mammalian or human) cell, or in an in vitro assay.

The targeter nucleic acid and/or the modulator nucleic acid can be synthesized chemically or produced in a biological process (e.g., catalyzed by an RNA polymerase in an in vitro reaction). Such reaction or process may limit the lengths of the targeter and modulator nucleic acids. In certain embodiments, the targeter nucleic acid is no more than 100, 90, 80, 70, 60, 50, 40, 30, or 25 nucleotides in length. In certain embodiments, the targeter nucleic acid is at least 20, 25, 30, 40, 50, 60, 70, 80, or 90 nucleotides in length. In certain embodiments, the targeter nucleic acid is 20-100, 20-90, 20-80, 20-70, 20-60, 20-50, 20-40, 20-30, 20-25, 25-100, 25-90, 25-80, 25-70, 25-60, 25-50, 25-40, 25-30, 30-100, 30-90, 30-80, 30-70, 30-60, 30-50, 30-40, 40-100, 40-90, 40-80, 40-70, 40-60, 40-50, 50-100, 50-90, 50-80, 50-70, 50-60, 60-100, 60-90, 60-80, 60-70, 70-100, 70-90, 70-80, 80-100, 80-90, or 90-100 nucleotides in length. In certain embodiments, the modulator nucleic acid is no more than 100, 90, 80, 70, 60, 50, 40, 30, or 20 nucleotides in length. In certain embodiments, the modulator nucleic acid is at least 10, 15, 20, 25, 30, 40, 50, 60, 70, 80, or 90 nucleotides in length. In certain embodiments, the modulator nucleic acid is 10-100, 10-90, 10-80, 10-70, 10-60, 10-50, 10-40, 10-30, 10-20, 15-100, 15-90, 15-80, 15-70, 15-60, 15-50, 15-40, 15-30, 15-20, 20-100, 20-90, 20-80, 20-70, 20-60, 20-50, 20-40, 20-30, 25-100, 25-90, 25-80, 25-70, 25-60, 25-50, 25-40, 25-30, 30-100, 30-90, 30-80, 30-70, 30-60, 30-50, 30-40, 40-100, 40-90, 40-80, 40-70, 40-60, 40-50, 50-100, 50-90, 50-80, 50-70, 50-60, 60-100, 60-90, 60-80, 60-70, 70-100, 70-90, 70-80, 80-100, 80-90, or 90-100 nucleotides in length.

In naturally occurring type V-A CRISPR-Cas systems, the crRNA comprises a scaffold sequence (also called direct repeat sequence) and a spacer sequence that hybridizes with the target nucleotide sequence. In certain naturally occurring type V-A CRISPR-Cas systems, the scaffold sequence forms a stem-loop structure in which the stem consists of five consecutive base pairs. A dual guide type V-A CRISPR-Cas system may be derived from a naturally occurring type V-A CRISPR-Cas system, or a variant thereof in which the Cas protein is guided to the target nucleotide sequence by a crRNA alone, such system referred to herein as a "single guide type V-A CRISPR-Cas system." In a dual guide type V-A CRISPR-Cas system disclosed herein, the targeter nucleic acid comprises the chain of the stem sequence between the spacer and the loop (the "targeter stem sequence") and the spacer sequence, and the modulator nucleic acid comprises the other chain of the stem sequence (the "modulator stem sequence") and the 5' tail positioned 5' to the modulator stem sequence. The targeter stem sequence is 100% complementary to the modulator stem sequence. As such, the double-stranded complex of the targeter nucleic acid and the modulator nucleic acid retains the orientation of the 5' tail, the modulator stem sequence, the targeter stem sequence, and the spacer sequence of a single guide type V-A CRISPR-Cas system but lacks the loop structure between the modulator stem sequence and the targeter stem sequence. A schematic representation of an exemplary double-stranded complex is shown in FIG. 1.

Notwithstanding the general structural similarity, it has been discovered that the stem-loop structure of the crRNA in a naturally occurring type V-A CRISPR complex is dispensable for the functionality of the CRISPR system. This discovery is surprising because the prior art has suggested that the stem-loop structure is critical (see, Zetsche et al. (2015) CELL, 163:759) and that removal of the loop structure by "splitting" the crRNA abrogated the activity of a AsCpf1 CRISPR system (see, Li et al. (2017) NAT. BIOMED. ENG., 1:0066).

It is contemplated that the length of the duplex may be a factor in providing an operative dual guide CRISPR system. In certain embodiments, the targeter stem sequence and the modulator stem sequence each consist of 4-10 nucleotides that base pair with each other. In certain embodiments, the targeter stem sequence and the modulator stem sequence each consist of 4-9, 4-8, 4-7, 4-6, 4-5, 5-10, 5-9, 5-8, 5-7, or 5-6 nucleotides that base pair with each other. In certain embodiments, the targeter stem sequence and the modulator stem sequence each consist of 4, 5, 6, 7, 8, 9, or 10 nucleotides. It is understood that the composition of the nucleotides in each sequence affects the stability of the duplex, and a C-G base pair confers greater stability than an A-U base pair. In certain embodiments, 20%-80%, 20%-70%, 20%-60%, 20%-50%, 20%-40%, 20%-30%, 30%-80%, 30%-70%, 30%-60%, 30%-50%, 30%-40%, 40%-80%, 40%-70%, 40%-60%, 40%-50%, 50%-80%, 50%-70%, 50%-60%, 60%-80%, 60%-70%, or 70%-80% of the base pairs are C-G base pairs.

In certain embodiments, the targeter stem sequence and the modulator stem sequence each consist of 5 nucleotides. As such, the targeter stem sequence and the modulator stem sequence form a duplex of 5 base pairs. In certain embodiments, 0-4, 0-3, 0-2, 0-1, 1-5, 1-4, 1-3, 1-2, 2-5, 2-4, 2-3, 3-5, 3-4, or 4-5 out of the 5 base pairs are C-G base pairs. In certain embodiments, 0, 1, 2, 3, 4, or 5 out of the 5 base pairs are C-G base pairs. In certain embodiments, the targeter stem sequence consists of 5'-GUAGA-3' and the modulator stem sequence consists of 5'-UCUAC-3'. In certain embodiments, the targeter stem sequence consists of 5'-GUGGG-3' and the modulator stem sequence consists of 5'-CCCAC-3'.

It is also contemplated that the compatibility of the duplex for a given Cas nuclease may be a factor in providing an operative dual guide CRISPR system. For example, the targeter stem sequence and the modulator stem sequence can be derived from a naturally occurring crRNA capable of activating a Cas nuclease in the absence of a tracrRNA. In certain embodiments, the nucleotide sequences of the targeter stem sequence and the modulator stem sequence are identical to the corresponding stem sequences of a stem-loop structure in such naturally occurring crRNA.

In certain embodiments, the targeter nucleic acid comprises, from 5' to 3', a targeter stem sequence and a spacer sequence. The spacer sequence is designed to hybridize with the target nucleotide sequence. To provide sufficient targeting to the target nucleotide sequence, the spacer sequence is generally 16 or more nucleotides in length. In certain embodiments, the spacer sequence is at least 16, 17, 18, 19, 20, 21, 22, 23, 24, 25, 26, 27, 28, 29, 30, 35, 40, 45, 50, or 75 nucleotides in length. In certain embodiments, the spacer sequence is shorter than or equal to 75, 50, 45, 40, 35, 30, 25, or 20 nucleotides in length. Shorter spacer sequence may be desirable for reducing off-target events. Accordingly, in certain embodiments, the spacer sequence is shorter than or equal to 19, 18, or 17 nucleotides. In certain embodiments, the spacer sequence is 17-30 nucleotides in length, e.g., 20-30 nucleotides, 20-25 nucleotides, 20-24 nucleotides, 20-23 nucleotides, 23-25 nucleotides, 20-22 nucleotides, or about 20 nucleotides in length. In certain embodiments, the spacer sequence is 20 nucleotides in length. In certain embodiments, the spacer sequence is at least about 50%, 60%, 70%, 75%, 80%, 85%, 90%, 95%, 96%, 97%, 98%, or 99% complementary to the target nucleotide sequence. In certain embodiments, the spacer sequence is 100% complementary to the target nucleotide sequence in the seed region (about 5 base pairs proximal to the PAM). In certain embodiments, the spacer sequence is 100% complementary to the target nucleotide sequence. It has been reported that compared to DNA binding, DNA cleavage is less tolerant to mismatches between the spacer sequence and the target nucleotide sequence (see, Klein et al. (2018) CELL REPORTS, 22:1413). Accordingly, in specific embodiments, when the engineered, non-naturally occurring system comprises a Cas nuclease, the spacer sequence is 100% complementary to the target nucleotide sequence.

Proper design of the spacer sequence is dependent upon the selection of target nucleotide sequence. For example, to select a target nucleotide sequence in a specific gene in a given genome, sequence analysis can be conducted to minimize potential hybridization of the spacer sequence with any other loci in the genome. The association of the target nucleotide sequence with a PAM recognized by the Cas protein is also considered by many design methods. In a type V-A CRISPR-Cas system, the PAM is immediately upstream from the target sequence when using the non-target strand (i.e., the strand not hybridized with the spacer sequence) as the coordinate. Computational models have been developed to assess the targetability of the target nucleotide sequence as well as any potential off-target effect, for example, as disclosed in Doench et al. (2016) NAT. BIOTECHNOL., 34:184; Chuai et al. (2018) GENOME BIOLOGY, 19:80; and Klein et al. (2018) CELL REPORTS, 22:1413. Although computational methods are useful for selection of spacer sequences, it is generally advisable to design multiple spacer sequences and select one or more with high efficiency and specificity based upon the results of in vitro and/or in vivo experiments.

In certain embodiments, the 3' end of the targeter stem sequence is linked by no more than 1, 2, 3, 4, 5, 6, 7, 8, 9, or 10 nucleotides to the 5' end of the spacer sequence. In certain embodiments, the targeter stem sequence and the spacer sequence are adjacent to each other, directly linked by an internucleotide bond. In certain embodiments, the targeter stem sequence and the spacer sequence are linked by one nucleotide, e.g., a uridine. In certain embodiments, the targeter stem sequence and the spacer sequence are linked by two or more nucleotides. In certain embodiments, the targeter stem sequence and the spacer sequence are linked by 1, 2, 3, 4, 5, 6, 7, 8, 9, or 10 nucleotides.

In certain embodiments, the targeter nucleic acid further comprises an additional nucleotide sequence 5' to the targeter stem sequence. In certain embodiments, the additional nucleotide sequence comprises at least 1 (e.g., at least 2, at least 3, at least 4, at least 5, at least 6, at least 7, at least 8, at least 9, at least 10, at least 15, at least 20, at least 25, at least 30, at least 35, at least 40, at least 45, or at least 50) nucleotides. In certain embodiments, the additional nucleotide sequence consists of 1, 2, 3, 4, 5, 6, 7, 8, 9, 10, 15, 20, 25, 30, 35, 40, 45, or 50 nucleotides. In certain embodiments, the additional nucleotide sequence consists of 2 nucleotides. In certain embodiments, the additional nucleotide sequence is reminiscent to the loop or a fragment thereof (e.g., one, two, three, or four nucleotides at the 3' end of the loop) in a crRNA of a corresponding single guide CRISPR-Cas system. It is understood that an additional nucleotide sequence 5' to the targeter stem sequence is dispensable. Accordingly, in certain embodiments, the targeter nucleic acid does not comprise any additional nucleotide 5' to the targeter stem sequence.

In certain embodiments, the targeter nucleic acid further comprises an additional nucleotide sequence containing one or more nucleotides at the 3' end that does not hybridize with the target nucleotide sequence. The additional nucleotide sequence may protect the targeter nucleic acid from degradation by 3'-5' exonuclease. In certain embodiments, the additional nucleotide sequence is no more than 100 nucleotides in length. In certain embodiments, the additional nucleotide sequence is no more than 90, 80, 70, 60, 50, 40, 30, 20, or 10 nucleotides in length. In certain embodiments, the additional nucleotide sequence is at least 1, 2, 3, 4, 5, 6, 7, 8, 9, 10, 15, 20, 25, 30, 35, 40, 45, or 50 nucleotides in length. In certain embodiments, the additional nucleotide sequence is 5-100, 5-50, 5-40, 5-30, 5-25, 5-20, 5-15, 5-10, 10-100, 10-50, 10-40, 10-30, 10-25, 10-20, 10-15, 15-100, 15-50, 15-40, 15-30, 15-25, 15-20, 20-100, 20-50, 20-40, 20-30, 20-25, 25-100, 25-50, 25-40, 25-30, 30-100, 30-50, 30-40, 40-100, 40-50, or 50-100 nucleotides in length.

In certain embodiments, the additional nucleotide sequence forms a hairpin with the spacer sequence. Such secondary structure may increase the specificity of the engineered, non-naturally occurring system (see, Kocak et al. (2019) NAT. BIOTECH. 37:657-66). In certain embodiments, the free energy change during the hairpin formation is greater than or equal to −20 kcal/mol, −15 kcal/mol, −14 kcal/mol, −13 kcal/mol, −12 kcal/mol, −11 kcal/mol, or −10 kcal/mol. In certain embodiments, the free energy change during the hairpin formation is greater than or equal to −5 kcal/mol, −6 kcal/mol, −7 kcal/mol, −8 kcal/mol, −9 kcal/mol, −10 kcal/mol, −11 kcal/mol, −12 kcal/mol, −13 kcal/mol, −14 kcal/mol, or −15 kcal/mol. In certain embodiments, the free energy change during the hairpin formation is in the range of −20 to −10 kcal/mol, −20 to −11 kcal/mol, −20 to −12 kcal/mol, −20 to −13 kcal/mol, −20 to −14 kcal/mol, −20 to −15 kcal/mol, −15 to −10 kcal/mol, −15 to −11 kcal/mol, −15 to −12 kcal/mol, −15 to −13 kcal/mol, −15 to −14 kcal/mol, −14 to −10 kcal/mol, −14 to −11 kcal/mol, −14 to −12 kcal/mol, −14 to −13 kcal/mol, −13 to −10 kcal/mol, −13 to −11 kcal/mol, −13 to −12 kcal/mol, −12 to −10 kcal/mol, −12 to −11 kcal/mol, or −11 to −10 kcal/mol. In other embodiments, the targeter nucleic acid does not comprise any nucleotide 3' to the spacer sequence.

In certain embodiments, the modulator nucleic acid further comprises an additional nucleotide sequence 3' to the modulator stem sequence. In certain embodiments, the additional nucleotide sequence comprises at least 1 (e.g., at least 2, at least 3, at least 4, at least 5, at least 6, at least 7, at least 8, at least 9, at least 10, at least 15, at least 20, at least 25, at least 30, at least 35, at least 40, at least 45, or at least 50) nucleotides. In certain embodiments, the additional nucleotide sequence consists of 1, 2, 3, 4, 5, 6, 7, 8, 9, 10, 15, 20, 25, 30, 35, 40, 45, or 50 nucleotides. In certain embodiments, the additional nucleotide sequence consists of 1 nucleotide (e.g., uridine). In certain embodiments, the additional nucleotide sequence consists of 2 nucleotides. In certain embodiments, the additional nucleotide sequence is reminiscent to the loop or a fragment thereof (e.g., one, two, three, or four nucleotides at the 5' end of the loop) in a crRNA of a corresponding single guide CRISPR-Cas system. It is understood that an additional nucleotide sequence 3' to the modulator stem sequence is dispensable. Accordingly, in certain embodiments, the modulator nucleic acid does not comprise any additional nucleotide 3' to the modulator stem sequence.

It is understood that the additional nucleotide sequence 5' to the targeter stem sequence and the additional nucleotide sequence 3' to the modulator stem sequence, if present, may interact with each other. For example, although the nucleotide immediately 5' to the targeter stem sequence and the nucleotide immediately 3' to the modulator stem sequence do not form a Watson-Crick base pair (otherwise they would constitute part of the targeter stem sequence and part of the modulator stem sequence, respectively), other nucleotides in the additional nucleotide sequence 5' to the targeter stem sequence and the additional nucleotide sequence 3' to the modulator stem sequence may form one, two, three, or more base pairs (e.g., Watson-Crick base pairs). Such interaction may affect the stability of the complex comprising the targeter nucleic acid and the modulator nucleic acid.

The stability of a complex comprising a targeter nucleic acid and a modulator nucleic acid can be assessed by the Gibbs free energy change ($\Delta G$) during the formation of the complex, either calculated or actually measured. Where all the predicted base pairing in the complex occurs between a base in the targeter nucleic acid and a base in the modulator nucleic acid, i.e., there is no intra-strand secondary structure, the $\Delta G$ during the formation of the complex correlates generally with the $\Delta G$ during the formation of a secondary structure within the corresponding single guide nucleic acid. Methods of calculating or measuring the $\Delta G$ are known in the art. An exemplary method is RNAfold (rna.tbi.univie.ac.at/cgi-bin/RNAWebSuite/RNAfold.cgi) as disclosed in Gruber et al. (2008) NUCLEIC ACIDS RES., 36 (Web Server issue): W70-W74. Unless indicated otherwise, the $\Delta G$ values in the present disclosure are calculated by RNAfold for the formation of a secondary structure within a corresponding single guide nucleic acid. In certain embodiments, the $\Delta G$ is lower than or equal to −1 kcal/mol, e.g., lower than or equal to −2 kcal/mol, lower than or equal to −3 kcal/mol, lower than or equal to −4 kcal/mol, lower than or equal to −5 kcal/mol, lower than or equal to −6 kcal/mol, lower than or equal to −7 kcal/mol, lower than or equal to −7.5 kcal/mol, or lower than or equal to −8 kcal/mol. In certain embodiments, the $\Delta G$ is greater than or equal to −10 kcal/mol, e.g., greater than or equal to −9 kcal/mol, greater than or equal to −8.5 kcal/mol, or greater than or equal to −8 kcal/mol. In certain embodiments, the $\Delta G$ is in the range of −10 to −4 kcal/mol. In certain embodiments, the $\Delta G$ is in the range of −8 to −4 kcal/mol, −7 to −4 kcal/mol, −6 to −4 kcal/mol, −5 to −4 kcal/mol, −8 to −4.5 kcal/mol, −7 to −4.5 kcal/mol, −6 to −4.5 kcal/mol, or −5 to −4.5 kcal/mol. In certain embodiments, the $\Delta G$ is about−8 kcal/mol, −7 kcal/mol, −6 kcal/mol, −5 kcal/mol, −4.9 kcal/mol, −4.8 kcal/mol, −4.7 kcal/mol, −4.6 kcal/mol, −4.5 kcal/mol, −4.4 kcal/mol, −4.3 kcal/mol, −4.2 kcal/mol, −4.1 kcal/mol, or −4 kcal/mol.

It is understood that the $\Delta G$ may be affected by a sequence in the targeter nucleic acid that is not within the targeter stem sequence, and/or a sequence in the modulator nucleic acid that is not within the modulator stem sequence. For example, one or more base pairs (e.g., Watson-Crick base pair) between an additional sequence 5' to the targeter stem sequence and an additional sequence 3' to the modulator stem sequence may reduce the $\Delta G$, i.e., stabilize the nucleic acid complex. In certain embodiments, the nucleotide immediately 5' to the targeter stem sequence comprises a uracil or is a uridine, and the nucleotide immediately 3' to the modulator stem sequence comprises a uracil or is a uridine, thereby forming a nonconventional U-U base pair.

In certain embodiments, the modulator nucleic acid comprises a nucleotide sequence referred to herein as a "5' tail" positioned 5' to the modulator stem sequence. Where the CRISPR system is a type V-A CRISPR system, the 5' tail in a dual guide system is reminiscent to the nucleotide sequence positioned 5' to the stem-loop structure of the scaffold sequence in a crRNA (the single guide). Accordingly, the 5' tail can comprise the corresponding nucleotide sequences when a dual guide system is engineered from a single guide system.

Without being bound by theory, it is contemplated that the 5' tail may participate in the formation of the CRISPR-Cas complex. For example, in certain embodiments, the 5' tail forms a pseudoknot structure with the modulator stem sequence, which is recognized by the Cas protein (see, Yamano et al. (2016) CELL, 165:949). In certain embodiments, the 5' tail is at least 3 (e.g., at least 4 or at least 5) nucleotides in length. In certain embodiments, the 5' tail is 3, 4, or 5 nucleotides in length. In certain embodiments, the nucleotide at the 3' end of the 5' tail comprises a uracil or is a uridine. In certain embodiments, the second nucleotide in the 5' tail, the position counted from the 3' end, comprises a uracil or is a uridine. In certain embodiments, the third nucleotide in the 5' tail, the position counted from the 3' end, comprises an adenine or is an adenosine. This third nucleotide may form a base pair (e.g., a Watson-Crick base pair) with a nucleotide 5' to the modulator stem sequence. Accordingly, in certain embodiments, the modulator nucleic acid comprises a uridine or a uracil-containing nucleotide 5' to the modulator stem sequence. In certain embodiments, the 5' tail comprises the nucleotide sequence of 5'-AUU-3'. In certain embodiments, the 5' tail comprises the nucleotide sequence of 5'-AAUU-3'. In certain embodiments, the 5' tail comprises the nucleotide sequence of 5'-UAAUU-3'. In certain embodiments, the 5' tail is positioned immediately 5' to the modulator stem sequence.

In certain embodiments, the targeter nucleic acid and/or the modulator nucleic acid are designed to reduce the degree of secondary structure other than the hybridization between the targeter stem sequence and the modulator stem sequence. In certain embodiments, no more than about 75%, 50%, 40%, 30%, 25%, 20%, 15%, 10%, 5%, 1%, or fewer of the nucleotides of the targeter nucleic acid and/or the modulator nucleic acid participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106 (1): 23-24; and PA Carr and GM Church, 2009, Nature Biotechnology 27 (12): 1151-62).

The targeter nucleic acid is directed to a specific target nucleotide sequence, and the donor template is designed to modify the target nucleotide sequence or a sequence nearby. It is understood, therefore, that association of the targeter or modulator nucleic acid with a donor template can increase editing efficiency and reduce off-targeting. In a multiplex method (e.g., as disclosed in the "Multiplex Methods" subsection of section II infra), association of a donor template with a modulator nucleic acid allows combination of a targeter nucleic acid library with a donor template library, making designs of screening or selection assays more efficient and flexible. Accordingly, in certain embodiments, the modulator nucleic acid further comprises a donor template-recruiting sequence capable of hybridizing with a donor template (see FIG. 1C). Donor templates are described in the "Donor Templates" subsection of section II infra. The donor template and donor template-recruiting sequence can be designed such that they bear sequence complementarity. In certain embodiments, the donor template-recruiting sequence is at least 90% (e.g., at least 91%, at least 92%, at least 93%, at least 94%, at least 95%, at least 96%, at least 97%, at least 98%, or at least 99%) complementary to at least a portion of the donor template. In certain embodiments, the donor template-recruiting sequence is 100% complementary to at least a portion of the donor template. In certain embodiments, where the donor template comprises an engineered sequence not homologous to the sequence to be repaired, the donor template-recruiting sequence is capable of hybridizing with the engineered sequence in the donor template. In certain embodiments, the donor template-recruiting sequence is at least 20, 25, 30, 35, 40, 45, 50, 55, 60, 65, 70, 75, 80, 85, 90, 95, or 100 nucleotides in length. In certain embodiments, the donor template-recruiting sequence is positioned at the 5' end of the modulator nucleic acid. In certain embodiments, the donor template-recruiting sequence is linked to the 5' tail, if present, or to the modulator stem sequence, of the modulator nucleic acid through an internucleotide bond or a nucleotide linker.

Figure 1D:
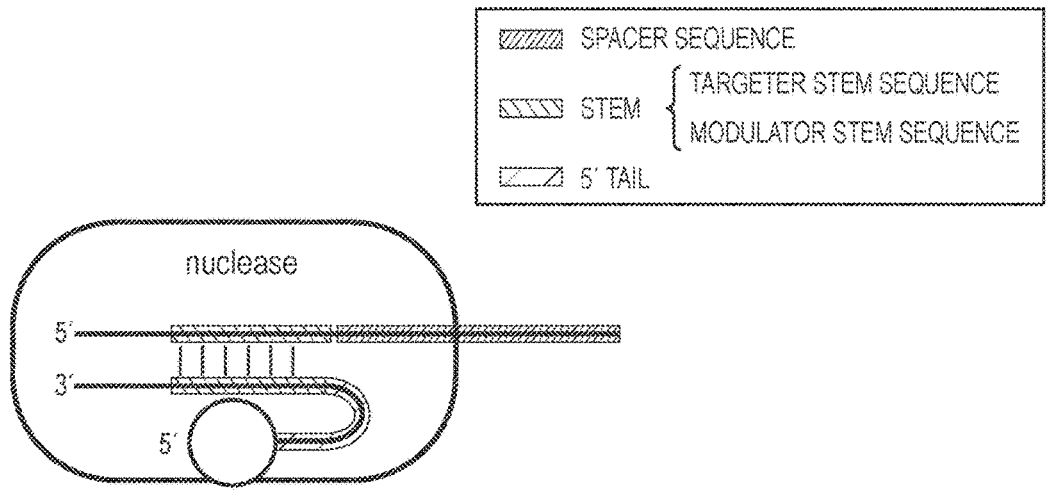

In certain embodiments, the modulator nucleic acid further comprises an editing enhancer sequence, which increases the efficiency of gene editing and/or homology-directed repair (HDR) (see FIG. 1D). Exemplary editing enhancer sequences are described in Park et al. (2018) NAT. COMMUN. 9:3313. In certain embodiments, the editing enhancer sequence is positioned 5' to the 5' tail, if present, or 5' to the modulator stem sequence. In certain embodiments, the editing enhancer sequence is 1-50, 4-50, 9-50, 15-50, 25-50, 1-25, 4-25, 9-25, 15-25, 1-15, 4-15, 9-15, 1-9, 4-9, or 1-4 nucleotides in length. In certain embodiments, the editing enhancer sequence is about 1, 2, 3, 4, 5, 6, 7, 8, 9, 10, 15, 20, 25, 30, 35, 40, 45, 50, or 55 nucleotides in length. The editing enhancer sequence is designed to minimize homology to the target nucleotide sequence or any other sequence that the engineered, non-naturally occurring system may be contacted to, e.g., the genome sequence of a cell into which the engineered, non-naturally occurring system is delivered. In certain embodiments, the editing enhancer is designed to minimize the presence of hairpin structure. The editing enhancer can comprise one or more of the chemical modifications disclosed herein.

The modulator and/or targeter nucleic acids can further comprise a protective nucleotide sequence that prevents or reduces nucleic acid degradation. In certain embodiments, the protective nucleotide sequence is at least 5 (e.g., at least 10, at least 15, at least 20, at least 25, at least 30, at least 35, at least 40, at least 45, or at least 50) nucleotides in length. The length of the protective nucleotide sequence increases the time for an exonuclease to reach the 5' tail, modulator stem sequence, targeter stem sequence, and/or spacer sequence, thereby protecting these portions of the modulator and/or targeter nucleic acids from degradation by an exonuclease. In certain embodiments, the protective nucleotide sequence forms a secondary structure, such as a hairpin or a tRNA structure, to reduce the speed of degradation by an exonuclease (see, for example, Wu et al. (2018) CELL. MOL. LIFE SCI., 75 (19): 3593-3607). Secondary structures can be predicted by methods known in the art, such as the online webserver RNAfold developed at University of Vienna using the centroid structure prediction algorithm (see, Gruber et al. (2008) NUCLEIC ACIDS RES., 36: W70). Certain chemical modifications, which may be present in the protective nucleotide sequence, can also prevent or reduce nucleic acid degradation, as disclosed in the "RNA Modifications" subsection infra.

A protective nucleotide sequence is typically located at the 5' end, at the 3' end, or at both ends, of the modulator or targeter nucleic acid. In certain embodiments, the modulator nucleic acid comprises a protective nucleotide sequence at the 5' end, optionally through a nucleotide linker (see FIG. 1B). In certain embodiments, the modulator nucleic acid comprises a protective nucleotide sequence at the 3' end. In certain embodiments, the modulator nucleic acid comprises a protective nucleotide sequence at the 5' end. In certain embodiments, the modulator nucleic acid comprises a protective nucleotide sequence at the 3' end.

As described above, various nucleotide sequences can be present in the 5' portion of a modulator nucleic acid, including but not limited to a donor template-recruiting sequence, an editing enhancer sequence, a protective nucleotide sequence, and a linker connecting such sequence to the 5' tail, if present, or to the modulator stem sequence. It is understood that the functions of donor template recruitment, editing enhancement, protection against degradation, and linkage are not exclusive to each other, and one nucleotide sequence can have one or more of such functions. For example, in certain embodiments, the modulator nucleic acid comprises a nucleotide sequence that is both a donor template-recruiting sequence and an editing enhancer sequence. In certain embodiments, the modulator nucleic acid comprises a nucleotide sequence that is both a donor template-recruiting sequence and a protective sequence. In certain embodiments, the modulator nucleic acid comprises a nucleotide sequence that is both an editing enhancer sequence and a protective sequence. In certain embodiments, the modulator nucleic acid comprises a nucleotide sequence that is a donor template-recruiting sequence, an editing enhancer sequence, and a protective sequence. In certain embodiments, the nucleotide sequence 5' to the 5' tail, if present, or 5' to the modulator stem sequence is 1-90, 1-80, 1-70, 1-60, 1-50, 1-40, 1-30, 1-20, 1-10, 10-90, 10-80, 10-70, 10-60, 10-50, 10-40, 10-30, 10-20, 20-90, 20-80, 20-70, 20-60, 20-50, 20-40, 20-30, 30-90, 30-80, 30-70, 30-60, 30-50, 30-40, 40-90, 40-80, 40-70, 40-60, 40-50, 50-90, 50-80, 50-70, 50-60, 60-90, 60-80, 60-70, 70-90, 70-80, or 80-90 nucleotides in length.

In certain embodiments, the engineered, non-naturally occurring system further comprises one or more compounds (e.g., small molecule compounds) that enhance HDR and/or inhibit NHEJ. Exemplary compounds having such functions are described in Maruyama et al. (2015) NAT BIOTECHNOL. 33 (5): 538-42; Chu et al. (2015) NAT BIOTECHNOL. 33 (5): 543-48; Yu et al. (2015) CELL STEM CELL 16 (2): 142-47; Pinder et al. (2015) NUCLEIC ACIDS RES. 43 (19): 9379-92; and Yagiz et al. (2019) COMMUN. BIOL. 2:198. In certain embodiments, the engineered, non-naturally occurring system further comprises one or more compounds selected from the group consisting of DNA ligase IV antagonists (e.g., SCR7 compound, Ad4 E1B55K protein, and Ad4 E4orf6 protein), RAD51 agonists (e.g., RS-1), DNA-dependent protein kinase (DNA-PK) antagonists (e.g., NU7441 and KU0060648), β3-adrenergic receptor agonists (e.g., L755507), inhibitors of intracellular protein transport from the ER to the Golgi apparatus (e.g., brefeldin A), and any combinations thereof.

The sequences of the modulator nucleic acid and the targeter nucleic acid should be compatible with the Cas protein. Exemplary sequences that are operative with certain type V-A Cas proteins are provided in Table 1. It is understood that these sequences are merely illustrative, and other guide nucleic acid sequences may also be used with these Cas proteins.

TABLE 1

Type V-A Cas Protein and Corresponding Guide Nucleic Acid Sequences

| Cas Protein[1] | Modulator Sequence[2] | Targeter Stem Sequence | PAM[3] |
|---|---|---|---|
| MAD7 (SEQ ID NO: 1) | UAAUUUCUAC (SEQ ID NO: 15) | GUAGA | 5' TTTN |
| MAD7 (SEQ ID NO: 1) | AUCUAC | GUAGA | 5' TTTN |
| MAD7 (SEQ ID NO: 1) | GGAAUUUCUAC (SEQ ID NO: 102) | GUAGA | 5' TTTN |
| MAD7 (SEQ ID NO: 1) | UAAUUCCCAC (SEQ ID NO: 17) | GUGGG | 5' TTTN |
| MAD2 (SEQ ID NO: 2) | AUCUAC | GUAGA | 5' TTTN |
| AsCpf1 (SEQ ID NO: 3) | UAAUUUCUAC (SEQ ID NO: 15) | GUAGA | 5' TTTN |
| LbCpf1 (SEQ ID NO: 4) | UAAUUUCUAC (SEQ ID NO: 15) | GUAGA | 5' TTTN |
| FnCpf1 (SEQ ID NO: 5) | UAAUUUUCUACU (SEQ ID NO: 18) | GUAGA | 5' TTN |
| *Prevotella bryantii* Cpf1 (SEQ ID NO: 6) | AAUUUCUAC | GUAGA | 5' TTTC |
| *Proteocatella sphenisci* Cpf1 (SEQ ID NO: 7) | AAUUUCUAC | GUAGA | 5' TTTC |
| *Anaerovibrio* sp. RM50 Cpf1 (SEQ ID NO: 8) | AAUUUCUAC | GUAGA | 5' TTTC |
| *Moraxella caprae* Cpf1 (SEQ ID NO: 9) | GAAUUUCUAC (SEQ ID NO: 20) | GUAGA | 5' TTTC |
| *Lachnospiraceae bacterium* COE1 Cpf1 (SEQ ID NO: 10) | GAAUUUCUAC (SEQ ID NO: 20) | GUAGA | 5' TTTC |
| *Eubacterium coprostanoligenes* Cpf1 (SEQ ID NO: 11) | GAAUUUCUAC (SEQ ID NO: 20) | GUAGA | 5' TTTC |
| *Smithella* sp. SCADC Csm1 (SEQ ID NO: 12) | GAAUUUCUAC (SEQ ID NO: 20) | GUAGA | 5' TTTC |
| *Sulfuricurvum* sp. Csm1 (SEQ ID NO: 13) | GAAUUUCUAC (SEQ ID NO: 20) | GUAGA | 5' TTTC |
| *Microgenomates* (*Roizmanbacteria*) bacterium Csm1 (SEQ ID NO: 14) | GAAUUUCUAC (SEQ ID NO: 20) | GUAGA | 5' TTTC |

[1] The amino acid sequences of the Cas proteins are provided at the end of the specification.
[2] It is understood that a "modulator sequence" listed herein may constitute the nucleotide sequence of a modulator nucleic acid. Alternatively, additional nucleotide sequences can be comprised in the modulator nucleic acid 5' and/or 3' to a "modulator sequence" listed herein.
[3] In the consensus PAM sequences, N represents A, C, G, or T. When the PAM sequence is preceded by "5'," it means that the PAM is immediately upstream from the target sequence when using the non-target strand (i.e., the strand not hybridized with the spacer sequence) as the coordinate.

In certain embodiments, the targeter nucleic acid of the engineered, non-naturally occurring system comprises a targeter stem sequence listed in Table 1. In certain embodiments, the targeter nucleic acid and the modulator nucleic acid of the engineered, non-naturally occurring system comprise, respectively, a targeter stem sequence and a modulator sequence listed in the same line of Table 1. In certain embodiments, the engineered, non-naturally occurring system further comprises a Cas nuclease comprising the amino acid sequence set forth in the SEQ ID NO listed in the same line of Table 1. In certain embodiments, the engineered, non-naturally occurring system is useful for targeting, editing, or modifying a nucleic acid comprising a target nucleotide sequence close or adjacent to (e.g., immediately downstream of) a PAM listed in the same line of Table 1 when using the non-target strand (i.e., the strand not hybridized with the spacer sequence) as the coordinate.

In certain embodiments, the engineered, non-naturally occurring system is tunable or inducible. For example, in certain embodiments, the targeter nucleic acid, the modulator nucleic acid, and/or the Cas protein can be introduced to the target nucleotide sequence at different times, the system becoming active only when all components are present. In certain embodiments, the amounts of the targeter nucleic acid, the modulator nucleic acid, and/or the Cas protein can be titrated to achieve desirable efficiency and specificity. In certain embodiments, excess amount of a nucleic acid comprising the targeter stem sequence or the modulator stem sequence can be added to the system, thereby dissociating the complex of the targeter nucleic and modulator nucleic acid and turning off the system.

RNA Modifications

The targeter nucleic acid may comprise a DNA (e.g., modified DNA), an RNA (e.g., modified RNA), or a combination thereof. The modulator nucleic acid may comprise a DNA (e.g., modified DNA), an RNA (e.g., modified RNA), or a combination thereof. In certain embodiments, the targeter nucleic acid is an RNA and the modulator nucleic acid is an RNA. A targer nucleic acid in the form of an RNA is also called targeter RNA, and a modulator nucleic acid in the form of an RNA is also called modulator RNA. The nucleotide sequences disclosed herein are presented as DNA sequences by including thymidines (T) and/or RNA sequences including uridines (U). It is understood that corresponding DNA sequences, RNA sequences, and DNA/RNA chimeric sequences are also contemplated. For example, where a spacer sequence is presented as a DNA sequence, a nucleic acid comprising this spacer sequence as an RNA can be derived from the DNA sequence disclosed herein by replacing each T with U. As a result, for the purpose of describing a nucleotide sequence, T and U are used interchangeably herein.

In certain embodiments, the targeter nucleic acid and/or the modulator nucleic acid are RNAs with one or more modifications in a ribose group, one or more modifications in a phosphate group, one or more modifications in a nucleobase, one or more terminal modifications, or a combination thereof. Exemplary modifications are disclosed in U.S. Patent Application Publication Nos. 2016/0289675, 2017/0355985, 2018/0119140, Watts et al. (2008) Drug Discov. Today 13:842-55, and Hendel et al. (2015) NAT. BIOTECHNOL. 33:985.

Modifications in a ribose group include but are not limited to modifications at the 2' position or modifications at the 4' position. For example, in certain embodiments, the ribose comprises 2'-O—C1-4alkyl, such as 2'-O-methyl (2'-OMe). In certain embodiments, the ribose comprises 2'-O—C1-3alkyl-O—C1-3alkyl, such as 2'-methoxyethoxy (2'-O—CH$_2$CH$_2$OCH$_3$) also known as 2'-O-(2-methoxyethyl) or 2'-MOE. In certain embodiments, the ribose comprises 2'-O-allyl. In certain embodiments, the ribose comprises 2'-O-2,4-Dinitrophenol (DNP). In certain embodiments, the ribose comprises 2'-halo, such as 2'-F, 2'-Br, 2'-Cl, or 2'-I. In certain embodiments, the ribose comprises 2'-NH$_2$. In certain embodiments, the ribose comprises 2'-H (e.g., a deoxynucleotide). In certain embodiments, the ribose comprises 2'-arabino or 2'-F-arabino. In certain embodiments, the ribose comprises 2'-LNA or 2'-ULNA. In certain embodiments, the ribose comprises a 4'-thioribosyl.

Modifications in a phosphate group include but are not limited to a phosphorothioate internucleotide linkage, a chiral phosphorothioate internucleotide linkage, a phosphorodithioate internucleotide linkage, a boranophosphonate internucleotide linkage, a C$_{1-4}$alkyl phosphonate internucleotide linkage such as a methylphosphonate internucleotide linkage, a boranophosphonate internucleotide linkage, a phosphonocarboxylate internucleotide linkage such as a phosphonoacetate internucleotide linkage, a phosphonocarboxylate ester internucleotide linkage such as a phosphonoacetate ester internucleotide linkage, an amide linkage, a thiophosphonocarboxylate internucleotide linkage such as a thiophosphonoacetate internucleotide linkage, a thiophosphonocarboxylate ester internucleotide linkage such as a thiophosphonoacetate ester internucleotide linkage, and a 2',5'-linkage having a phosphodiester linker or any of the linkers above. Various salts, mixed salts and free acid forms are also included.

Modifications in a nucleobase include but are not limited to 2-thiouracil, 2-thiocytosine, 4-thiouracil, 6-thioguanine, 2-aminoadenine, 2-aminopurine, pseudouracil, hypoxanthine, 7-deazaguanine, 7-deaza-8-azaguanine, 7-deazaadenine, 7-deaza-8-azaadenine, 5-methylcytosine, 5-methyluracil, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil, 5-allylcytosine, 5-aminoallyluracil, 5-aminoallyl-cytosine, 5-bromouracil, 5-iodouracil, diaminopurine, difluorotoluene, dihydrouracil, an abasic nucleotide, Z base, P base, Unstructured Nucleic Acid, isoguanine, isocytosine (see, Piccirilli et al. (1990) NATURE, 343:33), 5-methyl-2-pyrimidine (see, Rappaport (1993) BIOCHEMISTRY, 32:3047), x(A,G,C,T), and y(A,G,C,T).

Terminal modifications include but are not limited to polyethyleneglycol (PEG), hydrocarbon linkers (such as heteroatom (O,S,N)-substituted hydrocarbon spacers; halo-substituted hydrocarbon spacers; keto-, carboxyl-, amido-, thionyl-, carbamoyl-, thionocarbamaoyl-containing hydrocarbon spacers), spermine linkers, dyes such as fluorescent dyes (for example, fluoresceins, rhodamines, cyanines), quenchers (for example, dabcyl, BHQ), and other labels (for example biotin, digoxigenin, acridine, streptavidin, avidin, peptides and/or proteins). In certain embodiments, a terminal modification comprises a conjugation (or ligation) of the RNA to another molecule comprising an oligonucleotide (such as deoxyribonucleotides and/or ribonucleotides), a peptide, a protein, a sugar, an oligosaccharide, a steroid, a lipid, a folic acid, a vitamin and/or other molecule. In certain embodiments, a terminal modification incorporated into the RNA is located internally in the RNA sequence via a linker such as 2-(4-butylamidofluorescein) propane-1,3-diol bis (phosphodiester) linker, which is incorporated as a phosphodiester linkage and can be incorporated anywhere between two nucleotides in the RNA.

The modifications disclosed above can be combined in the targeter nucleic acid and/or the modulator nucleic acid that are in the form of RNA. In certain embodiments, the modification in the RNA is selected from the group consisting of incorporation of 2'-O-methyl-3'phosphorothioate, 2'-O-methyl-3'-phosphonoacetate, 2'-O-methyl-3'-thiophosphonoacetate, 2'-halo-3'-phosphorothioate (e.g., 2'-fluoro-3'-phosphorothioate), 2'-halo-3'-phosphonoacetate (e.g., 2'-fluoro-3'-phosphonoacetate), and 2'-halo-3'-thiophosphonoacetate (e.g., 2'-fluoro-3'-thiophosphonoacetate).

In certain embodiments, the modification alters the stability of the RNA. In certain embodiments, the modification enhances the stability of the RNA, e.g., by increasing nuclease resistance of the RNA relative to a corresponding RNA without the modification. Stability-enhancing modifications include but are not limited to incorporation of 2'-O-methyl, a 2'-O—$C_{1-4}$alkyl, 2'-halo (e.g., 2'-F, 2'-Br, 2'-Cl, or 2'-I), 2'MOE, a 2'-O—$C_{1-3}$alkyl-O—$C_{1-3}$alkyl, 2'-NH$_2$, 2'-H (or 2'-deoxy), 2'-arabino, 2'-F-arabino, 4'-thioribosyl sugar moiety, 3'-phosphorothioate, 3'-phosphonoacetate, 3'-thiophosphonoacetate, 3'-methylphosphonate, 3'-boranophosphate, 3'-phosphorodithioate, locked nucleic acid ("LNA") nucleotide which comprises a methylene bridge between the 2' and 4' carbons of the ribose ring, and unlocked nucleic acid ("ULNA") nucleotide. Such modifications are suitable for use as a protecting group to prevent or reduce degradation of the 5' tail, modulator stem sequence, targeter stem sequence, and/or spacer sequence (see, the "Targeter and Modulator nucleic acids" subsection supra).

In certain embodiments, the modification alters the specificity of the engineered, non-naturally occurring system. In certain embodiments, the modification enhances the specification of the engineered, non-naturally occurring system, e.g., by enhancing on-target binding and/or cleavage, or reducing off-target binding and/or cleavage, or a combination thereof. Specificity-enhancing modifications include but are not limited to 2-thiouracil, 2-thiocytosine, 4-thiouracil, 6-thioguanine, 2-aminoadenine, and pseudouracil.

In certain embodiments, the modification alters the immunostimulatory effect of the RNA relative to a corresponding RNA without the modification. For example, in certain embodiments, the modification reduces the ability of the RNA to activate TLR7, TLR8, TLR9, TLR3, RIG-I, and/or MDA5.

In certain embodiments, the targeter nucleic acid and/or the modulator nucleic acid comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified nucleotides. The modification can be made at one or more positions in the targeter nucleic acid and/or the modulator nucleic acid such that these nucleic acids retain functionality. For example, the modified nucleic acids can still direct the Cas protein to the target nucleotide sequence and allow the Cas protein to exert its effector function. It is understood that the particular modification(s) at a position may be selected based on the functionality of the nucleotide at the position. For example, a specificity-enhancing modification may be suitable for a nucleotide in the spacer sequence, the targeter stem sequence, or the modulator stem sequence. A stability-enhancing modification may be suitable for one or more terminal nucleotides in the targeter nucleic acid and/or the modulator nucleic acid. In certain embodiments, at least 1 (e.g., at least 2, at least 3, at least 4, or at least 5) terminal nucleotides at the 5' end and/or at least 1 (e.g., at least 2, at least 3, at least 4, or at least 5) terminal nucleotides at the 3' end of the targeter nucleic acid are modified nucleotides. In certain embodiments, 5 or fewer (e.g., 1 or fewer, 2 or fewer, 3 or fewer, or 4 or fewer) terminal nucleotides at the 5' end and/or 5 or fewer (e.g., 1 or fewer, 2 or fewer, 3 or fewer, or 4 or fewer) terminal nucleotides at the 3' end of the targeter nucleic acid are modified nucleotides. In certain embodiments, at least 1 (e.g., at least 2, at least 3, at least 4, or at least 5) terminal nucleotides at the 5' end and/or at least 1 (e.g., at least 2, at least 3, at least 4, or at least 5) terminal nucleotides at the 3' end of the modulator nucleic acid are modified nucleotides. In certain embodiments, 5 or fewer (e.g., 1 or fewer, 2 or fewer, 3 or fewer, or 4 or fewer) terminal nucleotides at the 5' end and/or 5 or fewer (e.g., 1 or fewer, 2 or fewer, 3 or fewer, or 4 or fewer) terminal nucleotides at the 3' end of the modulator nucleic acid are modified nucleotides. Selection of positions for modifications is described in U.S. Patent Application Publication Nos. 2016/0289675 and 2017/0355985. As used in this paragraph, where the targeter or modulator nucleic acid is a combination of DNA and RNA, the nucleic acid as a whole is considered as an RNA, and the DNA nucleotide(s) are considered as modification(s) of the RNA, including a 2'-H modification of the ribose and optionally a modification of the nucleobase.

It is understood that the targeter nucleic acid and the modulator nucleic acid, while not in the same nucleic acids, i.e., not linked end-to-end through a traditional internucleotide bond, can be covalently conjugated to each other through one or more chemical modifications introduced into these nucleic acids, thereby increasing the stability of the double-stranded complex and/or improving other characteristics of the system.

II. Methods of Targeting, Editing, and/or Modifying Genomic DNA

The engineered, non-naturally occurring system disclosed herein are useful for targeting, editing, and/or modifying a target nucleic acid, such as a DNA (e.g., genomic DNA) in a cell or organism. Accordingly, in one aspect, the present invention provides a method of modifying a target nucleic acid (e.g., DNA) having a target nucleotide sequence, the method comprising contacting the target nucleic acid with the engineered, non-naturally occurring system disclosed herein, thereby resulting in modification of the target nucleic acid.

The engineered, non-naturally occurring system can be contacted with the target nucleic acid as a complex. Accordingly, in certain embodiments, the method comprises contacting the target nucleic acid with a dual guide CRISPR-Cas complex comprising (a) a targeter nucleic acid comprising (i) a spacer sequence designed to hybridize with the target nucleotide sequence and (ii) a targeter stem sequence; (b) a modulator nucleic acid comprising a modulator stem sequence complementary to the targeter stem sequence; and (c) a Cas protein, wherein the targeter nucleic acid and the modulator nucleic acid are separate nucleic acids, and wherein the targeter nucleic acid and the modulator nucleic acid form a complex that is capable of activating a Cas nuclease that, in a naturally occurring system, is activated by a single crRNA in the absence of a tracrRNA, thereby resulting in modification of the target nucleic acid. In certain embodiments, the Cas protein comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to the Cas nuclease.

The Cas protein and the Cas nuclease can be identical. Accordingly, in certain embodiments, the present invention provides a method of cleaving a target nucleic acid (e.g., DNA) having a target nucleotide sequence, the method comprising contacting the target nucleic acid with the engineered, non-naturally occurring system disclosed herein, thereby resulting in leavage of the target DNA. In certain embodiments, the method comprises contacting the target nucleic acid with a dual guide CRISPR-Cas complex comprising (a) a targeter nucleic acid comprising (i) a spacer sequence designed to hybridize with the target nucleotide sequence and (ii) a targeter stem sequence; (b) a modulator nucleic acid comprising a modulator stem sequence complementary to the targeter stem sequence; and (c) a Cas nuclease, wherein the targeter nucleic acid and the modulator nucleic acid are separate nucleic acids, wherein in a naturally occurring system the Cas nuclease is activated by a single crRNA in the absence of a tracrRNA, thereby resulting in cleavage of the target nucleic acid by the Cas nuclease.

In certain embodiments, the Cas nuclease is a type V-A, type V-C, or type V-D Cas nuclease. In certain embodiments, the Cas nuclease is a type V-A Cas nuclease. In certain embodiments, the target nucleic acid further comprises a cognate PAM positioned relative to the target nucleotide sequence such that (a) the dual guide CRISPR-Cas complex binds the target nucleic acid; or (b) the Cas nuclease is activated when the dual guide CRISPR-Cas complex binds the target nucleic acid.

The dual guide CRISPR-Cas complex may be delivered to a cell by introducing a pre-formed ribonucleoprotein (RNP) complex into the cell. Alternatively, one or more components of the dual guide CRISPR-Cas complex may be expressed in the cell. Exemplary methods of delivery are known in the art and described in, for example, U.S. Pat. Nos. 10,113,167 and 8,697,359 and U.S. Patent Application Publication Nos. 2015/0344912, 2018/0044700, 2018/0003696, 2018/0119140, 2017/0107539, 2018/0282763, and 2018/0363009.

It is understood that contacting a DNA (e.g., genomic DNA) in a cell with a dual guide CRISPR-Cas complex does not require delivery of all components of the complex into the cell. For examples, one or more of the components may be pre-existing in the cell. In certain embodiments, the cell (or a parental/ancestral cell thereof) has been engineered to express the Cas protein, and the targeter nucleic acid (or a nucleic acid comprising a regulatory element operably linked to a nucleotide sequence encoding the targeter nucleic acid) and the modulator nucleic acid (or a nucleic acid comprising a regulatory element operably linked to a nucleotide sequence encoding the modulator nucleic acid) are delivered into the cell. In certain embodiments, the cell (or a parental/ancestral cell thereof) has been engineered to express the modulator nucleic acid, and the Cas protein (or a nucleic acid comprising a regulatory element operably linked to a nucleotide sequence encoding the Cas protein) and the targeter nucleic acid (or a nucleic acid comprising a regulatory element operably linked to a nucleotide sequence encoding the targeter nucleic acid) are delivered into the cell. In certain embodiments, the cell (or a parental/ancestral cell thereof) has been engineered to express the Cas protein and the modulator nucleic acid, and the targeter nucleic acid (or a nucleic acid comprising a regulatory element operably linked to a nucleotide sequence encoding the targeter nucleic acid) is delivered into the cell.

In certain embodiments, the target DNA is in the genome of a target cell.

Accordingly, in another aspect, the present invention provides a cell comprising the non-naturally occurring system or a CRISPR expression system described herein. In addition, the present invention provides a cell whose genome has been modified by the dual guide CRISPR-Cas system or complex disclosed herein.

The target cells can be mitotic or post-mitotic cells from any organism, such as a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens* C. Agardh, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, or a cell from a human. The types of target cells include but are not limited to a stem cell (e.g., an embryonic stem (ES) cell, an induced pluripotent stem (iPS) cell, a germ cell), a somatic cell (e.g., a fibroblast, a hematopoietic cell, a T lymphocyte (e.g., $CD8^+$ T lymphocyte), an NK cell, a neuron, a muscle cell, a bone cell, a hepatocyte, a pancreatic cell), an in vitro or in vivo embryonic cell of an embryo at any stage (e.g., a 1-cell, 2-cell, 4-cell, 8-cell; stage zebrafish embryo). Cells may be from established cell lines or may be primary cells (i.e., cells and cells cultures that have been derived from a subject and allowed to grow in vitro for a limited number of passages of the culture). For example, primary cultures are cultures that may have been passaged within 0 times, 1 time, 2 times, 4 times, 5 times, 10 times, or 15 times, but not enough times to go through the crisis stage. Typically, the primary cell lines of the present invention are maintained for fewer than 10 passages in vitro. If the cells are primary cells, they may be harvest from an individual by any suitable method. For example, leukocytes may be harvested by apheresis, leukocytapheresis, or density gradient separation, while cells from tissues such as skin, muscle, bone marrow, spleen, liver, pancreas, lung, intestine, or stomach can be harvested by biopsy. The harvested cells may be used immediately, or may be stored under frozen conditions with a cryopreservative and thawed at a later time in a manner as commonly known in the art.

Ribonucleoprotein (RNP) Delivery and "Cas RNA" Delivery

The engineered, non-naturally occurring system disclosed herein can be delivered into a cell by suitable methods known in the art, including but not limited to ribonucleoprotein (RNP) delivery and "Cas RNA" delivery described below.

In certain embodiments, a dual guide CRISPR-Cas system including a targeter nucleic acid, a modulator nucleic acid, and a Cas protein can be combined into a RNP complex and then delivered into the cell as a pre-formed complex. This method is suitable for active modification of the genetic or epigenetic information in a cell during a limited time period. For example, where the Cas protein has nuclease activity to modify the genomic DNA of the cell, the nuclease activity only needs to be retained for a period of time to allow DNA cleavage, and prolonged nuclease activity may increase off-targeting. Similarly, certain epigenetic modifications can be maintained in a cell once established and can be inherited by daughter cells.

A "ribonucleoprotein" or "RNP," as used herein, refers to a complex comprising a nucleoprotein and a ribonucleic acid. A "nucleoprotein" as provided herein refers to a protein capable of binding a nucleic acid (e.g., RNA, DNA). Where the nucleoprotein binds a ribonucleic acid it is referred to as "ribonucleoprotein." The interaction between the ribonucleoprotein and the ribonucleic acid may be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions, and the like). In certain embodiments, the ribonucleoprotein includes an RNA-binding motif non-covalently bound to the ribonucleic acid. For example, positively charged aromatic amino acid residues (e.g., lysine residues) in the RNA-binding motif may form electrostatic interactions with the negative nucleic acid phosphate backbones of the RNA.

To ensure efficient loading of the Cas protein, the targeter nucleic acid and the modulator nucleic acid can be provided in excess molar amount (e.g., about 2 fold, about 3 fold, about 4 fold, or about 5 fold) relative to the Cas protein. In certain embodiments, the targeter nucleic acid and the modulator nucleic acid are annealed under suitable conditions prior to complexing with the Cas protein. In other embodiments, the targeter nucleic acid, the modulator nucleic acid, and the Cas protein are directly mixed together to form an RNP.

A variety of delivery methods can be used to introduce an RNP disclosed herein into a cell. Exemplary delivery methods or vehicles include but are not limited to microinjection, liposomes (see, e.g., U.S. Patent Publication No. 2017/0107539) such as molecular trojan horses liposomes that delivers molecules across the blood brain barrier (see, Pardridge et al. (2010) COLD SPRING HARB. PROTOC., doi: 10.1101/pdb.prot5407), immunoliposomes, virosomes, microvesicles (e.g., exosomes and ARMMs), polycations, lipid: nucleic acid conjugates, electroporation, cell permeable peptides (see, U.S. Patent Publication No. 2018/0363009), nanoparticles, nanowires (see, Shalek et al. (2012) NANO LETTERS, 12:6498), exosomes, and perturbation of cell membrane (e.g., by passing cells through a constriction in a microfluidic system, see, U.S. Patent Publication No. 2018/0003696). Where the target cell is a proliferating cell, the efficiency of RNP delivery can be enhanced by cell cycle synchronization (see, U.S. Patent Publication No. 2018/0044700).

In other embodiments, the dual guide CRISPR-Cas system is delivered into a cell in a "Cas RNA" approach, i.e., delivering a targeter nucleic acid, a modulator nucleic acid, and an RNA (e.g., messenger RNA (mRNA)) encoding a Cas protein. The RNA encoding the Cas protein can be translated in the cell and form a complex with the targeter nucleic acid and the modulator nucleic acid intracellularly. Similar to the RNP approach, RNAs have limited half-lives in cells, even though stability-increasing modification(s) can be made in one or more of the RNAs. Accordingly, the "Cas RNA" approach is suitable for active modification of the genetic or epigenetic information in a cell during a limited time period, such as DNA cleavage, and has the advantage of reducing off-targeting.

The mRNA can be produced by transcription of a DNA comprising a regulatory element operably linked to a Cas coding sequence. Given that multiple copies of Cas protein can be generated from one mRNA, the targeter nucleic acid and the modulator nucleic acid are generally provided in excess molar amount (e.g., at least 5 fold, at least 10 fold, at least 20 fold, at least 30 fold, at least 50 fold, or at least 100 fold) relative to the mRNA. In certain embodiments, the targeter nucleic acid and the modulator nucleic acid are annealed under suitable conditions prior to delivery into the cells. In other embodiments, the targeter nucleic acid and the modulator nucleic acid are delivered into the cells without annealing in vitro.

A variety of delivery systems can be used to introduce an "Cas RNA" system into a cell. Non-limiting examples of delivery methods or vehicles include microinjection, biolistic particles, liposomes (see, e.g., U.S. Patent Publication No. 2017/0107539) such as molecular trojan horses liposomes that delivers molecules across the blood brain barrier (see, Pardridge et al. (2010) COLD SPRING HARB. PROTOC., doi: 10.1101/pdb.prot5407), immunoliposomes, virosomes, polycations, lipid: nucleic acid conjugates, electroporation, nanoparticles, nanowires (see, Shalek et al. (2012) NANO LETTERS, 12:6498), exosomes, and perturbation of cell membrane (e.g., by passing cells through a constriction in a microfluidic system, see, U.S. Patent Publication No. 2018/0003696). Specific examples of the "nucleic acid only" approach by electroporation are described in International (PCT) Publication No. WO2016/164356.

In other embodiments, the dual guide CRISPR-Cas system is delivered into a cell in the form of a targeter nucleic acid, a modulator nucleic acid, and a DNA comprising a regulatory element operably linked to a Cas coding sequence. The DNA can be provided in a plasmid, viral vector, or any other form described in the "CRISPR Expression Systems" subsection. Such delivery method may result in constitutive expression of Cas protein in the target cell (e.g., if the DNA is maintained in the cell in an episomal vector or is integrated into the genome), and may increase the risk of off-targeting which is undesirable when the Cas protein has nuclease activity. Notwithstanding, this approach is useful when the Cas protein comprises a non-nuclease effector (e.g., a transcriptional activator or repressor). It is also useful for research purposes and for genome editing of plants.

CRISPR Expression Systems

In another aspect, the present invention provides a CRISPR expression system comprising: (a) a nucleic acid comprising a first regulatory element operably linked to a nucleotide sequence encoding a targeter nucleic acid disclosed herein comprising (i) a spacer sequence designed to hybridize with a target nucleotide sequence and (ii) a targeter stem sequence; (b) a nucleic acid comprising a second regulatory element operably linked to a nucleotide sequence encoding a modulator nucleic acid disclosed herein comprising a modulator stem sequence complementary to the targeter stem sequence, wherein the targeter nucleic acid and the modulator nucleic acid are expressed as separate nucleic acids, and wherein a complex comprising the targeter nucleic acid and the modulator nucleic acid is capable of activating a Cas nuclease that, in a naturally occurring system, is activated by a single crRNA in the absence of a tracrRNA.

In certain embodiments, the CRISPR expression system further comprises (c) a nucleic acid comprising a third regulatory element operably linked to a nucleotide sequence encoding a Cas protein disclosed herein. In certain embodiments, the Cas protein comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to the Cas nuclease, thereby resulting in modification of the target nucleic acid (e.g., DNA). In certain embodiments, the Cas protein and the Cas nuclease are identical, and the method results in cleavage of the target nucleic acid. In certain embodiments, the Cas nuclease is a type V-A, type V-C, or type V-D Cas nuclease. In certain embodiments, the Cas nuclease is a type V-A Cas nuclease.

As used in this context, the term "operably linked" is intended to mean that the nucleotide sequence of interest is linked to the regulatory element in a manner that allows for expression of the nucleotide sequence (e.g., in an in vitro transcription/translation system or in a host cell when the vector is introduced into the host cell).

The form of elements (a), (b), and (c) of the CRISPR expression system described above may be independently selected from various nucleic acids such as DNA (e.g., modified DNA) and RNA (e.g., modified RNA). In certain embodiments, elements (a) and (b) are each in the form of DNA. In certain embodiments, the CRISPR expression system further comprises element (c) in the form of DNA. The third regulatory element can be a constitutive or inducible promoter that drives the expression of the Cas protein. In other embodiments, the CRISPR expression system further comprises element (c) in the form of RNA (e.g., mRNA).

Elements (a), (b), and/or (c) can be provided in one or more vectors. The term "vector," as used herein, refers to a nucleic acid molecule capable of transporting another nucleic acid to which it has been linked. Conventional viral and non-viral based gene transfer methods can be used to introduce nucleic acids in cells, such as prokaryotic cells, eukaryotic cells, mammalian cells, or target tissues. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. Gene therapy procedures are known in the art and disclosed in Van Brunt (1988) BIOTECHNOLOGY, 6:1149; Anderson (1992) SCIENCE, 256:808; Nabel & Feigner (1993) TIBTECH, 11:211; Mitani & Caskey (1993) TIBTECH, 11:162; Dillon (1993) TIBTECH, 11:167; Miller (1992) NATURE, 357:455; Vigne, (1995) RESTORATIVE NEUROLOGY AND NEUROSCIENCE, 8:35; Kremer & Perricaudet (1995) BRITISH MEDICAL BULLETIN, 51:31; Haddada et al. (1995) CURRENT TOPICS IN MICROBIOLOGY AND IMMUNOLOGY, 199:297; Yu et al. (1994) GENE THERAPY, 1:13; and Doerfler and Bohm (Eds.) (2012) The Molecular Repertoire of Adenoviruses II: Molecular Biology of Virus-Cell Interactions. In certain embodiments, at least one of the vectors is a DNA plasmid. In certain embodiments, at least one of the vectors is a viral vector (e.g., retrovirus, adenovirus, or adeno-associated virus).

Certain vectors are capable of autonomous replication in a host cell into which they are introduced (e.g., bacterial vectors having a bacterial origin of replication and episomal mammalian vectors). Other vectors (e.g., non-episomal mammalian vectors and replication defective viral vectors) do not autonomously replicate in the host cell. Certain vectors, however, may be integrated into the genome of the host cell and thereby are replicated along with the host genome. A skilled person in the art will appreciate that different vectors may be suitable for different delivery methods and have different host tropism, and will be able to select one or more vectors suitable for the use.

The term "regulatory element," as used herein, refers to a transcriptional and/or translational control sequence, such as a promoter, enhancer, transcription termination signal (e.g., polyadenylation signal), internal ribosomal entry sites (IRES), protein degradation signal, and the like, that provide for and/or regulate transcription of a non-coding sequence (e.g., a targeter nucleic acid or a modulator nucleic acid) or a coding sequence (e.g., a Cas protein) and/or regulate translation of an encoded polypeptide. Such regulatory elements are described, for example, in Goeddel, GENE EXPRESSION TECHNOLOGY: METHODS IN ENZYMOLOGY, 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In certain embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (see, Takebe et al. (1988) MOL. CELL. BIOL., 8:466); SV40 enhancer; and the intron sequence between exons 2 and 3 of rabbit β-globin (see, O'Hare et al. (1981) PROC. NATL. ACAD. SCI. USA., 78:1527). It will be appreciated by those skilled in the art that the design of the expression vector can depend on factors such as the choice of the host cell to be transformed, the level of expression desired, etc. A vector can be introduced into host cells to produce transcripts, proteins, or peptides, including fusion proteins or peptides, encoded by nucleic acids as described herein (e.g., CRISPR transcripts, proteins, enzymes, mutant forms thereof, or fusion proteins thereof).

In certain embodiments, the nucleotide sequence encoding the Cas protein is codon optimized for expression in a eukaryotic host cell, e.g., a yeast cell, a mammalian cell (e.g., a mouse cell, a rat cell, or a human cell), or a plant cell. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/ and these tables can be adapted in a number of ways (see, Nakamura et al. (2000) NUCL. ACIDS RES., 28:292). Computer algorithms for codon optimizing a particular sequence for expression in a particular host cell, such as Gene Forge (Aptagen; Jacobus, Pa.), are also available. In certain embodiments, the codon optimization facilitates or improves expression of the Cas protein in the host cell.

Donor Templates

Cleavage of a target nucleotide sequence in the genome of a cell by the dual guide CRISPR-Cas system or complex disclosed herein can activate the DNA damage pathways, which may rejoin the cleaved DNA fragments by NHEJ or HDR. HDR requires a repair template, either endogenous or exogenous, to transfer the sequence information from the repair template to the target.

In certain embodiments, the engineered, non-naturally occurring system or CRISPR expression system further comprises a donor template. As used herein, the term "donor template" refers to a nucleic acid designed to serve as a repair template at or near the target nucleotide sequence upon introduction into a cell or organism. In certain embodiments, the donor template is complementary to a polynucleotide comprising the target nucleotide sequence or a portion thereof. When optimally aligned, a donor template may overlap with one or more nucleotides of a target nucleotide sequences (e.g. about or more than about 1, 5, 10, 15, 20, 25, 30, 35, 40, or more nucleotides). The nucleotide sequence of the donor template is typically not identical to the genomic sequence that it replaces. Rather, the donor template may contain one or more substitutions, insertions, deletions, inversions or rearrangements with respect to the genomic sequence, so long as sufficient homology is present to support homology-directed repair. In certain embodiments, the donor template comprises a non-homologous sequence flanked by two regions of homology (i.e., homology arms), such that homology-directed repair between the target DNA region and the two flanking sequences results in insertion of the non-homologous sequence at the target region. In certain embodiments, the donor template comprises a non-homologous sequence 10-100 nucleotides, 50-500 nucleotides, 100-1,000 nucleotides, 200-2,000 nucleotides, or 500-5,000 nucleotides in length positioned between two homology arms.

Generally, the homologous region(s) of a donor template has at least 50% sequence identity to a genomic sequence with which recombination is desired. The homology arms are designed or selected such that they are capable of recombining with the nucleotide sequences flanking the target nucleotide sequence under intracellular conditions. In certain embodiments, where HDR of the non-target strand is desired, the donor template comprises a first homology arm homologous to a sequence 5' to the target nucleotide sequence and a second homology arm homologous to a sequence 3' to the target nucleotide sequence. In certain embodiments, the first homology arm is at least 50% (e.g., at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%) identical to a sequence 5' to the target nucleotide sequence. In certain embodiments, the second homology arm is at least 50% (e.g., at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%) identical to a sequence 3' to the target nucleotide sequence. In certain embodiments, when the donor template sequence and a polynucleotide comprising a target nucleotide sequence are optimally aligned, the nearest nucleotide of the donor template is within about 1, 5, 10, 15, 20, 25, 50, 75, 100, 200, 300, 400, 500, 1000, 2000, 3000, 4000, or more nucleotides from the target nucleotide sequence.

In certain embodiments, the donor template further comprises an engineered sequence not homologous to the sequence to be repaired. Such engineered sequence can harbor a barcode and/or a sequence capable of hybridizing with a donor template-recruiting sequence disclosed herein.

In certain embodiments, the donor template further comprises one or more mutations relative to the genomic sequence, wherein the one or more mutations reduce or prevent cleavage, by the same CRISPR-Cas system, of the donor template or of a modified genomic sequence with at least a portion of the donor template sequence incorporated. In certain embodiments, in the donor template, the PAM adjacent to the target nucleotide sequence and recognized by the Cas nuclease is mutated to a sequence not recognized by the same Cas nuclease. In certain embodiments, in the donor template, the target nucleotide sequence (e.g., the seed region) is mutated. In certain embodiments, the one or more mutations are silent with respect to the reading frame of a protein-coding sequence encompassing the mutated sites.

The donor template can be provided to the cell as single-stranded DNA, single-stranded RNA, double-stranded DNA, or double-stranded RNA. It is understood that the dual guide CRISPR-Cas system disclosed herein may possess nuclease activity to cleave the target strand, the non-target strand, or both. When HDR of the target strand is desired, a donor template having a nucleic acid sequence complementary to the target strand is also contemplated.

The donor template can be introduced into a cell in linear or circular form. If introduced in linear form, the ends of the donor template may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends (see, for example, Chang et al. (1987) Proc. Natl. Acad Sci USA, 84:4959; Nehls et al. (1996) Science, 272:886; see also the chemical modifications for increasing stability and/or specificity of RNA disclosed supra). Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor template, additional lengths of sequence may be included outside of the regions of homology that can be degraded without impacting recombination.

A donor template can be a component of a vector as described herein, contained in a separate vector, or provided as a separate polynucleotide, such as an oligonucleotide, linear polynucleotide, or synthetic polynucleotide. In certain embodiments, the donor template is a DNA. In certain embodiments, a donor template is in the same nucleic acid as a sequence encoding the targeter nucleic acid, a sequence encoding the modulator nucleic acid, and/or a sequence encoding the Cas protein, where applicable. In certain embodiments, a donor template is provided in a separate nucleic acid. A donor template polynucleotide may be of any suitable length, such as about or at least about 50, 75, 100, 150, 200, 500, 1000, 2000, 3000, 4000, or more nucleotides in length.

A donor template can be introduced into a cell as an isolated nucleic acid. Alternatively, a donor template can be introduced into a cell as part of a vector (e.g., a plasmid) having additional sequences such as, for example, replication origins, promoters and genes encoding antibiotic resistance, that are not intended for insertion into the DNA region of interest. Alternatively, a donor template can be delivered by viruses (e.g., adenovirus, adeno-associated virus (AAV)). In certain embodiments, the donor template is introduced as an AAV, e.g., a pseudotyped AAV. The capsid proteins of the AAV can be selected by a person skilled in the art based upon the tropism of the AAV and the target cell type. For example, in certain embodiments, the donor template is introduced into a hepatocyte as AAV8 or AAV9. In certain embodiments, the donor template is introduced into a hematopoietic stem cell, a hematopoietic progenitor cell, or a T lymphocyte (e.g., CD8+T lymphocyte) as AAV6 or an AAVHSC (see, U.S. Pat. No. 9,890,396). It is understood that the sequence of a capsid protein (VP1, VP2, or VP3) may be modified from a wild-type AAV capsid protein, for example, having at least 50% (e.g., at least 60%, at least 70%, at least 75%, at least 80%, at least 85%, at least 90%, at least 91%, at least 92%, at least 93%, at least 94%, at least 95%, at least 96%, at least 97%, at least 98%, or at least 99%) sequence identity to a wild-type AAV capsid sequence.

The donor template can be delivered to a cell (e.g., a primary cell) by various delivery methods, such as a viral or non-viral method disclosed herein. In certain embodiments, a non-viral donor template is introduced into the target cell as a naked nucleic acid or in complex with a liposome or poloxamer. In certain embodiments, a non-viral donor template is introduced into the target cell by electroporation. In other embodiments, a viral donor template is introduced into the target cell by infection. The engineered, non-naturally occurring system can be delivered before, after, or simultaneously with the donor template (see, International (PCT) Application Publication No. WO2017/053729). A skilled person in the art will be able to choose proper timing based upon the form of delivery (consider, for example, the time needed for transcription and translation of RNA and protein components) and the half-life of the molecule(s) in the cell. In particular embodiments, where the dual guide CRISPR-Cas system including the Cas protein is delivered by electroporation (e.g., as an RNP), the donor template (e.g., as an AAV) is introduced into the cell within 4 hours (e.g., within 1, 2, 3, 4, 5, 6, 7, 8, 9, 10, 11, 12, 13, 14, 15, 16, 17, 18, 19, 20, 25, 30, 35, 40, 45, 50, 55, 60, 90, 120, 150, 180, 210, or 240 minutes) after the introduction of the engineered, non-naturally occurring system.

In certain embodiments, the donor template is conjugated covalently to the modulator nucleic acid. Covalent linkages suitable for this conjugation are known in the art and are described, for example, in U.S. Pat. No. 9,982,278 and Savic et al. (2018) ELIFE 7: e33761. In certain embodiments, the donor template is covalently linked to the modulator nucleic acid (e.g., the 5' end of the modulator nucleic acid) through an internucleotide bond. In certain embodiments, the donor template is covalently linked to the modulator nucleic acid (e.g., the 5' end of the modulator nucleic acid) through a linker.

Efficiency and Specificity

The engineered, non-naturally occurring system of the present invention has the advantage that the efficiency of nucleic acid targeting, cleavage, or modification can be increased or decreased by, for example, adjusting the hybridization of dual guide nucleic acids and the length of the spacer sequence.

In certain embodiments, the engineered, non-naturally occurring system has high efficiency. For example, in certain embodiments, at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% of a population of nucleic acids having the target nucleotide sequence and a cognate PAM, when contacted with the engineered, non-naturally occurring system, is targeted, cleaved, or modified. In certain embodiments, the genomes of at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% of a population of cells, when contacted with the engineered, non-naturally occurring system, are targeted, cleaved, or modified.

It has been observed that the occurrence of on-target events and the occurrence of off-target events are generally correlated. For certain therapeutic purposes, low on-target efficiency can be tolerated and low off-target frequency is more desirable. For example, when editing or modifying a proliferating cell that will be delivered to a subject and proliferate in vivo, tolerance to off-target events is low. Prior to delivery, however, it is possible to assess the on-target and off-target events, thereby selecting one or more colonies that have the desired edit or modification and lack any undesired edit or modification.

The method disclosed herein is suitable for such use. In certain embodiments, when a population of nucleic acids having the target nucleotide sequence and a cognate PAM is contacted with the engineered, non-naturally occurring system disclosed herein, the frequency of off-target events (e.g., targeting, cleavage, or modification, depending on the function of the CRISPR-Cas system) is reduced by at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% relative to the frequency of off-target events when using the corresponding CRISPR system containing a single guide nucleic acid (e.g., a single crRNA consisting of the sequences of the targeter and modulator nucleic acids) under the same conditions. In certain embodiments, when genomic DNA having the target nucleotide sequence and a cognate PAM is contacted with the engineered, non-naturally occurring system disclosed herein in a population of cells, the frequency of off-target events (e.g., targeting, cleavage, or modification, depending on the function of the CRISPR-Cas system) is reduced by at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% relative to the frequency of off-target events when using the corresponding CRISPR system containing a single guide nucleic acid (e.g., a single crRNA consisting of the sequences of the targeter and modulator nucleic acids) under the same conditions. In certain embodiments, when delivered into a population of cells comprising genomic DNA having the target nucleotide sequence and a cognate PAM, the frequency of off-target events (e.g., targeting, cleavage, or modification, depending on the function of the CRISPR-Cas system) in the cells receiving the engineered, non-naturally occurring system disclosed herein is reduced by at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% relative to the frequency of off-target events in the cells receiving the corresponding CRISPR system containing a single guide nucleic acid (e.g., a single crRNA consisting of the sequences of the targeter and modulator nucleic acids) under the same conditions. Methods of assessing off-target events were summarized in Lazzarotto et al. (2018) NAT PROTOC. 13 (11): 2615-42, and include discovery of in situ Cas off-targets and verification by sequencing (DISCOVER-seq) as disclosed in Wienert et al. (2019) SCIENCE 364 (6437): 286-89; genome-wide unbiased identification of double-stranded breaks (DSBs) enabled by sequencing (GUIDE-seq) as disclosed in Kleinstiver et al. (2016) NAT. BIOTECH. 34:869-74; circularization for in vitro reporting of cleavage effects by sequencing (CIRCLE-seq) as described in Kocak et al. (2019) NAT. BIOTECH. 37:657-66. In certain embodiments, the off-target events include targeting, cleavage, or modification at a given off-target locus (e.g., the locus with the highest occurrence of off-target events detected). In certain embodiments, the off-target events include targeting, cleavage, or modification at all the loci with detectable off-target events, collectively.

Multiplex Methods

The method of targeting, editing, and/or modifying a genomic DNA disclosed herein can be conducted in multiplicity. For example, a library of targeter nucleic acids can be used to target multiple genomic loci; a library of donor templates can also be used to generate multiple insertions, deletions, and/or substitutions. The multiplex assay can be conducted in a screening method wherein each separate cell culture (e.g., in a well of a 96-well plate or a 384-well plate) is exposed to a different targeter nucleic acid or a different combination of targeter nucleic acid and donor template. The multiplex assay can also be conducted in a selection method wherein a cell culture is exposed to a mixed population of different targeter nucleic acids and/or donor templates, and the cells with desired characteristics (e.g., functionality) are enriched or selected by advantageous survival or growth, resistance to a certain agent, expression of a detectable protein (e.g., a fluorescent protein that is detectable by flow cytometry), etc.

In certain embodiments, the multiplex method employs a plurality of targeter nucleic acids that are capable of hybridizing with different target nucleotide sequences. In certain embodiments, the plurality of targeter nucleic acids comprise a common targeter stem sequence. In certain embodiments, the multiplex method employs a single modulator nucleic acid capable of hybridizing with the plurality of targeter nucleic acids. In certain embodiments, the multiplex method employs a single Cas protein (e.g., Cas nuclease) disclosed herein.

In certain embodiments, the multiplex method employs a plurality of targeter nucleic acids that are capable of hybridizing with different target nucleotide sequences that are close to or adjacent to different PAMs. In certain embodiments, the plurality of targeter nucleic acids comprise different targeter stem sequences. In certain embodiments, the multiplex method employs a plurality of modulator nucleic acids each capable of hybridizing with a different targeter nucleic acid. In certain embodiments, the multiplex method employs a plurality of Cas proteins (e.g., Cas nucleases) disclosed herein that have different PAM specificity.

In certain embodiments, the multiplex method further comprises introducing one or more donor templates into the population of cells. In certain embodiments, the multiplex method employs a plurality of modulator nucleic acids each comprising a different donor template-recruiting sequence, wherein each donor template-recruiting sequence is capable of hybridizing with a different donor template.

In certain embodiments, the plurality of targeter nucleic acids and/or the plurality of donor templates are designed for saturation editing. For example, in certain embodiments, each nucleotide position in a sequence of interest is systematically modified with each of all four traditional bases, A, T, G and C. In other embodiments, at least one sequence in each gene from a pool of genes of interest is modified, for example, according to a CRISPR design algorithm. In certain embodiments, each sequence from a pool of exogenous elements of interest (e.g., protein coding sequences, non-protein coding genes, regulatory elements) is inserted into one or more given loci of the genome.

It is understood that the multiplex methods suitable for the purpose of carrying out a screening or selection method, which is typically conducted for research purposes, may be different from the methods suitable for therapeutic purposes. For example, constitutive expression of certain elements (e.g., a Cas nuclease and/or a modulator nucleic acid) may be undesirable for therapeutic purposes due to the potential of increased off-targeting. Conversely, for research purposes, constitutive expression of a Cas nuclease and/or a modulator nucleic acid may be desirable. For example, the constitutive expression provides a large window during which other elements can be introduced. When a stable cell line is established for the constitutive expression, the number of exogenous elements that need to be co-delivered into a single cell is also reduced. Therefore, constitutive expression of certain elements can increase the efficiency and reduce the complexity of a screening or selection process. Inducible expression of certain elements of the system disclosed herein may also be used for research purposes given similar advantages. Expression may be induced by an exogenous agent (e.g., a small molecule) or by an endogenous molecule or complex present in a particular cell type (e.g., at a particular stage of differentiation). Methods known in the art, such as those described in the "CRISPR Expression Systems" subsection supra, can be used for constitutively or inducibly expressing one or more elements.

It is further understood that despite the need to introduce at least three elements—the targeter nucleic acid, the modulator nucleic acid, and the Cas protein—these three elements can be delivered into the cell as a single complex of pre-formed RNP. Therefore, the efficiency of the screening or selection process can also be achieved by pre-assembling a plurality of RNP complexes in a multiplex manner.

In certain embodiments, the method disclosed herein further comprises a step of identifying a targeter nucleic acid, a modulator nucleic acid, a Cas protein, a donor template, or a combination of two or more of these elements from the screening or selection process. A set of barcodes may be used, for example, in the donor template between two homology arms, to facilitate the identification. In specific embodiments, the method further comprises harvesting the population of cells; selectively amplifying a genomic DNA or RNA sample including the target nucleotide sequence(s) and/or the barcodes; and/or sequencing the genomic DNA or RNA sample and/or the barcodes that has been selectively amplified.

In another aspect, the present invention provides a library comprising a plurality of targeter nucleic acids disclosed herein, optionally further comprising one or more modulator nucleic acids disclosed herein. In another aspect, the present invention provides a library comprising a plurality of nucleic acids each comprising a regulatory element operably linked to a different targeter nucleic acid disclosed herein, optionally further comprising a regulatory element operably linked to a modulator nucleic acid disclosed herein. These libraries can be used in combination with one or more Cas proteins or Cas-coding nucleic acids disclosed herein, and/or one or more donor templates as disclosed herein for a screening or selection method.

III. Pharmaceutical Compositions

The present invention provides a composition (e.g., pharmaceutical composition) comprising an engineered, non-naturally occurring system or a eukaryotic cell disclosed herein. In certain embodiments, the composition comprises a complex of the targeter nucleic acid and the modulator nucleic acid. In certain embodiments, the composition comprises an RNP comprising the targeter nucleic acid, the modulator nucleic acid, and a Cas protein (e.g., the Cas nuclease that the targeter nucleic acid and the modulator nucleic acid are capable of activating or a related Cas protein).

In addition, the present invention provides a method of producing a composition, the method comprising incubating the targeter nucleic acid and the modulator nucleic acid of an engineered, non-naturally occurring system disclosed herein under suitable conditions, thereby producing a composition (e.g., pharmaceutical composition) comprising a complex of the targeter nucleic acid and the modulator nucleic acid. In certain embodiments, the method further comprises incubating the targeter nucleic acid and the modulator nucleic acid with a Cas protein (e.g., the Cas nuclease that the targeter nucleic acid and the modulator nucleic acid are capable of activating or a related Cas protein), thereby producing a complex of the targeter nucleic acid, the modulator nucleic acid, and the Cas protein (e.g., an RNP). In certain embodiments, the method further comprises purifying the complex (e.g., the RNP).

For therapeutic use, an engineered, non-naturally occurring system, a CRISPR expression system, or a cell comprising such system or modified by such system disclosed herein is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit-to-risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, PA (1975). Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, a pharmaceutical composition disclosed herein comprises a salt, e.g., NaCl, $MgCl_2$, KCl, $MgSO_4$, etc.; a buffering agent, e.g., a Tris buffer, N-(2-Hydroxyethyl) piperazine-N'-(2-ethanesulfonic acid) (HEPES), 2-(N-Morpholino) ethanesulfonic acid (MES), MES sodium salt, 3-(N-Morpholino) propanesulfonic acid (MOPS), N-tris [Hydroxymethyl] methyl-3-aminopropane-sulfonic acid (TAPS), etc.; a solubilizing agent; a detergent, e.g., a non-ionic detergent such as Tween-20, etc.; a nuclease inhibitor; and the like. For example, in certain embodiments, a subject composition comprises a subject DNA-targeting RNA and a buffer for stabilizing nucleic acids.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (see, Remington's Pharmaceutical Sciences, 18th ed. (Mack Publishing Company, 1990).

In certain embodiments, a pharmaceutical composition may contain nanoparticles, e.g., polymeric nanoparticles, liposomes, or micelles (See Anselmo et al. (2016) BIOENG. TRANSL. MED. 1:10-29). In certain embodiment, the pharmaceutical composition comprises an inorganic nanoparticle. Exemplary inorganic nanoparticles include, e.g., magnetic nanoparticles (e.g., $Fe_3MnO_2$) or silica. The outer surface of the nanoparticle can be conjugated with a positively charged polymer (e.g., polyethylenimine, polylysine, polyserine) which allows for attachment (e.g., conjugation or entrapment) of payload. In certain embodiment, the pharmaceutical composition comprises an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating. In certain embodiment, the pharmaceutical composition comprises a liposome, for example, a liposome disclosed in International Application Publication No. WO 2015/148863.

In certain embodiments, the pharmaceutical composition comprises a targeting moiety to increase target cell binding or update of nanoparticles and liposomes. Exemplary targeting moieties include cell specific antigens, monoclonal antibodies, single chain antibodies, aptamers, polymers, sugars, and cell penetrating peptides. In certain embodiments, the pharmaceutical composition comprises a fusogenic or endosome-destabilizing peptide or polymer.

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-inethacrylate), ethylene vinyl acetate, or poly-D (−)-3-hydroxybutyric acid. Sustained release compositions may also include liposomes that can be prepared by any of several methods known in the art.

A pharmaceutical composition of the invention can be administered by a variety of methods known in the art. The route and/or mode of administration vary depending upon the desired results. Administration can be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., the multispecific antibody of the invention, may be coated in a material to protect the compound from the action of acids and other natural conditions that may inactivate the compound.

Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, CREMOPHOR® ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethelyene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution. In certain embodiments, a multispecific antibody is lyophilized, and then reconstituted in buffered saline, at the time of administration.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the multispecific antibody of the invention is employed in the pharmaceutical compositions of the invention. The multispecific antibodies of the invention are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

IV. Therapeutic Uses

The engineered, non-naturally occurring system and CRISPR expression system disclosed herein are useful for targeting, editing, and/or modifying the genomic DNA in a cell or organism. These systems, as well as a cell comprising one of the systems or a cell whose genome has been modified by the engineered, non-naturally occurring system, can be used to treat a disease or disorder in which modification of genetic or epigenetic information is desirable. Accordingly, in another aspect, the present invention provides a method of treating a disease or disorder, the method comprising administering to a subject in need thereof a non-naturally occurring system, a CRISPR expression system, or a cell disclosed herein.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "treatment", "treating", "treat", "treated", and the like, as used herein, refer to obtaining a desired pharmacologic and/or physiologic effect. The effect may be therapeutic in terms of a partial or complete cure for a disease and/or adverse effect attributable to the disease or delaying the disease progression. "Treatment", as used herein, covers any treatment of a disease in a mammal, e.g., in a human, and includes: (a) inhibiting the disease, i.e., arresting its development; and (b) relieving the disease, i.e., causing regression of the disease. It is understood that a disease or disorder may be identified by genetic methods and treated prior to manifestation of any medical symptom.

For therapeutic purposes, the method disclosed herein is particularly suitable for editing or modifying a proliferating cell, such as a stem cell (e.g., a hematopoietic stem cell), a progenitor cell (e.g., a hematopoietic progenitor cell or a lymphoid progenitor cell), or a memory cell (e.g., a memory T cell). Given that such cell is delivered to a subject and will proliferate in vivo, tolerance to off-target events is low. Prior to delivery, however, it is possible to assess the on-target and off-target events, thereby selecting one or more colonies that have the desired edit or modification and lack any undesired edit or modification. Therefore, lower editing or modifying efficiency can be tolerated for such cell. The engineered, non-naturally occurring system of the present invention has the advantage of increasing or decreasing the efficiency of nucleic acid cleavage by, for example, adjusting the hybridization of dual guide nucleic acids. As a result, it can be used to minimize off-target events when creating genetically engineered proliferating cells.

For minimization of toxicity and off-target effect, it is important to control the concentration of the dual guide CRISPR-Cas system delivered. Optimal concentrations can be determined by testing different concentrations in a cellular, tissue, or non-human eukaryote animal model and using deep sequencing to analyze the extent of modification at potential off-target genomic loci. The concentration that gives the highest level of on-target modification while minimizing the level of off-target modification should be selected for ex vivo or in vivo delivery.

Gene Therapies

It is understood that the engineered, non-naturally occurring system and CRISPR expression system disclosed herein can be used to treat a genetic disease or disorder, i.e., a disease or disorder associated with or otherwise mediated by an undesirable mutation in the genome of a subject.

Exemplary genetic diseases or disorders include age-related macular degeneration, adrenoleukodystrophy (ALD), Alagille syndrome, alpha-1-antitrypsin deficiency, argininemia, argininosuccinic aciduria, ataxia (e.g., Friedreich ataxia, spinocerebellar ataxias, ataxia telangiectasia, essential tremor, spastic paraplegia), autism, biliary atresia, biotinidase deficiency, carbamoyl phosphate synthetase I deficiency, carbohydrate deficient glycoprotein syndrome (CDGS), a central nervous system (CNS)-related disorder (e.g., Alzheimer's disease, amyotrophic lateral sclerosis (ALS), canavan disease (CD), ischemia, multiple sclerosis (MS), neuropathic pain, Parkinson's disease), Bloom's syndrome, cancer, Charcot-Marie-Tooth disease (e.g., peroneal muscular atrophy, hereditary motor sensory neuropathy), congenital hepatic porphyria, citrullinemia, Crigler-Najjar syndrome, cystic fibrosis (CF), Dentatorubro-Pallidoluysian Atrophy (DRPLA). diabetes insipidus, Fabry, familial hypercholesterolemia (LDL receptor defect), Fanconi's anemia, fragile X syndrome, a fatty acid oxidation disorder, galactosemia, glucose-6-phosphate dehydrogenase (G6PD), glycogen storage diseases (e.g., type I (glucose-6-phosphatase deficiency, Von Gierke II (alpha glucosidase deficiency, Pompe), III (debrancher enzyme deficiency, Cori), IV (brancher enzyme deficiency, Anderson), V (muscle glycogen phosphorylase deficiency, McArdle), VII (muscle phosphofructokinase deficiency, Tauri), VI (liver phosphorylase deficiency, Hers), IX (liver glycogen phosphorylase kinase deficiency)), hemophilia A (associated with defective factor VIII), hemophilia B (associated with defective factor IX), Huntington's disease, glutaric aciduria, hypophosphatemia, Krabbe, lactic acidosis, Lafora disease, Leber's Congenital Amaurosis, Lesch Nyhan syndrome, a lysosomal storage disease, metachromatic leukodystrophy disease (MLD), mucopolysaccharidosis (MPS) (e.g., Hunter syndrome, Hurler syndrome, Maroteaux-Lamy syndrome, Sanfilippo syndrome, Scheie syndrome, Morquio syndrome, other, MPSI, MPSIII, MSIV, MPS 7), a muscular/skeletal disorder (e.g., muscular dystrophy, Duchenne muscular dystrophy), myotonic Dystrophy (DM), neoplasia, N-acetylglutamate synthase deficiency, ornithine transcarbamylase deficiency, phenylketonuria, primary open angle glaucoma, retinitis pigmentosa, schizophrenia, Severe Combined Immune Deficiency (SCID), Spinobulbar Muscular Atrophy (SBMA), sickle cell anemia, Usher syndrome, Tay-Sachs disease, thalassemia (e.g., β-Thalassemia), trinucleotide repeat disorders, tyrosinemia, Wilson's disease, Wiskott-Aldrich syndrome, X-linked chronic granulomatous disease (CGD), X-linked severe combined immune deficiency, and xeroderma pigmentosum.

Additional exemplary genetic diseases or disorders and associated information are available on the world wide web at kumc.edu/gec/support, genome.gov/10001200, and ncbi.nlm.nih.gov/books/NBK22183/. Additional exemplary genetic diseases or disorders, associated genetic mutations, and gene therapy approaches to treat genetic diseases or disorders are described in International (PCT) Publication Nos. WO2013/126794, WO2013/163628, WO2015/048577, WO2015/070083, WO2015/089354, WO2015/134812, WO2015/138510, WO2015/148670, WO2015/148860, WO2015/148863, WO2015/153780, WO2015/153789, and WO2015/153791, and U.S. Patent Publication Nos. 2009/0222937, 2009/0271881, 2009/0271881, 2010/0229252, 2010/0311124, 2011/0016540, 2011/0023139, 2011/0023144, 2011/0023145, 2011/0023145, 2011/0023146, 2011/0023153, 2011/0091441, 2011/0158957, 2011/0182867, 2011/0225664, 2012/0159653, 2012/0328580, 2013/0145487, and 2013/0202678.

Immune Cell Engineering

It is understood that the engineered, non-naturally occurring system and CRISPR expression system disclosed herein can be used to engineer an immune cell. Immune cells include but are not limited to lymphocytes (e.g., B lymphocytes or B cells, T lymphocytes or T cells, and natural killer cells), myeloid cells (e.g., monocytes, macrophages, eosinophils, mast cells, basophils, and granulocytes), and the stem and progenitor cells that can differentiate into these cell types (e.g., hematopoietic stem cells, hematopoietic progenitor cells, and lymphoid progenitor cells). The cells can include autologous cells derived from a subject to be treated, or alternatively allogenic cells derived from a donor.

In certain embodiments, the immune cell is a T cell, which can be, for example, a cultured T cell, a primary T cell, a T cell from a cultured T cell line (e.g., Jurkat, SupTi), or a T cell obtained from a mammal, for example, from a subject to be treated. If obtained from a mammal, the T cell can be obtained from numerous sources, including but not limited to blood, bone marrow, lymph node, the thymus, or other tissues or fluids. T cells can also be enriched or purified. The T cell can be any type of T cell and can be of any developmental stage, including but not limited to, $CD4^+/CD8^+$ double positive T cells, $CD4^+$ helper T cells (e.g., Th1 and Th2 cells), $CD8^+$ T cells (e.g., cytotoxic T cells), tumor infiltrating lymphocytes (TILs), memory T cells (e.g., central memory T cells and effector memory T cells), regulatory T cells, naive T cells, and the like.

In certain embodiments, an immune cell, e.g., a T cell, is engineered to express an exogenous gene. For example, in certain embodiments, an engineered CRISPR system disclosed herein may be used to engineer an immune cell to express an exogenous gene. For example, in certain embodiments, an engineered CRISPR system disclosed herein may catalyze DNA cleavage at a gene locus, allowing for site-specific integration of the exogenous gene at the gene locus by HDR.

In certain embodiments, an immune cell, e.g., a T cell, is engineered to express a chimeric antigen receptor (CAR), i.e., the T cell comprises an exogenous nucleotide sequence encoding a CAR. As used herein, the term "chimeric antigen receptor" or "CAR" refers to any artificial receptor including an antigen-specific binding moiety and one or more signaling chains derived from an immune receptor. CARs can comprise a single chain fragment variable (scFv) of an antibody specific for an antigen coupled via hinge and transmembrane regions to cytoplasmic domains of T cell signaling molecules, e.g. a T cell costimulatory domain (e.g., from CD28, CD137, OX40, ICOS, or CD27) in tandem with a T cell triggering domain (e.g. from CD32). A T cell expressing a chimeric antigen receptor is referred to as a CAR T cell. Exemplary CAR T cells include CD19 targeted CTL019 cells (see, Grupp et al. (2015) BLOOD, 126:4983), 19-28z cells (see, Park et al. (2015) J. CLIN. ONCOL., 33:7010), and KTE-C19 cells (see, Locke et al. (2015) BLOOD, 126:3991). Additional exemplary CAR T cells are described in U.S. Pat. Nos. 8,399,645, 8,906,682, 7,446,190, 9,181,527, 9,272,002, and 9,266,960, U.S. Patent Publication Nos. 2016/0362472, 2016/0200824, and 2016/0311917, and International (PCT) Publication Nos. WO2013/142034, WO2015/120180, WO2015/188141, WO2016/120220, and WO2017/040945. Exemplary approaches to express CARs using CRISPR systems are described in Hale et al. (2017) MOL THER METHODS CLIN DEV., 4:192, MacLeod et al. (2017) MOL THER, 25:949, and Eyquem et al. (2017) NATURE, 543:113.

In certain embodiments, an immune cell, e.g., a T cell, binds an antigen, e.g., a cancer antigen, through an endogenous T cell receptor (TCR). In certain embodiments, an immune cell, e.g., a T cell, is engineered to express an exogenous TCR, e.g., an exogenous naturally occurring TCR or an exogenous engineered TCR. T cell receptors comprise two chains referred to as the a-and-chains, that combine on the surface of a T cell to form a heterodimeric receptor that can recognize MHC-restricted antigens. Each of α- and β-chain comprises a constant region and a variable region. Each variable region of the α- and β-chains defines three loops, referred to as complementary determining regions (CDRs) known as CDR1, CDR2, and CDR3 that confer the T cell receptor with antigen binding activity and binding specificity.

In certain embodiments, a CAR or TCR binds a cancer antigen selected from B-cell maturation antigen (BCMA), mesothelin, prostate specific membrane antigen (PSMA), prostate stem cell antigen (PCSA), carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD70, CD74, CD123, CD133, CD138, epithelial glycoprotein2 (EGP 2), epithelial glycoprotein-40 (EGP-40), epithelial cell adhesion molecule (EpCAM), receptor-type tyrosine-protein kinase (FLT3), folate-binding protein (FBP), fetal acetylcholine receptor (AChR), folate receptor-a and β (FRa and β), Ganglioside G2 (GD2), Ganglioside G3 (GD3), epidermal growth factor receptor 2 (HER-2/ERB2), epidermal growth factor receptor vIII (EGFRvIII), ERB3, ERB4, human telom erase reverse transcriptase (hTERT), Interleukin-13 receptor subunit alpha-2 (IL-13Ra2), K-light chain, kinase insert domain receptor (KDR), Lewis A (CA19.9), Lewis Y (LeY), LI cell adhesion molecule (LICAM), melanoma-associated antigen 1 (melanoma antigen family Al, MAGE-A1), Mucin 16 (MUC-16), Mucin 1 (MUC-1; e.g., a truncated MUC-1), KG2D ligands, cancer-testis antigen NY-ESO-1, oncofetal antigen (h5T4), tumor-associated glycoprotein 72 (TAG-72), vascular endothelial growth factor R2 (VEGF-R2), Wilms tumor protein (WT-1), type 1 tyrosine-protein kinase transmembrane receptor (ROR1), B7-H3 (CD276), B7-H6 (Nkp30), Chondroitin sulfate proteoglycan-4 (CSPG4), DNAX Accessory Molecule (DNAM-1), Ephrin type A Receptor 2 (EpHA2), Fibroblast Associated Protein (FAP), Gpl00/HLA-A2, Glypican 3 (GPC3), HA-IH, HERK-V, IL-1 IRa, Latent Membrane Protein 1 (LMP1), Neural cell-adhesion molecule (N-CAM/CD56), and Trail Receptor (TRAIL-R).

Genetic loci suitable for insertion of a CAR- or exogenous TCR-encoding sequence include but are not limited to safe harbor loci (e.g., the AAVS1 locus), TCR subunit loci (e.g., the TCRα constant (TRAC) locus), and other loci associated with certain advantages (e.g., the CCR5 locus, the inactivation of which may prevent or reduce HIV infection). It is understood that insertion in the TRAC locus reduces tonic CAR signaling and enhances T cell potency (see, Eyquem et al. (2017) NATURE, 543:113). Furthermore, inactivation of the endogenous TRAC gene may reduce a graft-versus-host disease (GVHD) response, thereby allowing use of allogeneic T cells as starting materials for preparation of CAR-T cells. Accordingly, in certain embodiments, an immune cell, e.g., a T cell, is engineered to have reduced expression of an endogenous TCR or TCR subunit, e.g., TCRα subunit constant (TRAC). The cell may be engineered to have partially reduced or no expression of the endogenous TCR or TCR subunit. For example, in certain embodiments, the immune cell, e.g., a T cell, is engineered to have less than 80% (e.g., less than 70%, less than 60%, less than 50%, less than 40%, less than 30%, less than 20%, less than 10%, or less than 5%) of the expression of the endogenous TCR or TCR subunit relative to a corresponding unmodified or parental cell. In certain embodiments, the immune cell, e.g., a T cell, is engineered to have no detectable expression of the endogenous TCR or TCR subunit. Exemplary approaches to reduce expression of TCRs using CRISPR systems are described in U.S. Pat. No. 9,181,527, Liu et al. (2017) CELL RES, 27:154, Ren et al. (2017) CLIN CANCER RES, 23:2255, Cooper et al. (2018) LEUKEMIA, 32:1970, and Ren et al. (2017) ONCOTARGET, 8:17002.

It is understood that certain immune cells, such as T cells, also express major histocompatibility complex (MHC) or human leukocyte antigen (HLA) genes, and inactivation of these endogenous gene may reduce a GVHD response, thereby allowing use of allogeneic T cells as starting materials for preparation of CAR-T cells. Accordingly, in certain embodiments, an immune cell, e.g., a T-cell, is engineered to have reduced expression of one or more endogenous class I or class II MHCs or HLAs (e.g., beta 2-microglobulin (B2M), class II major histocompatibility complex transactivator (CIITA), HLA-E, and/or HLA-G). The cell may be engineered to have partially reduced or no expression of an endogenous MHC or HLA. For example, in certain embodiments, the immune cell, e.g., a T-cell, is engineered to have less than less than 80% (e.g., less than 70%, less than 60%, less than 50%, less than 40%, less than 30%, less than 20%, less than 10%, or less than 5%) of the expression of endogenous MHC (e.g., B2M, CIITA, HLA-E, or HLA-G) relative to a corresponding unmodified or parental cell. In certain embodiments, the immune cell, e.g., a T cell, is engineered to have no detectable expression of an endogenous MHC (e.g., B2M, CIITA, HLA-E, or HLA-G). Exemplary approaches to reduce expression of MHCs using CRISPR systems are described in Liu et al. (2017) CELL RES, 27:154, Ren et al. (2017) CLIN CANCER RES, 23:2255, and Ren et al. (2017) ONCOTARGET, 8:17002.

Other genes that may be inactivated to reduce a GVHD response include but are not limited to CD3, CD52, and deoxycytidine kinase (DCK). For example, inactivation of CK may render the immune cells (e.g., T cells) resistant to purine nucleotide analogue (PNA) compounds, which are often used to compromise the host immune system in order to reduce a GVHD response during an immune cell therapy.

In certain embodiments, an immune cell, e.g., a T cell, is engineered to have reduced expression of an endogenous gene. For example, in certain embodiments, an engineered CRISPR system disclosed herein may be used to engineer an immune cell to have reduced expression of an endogenous gene. For example, in certain embodiments, an engineered CRISPR system disclosed herein may result in DNA cleavage at a gene locus, thereby inactivating the targeted gene. In other embodiments, an engineered CRISPR system disclosed herein may be fused to an effector domain (e.g., a transcriptional repressor or histone methylase) to reduce the expression of the target gene.

It is understood that the activity of an immune cell (e.g., T cell) may be enhanced by inactivating or reducing the expression of an immune suppressor such as an immune checkpoint protein. Accordingly, in certain embodiments, an immune cell, e.g., a T cell, is engineered to have reduced expression of an immune checkpoint protein. Exemplary immune checkpoint proteins expressed by wild-type T cells include but are not limited to PD-1, CTLA-4, A2AR, B7-H3, B7-H4, BTLA, KIR, LAG3, TIM-3, TIGIT, VISTA, PTPN6 (SHP-1), and FAS. The cell may be modified to have partially reduced or no expression of the immune checkpoint protein. For example, in certain embodiments, the immune cell, e.g., a T cell, is engineered to have less than 80% (e.g., less than 70%, less than 60%, less than 50%, less than 40%, less than 30%, less than 20%, less than 10%, or less than 5%) of the expression of the immune checkpoint protein relative to a corresponding unmodified or parental cell. In certain embodiments, the immune cell, e.g., a T cell, is engineered to have no detectable expression of the immune checkpoint protein. Exemplary approaches to reduce expression of immune checkpoint proteins using CRISPR systems are described in International (PCT) Publication No. WO2017/017184, Cooper et al. (2018) LEUKEMIA, 32:1970, Su et al. (2016) ONCOIMMUNOLOGY, 6: e1249558, and Zhang et al. (2017) FRONT MED, 11:554.

In certain embodiments, an immune cell, e.g., a T cell, is modified to express a dominant-negative form of an immune checkpoint protein. In certain embodiments, the dominant-negative form of the checkpoint inhibitor can act as a decoy receptor to bind or otherwise sequester the natural ligand that would otherwise bind and activate the wild-type immune checkpoint protein. Examples of engineered immune cells, for example, T cells containing dominant-negative forms of an immune suppressor are described, for example, in International (PCT) Publication No. WO2017/040945.

In certain embodiments, an immune cell, e.g., a T cell, is modified to express a gene (e.g., a transcription factor, a cytokine, or an enzyme) that regulates the survival, proliferation, activity, or differentiation (e.g., into a memory cell) of the immune cell. In certain embodiments, the immune cell is modified to express TET2, FOXO1, IL-12, IL-15, IL-18, IL-21, IL-7, GLUT1, GLUT3, HK1, HK2, GAPDH, LDHA, PDK1, PKM2, PFKFB3, PGK1, ENO1, GYS1, and/or ALDOA. In certain embodiments, the modification is an insertion of a nucleotide sequence encoding the protein operably linked to a regulatory element. In certain embodiments, the modification is a substitution of a single nucleotide polymorphism (SNP) site in the endogenous gene.

In certain embodiments, an immune cell, e.g., a T cell, is modified to express a protein (e.g., a cytokine or an enzyme) that regulates the microenvironment that the immune cell is designed to migrate to (e.g., a tumor microenvironment). In certain embodiments, the immune cell is modified to express CA9, CA12, a V-ATPase subunit, NHE1, and/or MCT-1.

V. Kits

It is understood that the engineered, non-naturally occurring system, the CRISPR expression system, and the library disclosed herein can be packaged in a kit suitable for use by a medical provider. Accordingly, in another aspect, the invention provides kits containing any one or more of the elements disclosed in the above systems, libraries, methods, and compositions. In certain embodiments, the kit comprises an engineered, non-naturally occurring system as disclosed herein and instructions for using the kit. The instructions may be specific to the applications and methods described herein. In certain embodiments, one or more of the elements of the system are provided in a solution. In certain embodiments, one or more of the elements of the system are provided in lyophilized form, and the kit further comprises a diluent. Elements may be provided individually or in combinations, and may be provided in any suitable container, such as a vial, a bottle, a tube, or immobilized on the surface of a solid base (e.g., chip or microarray). In certain embodiments, the kit comprises one or more of the nucleic acids and/or proteins described herein. In certain embodiments, the kit provides all elements of the systems of the invention.

In certain embodiments of a kit comprising the engineered, non-naturally occurring system, the targeter nucleic acid and the modulator nucleic acid are provided in separate containers. In other embodiments, the targeter nucleic acid and the modulator nucleic acid are pre-complexed, and the complex is provided in a single container. In certain embodiments, the kit comprises a Cas protein or a nucleic acid comprising a regulatory element operably linked to a nucleic acid encoding a Cas protein provided in a separate container. In other embodiments, the kit comprises a Cas protein pre-complexed with the targeter nucleic acid and the modulator nucleic acid, and the complex is provided in a single container.

In order to target multiple target nucleotide sequences, e.g., for use in a screening or selection process, a kit may be provided comprising multiple targeter nucleic acids. Accordingly, in certain embodiments, the kit comprises a plurality of targeter nucleic acids as disclosed herein (e.g., in separate tubes or immobilized on the surface of a solid base such as a chip or a microarray), optionally one or more modulator nucleic acids as disclosed herein, and optionally a Cas protein or a regulatory element operably linked to a nucleic acid encoding a Cas protein as disclosed herein. Such kits are useful for identifying a targeter nucleic acid with the highest efficiency and/or specificity to target a given gene, for identifying a gene implicated in a physiological or pathological pathway, or for engineering a cell to achieve desired functionality in a multiplex assay. In certain embodiments, the kit further comprises one or more donor templates provided in one or more separate containers. In certain embodiments, the kit comprises a plurality of donor templates as disclosed herein (e.g., in separate tubes or immobilized on the surface of a solid base such as a chip or a microarray), one or more targeter nucleic acids disclosed herein, and one or more modulator nucleic acids as disclosed herein, and optionally a Cas protein or a regulatory element operably linked to a nucleic acid encoding a Cas protein as disclosed herein. Such kits are useful for identifying a donor template that introduces optimal genetic modification in a multiplex assay. The CRISPR expression systems as disclosed herein are also suitable for use in a kit.

In certain embodiments, a kit further comprises one or more reagents and/or buffers for use in a process utilizing one or more of the elements described herein. Reagents may be provided in any suitable container and may be provided in a form that is usable in a particular assay, or in a form that requires addition of one or more other components before use (e.g., in concentrate or lyophilized form). A buffer may be a reaction or storage buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In certain embodiments, the buffer has a pH from about 7 to about 10. In certain embodiments, the kit further comprises a pharmaceutically acceptable carrier. In certain embodiments, the kit further comprises one or more devices or other materials for administration to a subject.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The terms "a" and "an" and "the" and similar references in the context of describing the invention (especially in the context of the following claims) are to be construed to cover both the singular and the plural, unless otherwise indicated herein or clearly contradicted by context. For example, the term "a cell" includes a plurality of cells, including mixtures thereof. Where the plural form is used for compounds, salts, and the like, this is taken to mean also a single compound, salt, or the like.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1. In Vitro Cleavage of Target DNA by Dual Guide MAD7 CRISPR-Cas Systems MAD7 is a type V-A Cas protein that has endonuclease activity when complexed with a single guide RNA, also known as a crRNA in a type V-A system (see, U.S. Pat. No. 9,982,279). This example describes cleavage of target DNA using MAD7 in complex with dual guide nucleic acids in an in vitro cleavage assay.

Briefly, two different crRNAs, named crRNA1 and crRNA2, were designed to target the DNMT1 gene. In particular, crRNA2 has been reported to have better ability to activate LbCas12a and FnoCas12a in zebrafish (see, Liu et al. (2019) NUC. ACIDS RES. 47 (8): 4169-80). Predicted secondary structures of crRNA1 and crRNA2 are shown in FIG. 2A. Also designed were a set of targeter and modulator RNAs corresponding to crRNA1, named crRNA1_targeter1 and crRNA1_modulator1, respectively, and a set of targeter and modulator RNAs corresponding to crRNA2, named crRNA2_targeter1 and crRNA2_modulator1, respectively. Each set of dual guide RNAs represents split of the corresponding single guide RNA at the middle position of the loop region. The nucleotide sequences of these guide RNAs are provided in Table 2.

TABLE 2

Nucleotide Sequences of Tested Single and Dual Guide RNAs

| Guide RNA | Nucleotide Sequence | SEQ ID NO |
|---|---|---|
| crRNA1 | UAAUUUCUACUCUUGUAGAUCUGAUGGU CCAUGUCUGUUA | 41 |
| crRNA1_ modulator1 | UAAUUUCUACUC | 42 |

TABLE 2-continued

Nucleotide Sequences of Tested Single and Dual Guide RNAs

| Guide RNA | Nucleotide Sequence | SEQ ID NO |
|---|---|---|
| crRNA1_targeter1 | UUGUAGAUCUGAUGGUCCAUGUCUGUUA | 43 |
| crRNA2 | UAAUUCCCACUCUUGUGGGUCUGAUGGUCCAUGUCUGUUA | 44 |
| crRNA2_modulator1 | UAAUUCCCACUC | 45 |
| crRNA2_targeter1 | UUGUGGGUCUGAUGGUCCAUGUCUGUUA | 46 |

These guide RNAs were chemically synthesized. Human DNMT1 target DNA was prepared by PCR and contained the nucleotide sequence of 5'-CGAGAGAGT-GCCTCAGGTATGGTGGGGTGGGCCAGGCTTCCTC-TGGGGCCTGACTG CCCTCTGGGGGTACATGTGG-GGGCAGTTGCTGGCCACCGTTTTGGGCTCT-GGGACTC AGGCGGGTCACCTACCCACGTTCGT-GGCCCCATCTTTCTCAAGGGGCTGCTGTGAGG ATT-GAGTGAGTTGCACGTGTCAAGTGCTTAGAGCA-GGCGTGCTGCACACAGCAGGC CTTTGGTCAGG-TTGGCTGCTGGGCTGGCCCTGGGGCCGTTTCCCT-CACTCCTGCTCGG TGAATTTGGCTCAGCAGGCA-CCTGCCTCAGCTGCTCACTTGAGCCTCTGGGT-CTAGA ACCCTCTGGGGACCGTTTGAGGAGTGTTC-AGTCTCCGTGAACGTTCCCTTAGCACTC TGCCACT-TATTGGGTCAGCTGTTAACATCAGTACGTTAATG-TTTCCTGATGGTCCATG TCTGTTACTCGCCTGT-CAAGTGGCGTGACACCGGGCGTGTTCCCCAGAG-TGACTTTT CCTTTTATTTCCCTTCAGCTAAAATAAA-GGAGGAGGAAGCTGCTAAGGACTAGTTCT GCCCTCCCGTCACCCCTGTTTCTGGCACCAG-GAATCCCCAACATGCACTGATGTTGT GTTTTTAA-CATGTCAATCTGTCCGTTCACATGTGTGGTA-CATGGTGTTTGTGGCC-3' (SEQ ID NO: 40). MAD7 protein, which contained a nucleoplasmin NLS at the C-terminus, was expressed in E. Coli and purified by fast protein liquid chromatography (FPLC).

The single guide and dual guide CRISPR-Cas systems were tested in an in vitro cleavage assay. Briefly, 1 µM MAD7 protein was incubated for 10 minutes at room temperature with 1 µM crRNA1, 1 µM crRNA1_modulator1, 1 µM crRNA1_targeter1, a combination of 1 UM crRNA1_modulator1 and 1 µM crRNA1_targeter1, 1 µM crRNA2, 1 µM crRNA2_modulator1, 1 µM crRNA2_targeter1, or a combination of 1 µM crRNA2_modulator1 and 1 µM crRNA2_targeter1 to form an RNP complex. Then DNMT1 target DNA was added into the solution at a 10:1 or 1:1 molar ratio of MAD7 to target DNA. After a 10-minute incubation at 37° C., the samples were analyzed by electrophoresis in an agarose gel.

Figure 2B:
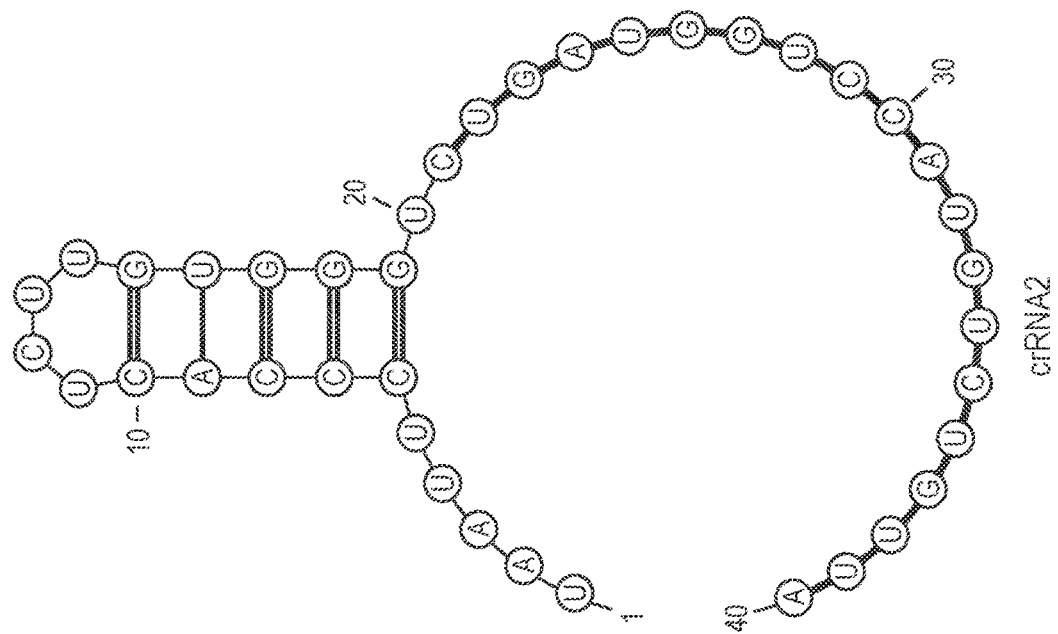
FIG. 2B is a schematic representation showing the predicted secondary structure of a second crRNA tested in an in vitro cleavage experiment (SEQ ID NO: 44).
Figure 2A:
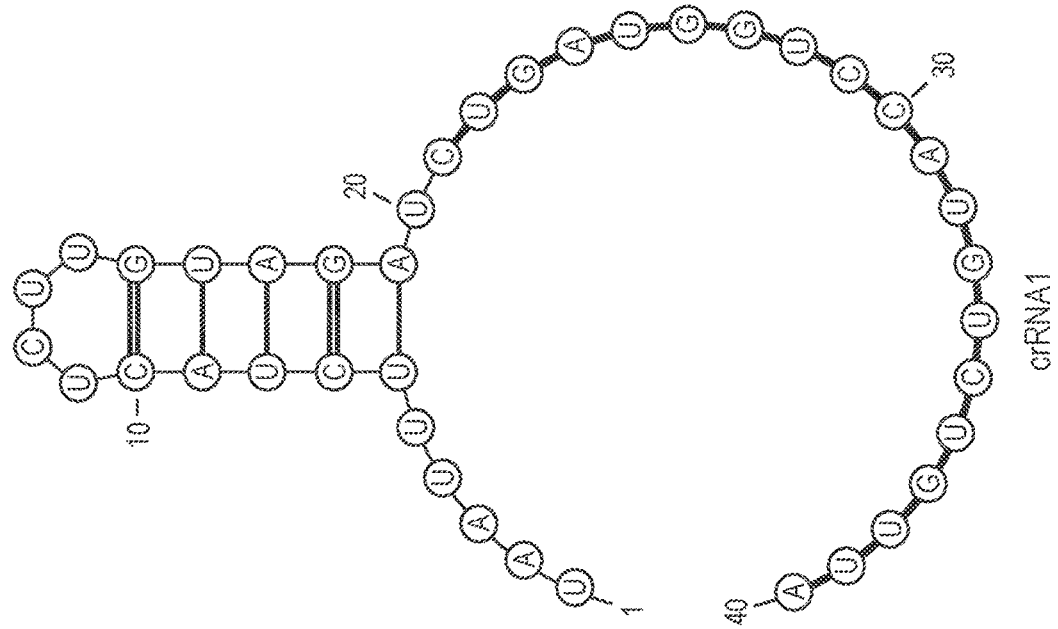
FIG. 2A is a schematic representation showing the predicted secondary structure of a first crRNA tested in an in vitro cleavage experiment (SEQ ID NO: 41).
Figure 2C:
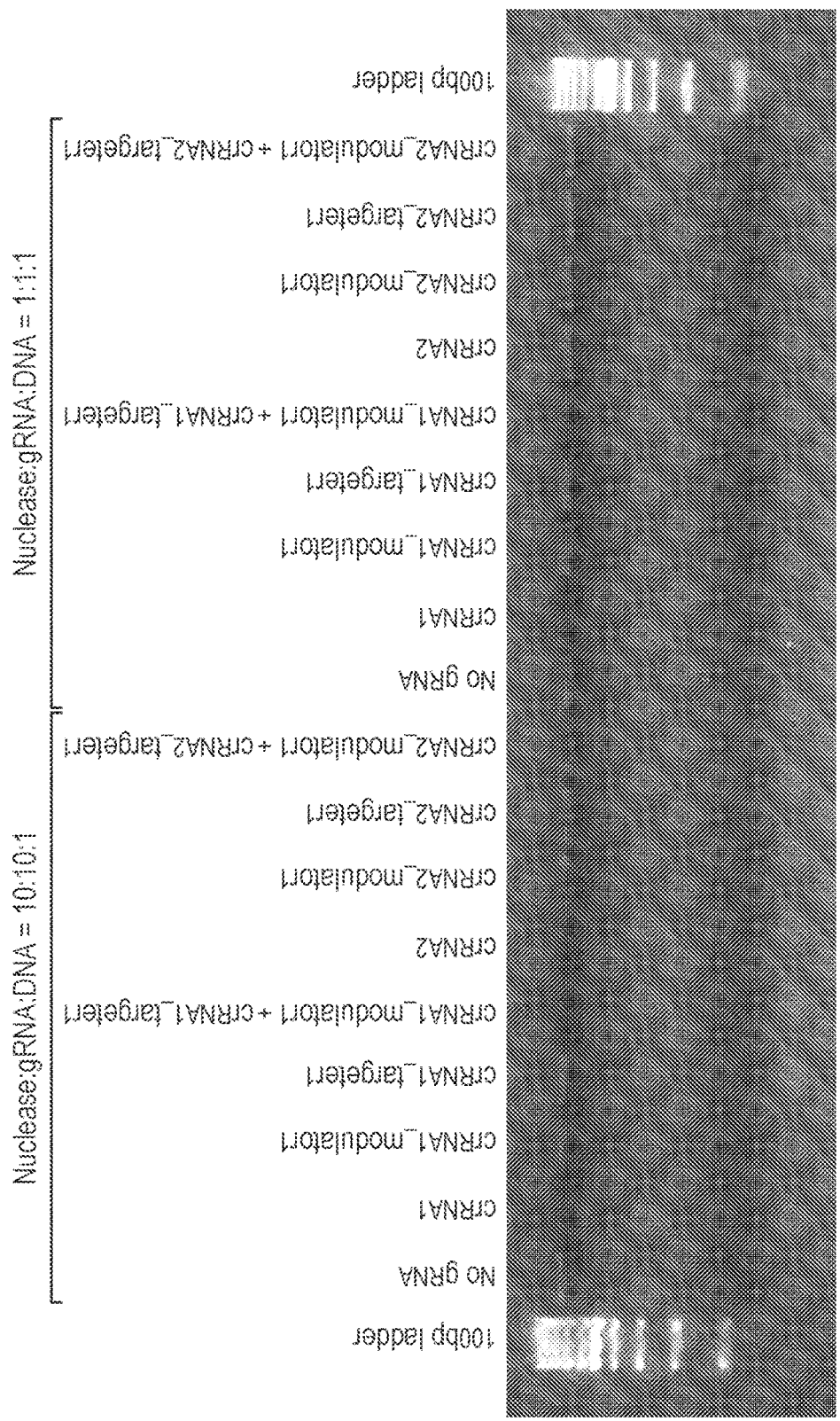
FIG. 2C is a photograph showing gel electrophoresis results from an in vitro cleavage experiment using MAD7 complexed with two different crRNAs, referred to as "crRNA1" and "crRNA2," and their corresponding sets of targeter RNAs and modulator RNAs that were chemically transcribed.

As shown in FIG. 2B, crRNA1, crRNA2, and their corresponding sets of dual guide RNAs activated the nuclease activity of MAD7 to cleave the DNMT1 target DNA. By contrast, crRNA1_modulator1, crRNA1_targeter1, crRNA2_modulator1, or crRNA2_targeter1 alone did not exhibit such activity. The ability of crRNA1 to activate MAD7 nuclease under these conditions was greater than that of crRNA2. For each of crRNA1 and crRNA2, the ability of the single guide RNA to activate MAD7 nuclease was greater than that of the corresponding dual guide system.

Extension of Modulator RNAs at the 5' End

Next assessed was whether the CRISPR-Cas system could tolerate the addition of a nucleotide sequence at the 5' end of the crRNAs or modulator RNAs. Two crRNA sequences, named crRNA3 and crRNA4, were designed to contain additional nucleotide sequences at the 5' end of crRNA1. The corresponding dual guide systems included modulator RNAs, named crRNA3_modulator1 and crRNA4_modulator1, paired with crRNA1_targeter1 as the targeter RNA. The sequences of these newly designed guide RNAs are provided in Table 3. The additional nucleotide sequences at the 5' end of the RNAs are underlined.

TABLE 3

Nucleotide Sequences of Tested crRNAs and Modulator RNAs

| Guide RNA | Nucleotide Sequence | SEQ ID NO |
|---|---|---|
| crRNA3 | UCCCAUAGAUGAUAAUUUCUACUCUUGUAGAUCUGAUGGUCCAUGUCUGUUA | 47 |
| crRNA3_modulator1 | UCCCAUAGAUGAUAAUUUCUACUC | 48 |
| crRNA4 | UCCCAUAGAUGACCGCACUCAUAGUAAUUUCUACUCUUGUAGAUCUGAUGGUCCAUGUCUGUUA | 49 |
| crRNA4_modulator1 | UCCCAUAGAUGACCGCACUCAUAGUAAUUUCUACUC | 50 |

These guide RNAs were chemically synthesized. An in vitro cleavage assay was conducted using the method described above. Each guide RNA was used at the concentration of 1 µM when incubated with MAD7 to form an RNP. The molar ratio of MAD7 and target DNA was 10:1.

Figure 3:
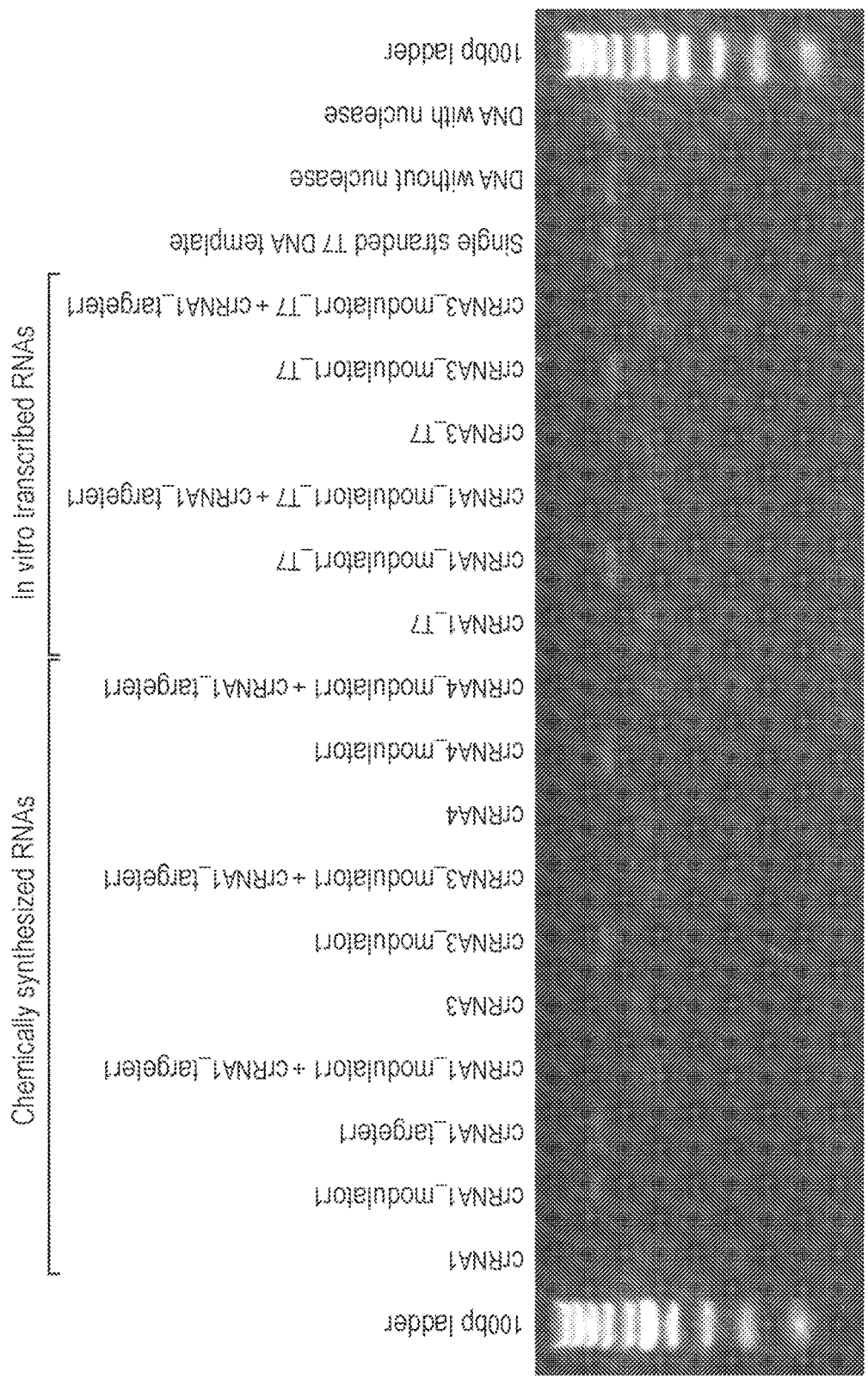
FIG. 3 is a photograph showing gel electrophoresis results from an in vitro cleavage experiment using MAD7 complexed with three different crRNAs, referred to as "crRNA1," "crRNA3," and "crRNA4," and their corresponding sets of targeter RNA and modulator RNAs, either chemically synthesized or produced by in vitro transcription.

As shown in FIG. 3, crRNA1, crRNA3, and crRNA4 all activated the nuclease activity of MAD7 to cleave the DNMT1 target DNA. Moreover, each of crRNA1_modulator1, crRNA3_modulator1, and crRNA4_modulator1, in combination with crRNA1_targeter1, activated MAD7 nuclease. By contrast, none of the targeter or modulator RNAs alone exhibited such activity. Therefore, under these conditions, the additional nucleotide sequences at the 5' end of a crRNA or a modulator RNA did not appear to have any negative impact on the ability of the guide RNA to activate MAD7 nuclease.

In Vitro Transcribed Modulator RNAs

Next assessed was the activity of in vitro transcribed RNAs in a single guide or dual guide CRISPR-Cas system. Briefly, crRNA1 and crRNA3 were transcribed in vitro from chemically synthesized double-stranded template DNAs using the MegaScript kit (Ambion). The template DNAs contained a T7 promoter, which had the nucleotide sequence of GCAGCTAATACGACTCACTATAGG (SEQ ID NO: 51), immediately upstream of the sequence encoding the RNA of interest. As a result, the in vitro transcribed RNAs, named crRNA1_T7 and crRNA3_T7, contained the nucleotide sequence of GG at the 5' end of the transcribed RNA. The RNAs were purified with the Oligo Clean and Concentration kit (Zymogen) and quantified on a Nanodrop. The quality of the in vitro transcribed RNAs was assessed on an agarose gel.

To generate corresponding dual guide systems, template DNAs containing a T7 promoter immediately upstream of a sequence encoding crRNA1_modulator1 or crRNA3 modulator1 were in vitro transcribed. The resulting RNAs, named crRNA1_modulator1_T7 and crRNA3_modulator1_T7, each contained the nucleotide sequence of GG at the 5' end of the transcribed RNA. The RNA samples were purified, and their quantity and quality were assessed as described above. These in vitro transcribed modulator RNAs were used in combination with chemically synthesized crRNA1_targeter1.

The in vitro transcribed RNAs were tested in an in vitro cleavage assay using the method described above. Each guide RNA was used at the concentration of 1 µM when incubated with MAD7 to form an RNP. The molar ratio of MAD7 and target DNA was 10:1.

As shown in FIG. 3, crRNA1_T7 and crRNA3_T7 retained the ability to activate MAD7 nuclease. Similarly, the combinations of (1) crRNA1_modulator1_T7 and crRNA1_targeter1 and (2) crRNA3_modulator1_T7 and crRNA1_targeter1 retained their ability to activate MAD7 nuclease. Therefore, under these conditions, the in vitro transcribed crRNAs and modulator RNAs, despite containing additional nucleotide sequences at the 5' end, were suitable for use in the single and dual guide CRISPR-Cas systems, respectively.

"Loop" Termini of Modulator and Targeter RNAs

The dual guide RNAs described above were designed by splitting single guide RNAs at the middle position of the crRNA loop. Next assessed were variants of the dual guide RNA systems in which a single guide RNA was split at different positions in the loop. As shown in FIGS. 4A-4F, crRNA1 (also called RNA #1 herein) was split at different positions in the loop to generate modulator RNAs named RNAs #2, #4, #6, #8, and #10, and targeter RNAs named RNAs #3, #5, #7, #9, and #11. The nucleotide sequences of these guide RNAs are provided in Table 4.

TABLE 4

Nucleotide Sequences of Tested Single and Dual Guide RNAs

| Guide RNA | Nucleotide Sequence | SEQ ID NO |
|---|---|---|
| RNA #1 | UAAUUUCUACUCUUGUAGAUCUGAUGGUCC AUGUCUGUUA | 41 |
| RNA #2 | UAAUUUCUACUC | 42 |
| RNA #3 | UUGUAGAUCUGAUGGUCCAUGUCUGUUA | 43 |
| RNA #4 | UAAUUUCUAC | 15 |
| RNA #5 | UCUUGUAGAUCUGAUGGUCCAUGUCUGUUA | 52 |
| RNA #6 | UAAUUUCUACU | 53 |
| RNA #7 | CUUGUAGAUCUGAUGGUCCAUGUCUGUUA | 54 |
| RNA #8 | UAAUUUCUACUCU | 55 |
| RNA #9 | UGUAGAUCUGAUGGUCCAUGUCUGUUA | 56 |
| RNA #10 | UAAUUUCUACUCUU | 57 |
| RNA #11 | GUAGAUCUGAUGGUCCAUGUCUGUUA | 58 |

These guide RNAs were chemically synthesized. An in vitro cleavage assay was conducted using the method described above. Each guide RNA was used at the concentration of 1 µM when incubated with MAD7 to form an RNP. The molar ratio of MAD7 and target DNA was 10:1.

As shown in FIG. 4I, the pairs of guide RNAs #2 and #3, #4 and #5, #6 and #7, #8 and #9, and #10 and #11 activated the nuclease activity of MAD7 to cleave the DNMT1 target DNA. None of these targeter or modulator RNAs alone exhibited such activity. Therefore, under these conditions, the position in the loop at which crRNA1 was split did not appear to affect the activity of the dual guide RNA system.

Surprisingly, combinations of any modulator RNA selected from RNAs #2, #4, #6, #8, and #10 with any targeter RNA selected from RNAs #3, #5, #7, #9, and #11 were shown to activate MAD7 nuclease (FIG. 4I). In particular, the combination of RNAs #4 and #11 contained no sequence from the loop of crRNA1, and the combination of RNAs #10 and #5 contained the loop sequence of crRNA1 in both the modulator RNA and the targeter RNA. Therefore, under these conditions, the loop of a corresponding single guide RNA or a fragment of the loop was dispensable in the dual guide system. When the loop or a loop fragment was present, its length in either the targeter RNA or the modulator RNA did not appear to affect the activity of the dual guide RNA system.

Inclusion of Additional Hairpin Sequences

Figure 4B:
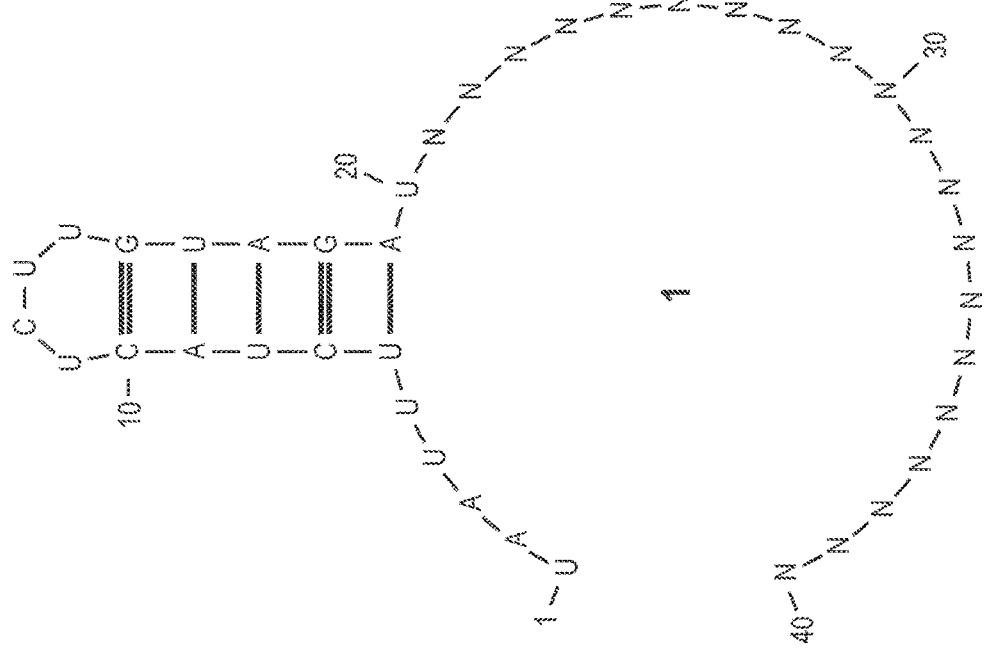
FIGS. 4A-4H are a series of schematic representations showing the predicted secondary structure of hybridized targeter and modulator RNAs. Crosses (within the loop regions) indicate the sites where the RNAs are split into a targeter RNA and a modulator RNA.
Figure 4A:
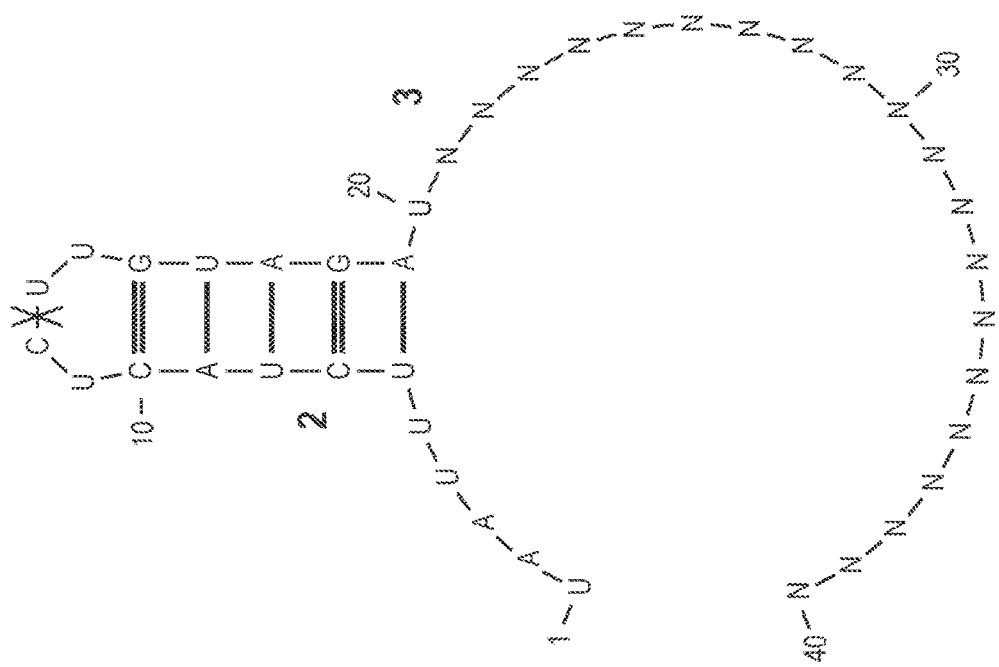
Figure 4C:
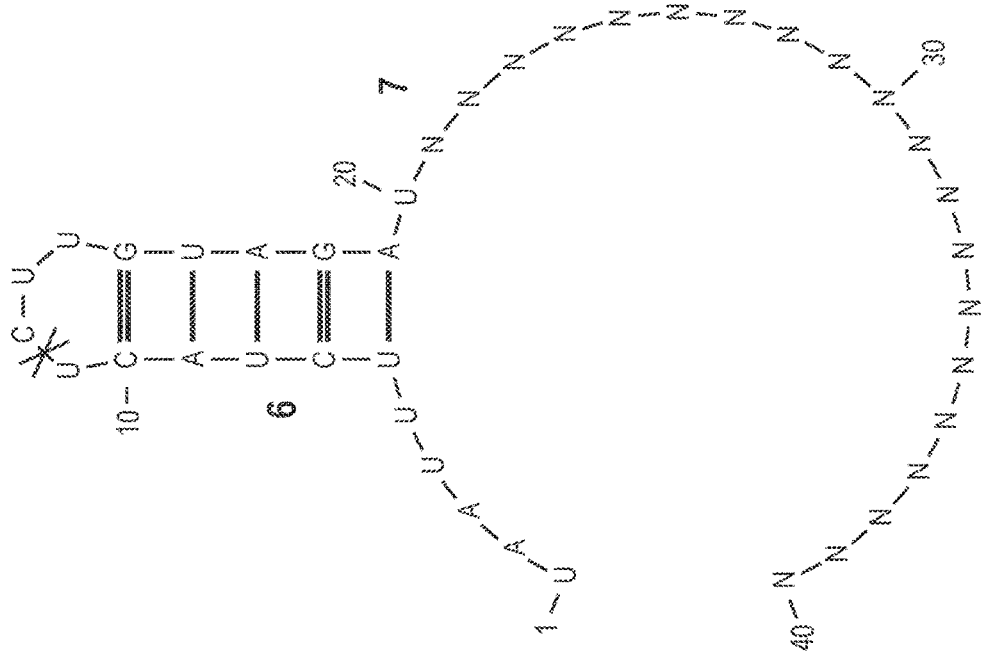
Figure 4D:
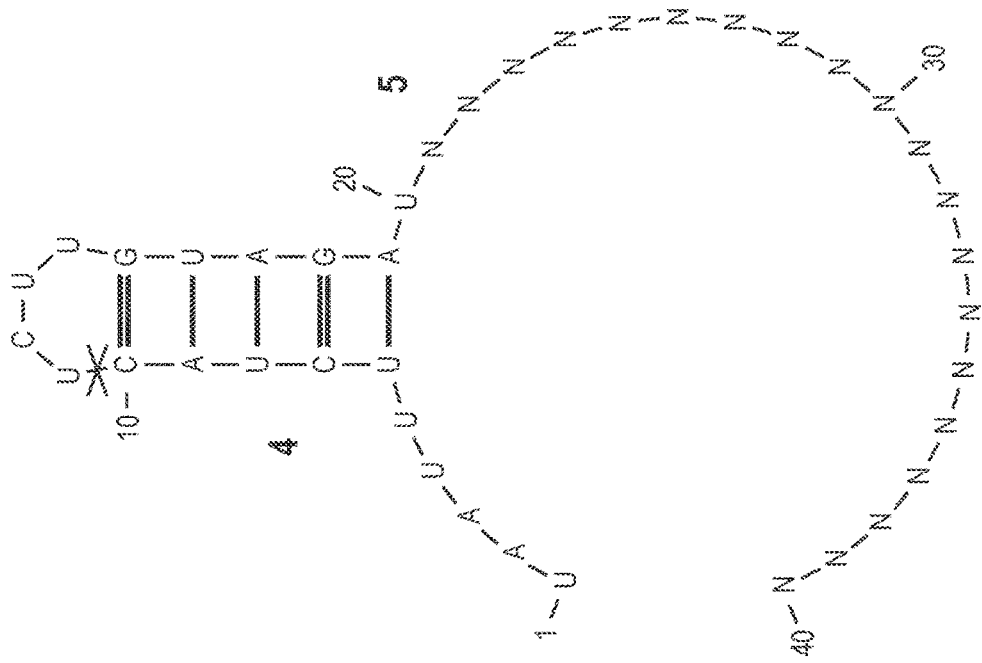
Figure 4F:
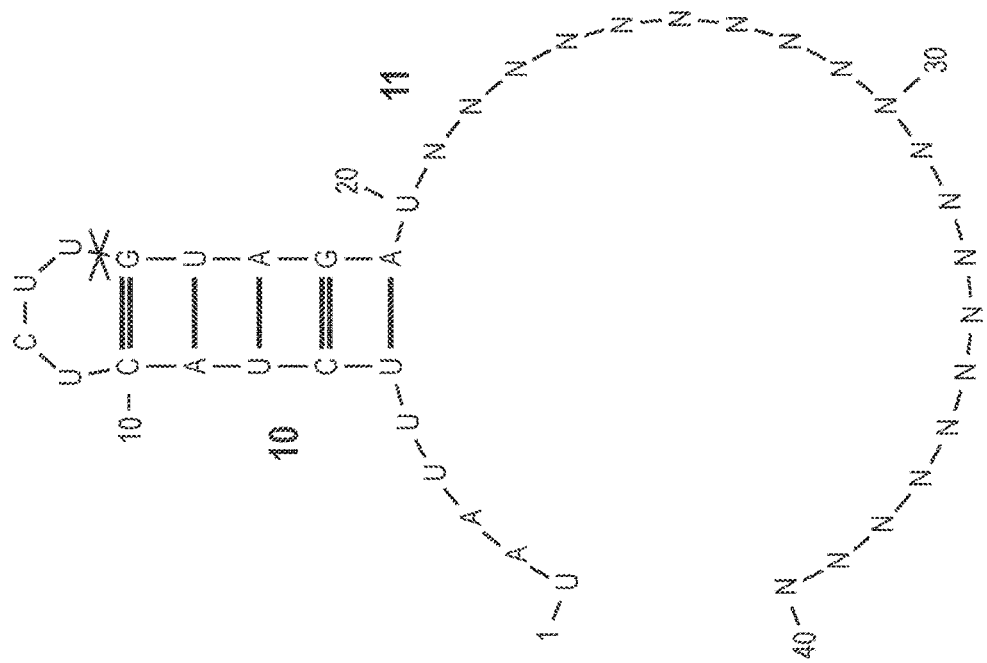
Figure 4E:
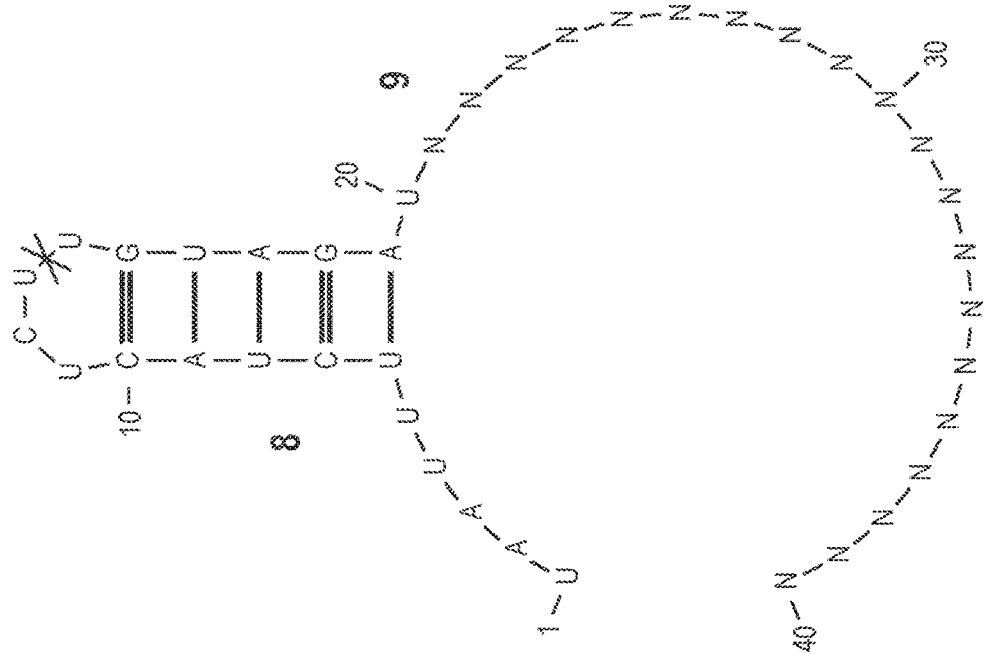
Figure 4H:
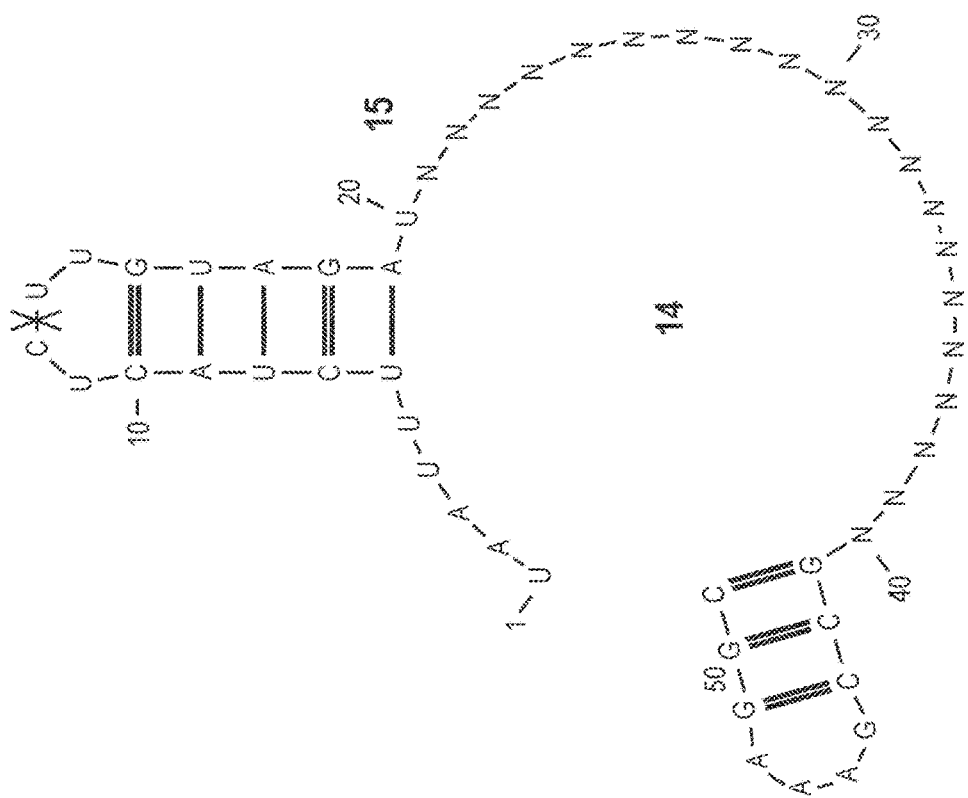
Figure 4G:
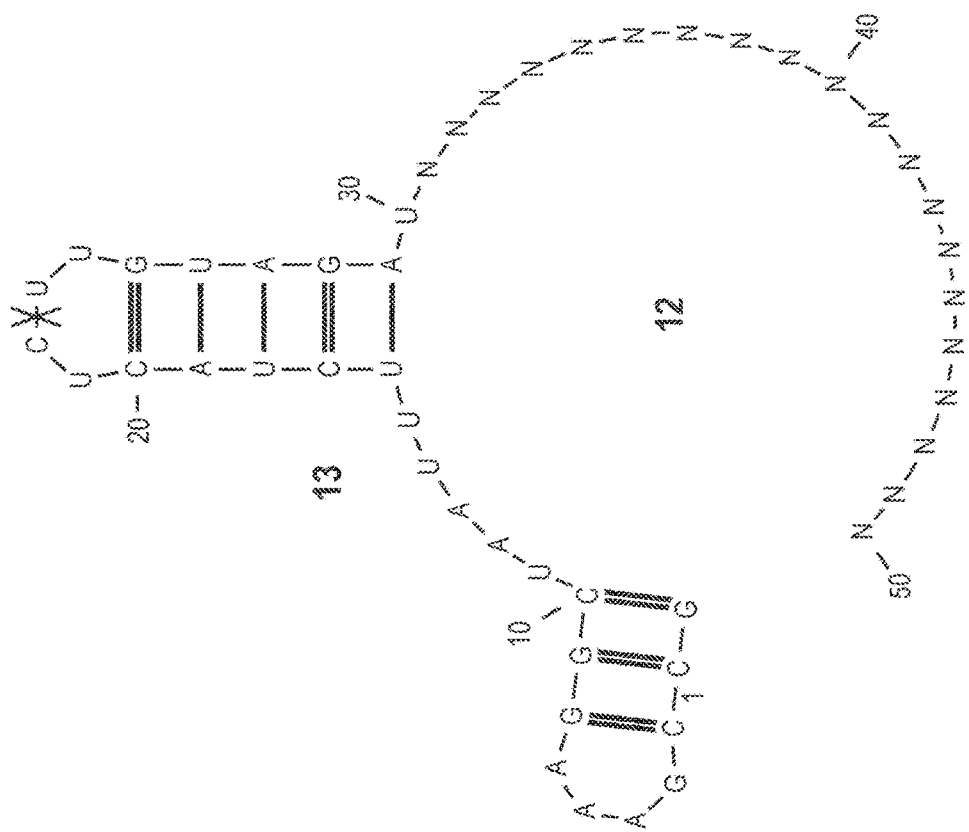
Figure 41:
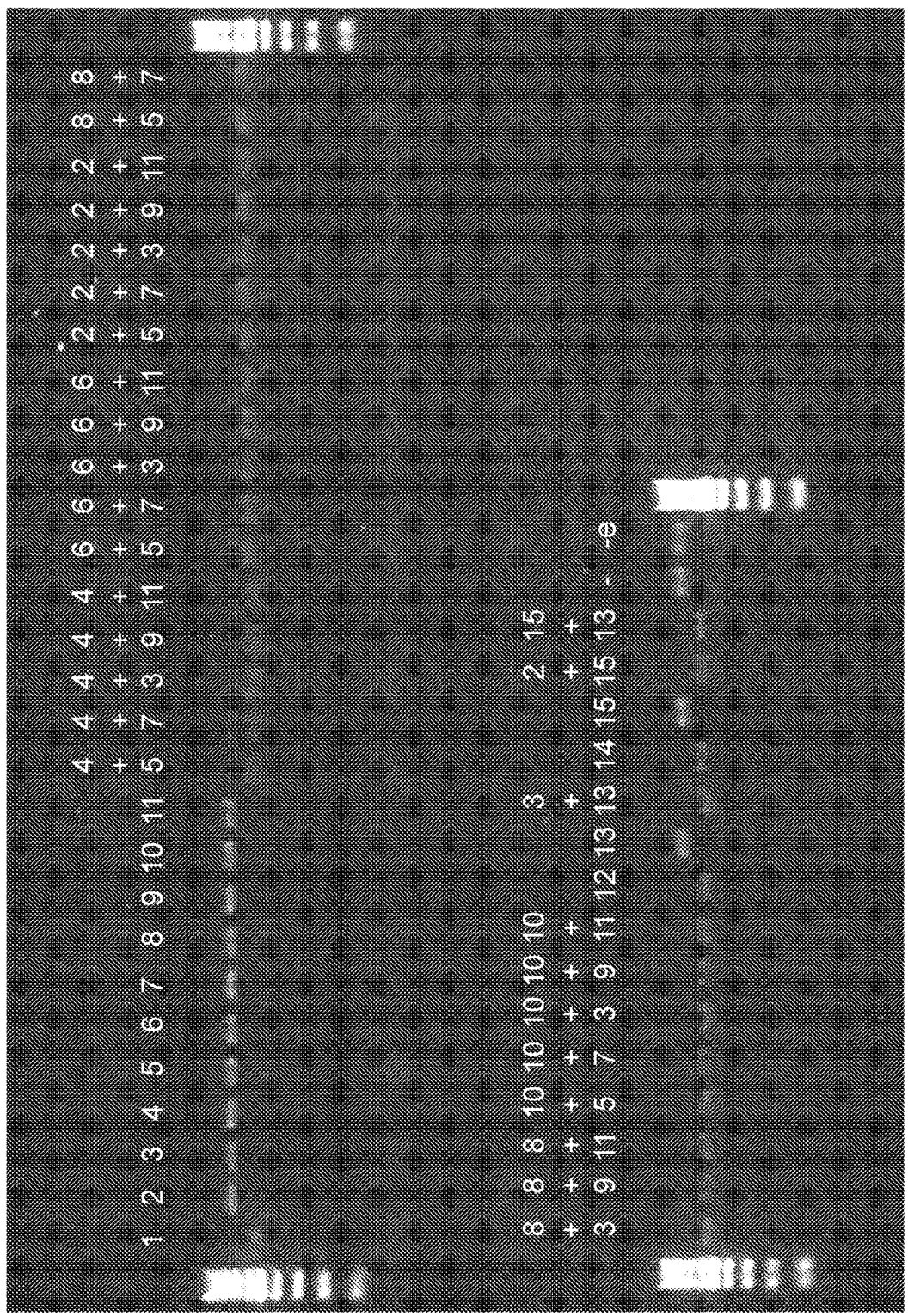

Next assessed were dual guide RNA systems including a hairpin sequence at the 5' end of a modulator RNA or at the 3' end of a targeter RNA. As shown in FIGS. 4G-4H, a hairpin sequence was added at the 5' end or 3' end of crRNA1 to generate single guide RNA named RNAs #12 and 14, respectively. A modulator RNA corresponding to RNA #12, which included the hairpin sequence added at the 5' end of crRNA1_modulator1, was designed and named RNA #13. A targeter RNA corresponding to RNA #14, which included the hairpin sequence added at the 3' end of crRNA1_targeter1, was designed and named RNA #15. The nucleotide sequences of these guide RNAs are provided in Table 5. The hairpin sequences in the guide RNAs are underlined.

TABLE 5

Nucleotide Sequences of Tested Single and Dual Guide RNAs

| Guide RNA | Nucleotide Sequence | SEQ ID NO |
|---|---|---|
| RNA #12 | GCCGAAAGGCUAAUUUCUACUCUUGUAGAU CUGAUGGUCCAUGUCUGUUA | 59 |
| RNA #13 | GCCGAAAGGCUAAUUUCUACUC | 60 |
| RNA #14 | UAAUUUCUACUCUUGUAGAUCUGAUGGUCC AUGUCUGUUAGCCGAAAGGC | 61 |
| RNA #15 | UUGUAGAUCUGAUGGUCCAUGUCUGUUAGC CGAAAGGC | 62 |

These guide RNAs were chemically synthesized. An in vitro cleavage assay was conducted using the method described above. Each guide RNA was used at the concentration of 1 µM when incubated with MAD7 to form an RNP. The molar ratio of MAD7 and target DNA was 10:1.

As shown in FIG. 4I, the hairpin-containing single guide RNAs #12 and 14 activated the nuclease activity of MAD7 to cleave the DNMT1 target DNA. The corresponding modulator RNA #13 and targeter RNA #15, which contained the hairpin sequence at the 5' end and the 3' end, respectively, did not show such activity alone. However, when modulator RNA #13 was combined with targeter RNA #3 (as described in the "'Loop' Termini of Modulator and Targeter RNAs" subsection) to form a dual guide system, this pair of RNAs activated MAD7 nuclease. Similarly, when targeter RNA #15 was combined with modulator RNA #2 (as described in the "'Loop' Termini of Modulator and Targeter RNAs" subsection) to form a dual guide system, this pair of RNAs activated MAD7 nuclease. Notably, the combination of modulator RNA #13 and targeter RNA #15, each containing a pairpin sequence, also activated MAD7 nuclease. Therefore, under these conditions, the hairpin sequence added at the 5' end of a modulator RNA or at the 3' end of a targeter RNA did not appear to negatively affect the activity of a dual guide system.

Base Pairing Between Modulator RNA and Targeter RNA

To assess the impact of modulator RNA-targeter RNA base pairing on the activity of dual guide systems, more single and dual guide systems were designed and tested. Specifically, crRNA constructs were designed to introduce additional base pairing between the modulator RNA and the targeter RNA. The nucleotides in the modulator RNA that formed these base pairs were positioned 3' to the modulator stem sequence, and the nucleotides in the targeter RNA that formed these base pairs were positioned 5' to the targeter stem sequence. As shown in FIGS. 5A-5I, constructs 1 and 2 were identical to crRNA1 and crRNA2 described above. The other constructs were split either within the loop regions to generate combinations 3, 5, 7, 9, 11, 13, and 15 or within the stem regions to generate combinations 4, 6, 8, 10, 12, 14, and 16. The nucleotides sequences of these guide RNAs are provided in Table 6. The Gibbs free energy change (ΔG) of the corresponding crRNAs was calculated by the RNAfold program and are noted in FIGS. 5A-5I.

TABLE 6

Nucleotide Sequences of Tested Single and Dual Guide RNAs

| Construct | crRNA Sequence | SEQ ID NO |
|---|---|---|
| 1 | UAAUUUCUACUCUUGUAGAUCTGATGGTCCATGTCTGTTA | 63 |
| 2 | UAAUUCCCACUCUUGUGGGUCTGATGGTCCATGTCTGTTA | 64 |

| Combination | Modulator RNA Sequence | SEQ ID NO | Targeter RNA Sequence | SEQ ID NO |
|---|---|---|---|---|
| 3 | UAAUUCCCACUC | 45 | UUGUGGGUCTGATGGTCCATGTCTGTTA | 78 |
| 4 | UAAUUCCCACUCUUG | 65 | UGGGUCTGATGGTCCATGTCTGTTA | 79 |
| 5 | UAAUUCCCACUCUC | 66 | UUGUGUGGGUCTGATGGTCCATGTCTGTTA | 80 |
| 6 | UAAUUCCCACUCUCUUGUG | 67 | UGGGUCTGATGGTCCATGTCTGTTA | 81 |
| 7 | UAAUUCCCACUCCUC | 68 | UUGUUGUGGGUCTGATGGTCCATGTCTGTTA | 82 |
| 8 | UAAUUCCCACUCCUCUUGUUG | 69 | UGGGUCTGATGGTCCATGTCTGTTA | 83 |
| 9 | UAAUUCCCACUGCUC | 70 | UUGCUGUGGGUCTGATGGTCCATGTCTGTTA | 84 |
| 10 | UAAUUCCCACUGCUCUUGCUG | 71 | UGGGUCTGATGGTCCATGTCTGTTA | 85 |
| 11 | UAAUUCCCACUCGCUC | 72 | UUGCUUGUGGGUCTGATGGTCCATGTCTGTTA | 86 |
| 12 | UAAUUCCCACUCGCUCUUGCUUG | 73 | UGGGUCTGATGGTCCATGTCTGTTA | 87 |
| 13 | UAAUUCCCACUCGCUC | 74 | UUGCGUGUGGGUCTGATGGTCCATGTCTGTTA | 88 |
| 14 | UAAUUCCCACUCGCUCUUGCGUG | 75 | UGGGUCTGATGGTCCATGTCTGTTA | 89 |
| 15 | UAAUUCCCACUCCGCUC | 76 | UUGCGUUGUGGGUCTGATGGTCCATGTCTGTTA | 90 |
| 16 | UAAUUCCCACUCCGCUCUUGCGUUG | 77 | UGGGUCTGATGGTCCATGTCTGTTA | 91 |

The guide RNAs were chemically synthesized. An in vitro cleavage assay was conducted using the method described above, except that the MAD7 protein was incubated with an equimolar amount of RNA(s) at 25° C. for 20 min to form an RNP, and the RNPs were incubated with the target DNA for 30 minutes. Each guide RNA was used at the concentration of 1 μM when incubated with MAD7 to form an RNP. The molar ratio of MAD7 and target DNA was 10:1.

Figure 5B:
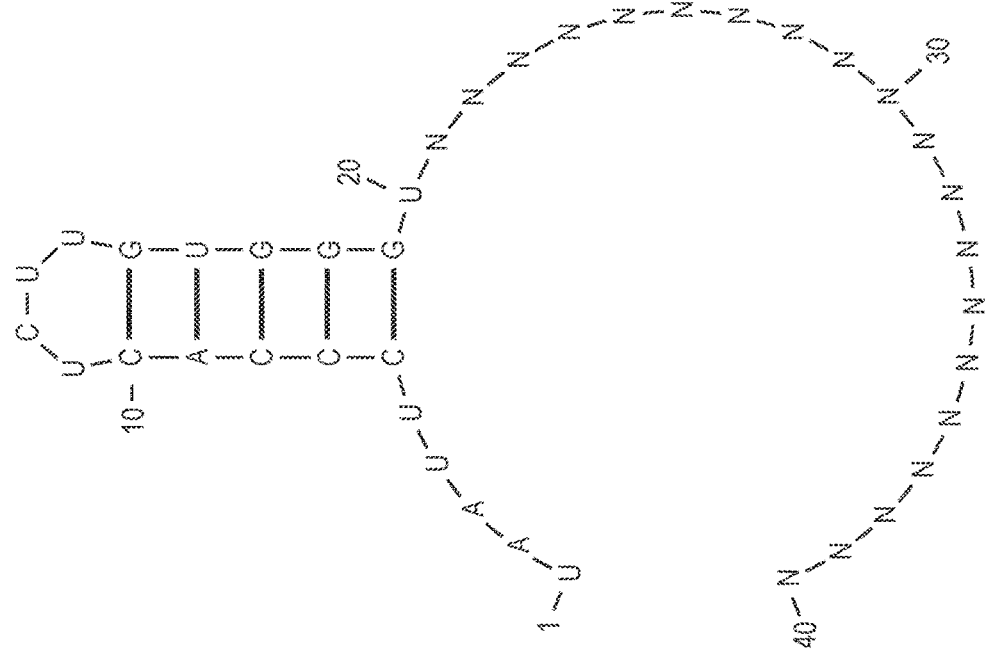
FIGS. 5A-5I are a series of schematic representations showing the predicted secondary structures of crRNAs.
Figure 5A:
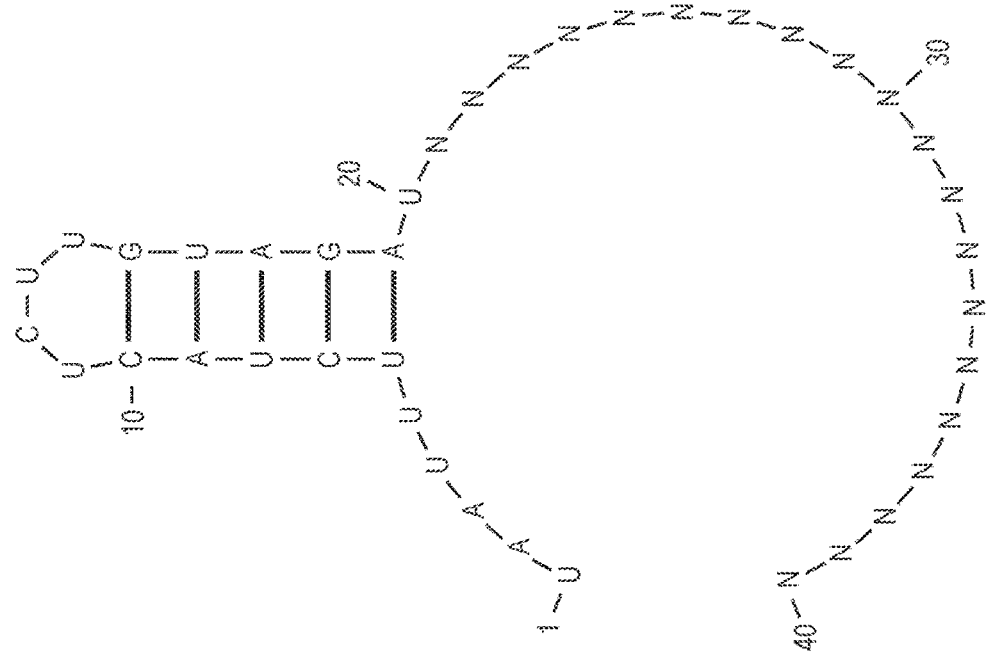
Figure 5D:
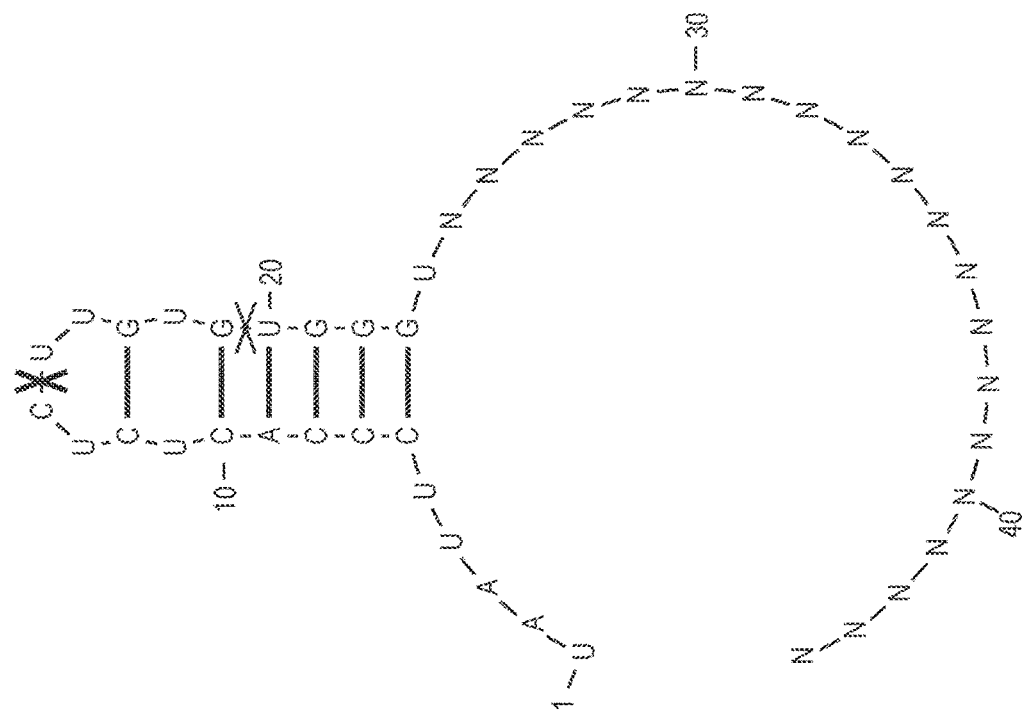
Figure 5C:
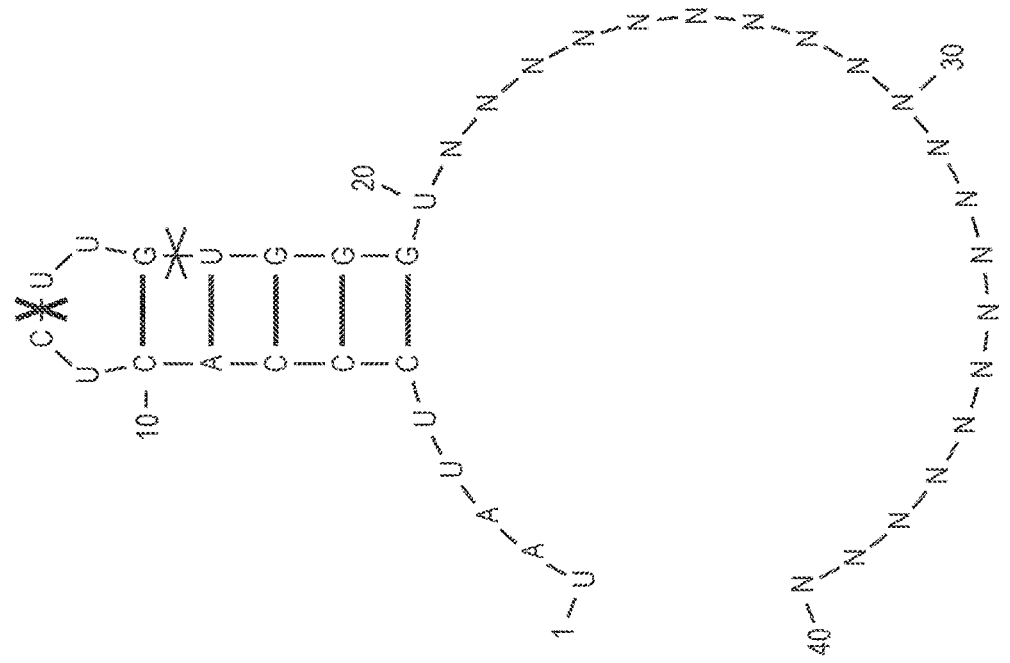
Figure 5F:
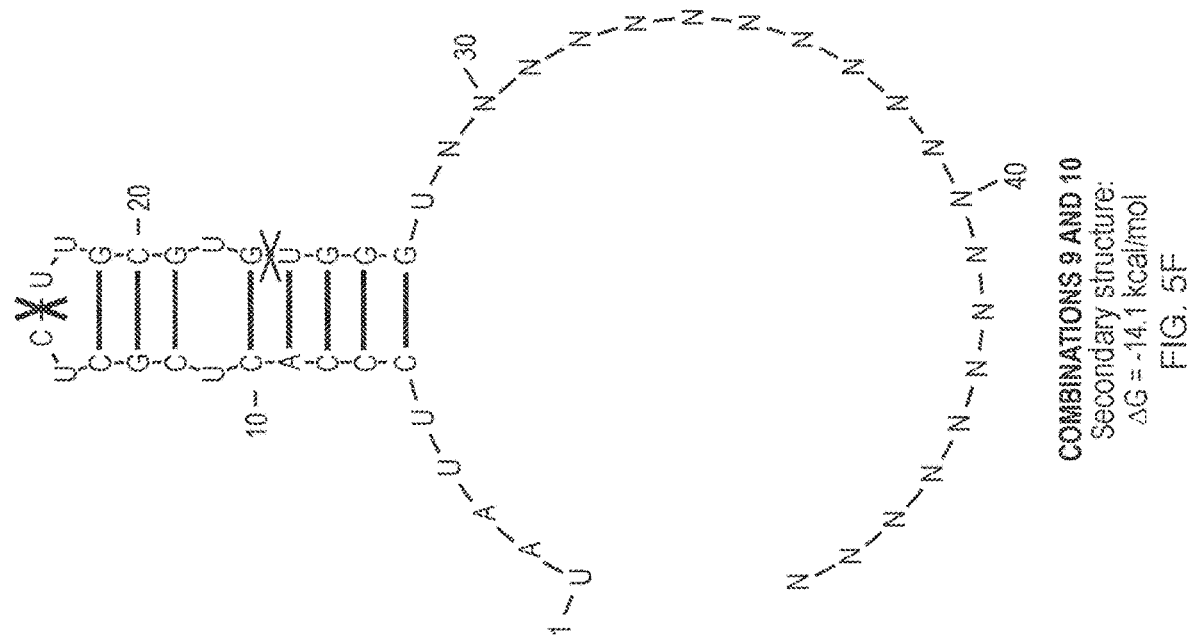
Figure 5E:
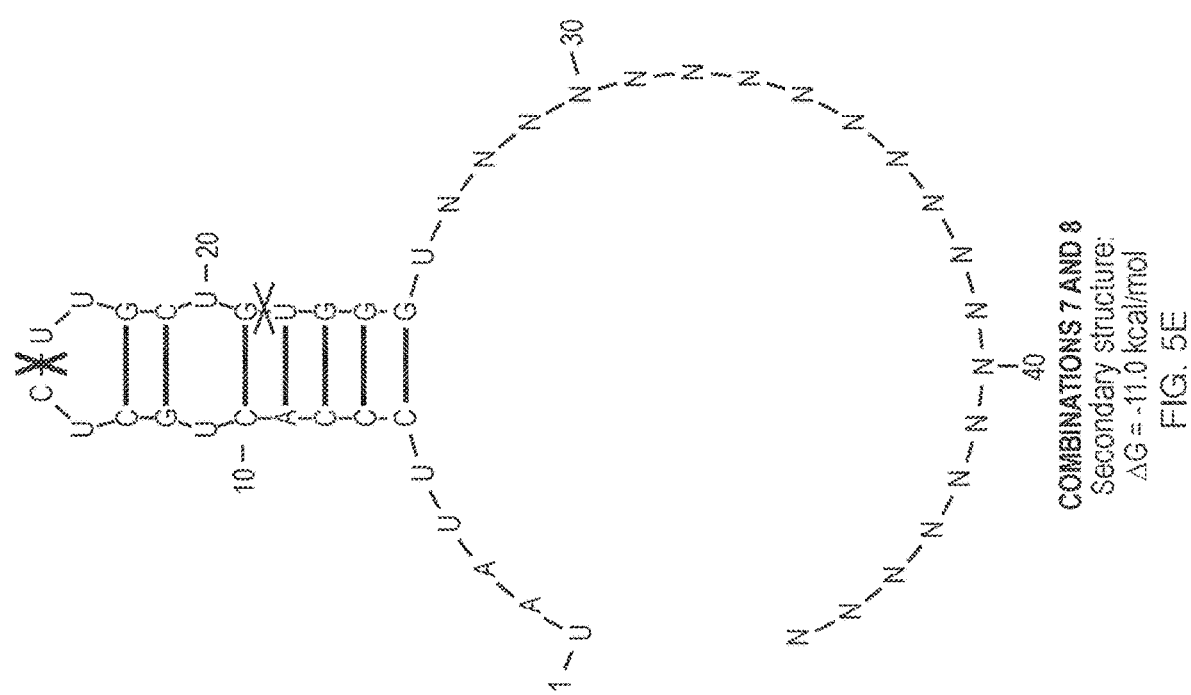
Figure 5H:
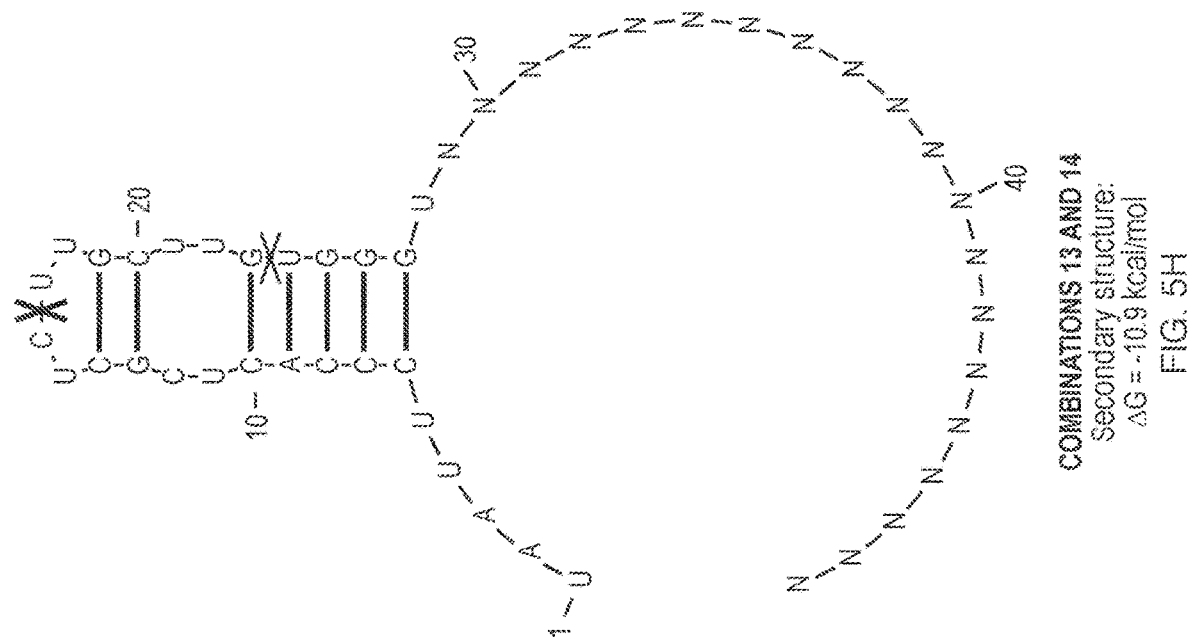
Figure 5G:
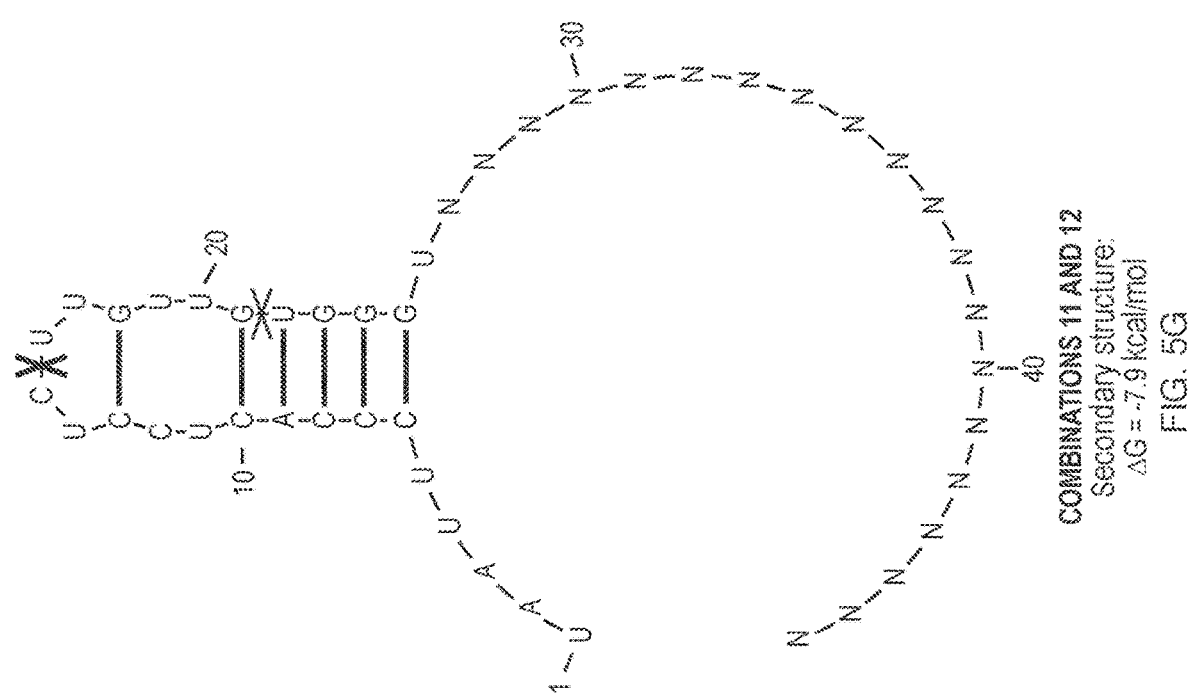
Figure 5I:
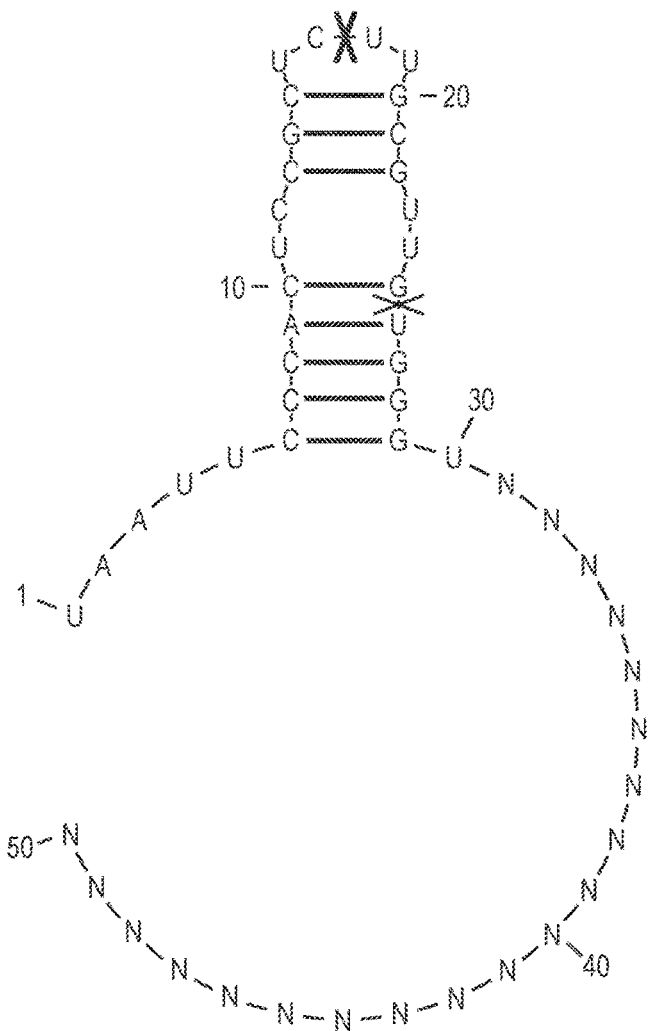
Figures 5J, 5K:
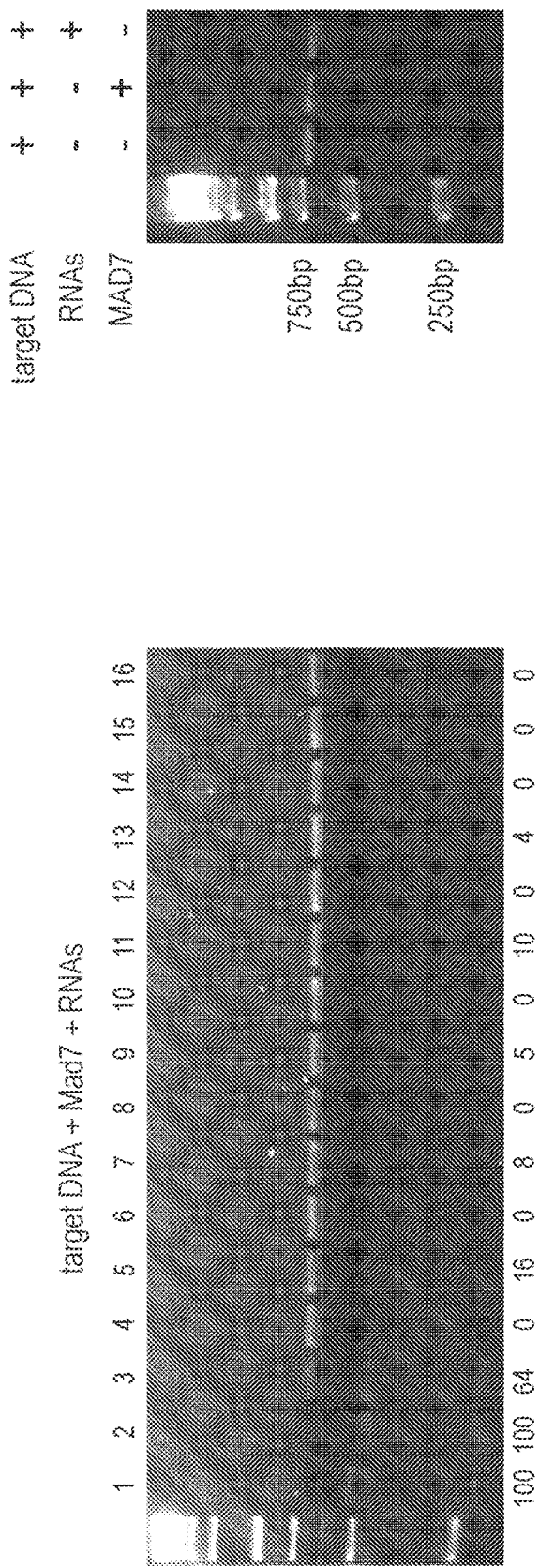
FIGS. 5J-5K are photographs showing gel electrophoresis results from an in vitro cleavage experiment using MAD7 complexed with crRNA constructs or combinations of targeter and modulator RNAs. The ratio of cleaved product in FIG. 5J was determined by measuring the relative intensities of the bands.

As shown in FIGS. 5J-5K, splitting the crRNAs within the stem regions into dual guides abrogated the activity of the CRISPR-Cas system. However, where the crRNAs were split within the loop regions, the ability of the dual guide system to activate MAD7 nuclease was reduced in the systems that contained additional base pairing between the modulator RNA and the targeter RNA.

Example 2. Cleavage of Genomic DNA by Dual Guide MAD7 CRISPR-Cas Systems

This example describes cleavage of the genomic DNA of Jurkat cells using MAD7 in complex with single guide or dual guide nucleic acids.

Briefly, Jurkat cells were grown in RPMI 1640 medium (Thermo Fisher Scientific, A1049101) supplemented with 10% fetus bovine serum at 37° C. in a 5% $CO_2$ environment, and split every 2-3 days to a density of 100,000 cells/mL. MAD7 protein, which contained a nucleoplasmin NLS at the C-terminus, was expressed in *E. Coli* and purified by FPLC. RNP complexes were prepared by incubating 150 pmol MAD7 protein with 150 pmol crRNA1 or a combination of 150 pmol crRNA1_modulator1 and 150 pmol crRNA1_targeter1, as described in Example 1, for 10 minutes at room temperature. The RNPs were mixed with 200,000 Jurkat cells in a final volume of 25 μL. Electroporation was carried out on a 4D-NUCLEOFECTOR® (Lonza) using program CA-137. Following electroporation, the cells were cultured for three days.

Genomic DNA of the cells was extracted using the Quick Extract DNA extraction solution 1.0 (Epicentre). The DNMT1 gene was amplified from the genomic DNA samples in a PCR reaction using a forward primer having the nucleotide sequence of TCGTCGGCAGCGTCA-GATGTGTATAAGAGACAGAGTGTTCAGTCTCCGT-GAACGT (SEQ ID NO: 92) and a reverse primer having the nucleotide sequence of GTCTCGTGGGCTCG-GAGATGTGTATAAGAGACAGGTCCT-TAGCAGCTTCCTCCTCC (SEQ ID NO: 93). The amplified DNA was purified and used as template in a second PCR reaction using Nextera indexing primers Index 1 and Index 2. The sequence of Index 1 was CAAGCAGAAGACGG-CATACGAGAT [17] GTCTCGTGGGCTCGG (SEQ ID NOS 94 and 141, respectively)) and the sequence of Index 2 was AATGATACGGCGACCACCGAGATCTACAC [15] TCGTCGGCAGCGTC (SEQ ID NOS 95 and 142, respectively), where i7 and i5 represented barcodes for multiplexing. The PCR products were analyzed by next-generation sequencing, and the data were analyzed with the AmpliCan package (see, Labun et al. (2019), *Accurate analysis of genuine CRISPR editing events with ampliCan*, GENOME RES., electronically published in advance). The quality of the sequencing results was verified in FIG. 6B. Editing efficiency was determined by the number of edited reads relative to the total number of reads obtained under each condition. The experiment was conducted in duplicate.

Figure 6A:
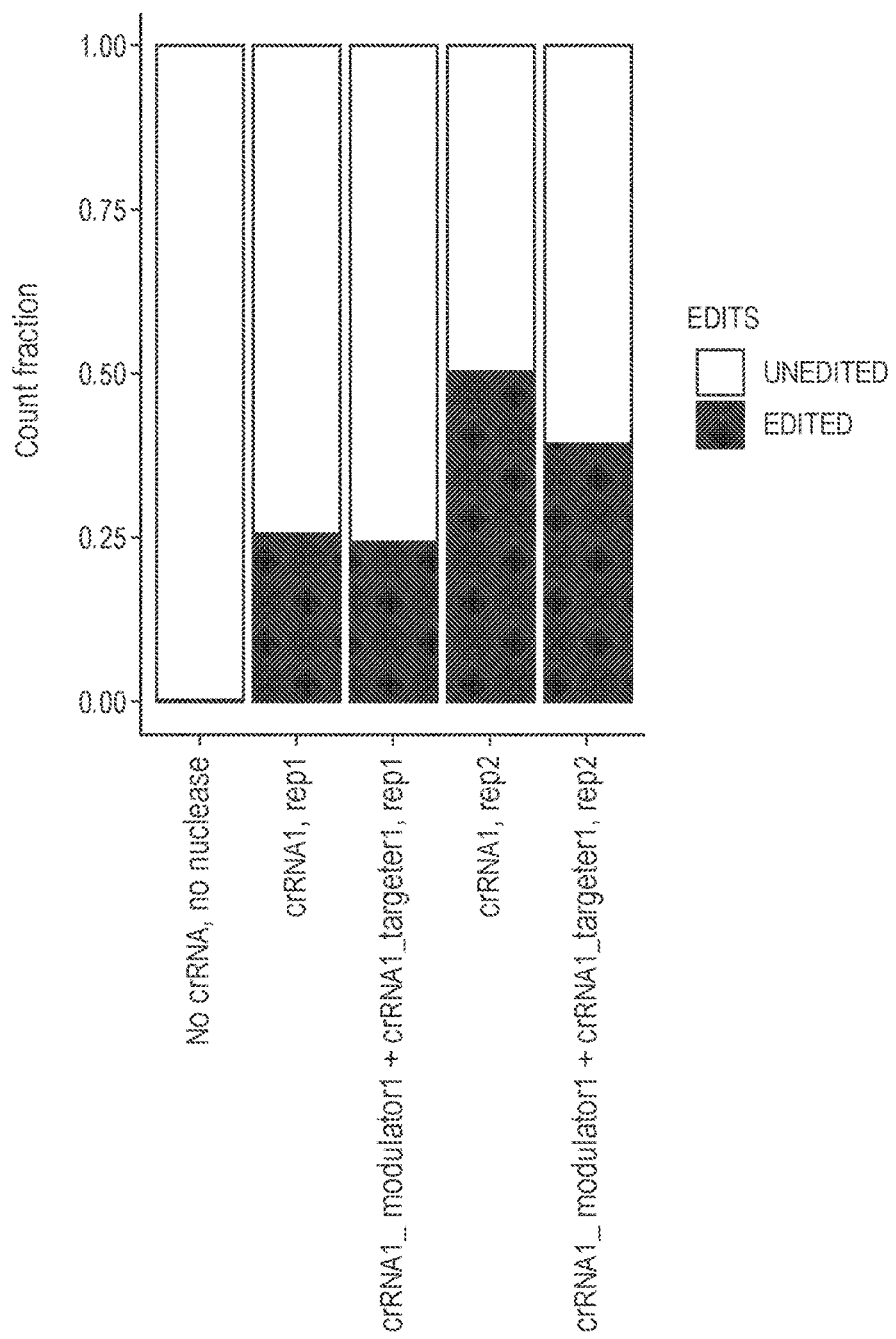
FIG. 6A is a bar graph showing the read fraction of edited and unedited copies of target DNA by each crRNA or a corresponding set of targeter RNA and modulator RNA tested. "Rep1" and "rep2" means the first and second replicates, respectively, of the same experiment.
Figure 6B:
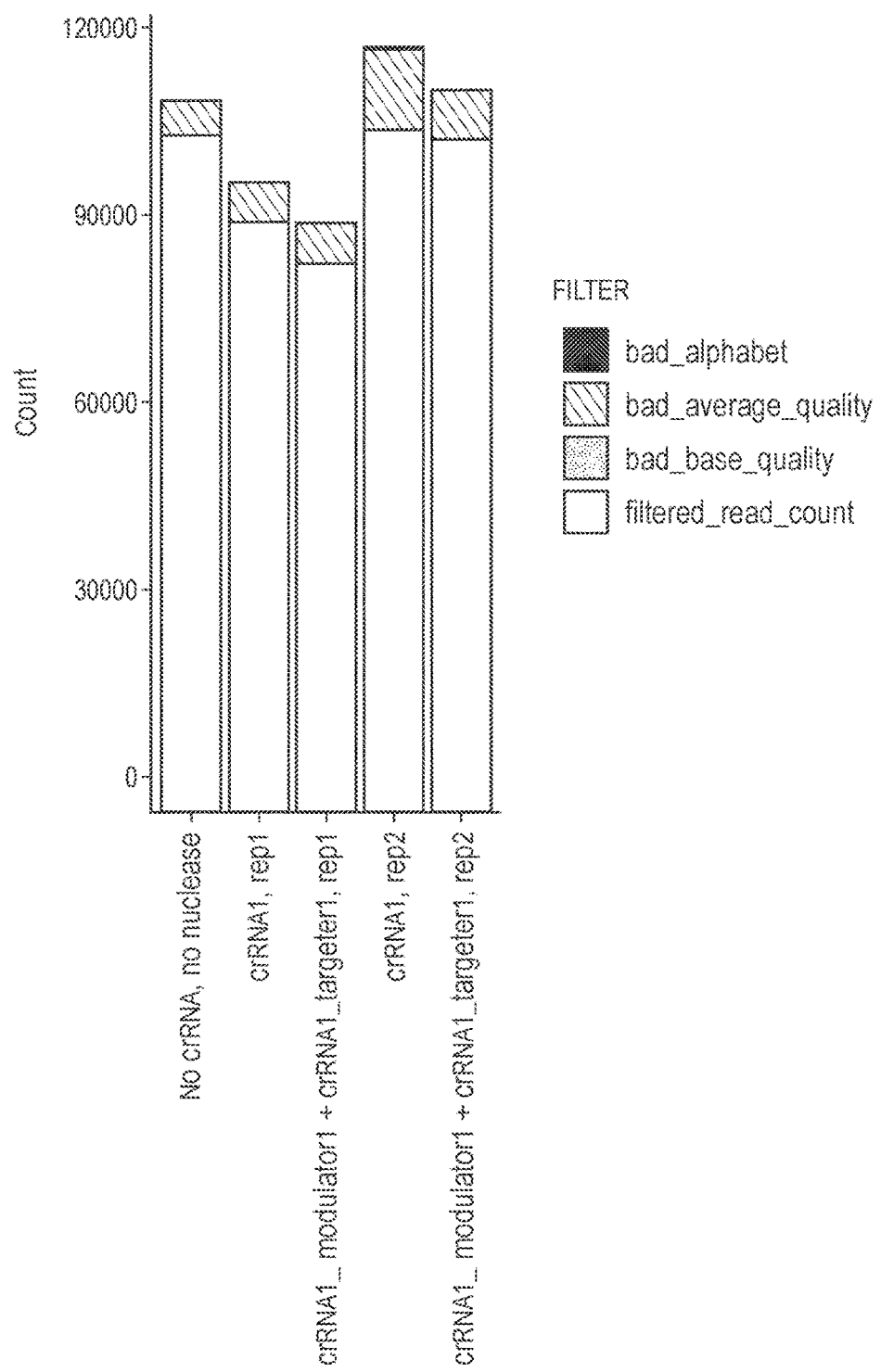
FIG. 6B is a bar graph showing the number of sequencing reads obtained in each condition. The colors indicate the quality of the reads.

As shown in FIG. 6A, the combination of crRNA1_modulator1 and crRNA1_targeter1, in complex with MAD7, edited 25-40% of the DNMT1 genomic locus in the population of Jurkat cells. This observed efficiency was similar to the efficiency achieved by using crRNA1 and MAD7.

Example 3. Cleavage of Other Target Sites by Dual Guide MAD7 CRISPR-Cas Systems

Examples 1 and 2 describe cleavage of a target DNA having the sequence of the human DNMT1 gene. This example describes cleavage of other target DNAs using MAD7 in complex with dual guide nucleic acids.

Briefly, crRNAs and corresponding targeter RNAs were designed to target other human genes. These targeter RNAs can be combined with crRNA1_modulator1 to generate a dual guide system. The sequences of the guide RNAs used in this experiment are provided in Table 7. Guide RNAs targeting other human genes are also designed.

TABLE 7

Nucleotide Sequences of Exemplary Single and Dual Guide RNAs

| Guide RNA | Nucleotide Sequence | Target Gene | SEQ ID NO |
| --- | --- | --- | --- |
| crRNA1_modulator1 | UAAUUUCUACUC | N/A | 42 |
| crRNA_CD90 | UAAUUUCUACUCUUGUAGAUCUGGUGAAGTTGGTTCGGGAG | CD90 | 100 |
| crRNA_CD90_targeter | UUGUAGAUCUGGUGAAGTTGGTTCGGGAG | CD90 | 101 |
| crRNA_PDCD1_23 | UAAUUUCUACUCUUGUAGAUCUGCAGGGACAAUAGGAGCC | PDCD1 | 103 |
| crRNA_PDCD1_23_targeter | UUGUAGAUCUGCAGGGACAAUAGGAGCC | PDCD1 | 104 |

TABLE 7-continued

Nucleotide Sequences of Exemplary Single and Dual Guide RNAs

| Guide RNA | Nucleotide Sequence | Target Gene | SEQ ID NO |
|---|---|---|---|
| crRNA_LAG3 | UAAUUUCUACUCUUGUAGAUGGGTGCATAC CTGTCTGGCTG | LAG3 | 105 |
| crRNA_LAG3_targeter | UUGUAGAUGGGTGCATACCTGTCTGGCTG | LAG3 | 106 |
| crRNA_PTPN11 | UAAUUUCUACUCUUGUAGAUUAUGACCUG UAUGGAGGGGAG | PTPN11 | 107 |
| crRNA_PTPN11_targeter | UUGUAGAUUAUGACCUGUAUGGAGGGGAG | PTPN11 | 108 |
| crRNA_PDCD1_8 | UAAUUUCUACUCUUGUAGAUGCACGAAGC TCTCCGATGTGT | PDCD1 | 109 |
| crRNA_PDCD1_8_targeter | UUGUAGAUGCACGAAGCTCTCCGATGTGT | PDCD1 | 110 |
| crRNA_FAS | UAAUUUCUACUCUUGUAGAUGTGTAACATA CCTGGAGGACA | FAS | 111 |
| crRNA_FAS_targeter | UUGUAGAUGTGTAACATACCTGGAGGACA | FAS | 112 |
| crRNA_TIGIT | UAAUUUCUACUCUUGUAGAUGTCCTCCCTC TAGTGGCTGAG | TIGIT | 113 |
| crRNA_TIGIT_targeter | UUGUAGAUGTCCTCCCTCTAGTGGCTGAG | TIGIT | 114 |
| crRNA_CTLA4 | UAAUUUCUACUCUUGUAGAUAGCGGCACA AGGCTCAGCTGA | CTLA4 | 115 |
| crRNA_CTLA4_targeter | UUGUAGAUAGCGGCACAAGGCTCAGCTGA | CTLA4 | 116 |
| crRNA_B2M | UAAUUUCUACUCUUGUAGAUACTTTCCATT CTCTGCTGGAT | B2M | 117 |
| crRNA_B2M_targeter | UUGUAGAUACTTTCCATTCTCTGCTGGAT | B2M | 118 |
| crRNA_PDCD1_2 | UAAUUUCUACUCUUGUAGAUCCTTCCGCTC ACCTCCGCCTG | PDCD1 | 119 |
| crRNA_PDCD1_2_targeter | UUGUAGAUCCTTCCGCTCACCTCCGCCTG | PDCD1 | 120 |
| crRNA_CD52 | UAAUUUCUACUCUUGUAGAUCTCTTCCTCC TACTCACCATC | CD52 | 121 |
| crRNA_CD52_targeter | UUGUAGAUCTCTTCCTCCTACTCACCATC | CD52 | 122 |

The guide RNAs were chemically synthesized. In cell cleavage assay was conducted using the method described in Example 2.

Figure 7:
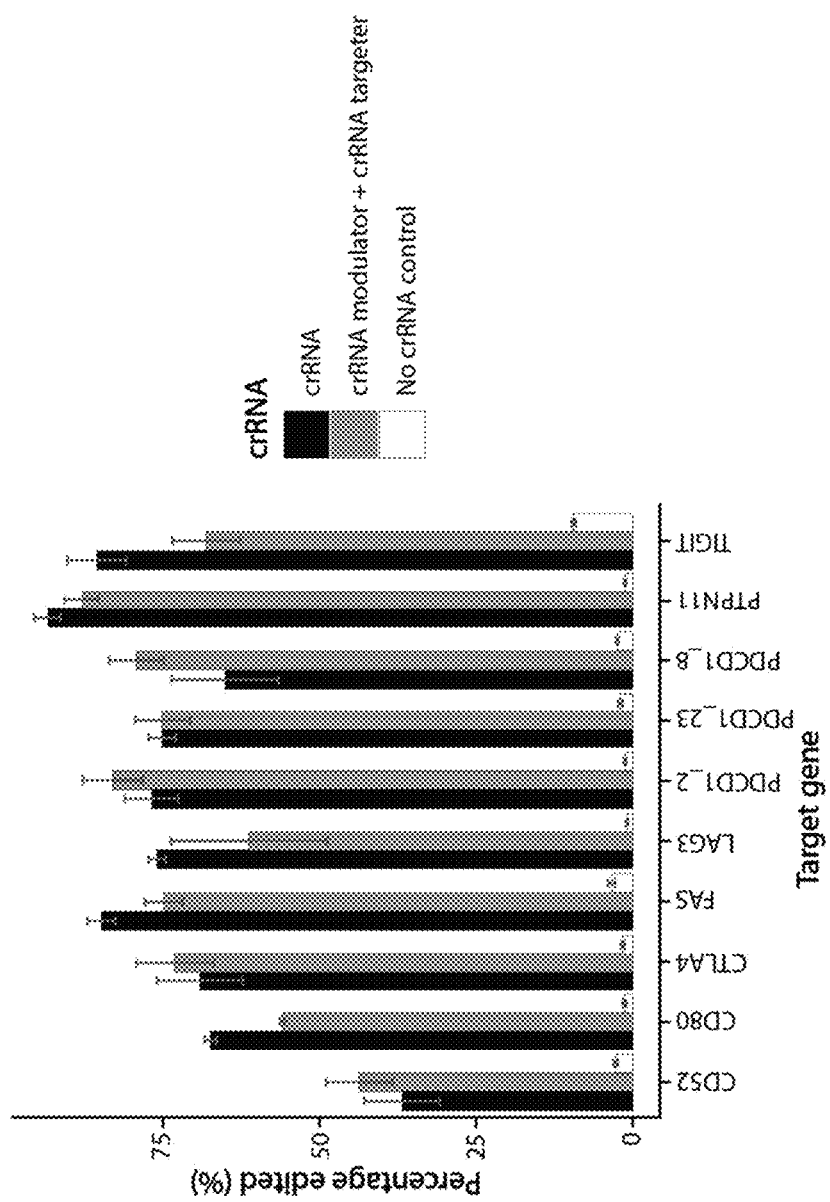
FIG. 7 is a bar graph showing the percentage of edited copies of the target locus (shown on the x-axis) in the genome of Jurkat cells.

As shown in FIG. 7, in each of the target loci tested, the dual guide RNAs edited the human genome at similar efficiencies as the respective single guide RNA.

Example 4. Cleavage of Other Target Sites by Dual Guide MAD7 CRISPR-Cas Systems Using Different Splits in the crRNA Loops This example describes cleavage of DNAs using MAD7 in complex with dual guide nucleic acids split at different positions in the cRNA loop.

Briefly, the crRNAs targeting CD52, PDCD1, and TIGIT and modulator RNAs and targeter RNAs in a dual guide CRISPR system were chemically synthesized. The nucleotide sequences of these RNAs are shown in Table 8 below.

TABLE 8

| Guide RNA | Nucleotide Sequence | Target Gene | SEQ ID NO |
|---|---|---|---|
| crRNA_modulator1 | UAAUUUCUAC | N/A | 96 |
| crRNA_modulator2 | UAAUUUCUACU | N/A | 97 |
| crRNA_modulator3 | UAAUUUCUACUC | N/A | 42 |
| crRNA_modulator4 | UAAUUUCUACUCU | N/A | 98 |
| crRNA_modulator5 | UAAUUUCUACUCUU | N/A | 99 |
| crRNA_CD52 | UAAUUUCUACUCUUGUAGAUCUCUUCCUCCUACUCACCAUC | CD52 | 123 |
| crRNA_CD52_targeter1 | UCUUGUAGAUCUCUUCCUCCUACUCACCAUC | CD52 | 124 |
| crRNA_CD52_targeter2 | CUUGUAGAUCUCUUCCUCCUACUCACCAUC | CD52 | 125 |
| crRNA_CD52_targeter3 | UUGUAGAUCUCUUCCUCCUACUCACCAUC | CD52 | 126 |
| crRNA_CD52_targeter4 | UGUAGAUCUCUUCCUCCUACUCACCAUC | CD52 | 127 |
| crRNA_CD52_targeter5 | GUAGAUCUCUUCCUCCUACUCACCAUC | CD52 | 128 |
| crRNA_PDCD1 | UAAUUUCUACUCUUGUAGAUGCACGAAGCUCUCCGAUGUGU | PDCD1 | 129 |
| crRNA_PDCD1_targeter1 | UCUUGUAGAUGCACGAAGCUCUCCGAUGUGU | PDCD1 | 130 |
| crRNA_PDCD1_targeter2 | CUUGUAGAUGCACGAAGCUCUCCGAUGUGU | PDCD1 | 131 |
| crRNA_PDCD1_targeter3 | UUGUAGAUGCACGAAGCUCUCCGAUGUGU | PDCD1 | 132 |
| crRNA_PDCD1_targeter4 | UGUAGAUGCACGAAGCUCUCCGAUGUGU | PDCD1 | 133 |
| crRNA_PDCD1_targeter5 | GUAGAUGCACGAAGCUCUCCGAUGUGU | PDCD1 | 134 |
| crRNA_TIGIT | UAAUUUCUACUCUUGUAGAUGUCCUCCCUCUAGUGGCUGAG | TIGIT | 135 |
| crRNA_TIGIT_targeter1 | UCUUGUAGAUGUCCUCCCUCUAGUGGCUGAG | TIGIT | 136 |

TABLE 8-continued

Nucleotide Sequences of Exemplary Single and Dual Guide RNAs

| Guide RNA | Nucleotide Sequence | Target Gene | SEQ ID NO |
|---|---|---|---|
| crRNA_TIGIT_targeter2 | CUUGUAGAUGUCCUCCCUCUAGUGGCUGAG | TIGIT | 137 |
| crRNA_TIGIT_targeter3 | UUGUAGAUGUCCUCCCUCUAGUGGCUGAG | TIGIT | 138 |
| crRNA_TIGIT_targeter4 | UGUAGAUGUCCUCCCUCUAGUGGCUGAG | TIGIT | 139 |
| crRNA_TIGIT_targeter5 | GUAGAUGUCCUCCCUCUAGUGGCUGAG | TIGIT | 140 |

In Table 8, crRNA_CD52, crRNA_PDCD1, and crRNA_TIGIT were used as single guide RNAs targeting CD52, PDCD1, and TIGIT, respectively. crRNA_modulator1 was used in combination with crRNA_CD52_targeter1, crRNA_PDCD1_targeter1, or crRNA_TIGIT_targeter1 as dual guide RNAs corresponding to the respective single guide RNA, wherein the single guide RNA is split at the first internucleotide bond from the 5'end of the loop. crRNA_modulator2 was used in combination with crRNA_CD52_targeter2, crRNA_PDCD1_targeter2, or crRNA_TIGIT_targeter2 as dual guide RNAs corresponding to the respective single guide RNA, wherein the single guide RNA is split at the second internucleotide bond from the 5'end of the loop. crRNA_modulator3 was used in combination with crRNA_CD52_targeter3, crRNA_PDCD1_targeter3, or crRNA_TIGIT_targeter3 as dual guide RNAs corresponding to the respective single guide RNA, wherein the single guide RNA is split at the third internucleotide bond from the 5'end of the loop. crRNA_modulator4 was used in combination with crRNA_CD52_targeter4, crRNA_PDCD1_targeter4, or crRNA TIGIT_targeter4 as dual guide RNAs corresponding to the respective single guide RNA, wherein the single guide RNA is split at the fourth internucleotide bond from the 5'end of the loop. crRNA_modulator5 was used in combination with crRNA_CD52_targeter5, crRNA PDCD1_targeter5, or crRNA_TIGIT_targeter5 as dual guide RNAs corresponding to the respective single guide RNA, wherein the single guide RNA is split at the fifth internucleotide bond from the 5'end of the loop. An in-cell cleavage assay was conducted using the method described in Examples 1 above.

As shown in FIG. 8, for each target gene tested, the dual guide CRISPR system edited the genomes of cells in the in-cell cleavage assay at similar efficiencies where the split position is 2, 3, 4, or 5, and at significantly lower efficiencies where the split position is 1 (i.e., split at the first internucleotide bond of the loop from the 5' end). This result suggested that the modulator RNA should include at least one nucleotide (e.g., uridine) 3' to the modulator stem sequence for optimal activity in cells.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

The invention claimed is:

1. An engineered, non-naturally occurring system comprising:
   (a) a targeter nucleic acid comprising, from 5' to 3':
      (i) a targeter stem sequence;
      (ii) a spacer sequence designed to hybridize with a target nucleotide sequence; and
      (iii) an optional additional nucleotide sequence;
   (b) a modulator nucleic acid comprising a modulator stem sequence complementary to the targeter stem sequence, wherein the targeter nucleic acid and the modulator nucleic acid are separate nucleic acids, wherein the targeter nucleic acid, the modulator nucleic acid, or both, comprises a chemically modified RNA, and wherein a complex comprising the targeter nucleic acid and the modulator nucleic acid is capable of activating a CRISPR Associated (Cas) nuclease that, in a naturally occurring system, is activated by a single crRNA in the absence of a tracrRNA, wherein the Cas nuclease comprises a Type V-A Cas nuclease; and
   (c) the Type V-A Cas nuclease.

2. The engineered, non-naturally occurring system of claim 1 wherein the targeter stem sequence and the modulator stem sequence are each 4-10 nucleotides in length.

3. The engineered, non-naturally occurring system of claim 1 wherein the spacer sequence is 18 nucleotides in length or shorter.

4. The engineered, non-naturally occurring system of claim 1 wherein the chemical modification is present in one or more nucleotides at the 3' end of the targeter nucleic acid, in one or more nucleotides at the 5' end of the modulator nucleic acid, or both.

5. The engineered, non-naturally occurring system of claim 4 wherein the chemical modification is selected from the group consisting of 2'-O-methyl, 2'-fluoro, 2'-O-methoxyethyl, phosphorothioate, phosphorodithioate, pseudouridine, and any combinations thereof.

6. The engineered, non-naturally occurring system of claim 1 wherein the modulator nucleic acid further comprises an additional nucleotide sequence positioned 5' to the modulator stem sequence, and 4-50 nucleotides in length.

7. The engineered, non-naturally occurring system of claim 6 wherein the additional nucleotide sequence comprises a donor template-recruiting sequence capable of hybridizing with a donor template.

8. The engineered, non-naturally occurring system of claim 7 further comprising the donor template.

9. The engineered, non-naturally occurring system of claim 1 wherein the targeter nucleic acid and the modulator nucleic acid are not covalently linked.

10. The engineered, non-naturally occurring system of claim 1 wherein the Cas nuclease comprises an amino acid sequence at least 80% identical to SEQ ID NO: 1.

11. The engineered, non-naturally occurring system of claim 1 wherein the Cas nuclease comprises an amino acid sequence at least 95% identical to SEQ ID NO: 1.

12. The engineered, non-naturally occurring system of claim 1 wherein the targeter nucleic acid, the modulator nucleic acid, and the Cas nuclease are present in a ribonucleoprotein (RNP) complex.

13. A cell comprising
   (a) a targeter nucleic acid comprising from 5' to 3':
      (i) a targeter stem sequence;
      (ii) a spacer sequence designed to hybridize with a target nucleotide sequence; and
      (iii) an optional additional nucleotide sequence;
   (b) a modulator nucleic acid comprising a modulator stem sequence complementary to the targeter stem sequence, wherein the targeter nucleic acid and the modulator nucleic acid are expressed as separate nucleic acids, wherein the targeter nucleic acid, the modulator nucleic acid, or both, comprises a chemically modified RNA, and wherein a complex comprising the targeter nucleic acid and the modulator nucleic acid is capable of activating a Cas nuclease that, in a naturally occurring system, is activated by a single crRNA in the absence of a tracrRNA, wherein the Cas nuclease comprises a Type V-A nuclease; and
   (c) a Type V-A Cas nuclease, or a polynucleotide encoding the Type V-A Cas nuclease.

14. The cell of claim 13 wherein the cell is an immune cell or a stem cell.

15. The cell of claim 13 wherein the cell is an induced pluripotent stem cell.

16. The cell of claim 13 wherein the cell is an immune cell that is a T lymphocyte.

17. A method of cleaving a target DNA having a target nucleotide sequence, the method comprising contacting the target DNA with an engineered, non-naturally occurring system comprising
   (a) a targeter nucleic acid comprising from 5' to 3':
      (i) a targeter stem sequence;
      (ii) a spacer sequence designed to hybridize with the target nucleotide sequence; and
      (iii) an optional additional nucleotide sequence; and
   (b) a modulator nucleic acid comprising a modulator stem sequence complementary to the targeter stem sequence, wherein the targeter nucleic acid and the modulator nucleic acid are separate nucleic acids, wherein the targeter nucleic acid, the modulator nucleic acid, or both, comprises a chemically modified RNA, and wherein a complex comprising the targeter nucleic acid and the modulator nucleic acid is capable of activating a CRISPR Associated (Cas) nuclease that, in a naturally occurring system, is activated by a single crRNA in the absence of a tracrRNA, wherein the Cas nuclease comprises a type V-A Cas nuclease, and (c) the Cas nuclease;

thereby resulting in cleavage of the target DNA.

18. The method of claim 17 wherein the contacting occurs in vitro.

19. The method of claim 17 wherein the contacting occurs in a cell ex vivo.

20. The method of claim 19 wherein the target DNA is genomic DNA of the cell.

21. The method of claim 19 wherein the system is delivered into the cell as a pre-formed RNP complex.

22. The method of claim 21 wherein the pre-formed RNP complex is delivered into the cell by electroporation.

23. A method of editing a genome of a eukaryotic cell, the method comprising delivering an engineered, non-naturally occurring system comprising (a) a targeter nucleic acid comprising from 5' to 3':
   (i) a targeter stem sequence;
   (ii) a spacer sequence designed to hybridize with a target nucleotide sequence within the genome; and
   (iii) an optional additional nucleotide sequence; and (b) a modulator nucleic acid comprising a modulator stem sequence complementary to the targeter stem sequence, wherein the targeter nucleic acid and the modulator nucleic acid are separate nucleic acids, wherein the targeter nucleic acid, the modulator nucleic acid, or both, comprises a chemically modified RNA and wherein a complex comprising the targeter nucleic acid and the modulator nucleic acid is capable of activating a CRISPR Associated (Cas) nuclease that, in a naturally occurring system, is activated by a single crRNA in the absence of a tracrRNA, wherein the Cas nuclease comprises a type V-A Cas nuclease, and (c) the Cas nuclease or a polynucleotide encoding the Cas nuclease, into the eukaryotic cell, thereby resulting in editing of the genome of the eukaryotic cell.

24. The method of claim 23 wherein the system is delivered into the cell as a pre-formed RNP complex.

25. The method of claim 24 wherein the system is delivered into the cell by electroporation.

26. The method of claim 23 wherein the cell is an immune cell or a stem cell.

27. The method of claim 26 wherein the cell is an immune cell that is a T lymphocyte.

* * * * *

SEQUENCE LISTING

```
Sequence total quantity: 159
SEQ ID NO: 1            moltype = AA  length = 1263
FEATURE                 Location/Qualifiers
REGION                  1..1263
                        note = source = /note="Description of Unknown: MAD7
                         sequence"
source                  1..1263
                        mol_type = protein
                        organism = unidentified
SEQUENCE: 1
MNNGTNNFQN FIGISSLQKT LRNALIPTET TQQFIVKNGI IKEDELRGEN RQILKDIMDD  60
YYRGFISETL SSIDDIDWTS LFEKMEIQLK NGDNKDTLIK EQTEYRKAIH KKFANDDRFK  120
NMFSAKLISD ILPEFVIHNN NYSASEKEEK TQVIKLFSRF ATSFKDYFKN RANCFSADDI  180
SSSSCHRIVN DNAEIFFSNA LVYRRIVKSL SNDDINKISG DMKDSLKEMS LEEIYSYEKY  240
GEFITQEGIS FYNDICGKVN SFMNLYCQKN KENKNLYKLQ KLHKQILCIA DTSYEVPYKF  300
ESDEEVYQSV NGFLDNISSK HIVERLRKIG DNYNGYNLDK IYIVSKFYES VSQKTYRDWE  360
TINTALEIHY NNILPGNGKS KADKVKKAVK NDLQKSITEI NELVSNYKLC SDDNIKAETY  420
IHEISHILNN FEAQELKYNP EIHLVESELK ASELKNVLDV IMNAFHWCSV FMTEELVDKD  480
NNFYAELEEI YDEIYPVISL YNLVRNYVTQ KPYSTKKIKL NFGIPTLADG WSKSKEYSNN  540
AIILMRDNLY YLGIFNAKNK PDKKIIEGNT SENKGDYKKM IYNLLPGPNK MIPKVFLSSK  600
```

-continued

```
TGVETYKPSA YILEGYKQNK HIKSSKDFDI TFCHDLIDYF KNCIAIHPEW KNFGFDFSDT    660
STYEDISGFY REVELQGYKI DWTYISEKDI DLLQEKGQLY LFQIYNKDFS KKSTGNDNLH    720
TMYLKNLFSE ENLKDIVLKL NGEAEIFFRK SSIKNPIIHK KGSILVNRTY EAEEKDQFGN    780
IQIVRKNIPE NIYQELYKYF NDKSDKELSD EAAKLKNVVG HHEAATNIVK DYRYTYDKYF    840
LHMPITINFK ANKTGFINDR ILQYIAKEKD LHVIGIDRGE RNLIYVSVID TCGNIVEQKS    900
FNIVNGYDYQ IKLKQQEGAR QIARKEWKEI GKIKEIKEGY LSLVIHEISK MVIKYNAIIA    960
MEDLSYGFKK GRFKVERQVY QKFETMLINK LNYLVFKDIS ITENGGLLKG YQLTYIPDKL   1020
KNVGHQCGCI FYVPAAYTSK IDPTTGFVNI FKFKDLTVDA KREFIKKFDS IRYDSEKNLF   1080
CFTFDYNNFI TQNTVMSKSS WSVYTYGVRI KRRFVNGRFS NESDTIDITK DMEKTLEMTD   1140
INWRDGHDLR QDIIDYEIVQ HIFEIFRLTV QMRNSLSELE DRDYDRLISP VLNENNIFYD   1200
SAKAGDALPK DADANGAYCI ALKGLYEIKQ ITENWKEDGK FSRDKLKISN KDWFDFIQNK   1260
RYL                                                                1263

SEQ ID NO: 2            moltype = AA  length = 1334
FEATURE                 Location/Qualifiers
REGION                  1..1334
                        note = source = /note="Description of Unknown: MAD2
                         sequence"
source                  1..1334
                        mol_type = protein
                        organism = unidentified
SEQUENCE: 2
MSSLTKFTNK YSKQLTIKNE LIPVGKTLEN IKENGLIDGD EQLNENYQKA KIIVDDFLRD     60
FINKALNNTQ IGNWRELADA LNKEDEDNIE KLQDKIRGII VSKFETFDLF SSYSIKKDEK    120
IIDDDNDVEE EELDLGKKTS SFKYIFKKNL FKLVLPSYLK TTNQDLKII SSFDNFSTYF    180
RGFFENRKNI FTKKPISTSI AYRIVHDNFP KFLDNIRCFN VWQTECPQLI VKADNYLKSK    240
NVIAKDKSLA NYFTVGAYDY FLSQNGIDFY NNIIGGLPAF AGHEKIQGLN EFINQECQKD    300
SELKSKLKNR HAFKMAVLFK QILSDREKSF VIDEFESDAQ VIDAVKNFYA EQCKDNNVIF    360
NLLNLIKNIA FLSDDELDGI FIEGKYLSSV SQKLYSDWSK LRNDIEDSAN SKQGNKELAK    420
KIKTNKGDVE KAISKYEFSL SELNSIVHDN TKFSDLLSCT LHKVASEKLV KVNEGDWPKH    480
LKNNEEKQKI KEPLDALLEI YNTLLIFNCK SFNKNGNFYV DYDRCINELS SVVYLYNKTR    540
NYCTKKPYNT DKFKLNFNSP QLGEGFSKSK ENDCLTLLFK KDDNYYVGII RKGAKINFDD    600
TQAIADNTDN CIFKMNYFLL KDAKKFIPKC SIQLKEVKAH FKKSEDDYIL SDKEKFASPL    660
VIKKSTFLLA TAHVKGKKGN IKKFQKEYSK ENPTEYRNSL NEWIAFCKEF LKTYKAATIF    720
DITTLKKAEE YADIVEFYKD VDNLCYKLEF CPIKTSFIEN LIDNGDLYLF RINNKDFSSK    780
STGTKNLHTL YLQAIFDERN LNNPTIMLNG GAELFYRKES IEQKNRITHK AGSILVNKVC    840
KDGTSLDDKI RNEIYQYENK FIDTLSDEAK KVLPNVIKKE ATHDITKDKR FTSDKFFFHC    900
PLTINYKEGD TKQFNNEVLS FLRGNPDINI IGIDRGERNL IYVTVINQKG EILDSVSFNT    960
VTNKSSKIEQ TVDYEEKLAV REKERIEAKR SWDSISKIAT LKEGYLSAIV HEICLLMIKH   1020
NAIVVLENLN AGFKRIRGGL SEKSVYQKFE KMLINKLWKF VSKKESDWNK PSGLLNGLQL   1080
SDQFESFEKL GIQSGFIFYV PAAYTSKIDP TTGFANVLNL SKVRNVDAIK SFFSNFNEIS   1140
YSKKEALFKF SFDLDSLSKK GFSSFVKFSK SKWNVYTFGE RIIKPKNKQG YREDKRINLT   1200
FEMKKLLNEY KVSFDLENNL IPNLTSANLK DTFWKELFFI FKTTLQLRNS VTNGKEDVLI   1260
SPVKNAKGEF FVSGTHNKTL PQDCDANGAY HIALKGLMIL ERNNLVREEK DTKKIMAISN   1320
VDWFEYVQKR RGVL                                                    1334

SEQ ID NO: 3            moltype = AA  length = 1307
FEATURE                 Location/Qualifiers
source                  1..1307
                        mol_type = protein
                        organism = Acidaminococcus sp.
SEQUENCE: 3
MTQFEGFTNL YQVSKTLRFE LIPQGKTLKH IQEQGFIEED KARNDHYKEL KPIIDRIYKT     60
YADQCLQLVQ LDWENLSAAI DSYRKEKTEE TRNALIEEQA TYRNAIHDYF IGRTDNLTDA    120
INKRHAEIYK GLFKAELFNG KVLKQLGTVT TTEHENALLR SFDKFTTYFS GFYENRKNVF    180
SAEDISTAIP HRIVQDNFPK FKENCHIFTR LITAVPSLRE HFENVKKAIG IFVSTSIEEV    240
FSFPFYNQLL TQTQIDLYNQ LLGGISREAG TEKIKGLNEV LNLAIQKNDE TAHIIASLPH    300
RFIPLFKQIL SDRNTLSFIL EEFKSDEEVI QSFCKYKTLL RNENVLETAE ALFNELNSID    360
LTHIFISHKK LETISSALCD HWDTLRNALY ERRISELTGK ITKSAKEKVQ RSLKHEDINL    420
QEIISAAGKE LSEAFKQKTS EILSHAHAAL DQPLPTTLKK QEEKEILKSQ LDSLLGLYHL    480
LDWFAVDESN EVDPEFSARL TGIKLEMEPS LSFYNKARNY ATKKPYSVEK FKLNFQMPTL    540
ASGWDVNKEK NNGAILFVKN GLYYLGIMPK QKGRYKALSF EPTEKTSEGF DKMYYDYFPD    600
AAKMIPKCST QLKAVTAHFQ THTTPILLSN NFIEPLEITK EIYDLNNPEK EPKKFQTAYA    660
KKTGDQKGYR EALCKWIDFT RDFLSKYTKT TSIDLSSLRP SSQYKDLGEY YAELNPLLYH    720
ISFQRIAEKE IMDAVETGKL YLFQIYNKDF AKGHHGKPNL HTLYWTGLFS PENLAKTSIK    780
LNGQAELFYR PKSRMKRMAH RLGEKMLNKK LKDQKTPIPD TLYQELYDYV NHRLSHDLSD    840
EARALLPNVI TKEVSHEIIK DRRFTSDKFF FHVPITLNYQ AANSPSKFNQ RVNAYLKEHP    900
ETPIIGIDRG ERNLIYITVI DSTGKILEQR SLNTIQQFDY QKKLDNREKE RVAARQAWSV    960
VGTIKDLKQG YLSQVIHEIV DLMIHYQAVV VLENLNFGFK SKRTGIAEKA VYQQFEKMLI   1020
DKLNCLVLKD YPAEKVGGVL NPYQLTDQFT SFAKMGTQSG FLFYVPAPYT SKIDPLTGFV   1080
DPFKHIYTIKN HESRKHFLEG FDFLHYDVKT GDFILHFKMN RNLSFQRGLP GFMPAWDIVF   1140
EKNETQFDAK GTPFIAGKRI VPVIENHRFT GRYRDLYPAN ELIALLEEKG IVFRDGSNIL   1200
PKLLENDDSH AIDTMVALIR SVLQMRNSNA ATGEDYINSP VRDLNGVCFD SRFQNPEWPM   1260
DADANGAYHI ALKGQLLLNH LKESKDLKLQ NGISNQDWLA YIQELRN                1307

SEQ ID NO: 4            moltype = AA  length = 1228
FEATURE                 Location/Qualifiers
```

-continued

REGION 1..1228
note = source = /note="Description of Unknown: Lachnospiraceae bacterium ND2006 sequence"
source 1..1228
mol_type = protein
organism = unidentified
SEQUENCE: 4
MSKLEKFTNC YSLSKTLRFK AIPVGKTQEN IDNKRLLVED EKRAEDYKGV KKLLDRYYLS 60
FINDVLHSIK LKNLNNYISL FRKKTRTEKE NKELENLEIN LRKEIAKAFK GNEGYKSLFK 120
KDIIETILPE FLDDKDEIAL VNSFNGFTTA FTGFFDNREN MFSEEAKSTS IAFRCINENL 180
TRYISNMDIF EKVDAIFDKH EVQEIKEKIL NSDYDVEDFF EGEFFNFVLT QEGIDVYNAI 240
IGGFVTESGE KIKGLNEYIN LYNQKTKQKL PKFKPLYKQV LSDRESLSFY GEGYTSDEEV 300
LEVFRNTLNK NSEIFSSIKK LEKLFKNFDE YSSAGIFVKN GPAISTISKD IFGEWNVIRD 360
KWNAEYDDIH LKKKAVVTEK YEDDRRKSFK KIGSFSLEQL QEYADADLSV VEKLKEIIIQ 420
KVDEIYKVYG SSEKLFDADF VLEKSLKKND AVVAIMKDLL DSVKSFENYI KAFFGEGKET 480
NRDESFYGDF VLAYDILLKV DHIYDAIRNY VTQKPYSKDK FKLYFQNPQF MGGWDKDKET 540
DYRATILRYG SKYYLAIMDK KYAKCLQKID KDDVNGNYEK INYKLLPGPN KMLPKVFFSK 600
KWMAYYNPSE DIQKIYKNGT FKKGDMFNLN DCHKLIDFFK DSISRYPKWS NAYDFNFSET 660
EKYKDIAGFY REVEEQGYKV SFESASKKEV DKLVEEGKLY MFQIYNKDFS DKSHGTPNLH 720
TMYFKLLFDE NNHGQIRLSG GAELFMRRAS LKKEELVVHP ANSPIANKNP DNPKKTTTLS 780
YDVYKDKRFS EDQYELHIPI AINKCPKNIF KINTEVRVLL KHDDNPYVIG IDRGERNLLY 840
IVVVDGKGNI VEQYSLNEII NNFNGIRIKT DYHSLLDKKE KERFEARQNW TSIENIKELK 900
AGYISQVVHK ICELVEKYDA VIALEDLNSG FKNSRVKVEK QVYQKFEKML IDKLNYMVDK 960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IAISNKEWLE YAQTSVKH 1228

SEQ ID NO: 5 moltype = AA length = 1300
FEATURE Location/Qualifiers
source 1..1300
mol_type = protein
organism = Francisella tularensis
SEQUENCE: 5
MSIYQEFVNK YSLSKTLRFE LIPQGKTLEN IKARGLILDD EKRAKDYKKA KQIIDKYHQF 60
FIEEILSSVC ISEDLLQNYS DVYFKLKKSD DDNLQKDFKS AKDTIKKQIS EYIKDSEKFK 120
NLFNQNLIDA KKGQESDLIL WLKQSKDNGI ELFKANSDIT DIDEALEIIK SFKGWTTYFK 180
GFHENRKNVY SSNDIPTSII YRIVDDNLPK FLENKAKYES LKDKAPEAIN YEQIKKDLAE 240
ELTFDIDYKT SEVNQRVFSL DEVFEIANFN NYLNQSGITK FNTIIGGKFV NGENTKRKGI 300
NEYINLYSQQ INDKTLKKYK MSVLFKQILS DTESKSFVID KLEDDSDVVT TMQSFYEQIA 360
AFKTVEEKSI KETLSLLFDD LKAQKLDLSK IYFKNDKSLT DLSQQVFDDY SVIGTAVLEY 420
ITQQIAPKNL DNPSKKEQEL IAKKTEKAKY LSLETIKLAL EEFNKHRDID KQCRFEEILA 480
NFAAIPMIFD EIAQNKDNLA QISIKYQNQG KKDLLQASAE DDVKAIKDLL DQTNNLLHKL 540
KIFHISQSED KANILDKDEH FYLVFEECYF ELANIVPLYN KIRNYITQKP YSDEKFKLNF 600
ENSTLANGWD KNKEPDNTAI LFIKDDKYYL GVMNKKNNKI FDDKAIKENK GEGYKKIVYK 660
LLPGANKMLP KVFFSAKSIK FYNPSEDILR IRNHSTHTKN GSPQKGYEKF EFNIEDCRKF 720
IDFYKQSISK HPEWKDFGFR FSDTQRYNSI DEFYREVENQ GYKLTFENIS ESYIDSVVNQ 780
GKLYLFQIYN KDFSAYSKGR PNLHTLYWKA LFDERNLQDV VYKLNGEAEL FYRKQSIPKK 840
ITHPAKEAIA NKNKDNPKKE SVFEYDLIKD KRFTEDKFFF HCPITINFKS SGANKFNDEI 900
NLLLKEKAND VHILSIDRGE RHLAYYTLVD GKGNIIKQDT FNIIGNDRMK TNYHDKLAAI 960
EKDRDSARKD WKKINNIKEM KEGYLSQVVH EIAKLVIEYN AIVVFEDLNF GFKRGRFKVE 1020
KQVYQKLEKM LIEKLNYLVF KDNEFDKTGG VLRAYQLTAP FETFKKMGKQ TGIIYYVPAG 1080
FTSKICPVTG FVNQLYPKYE SVSKSQEFFS KFDKICYNLD KGYFEFSFDY KNFGDKAAKG 1140
KWTIASFGSR LINFRNSDKN HNWDTREVYP TKELEKLLKD YSIEYGHGEC IKAAICGESD 1200
KKFFAKLTSV LNTILQMRNS KTGTELDYLI SPVADVNGNF FDSRQAPKNM PQDADANGAY 1260
HIGLKGLMLL GRIKNNQEGK KLNLVIKNEE YFEFVQNRNN 1300

SEQ ID NO: 6 moltype = AA length = 1257
FEATURE Location/Qualifiers
source 1..1257
mol_type = protein
organism = Prevotella bryantii
SEQUENCE: 6
MQINNLKIIY MKFTDFTGLY SLSKTLRFEL KPIGKTLENI KKAGLLEQDQ HRADSYKKVK 60
KIIDEYHKAF IEKSLSNFEL KYQSEDKLDS LEEYLMYYSM KRIEKTEKDK FAKIQDNLRK 120
QIADHLKGDE SYKTIFSKDL IRKNLPDFVK SDEERTLIKE FKDFTTYFKG FYENRENMYS 180
AEDKSTAISH RIIHENLPKF VDNINAFSKI ILIPELREKL NQIYQDFEEY LNVESIDEIF 240
HLDYFSMVMT QKQIEVYNAI IGGKSTNDKK IQGLNEYINL YNQKHKDCKL PKLKLLFKQI 300
LSDRIAISWL PDNFKDDQEA LDSIDTCYKN LLNDGNVLGE GNLKLLLENI DTYNLKGIFI 360
RNDLQLTDIS QKMYASWNVI QDAVILDLKK QVSRKKKESA EDYNDRLKKL YTSQESFSIQ 420
YLNDCLRAYG KTENIQDYFA KLGAVNNEHE QTINLFAQVR NAYTSVQAIL TTPYPENANL 480
AQDKETVALI KNLLDSLKRL QRFIKPLLGK GDESDKDERF YGDFTPLWET LNQITPLYNM 540
VRNYMTRKPY SQEKIKLNFE NSTLLGGWDL NKEHDNTAII LRKNGLYYLA IMKKSANKIF 600
DKDKLDNSGD CYEKMVYKLL PGANKMLPKV FFSKSRIDEF KPSENIIENY KKGTHKKGAN 660
FNLADCHNLI DFFKSSISKH EDWSKFNFHF SDTSSYEDLS DFYREVEQQG YSISFCDVSV 720
EYINKMVEKG DLYLFQIYNK DFSEFSKGTP NMHTLYWNSL FSKENLNNII YKLNGQAEIF 780
FRKKSLNYKR PTHPAHQAIK NKNKCNEKKE SIFDYDLVKD KRYTVDKFQF HVPITMNFKS 840
TGNTNINQQV IDYLRTEDDT HIIGIDRGER HLLYLVVIDS HGKIVEQFTL NEIVNEYGGN 900

```
IYRTNYHDLL DTREQNREKA RESWQTIENI KELKEGYISQ VIHKITDLMQ KYHAVVVLED   960
LNMGFMRGRQ KVEKQVYQKF EEMLINKLNY LVNKKADQNS AGGLLHAYQL TSKFESFQKL  1020
GKQSGFLFYI PAWNTSKIDP VTGFVNLFDT RYESIDKAKA FFGKFDSIRY NADKDWFEFA  1080
FDYNNFTTKA EGTRTNWTIC TYGSRIRTFR NQAKNSQWDN EEIDLTKAYK AFFAKHGINI  1140
YDNIKEAIAM ETEKSFFEDL LHLLKLTLQM RNSITGTTTD YLISPVHDSK GNFYDSRICD  1200
NSLPANADAN GAYNIARKGL MLIQQIKDST SSNRFKFSPI TNKDWLIFAQ EKPYLND    1257

SEQ ID NO: 7            moltype = AA  length = 1154
FEATURE                 Location/Qualifiers
source                  1..1154
                        mol_type = protein
                        organism = Proteocatella sphenisci
SEQUENCE: 7
MENFKNLYPI NKTLRFELRP YGKTLENFKK SGLLEKDAFK ANSRRSMQAI IDEKFKETIE    60
ERLKYTEFSE CDLGNMTSKD KKITDKAATN LKKQVILSFD DEIFNNYLKP DKNIDALFKN   120
DPSNPVISTF KGFTTYFVNF FEIRKHIFKG ESSGSMAYRI IDENLTTYLN NIEKIKKLPE   180
ELKSQLEGID QIDKLNNYNE FITQSGITHY NEIIGGISKS ENVKIQGINE GINLYCQKNK   240
VKLPRLTPLY KMILSDRVSN SFVLDTIEND TELIEMISDL INKTEISQDV IMSDIQNIFI   300
KYKQLGNLPG ISYSSIVNAI CSDYDNNFGD GKRKKSYEND RKKHLETNVY SINYISELLT   360
DTDVSSNIKM RYKELEQNYQ VCKENFNATN WMNIKNIKQS EKTNLIKDLL DILKSIQRFY   420
DLFDIVDEDK NPSAEFYTWL SKNAEKLDFE FNSVYNKSRN YLTRKQYSDK KIKLNFDSPT   480
LAKGWDANKE IDNSTIIMRK FNNDRGDYDY FLGIWNKSTP ANEKIIPLED NGLFEKMQYK   540
LYPDPSKMLP KQFLSKIWKA KHPTTPEFDK KYKEGRHKKG PDFEKEFLHE LIDCFKHGLV   600
NHDEKYQDVF GFNLRNTEDY NSYTEFLEDV ERCNYNLSFN KIADTSNLIN DGKLYVFQIW   660
SKDFSIDSKG TKNLNTIYFE SLFSEENMIE KMFKLSGEAE IFYRPASLNY CEDIIKKGHH   720
HAELKDKFDY PIIKDKRYSQ DKFFFHVPMV INYKSEKLNS KSLNNRTNEN LGQFTHIIGI   780
DRGERHLIYL TVVDVSTGEI VEQKHLDEII NTDTKGVEHK THYLNKLEEK SKTRDNERKS   840
WEAIETIKEL KEGYISHVIN EIQKLQEKYN ALIVMENLNY GFKNSRIKVE KQVYQKFETA   900
LIKKFNYIID KKDPETYIHG YQLTNPITTL DKIGNQSGIV LYIPAWNTSK IDPVTGFVNL   960
LYADDLKYKN QEQAKSFIQK IDNIYFENGE FKFDIDFSKW NNRYSISKTK WTLTSYGTRI  1020
QTFRNPQKNN KWDSAEYDLT EEFKLILNID GTLKSQDVET YKKFMSLFKL MLQLRNSVTG  1080
TDIDYMISPV TDKTGTHFDS RENIKNLPAD ADANGAYNIA RKGIMAIENI MNGISDPLKI  1140
SNEDYLKYIQ NQQE                                                   1154

SEQ ID NO: 8            moltype = AA  length = 1235
FEATURE                 Location/Qualifiers
source                  1..1235
                        mol_type = protein
                        organism = Anaerovibrio sp.
SEQUENCE: 8
MVAFIDEFVG QYPVSKTLRF EARPVPETKK WLESDQCSVL FNDQKRNEYY GVLKELLDDY    60
YRAYIEDALT SFTLDKALLE NAYDLYCNRD TNAFSSCCEK LRKDLVKAFG NLKDYLLGSD   120
QLKDLVKLKA KVDAPAGKGK KKIEVDSRLI NWLNNNAKYS AEDREKYIKA IESFEGFVTY   180
LTNYKQAREN MFSSEDKSTA IAFRVIDQNM VTYFGNIRIY EKIKAKYPEL YSALKGFEKF   240
FSPTAYSEIL SQSKIDEYNY QCIGRPIDDA DFKGVNSLIN EYRQKNGIKA RELPVMSMLY   300
KQILSDRDNS FMSEVINRNE EAIECAKNGY KVSYALFNEL LQLYKKIFTE DNYGNIYVKT   360
QPLTELSQAL FGDWSILRNA LDNGKYDKDI INLAELEKYF SEYCKVLDAD DAAKIQDKFN   420
LKDYFIQKNA LDATLPDLDK ITQYKPHLDA MLQAIRKYKL FSMYNGRKKM DVPENGIDFS   480
NEFNAIYDKL SEFSILYDRI RNFATKKPYS DEKMKLSFNM PTMLAGWDYN NETANGCFLF   540
IKDGKYFLGV ADSKSKNIFD FKKNPHLLDK YSSKDIYYKV KYKQVSGSAK MLPKVVFAGS   600
NEKIFGHLIS KRILEIREKK LYTAAAGDRK AVAEWIDFMK SAIAIHPEWN EYFKFKFKNT   660
AEYDNANKFY EDIDKQTYSL EKVEIPTEYI DEMVSQHKLY LFQLYTKDFS DKKKKKGTDN   720
LHTMYWHGVF SDENLKAVTE GTQPIIKLNG EAEMFMRNPS IEFQVTHEHN KPIANKNPLN   780
TKKESVFNYD LIKDKRYTER KFYFHCPITL NFRADKPIKY NEKINRFVEN NPDVCIIGID   840
RGERHLLYYT VINQTGDILE QGSLNKISGS YTNDKGEVIK KETDYHDLLD RKEKGKHVAQ   900
QAWETIENIK ELKAGYLSQV VYKLTQLMLQ YNAVIVLENL NVGFKRGRTK VEKQVYQKFE   960
KAMIDKLNYL VFKDRGYEMN GSYAKGLQLT DKFESFDKIG KQTGCIYYVI PSYTSHIDPK  1020
TGFVNLLNAK LRYENITKAQ DTIRKFDSIS YNAKADYFEF AFDYRSFGVD MARNEWVVCT  1080
CGDLRWEYSA KTRETKAYSV TDRLKELFKA HGIDYVGCEM LVSHITEVAD KHFLSTLLFY  1140
LRLVLKMRYT VSGTENENDF ILSPVEYAPG KFFDSREATS TEPMNADANG AYHIALKGLM  1200
TIRGIEDGKL HNYGKGGENA AWFKFMQNQE YKNNG                            1235

SEQ ID NO: 9            moltype = AA  length = 1264
FEATURE                 Location/Qualifiers
source                  1..1264
                        mol_type = protein
                        organism = Moraxella caprae
SEQUENCE: 9
MLFQDFTHLY PLSKTMRFEL KPIGKTLEHI HAKNFLSQDE TMADMYQKVK AILDDYHRDF    60
IADMMGEVKL TKLAEFYDVY LKFRKNPKDD GLQKQLKDLQ AVLRKEIVKP IGNGGKYKAG   120
YDRLFGAKLF KDGKELGDLA KFVIAQEGES SPKLAHLAHF EKFSTYFTGF HDNRKNMYSD   180
EDKHTAITYR LIHENLPRFI DNLQILATIK QKHSALYDQI INELTASGLD VSLASHLDGY   240
HKLLTQEGIT AYNTLLGGIS GEAGSRKIQG INELINSHHN QHCHKSERIA KLRPLHKQIL   300
SDGMGVSFLP SKFADDSEMC QAVNEFYRHY ADVFAKVQSL FDGFDDHQKD GIYVEHKNLN   360
ELSKQAFGDK ALLGRVLDGY YVDVVNPEFN ERFAKAKTDN AKAKLTKEKD KFIKGVHSLA   420
SLEQAIEHYT ARHDDESVQA GKLGYYFKHG LAGVDNPIQK IHNNHSTIKG FLERERPAGE   480
RALPKIKSGK NPEMTQLRQL KELLDNALNV AHFAKLLTTK TTLDNQDGNF YGEFGALYDE   540
LAKIPTLYNK VRDYLSQKPF STEKYKLNFG NPTLLNGWDL NKEKDNFGII LQKDGCYYLA   600
LLDKAHKKVF DNAPNTGKNV YQKMIYKLLP GPNKMLPKVF FAKSNLDYYN PSAELLDKYA   660
```

-continued

```
QGTHKKGNNF NLKDCHALID FFKAGINKHP EWQHFGFKFS PTSSYQDLSD FYREVEPQGY    720
QVKFVDINAD YINELVEQGQ LYLFQIYNKD FSPKAHGKPN LHTLYFKALF SKDNLANPIY    780
KLNGEAQIFY RKASLDMNET TIHRAGEVLE NKNPDNPKKR QFVYDIIKDK RYTQDKFMLH    840
VPITMNFGVQ GMTIKEFNKK VNQSIQQYDE VNVIGIDRGE RHLLYLTVIN SKGEILEQRS    900
LNDITTASAN GTQMTTPYHK ILDKREIERL NARVGWGEIE TIKELKSGYL SHVVHQISQL    960
MLKYNAIVVL EDLNFGFKRG RFKVEKQIYQ NFENALIKKL NHLVLKDEAD DEIGSYKNAL   1020
QLTNNFTDLK SIGKQTGFLF YVPAWNTSKI DPETGFVDLL KPRYENIAQS QAFFGKFDKI   1080
CYNADKDYFE FHIDYAKFTD KAKNSRQIWK ICSHGDKRYV YDKTANQNKG ATKGINVNDE   1140
LKSLFARHHI NDKQPNLVMD ICQNNDKEPH KSLIYLLKTL LALRYSNASS DEDFILSPVA   1200
NDEGMFFNSA LADDTQPQNA DANGAYHIAL KGLWVLEQIK NSDDLNKVKL AIDNQTWLNF   1260
AQNR                                                                1264

SEQ ID NO: 10           moltype = AA  length = 1230
FEATURE                 Location/Qualifiers
REGION                  1..1230
                        note = source = /note="Description of Unknown:
                        Lachnospiraceae bacterium COE1 sequence"
source                  1..1230
                        mol_type = protein
                        organism = unidentified
SEQUENCE: 10
MHENNGKIAD NFIGIYPVSK TLRFELKPVG KTQEYIEKHG ILDEDLKRAG DYKSVKKIID     60
AYHKYFIDEA LNGIQLDGLK NYYELYEKKR DNNEEKEFQK IQMSLRKQIV KRFSEHPQYK    120
YLFKKELIKN VLPEFTKDNA EEQTLVKSFQ EFTTYFEGFH QNRKNMYSDE EKSTAIAYRV    180
VHQNLPKYID NMRIFSMILN TDIRSDLTEL FNNLKTKMDI TIVEEYFAID GFNKVVNQKG    240
IDVYNTILGA FSTDDNTKIK GLNEYINLYN QKNKAKLPKL KPLFKQILSD RDKISFIPEQ    300
FDSDTEVLEA VDMFYNRLLQ FVIENEGQIT ISKLLTNFSA YDLNKIYVKN DTTISAISND    360
LFDDWSYISK AVRENYDSEN VDKKNRAAAY EEKKEKALSK IKMYSIEELN FFVKKYSCNE    420
CHIEGYFERR ILEILDKMRY AYESCKILHD KGLINNISLC QDRQAISELK DFLDSIKEVQ    480
WLLKPLMIGQ EQADKEEAFY TELLRIWEEL EPITLLYNKV RNYVTKKPYT LEKVKLNFYK    540
STLLDGWDKN KEKDNLGIIL LKDGQYYLGI MNRRNNKIAD DAPLAKTDNV YRKMEYKLLT    600
KVSANLPRIF LKDKYNPSEE MLEKYEKGTH LKGENFCIDD CRELIDFFKK GIKQYEDWGQ    660
FDFKFSDTES YDDISAFYKE VEHQGYKITF RDIDETYIDS LVNEGKLYLF QIYNKDFSPY    720
SKGTKNLHTL YWMLFSQQN LQNIVYKLNG NAEIFYRKAS INQKDVVVHK ADLPIKNKDP     780
QNSKKESMFD YDIIKDKRFT CDKYQFHVPI TMNFKALGEN FMNRKVNRLI HDAENMHIIG    840
IDRGERNLIY LCMIDMKGNI VKQISLNEII SYDKNKLEHK RNYHQLLKTR EDENKSARQS    900
WQTIHTIKEL KEGYLSQVIH VITDLMVEYN AIVVLEDLNF GFKQGRQKFE RQVYQKFEKM    960
LIDKLNYLVD KSKGMDEDGG LLHAYQLTDE FKSFKQLGKQ SGFLYYIPAW NTSKLDPTTG   1020
FVNLFYTKYE SVEKSKEFIN NFTSILYNQE REYFEFLFDY SAFTSKAEGS RLKWTVCSKG   1080
ERVETYRNPK KNNEWDTQKI DLTFELKKLF NDYSISLLDG DLREQMGKID KADFYKKFMK   1140
LFALIVQMRN SDEREDKLIS PVLNKYGAFF ETGKNERMPL DADANGAYNI ARKGLWIIEK   1200
IKNTDVEQLD KVKLTISNKE WLQYAQEHIL                                   1230

SEQ ID NO: 11           moltype = AA  length = 1261
FEATURE                 Location/Qualifiers
source                  1..1261
                        mol_type = protein
                        organism = Eubacterium coprostanoligenes
SEQUENCE: 11
MDFFKNDMYF LCINGIIVIS KLFAYLFLMY KRGVVMIKDN FVNVYSLSKT IRMALIPWGK     60
TEDNFYKKFL LEEDEERAKN YIKVKGYMDE YHKNFIESAL NSVVLNGVDE YCELYFKQNK    120
SDSEVKKIES LEASMRKQIS KAMKEYTVDG VKIYPLLSKK EFIRELLPEF LTQDEEIETL    180
EQFNDFSTYF QGFWENRKNI YTDEEKSTGV PYRCINDNLP KFLDNVKSFE KVILALPQKA    240
VDELNANFNG VYNVDVQDVF SVDYFNFVLS QSGIEKYNNI IGGYSNSDAS KVQGLNEKIN    300
LYNQQIAKSD KSKKLPLLKP LYKQILSDRS SLSFIPEKFK DDNEVLNSIN VLYDNIAESL    360
EKANDLMSDI ANYNTDNIFI SSGVAVTDIS KKVFGDWSLI RNNWNDEYES THKKGKNSEL    420
FYEKEDKEFK KIKSFSVSEL QRLANSDLSI VDYLVDESAS LYADIKTAYN NAKDLLSNEY    480
SHSKRLSKND DAIELIKSFL DSIKNYEAFL KPLCGTGKEE SKDNAFYGAF LECFEEIRQV    540
DAVYNKVRNH ITQKPYSNDK IKLNFQNPQF LAGWDKNKER AYRSVLLRNG EKYYLAIMEK    600
GKSKLFEDFP EDESSPFEKI DYKLLPEPSK MLPKVFFATS NKDLFNPSDE ILNIRATGSF    660
KKGDSFNLDD CHKFIDFYKA SIENHPDWSK FDFDFSETND TEDISKFFKE VSDQGYSIGY    720
RKISESYLEE MVDNGSLYMF QLYNKDFSEN RKSKGTPNLH TLYFKMLFDE RNLEDVVYKL    780
SGGAEMFYRK PSIDKNEMIV HPKNQPIDNK NPNNVKKTST FEYDIVKDMR YTKPQFQLHL    840
PIVLNFKANS KGYINDDVRN VLKNSEDTYV IGIDRGERNL VYACVVDGNG KLVEQVPLNV    900
IEADNGYKTD YHKLLNDREE KRNEARKSWK TIGNIKELKE GYISQVVHKI CQLVVKYDAV    960
IAMEDLNSGF VNSRKKVEKQ VYQKFERMLT QKLNYLVDKK LDPNEMGGLL NAYQLTNEAT   1020
KVRNGRQDGI IFYIPAWLTS KIDPTTGFVN LLKPKYNSVS ASKEFFSKFD EIRYNEKENY   1080
FEFSFNYDNF PKCNADFKRE WTVCTYGDRI RTFRDPENNN KFNSEVVVLN DEFKNLVYEF   1140
DIDYTDNLKE QILAMDEKSF YKKLMGLLSL TLQMRNSISK NVDVDYLISP VKNSNGEFYD   1200
SRNYDITSSL PCDADSNGAY NIARKGLWAI NQIKQADDET KANISIKNSE WLQYAQNCDE   1260
V                                                                  1261

SEQ ID NO: 12           moltype = AA  length = 1064
FEATURE                 Location/Qualifiers
source                  1..1064
                        mol_type = protein
                        organism = Smithella sp.
```

```
SEQUENCE: 12
MEKYKITKTI RFKLLPDKIQ DISRQVAVLQ NSTNAEKKNN LLRLVQRGQE LPKLLNEYIR    60
YSDNHKLKSN VTVHFRWLRL FTKDLFYNWK KDNTEKKIKI SDVVYLSHVF EAFLKEWEST   120
IERVNADCNK PEESKTRDAE IALSIRKLGI KHQLPFIKGF VDNSNDKNSE DTKSKLTALL   180
SEFEAVLKIC EQNYLPSQSS GIAIAKASFN YYTINKKQFD FEAEIVALKK QLHARYGNKK   240
YDQLLRELNL IPLKELPLKE LPLIEFYSEI KKRKSTKKSE FLEAVSNGLV FDDLKSKFPL   300
FQTESNKYDE YLKLSNKITQ KSTAKSLLSK DSPEAQKLQT EITKLKKNRG EYFKKAFGKY   360
VQLCELYKEI AGKRGLKGQ IKGIENERID SQRLQYWALV LEDNLKHSLI LIPKEKTNEL    420
YRKVWGAKDD GASSSSSSTL YYFESMTYRA LRKLCFGING NTFLPEIQKE LPQYNQKEFG   480
EFCFHKSNDD KEIDEPKLIS FYQSVLKTDF VKNTLALPQS VFNEVAIQSF ETRQDFQIAL   540
EKCCYAKKQI ISESLKKEIL ENYNTQIFKI TSLDLQRSEQ KNLKGHTRIW NRFWTKQNEE   600
INYNLRLNPE IAIVWRKAKK TRIEKYGERS VLYEPEKRNR YLHEQYTLCT TVTDNALNNE   660
ITFAFEDTKK KGTEIVKYNE KINQTLKKEF NKNQLWFYGI DAGEIELATL ALMNKDKEPQ   720
LFTVYELKKL DFFKHGYIYN KERELVIREK PYKAIQNLSY FLNEELYEKT FRDGKFNETY   780
NELFKEKHVS AIDLTTAKVI NGKIILNGDM ITFLNLRILH AQRKIYEELI ENPHAELKEK   840
DYKLYFEIEG KDKDIYISRL DFEYIKPYQE ISNYLFAYFA SQQINEAREE EQINQTKRAL   900
AGNMIGVIYY LYQKYRGIIS IEDLKQTKVE SDRNKFEGNI ERPLEWALYR KFQQEGYVPP   960
ISELIKLREL EKFPLKDVKQ PKYENIQQFG IIKFVSPEET STTCPKCLRR FKDYDKNKQE  1020
GFCKCQCGFD TRNDLKGFEG LNDPDKVAAF NIAKRGFEDL QKYK                   1064

SEQ ID NO: 13           moltype = AA  length = 1232
FEATURE                 Location/Qualifiers
source                  1..1232
                        mol_type = protein
                        organism = Sulfuricurvum sp.
SEQUENCE: 13
MLHAFTNQYQ LSKTLRFGAT LKEDEKKCKS HEELKGFVDI SYENMKSSAT IAESLNENEL    60
VKKCERCYSE IVKFHNAWEK IYYRTDQIAV YKDFYRQLSR KARFDAGKQN SQLITLASLC   120
GMYQGAKLSR YITNYWKDNI TRQKSFLKDF SQQLHQYTRA LEKSDKAHTK PNLINFNKTF   180
MVLANLVNEI VIPLSNGAIS FPNISKLEDG EESHLIEFAL NDYSQLSELI GELKDAIATN   240
GGYTPFAKVT LNHYTAEQKP HVFKNDIDAK IRELKLIGLV ETLGKSSEQ IEEYFSNLDK    300
FSTYNDRNQS VIVRTQCFKY KPIPPLVKHQ LAKYISEPNG WDEDAVAKVL DAVGAIRSPA   360
HDYANNQEGF DLNHYPIKVA FDYAWEQLAN SLYTTVTFPQ EMCEKYLNSI YGCEVSKEPV   420
FKFYADLLYI RKNLAVLEHK NNLPSNQEEF ICKINNTFEN IVLPYKISQF ETYKKDILAW   480
INDGHDHKKY TDAKQQLGFI RGGLKGRIKA EEVSQKDKYG KIKSYYENPY TKLTNEFKQI   540
SSTYGKTFAE LRDKFKEKNE ITKITHFGII IEDKNRDRYL LASELKHEQI NHVSTILNKL   600
DKSSEFITYQ VKSLTSKTLI KLIKNHTTKK GAISPYADFH TSKTGFNKNE IEKNWDNYKR   660
EQVLVEYVKD CLTDSTMAKN QNWAEFGWNF EKCNSYEDIE HEIDQKSYLL QSDTISKQSI   720
ASLVEGGCLL LPIINQDITS KERKDKNQFS KDWNHIFEGS KEFRLHPEFA VSYRTPIEGY   780
PVQKRYGRLQ FVCAFNAHIV PQNGEFINLK KQIENFNDED VQKRNVTEFN KKVNHALSDK   840
EYVVIGIDRG LKQLATLCVL DKRGKILGDF EIYKKEFVRA EKRSESHWEH TQAETRHILD   900
LSNLRVETTI EGKKVLVDQS LTLVKKNRDT PDEEATEENK QKIKLKQLSY IRKLQHKMQT   960
NEQDVLDLIN NEPSDEEFKK RIEGLISSFG EGQKYADLPI NTMREMISDL QGVIARGNNQ  1020
TEKNKIIELD AADNLKQGIV ANMIGIVNYI FAKYSYKAYI SLEDLSRAYG GAKSGYDGRY  1080
LPSTSQDEDV DFKEQQNQML AGLGTYQFFE MQLLKKLQKI QSDNTVLRFV PAFRSADNYR  1140
NILRLEETKY KSKPFGVVHF IDPKFTSKKC PVCSKTNVYR DKDDILVCKE CGFRSDSQLK  1200
ERENNIHYIH NGDDNGAYHI ALKSVENLIQ MK                                1232

SEQ ID NO: 14           moltype = AA  length = 1057
FEATURE                 Location/Qualifiers
REGION                  1..1057
                        note = source = /note="Description of Unknown:
                         Microgenomates (Roizmanbacteria) bacterium sequence"
source                  1..1057
                        mol_type = protein
                        organism = unidentified
SEQUENCE: 14
MEIQELKNLY EVKKTVRFEL KPSKKKIFEG GDVIKLQKDF EKVQKFFLDI FVYKNEHTKL    60
EFKKKREIKY TWLRTNTKNE FYNWRGKSDT GKNYALNKIG FLAEEILRWL NEWQELTKSL   120
KDLTQREEHK QERKSDIAFV LRNFLKRQNL PFIKDFFNAV IDIQGKQGKE SDDKIRKFRE   180
EIKEIEKNLN ACSREYLPTQ SNGVLLYKAS FSYYTLNKTP KEYEDLKKEK ESELSSVLLK   240
EIYRRKRFNR TTNQKDTLFE CTSDWLVKIK LGKDIYEWTL DEAYQKMKIW KANQKSNFIE   300
AVAGDKLTHQ NFRKQFPLFD ASDEDFETFY RLTKALDKNP ENAKKIAQKR GKFFNAPNET   360
VQTKNYHELC ELYKRIAVKR GKIIAEIKGI ENEEVQSQLL THWAVIAEER DKKFIVLIPR   420
KNGGKLENHK NAHAFLQEKD RKEPNDIKVY HFKSLTLRSL EKLCFKEAKN TFAPEIKKET   480
NPKIWFPTYK QEWNSTPERL IKFYKQVLQS NYAQTYLDLV DFGNLNTFLE THFTTLEEFE   540
SDLEKTCYTK VPVYFAKKEL ETFADEFEAE VFEITTRSIS TESKRKENAH AEIWRDFWSR   600
ENEEENHITR LNPEVSVLYR DEIKEKSNTS RKNRKSNANN RFSDPRFTLA TTITLNADKK   660
KSNLAFKTVE DINIHIDNFN KKFSKNFSGE WVYGIDRGLK ELATLNVVKF SDVKNVFGVS   720
QPKEFAKIPI YKLRDEKAIL KDENGLSLKN AKGEARKVID NISDVLEEGK EPDSTLFEKR   780
EVSSIDLTRA KLIKGHIISN GDQKTYLKLK ETSAKRRIFE LFSTAKIDKS SQFHVRKTIE   840
LSGTKIYWLC EWQRQDSWRT EKVSLRNTLK GYLQNLDLKN RFENIETIEK INHLRDAITA   900
NMVGILSHLQ NKLEMQGVIA LENLDTVREQ SNKKMIDEHF EQSNEHVSRR LEWALYCKFA   960
NTGEVPPQIK ESIFLRDEFK VCQIGILNFI DVKGTSSNCP NCDQESRKTG SHFICNFQNN  1020
CIFSSKENRN LLEQNLHNSD DVAAFNIAKR GLEIVKV                           1057

SEQ ID NO: 15           moltype = RNA  length = 10
FEATURE                 Location/Qualifiers
```

```
misc_feature            1..10
                        note = source = /note="Description of Artificial Sequence:
                         Synthetic oligonucleotide"
source                  1..10
                        mol_type = other RNA
                        organism = synthetic construct
SEQUENCE: 15
taatttctac                                                                      10

SEQ ID NO: 16           moltype =    length =
SEQUENCE: 16
000

SEQ ID NO: 17           moltype = RNA   length = 10
FEATURE                 Location/Qualifiers
misc_feature            1..10
                        note = source = /note="Description of Artificial Sequence:
                         Synthetic oligonucleotide"
source                  1..10
                        mol_type = other RNA
                        organism = synthetic construct
SEQUENCE: 17
taattcccac                                                                      10

SEQ ID NO: 18           moltype = RNA   length = 12
FEATURE                 Location/Qualifiers
misc_feature            1..12
                        note = source = /note="Description of Artificial Sequence:
                         Synthetic oligonucleotide"
source                  1..12
                        mol_type = other RNA
                        organism = synthetic construct
SEQUENCE: 18
taattttcta ct                                                                   12

SEQ ID NO: 19           moltype =    length =
SEQUENCE: 19
000

SEQ ID NO: 20           moltype = RNA   length = 10
FEATURE                 Location/Qualifiers
misc_feature            1..10
                        note = source = /note="Description of Artificial Sequence:
                         Synthetic oligonucleotide"
source                  1..10
                        mol_type = other RNA
                        organism = synthetic construct
SEQUENCE: 20
gaatttctac                                                                      10

SEQ ID NO: 21           moltype =    length =
SEQUENCE: 21
000

SEQ ID NO: 22           moltype =    length =
SEQUENCE: 22
000

SEQ ID NO: 23           moltype = AA   length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 23
PKKKRKV                                                                          7

SEQ ID NO: 24           moltype = AA   length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 24
KRPAATKKAG QAKKKK                                                               16
```

```
SEQ ID NO: 25          moltype = AA   length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 25
PAAKRVKLD                                                                9

SEQ ID NO: 26          moltype = AA   length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 26
RQRRNELKRS P                                                            11

SEQ ID NO: 27          moltype = AA   length = 38
FEATURE                Location/Qualifiers
REGION                 1..38
                       note = source = /note="Description of Artificial Sequence:
                        Synthetic polypeptide"
source                 1..38
                       mol_type = protein
                       organism = synthetic construct
SEQUENCE: 27
NQSSNFGPMK GGNFGGRSSG PYGGGGQYFA KPRNQGGY                                38

SEQ ID NO: 28          moltype = AA   length = 42
FEATURE                Location/Qualifiers
REGION                 1..42
                       note = source = /note="Description of Artificial Sequence:
                        Synthetic polypeptide"
source                 1..42
                       mol_type = protein
                       organism = synthetic construct
SEQUENCE: 28
RMRIZFKNKG KDTAELRRRR VEVSVELRKA KKDEQILKRR NV                           42

SEQ ID NO: 29          moltype = AA   length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 29
VSRKRPRP                                                                 8

SEQ ID NO: 30          moltype = AA   length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 30
PPKKARED                                                                 8

SEQ ID NO: 31          moltype = AA   length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 31
PQPKKKPL                                                                 8

SEQ ID NO: 32          moltype = AA   length = 12
```

```
FEATURE            Location/Qualifiers
REGION             1..12
                   note = source = /note="Description of Artificial Sequence:
                    Synthetic peptide"
source             1..12
                   mol_type = protein
                   organism = synthetic construct
SEQUENCE: 32
SALIKKKKKM AP                                                              12

SEQ ID NO: 33      moltype = AA  length = 5
FEATURE            Location/Qualifiers
REGION             1..5
                   note = source = /note="Description of Artificial Sequence:
                    Synthetic peptide"
source             1..5
                   mol_type = protein
                   organism = synthetic construct
SEQUENCE: 33
DRLRR                                                                       5

SEQ ID NO: 34      moltype = AA  length = 7
FEATURE            Location/Qualifiers
REGION             1..7
                   note = source = /note="Description of Artificial Sequence:
                    Synthetic peptide"
source             1..7
                   mol_type = protein
                   organism = synthetic construct
SEQUENCE: 34
PKQKKRK                                                                     7

SEQ ID NO: 35      moltype = AA  length = 10
FEATURE            Location/Qualifiers
REGION             1..10
                   note = source = /note="Description of Artificial Sequence:
                    Synthetic peptide"
source             1..10
                   mol_type = protein
                   organism = synthetic construct
SEQUENCE: 35
RKLKKKIKKL                                                                 10

SEQ ID NO: 36      moltype = AA  length = 10
FEATURE            Location/Qualifiers
REGION             1..10
                   note = source = /note="Description of Artificial Sequence:
                    Synthetic peptide"
source             1..10
                   mol_type = protein
                   organism = synthetic construct
SEQUENCE: 36
REKKKFLKRR                                                                 10

SEQ ID NO: 37      moltype = AA  length = 20
FEATURE            Location/Qualifiers
REGION             1..20
                   note = source = /note="Description of Artificial Sequence:
                    Synthetic peptide"
source             1..20
                   mol_type = protein
                   organism = synthetic construct
SEQUENCE: 37
KRKGDEVDGV DEVAKKKSKK                                                      20

SEQ ID NO: 38      moltype = AA  length = 17
FEATURE            Location/Qualifiers
REGION             1..17
                   note = source = /note="Description of Artificial Sequence:
                    Synthetic peptide"
source             1..17
                   mol_type = protein
                   organism = synthetic construct
SEQUENCE: 38
RKCLQAGMNL EARKTKK                                                         17

SEQ ID NO: 39      moltype = AA  length = 9
FEATURE            Location/Qualifiers
```

| | | |
|---|---|---|
| REGION | 1..9 | |
| | note = source = /note="Description of Artificial Sequence: Synthetic peptide" | |
| source | 1..9 | |
| | mol_type = protein | |
| | organism = synthetic construct | |

SEQUENCE: 39
PAAKKKKLD                                                                 9

| | | |
|---|---|---|
| SEQ ID NO: 40 | moltype = DNA   length = 682 | |
| FEATURE | Location/Qualifiers | |
| source | 1..682 | |
| | mol_type = genomic DNA | |
| | organism = Homo sapiens | |

SEQUENCE: 40
```
cgagagagtg cctcaggtat ggtggggtgg gccaggcttc ctctggggcc tgactgccct    60
ctggggtac atgtggggc agttgctggc caccgttttg ggctctggga ctcaggcggg   120
tcacctaccc acgttcgtgg ccccatcttt ctcaagggc tgctgtgagg attgagtgag   180
ttgcacgtgt caagtgctta gagcaggcgt gctgcacaca gcaggccttt ggtcaggttg   240
gctgctgggc tggccctggg gccgtttccc tcactcctgc tcggtgaatt tggctcagca   300
ggcacctgcc tcagctgctc acttgagcct ctgggtctag aaccctctgg ggaccgtttg   360
aggagtgttc agtctccgtg aacgttccct tagcactctg ccacttattg ggtcagctgt   420
taacatcagt acgttaatgt ttcctgatgg tccatgtctg ttactcgcct gtcaagtggc   480
gtgacaccgg gcgtgttccc cagagtgact tttccttta tttcccttca gctaaaataa   540
aggaggagga agctgctaag gactagttct gccctcccgt caccctgtt tctggcacca   600
ggaatcccca acatgcactg atgttgtgtt tttaacatgt caatctgtcc gttcacatgt   660
gtggtacatg gtgtttgtgg cc                                            682
```

| | | |
|---|---|---|
| SEQ ID NO: 41 | moltype = RNA   length = 40 | |
| FEATURE | Location/Qualifiers | |
| misc_feature | 1..40 | |
| | note = source = /note="Description of Artificial Sequence: Synthetic oligonucleotide" | |
| source | 1..40 | |
| | mol_type = other RNA | |
| | organism = synthetic construct | |

SEQUENCE: 41
taatttctac tcttgtagat ctgatggtcc atgtctgtta                         40

| | | |
|---|---|---|
| SEQ ID NO: 42 | moltype = RNA   length = 12 | |
| FEATURE | Location/Qualifiers | |
| misc_feature | 1..12 | |
| | note = source = /note="Description of Artificial Sequence: Synthetic oligonucleotide" | |
| source | 1..12 | |
| | mol_type = other RNA | |
| | organism = synthetic construct | |

SEQUENCE: 42
taatttctac tc                                                       12

| | | |
|---|---|---|
| SEQ ID NO: 43 | moltype = RNA   length = 28 | |
| FEATURE | Location/Qualifiers | |
| misc_feature | 1..28 | |
| | note = source = /note="Description of Artificial Sequence: Synthetic oligonucleotide" | |
| source | 1..28 | |
| | mol_type = other RNA | |
| | organism = synthetic construct | |

SEQUENCE: 43
ttgtagatct gatggtccat gtctgtta                                      28

| | | |
|---|---|---|
| SEQ ID NO: 44 | moltype = RNA   length = 40 | |
| FEATURE | Location/Qualifiers | |
| misc_feature | 1..40 | |
| | note = source = /note="Description of Artificial Sequence: Synthetic oligonucleotide" | |
| source | 1..40 | |
| | mol_type = other RNA | |
| | organism = synthetic construct | |

SEQUENCE: 44
taattcccac tcttgtgggt ctgatggtcc atgtctgtta                         40

| | | |
|---|---|---|
| SEQ ID NO: 45 | moltype = RNA   length = 12 | |
| FEATURE | Location/Qualifiers | |
| misc_feature | 1..12 | |
| | note = source = /note="Description of Artificial Sequence: Synthetic oligonucleotide" | |

```
source                  1..12
                        mol_type = other RNA
                        organism = synthetic construct
SEQUENCE: 45
taattcccac tc                                                           12

SEQ ID NO: 46           moltype = RNA   length = 28
FEATURE                 Location/Qualifiers
misc_feature            1..28
                        note = source = /note="Description of Artificial Sequence:
                        Synthetic oligonucleotide"
source                  1..28
                        mol_type = other RNA
                        organism = synthetic construct
SEQUENCE: 46
ttgtgggtct gatggtccat gtctgtta                                          28

SEQ ID NO: 47           moltype = RNA   length = 52
FEATURE                 Location/Qualifiers
misc_feature            1..52
                        note = source = /note="Description of Artificial Sequence:
                        Synthetic oligonucleotide"
source                  1..52
                        mol_type = other RNA
                        organism = synthetic construct
SEQUENCE: 47
tcccatagat gataatttct actcttgtag atctgatggt ccatgtctgt ta               52

SEQ ID NO: 48           moltype = RNA   length = 24
FEATURE                 Location/Qualifiers
misc_feature            1..24
                        note = source = /note="Description of Artificial Sequence:
                        Synthetic oligonucleotide"
source                  1..24
                        mol_type = other RNA
                        organism = synthetic construct
SEQUENCE: 48
tcccatagat gataatttct actc                                              24

SEQ ID NO: 49           moltype = RNA   length = 64
FEATURE                 Location/Qualifiers
misc_feature            1..64
                        note = source = /note="Description of Artificial Sequence:
                        Synthetic oligonucleotide"
source                  1..64
                        mol_type = other RNA
                        organism = synthetic construct
SEQUENCE: 49
tcccatagat gaccgcactc atagtaattt ctactcttgt agatctgatg gtccatgtct       60
gtta                                                                    64

SEQ ID NO: 50           moltype = RNA   length = 36
FEATURE                 Location/Qualifiers
misc_feature            1..36
                        note = source = /note="Description of Artificial Sequence:
                        Synthetic oligonucleotide"
source                  1..36
                        mol_type = other RNA
                        organism = synthetic construct
SEQUENCE: 50
tcccatagat gaccgcactc atagtaattt ctactc                                 36

SEQ ID NO: 51           moltype = DNA   length = 24
FEATURE                 Location/Qualifiers
misc_feature            1..24
                        note = source = /note="Description of Artificial Sequence:
                        Synthetic oligonucleotide"
source                  1..24
                        mol_type = other DNA
                        organism = synthetic construct
SEQUENCE: 51
gcagctaata cgactcacta tagg                                              24

SEQ ID NO: 52           moltype = RNA   length = 30
FEATURE                 Location/Qualifiers
misc_feature            1..30
                        note = source = /note="Description of Artificial Sequence:
                        Synthetic oligonucleotide"
```

```
source                  1..30
                        mol_type = other RNA
                        organism = synthetic construct
SEQUENCE: 52
tcttgtagat ctgatggtcc atgtctgtta                                            30

SEQ ID NO: 53           moltype = RNA   length = 11
FEATURE                 Location/Qualifiers
misc_feature            1..11
                        note = source = /note="Description of Artificial Sequence:
                         Synthetic oligonucleotide"
source                  1..11
                        mol_type = other RNA
                        organism = synthetic construct
SEQUENCE: 53
taatttctac t                                                                11

SEQ ID NO: 54           moltype = RNA   length = 29
FEATURE                 Location/Qualifiers
misc_feature            1..29
                        note = source = /note="Description of Artificial Sequence:
                         Synthetic oligonucleotide"
source                  1..29
                        mol_type = other RNA
                        organism = synthetic construct
SEQUENCE: 54
cttgtagatc tgatggtcca tgtctgtta                                             29

SEQ ID NO: 55           moltype = RNA   length = 13
FEATURE                 Location/Qualifiers
misc_feature            1..13
                        note = source = /note="Description of Artificial Sequence:
                         Synthetic oligonucleotide"
source                  1..13
                        mol_type = other RNA
                        organism = synthetic construct
SEQUENCE: 55
taatttctac tct                                                              13

SEQ ID NO: 56           moltype = RNA   length = 27
FEATURE                 Location/Qualifiers
misc_feature            1..27
                        note = source = /note="Description of Artificial Sequence:
                         Synthetic oligonucleotide"
source                  1..27
                        mol_type = other RNA
                        organism = synthetic construct
SEQUENCE: 56
tgtagatctg atggtccatg tctgtta                                               27

SEQ ID NO: 57           moltype = RNA   length = 14
FEATURE                 Location/Qualifiers
misc_feature            1..14
                        note = source = /note="Description of Artificial Sequence:
                         Synthetic oligonucleotide"
source                  1..14
                        mol_type = other RNA
                        organism = synthetic construct
SEQUENCE: 57
taatttctac tctt                                                             14

SEQ ID NO: 58           moltype = RNA   length = 26
FEATURE                 Location/Qualifiers
misc_feature            1..26
                        note = source = /note="Description of Artificial Sequence:
                         Synthetic oligonucleotide"
source                  1..26
                        mol_type = other RNA
                        organism = synthetic construct
SEQUENCE: 58
gtagatctga tggtccatgt ctgtta                                                26

SEQ ID NO: 59           moltype = RNA   length = 50
FEATURE                 Location/Qualifiers
misc_feature            1..50
                        note = source = /note="Description of Artificial Sequence:
                         Synthetic oligonucleotide"
```

```
                        -continued source                  1..50
                        mol_type = other RNA
                        organism = synthetic construct
SEQUENCE: 59
gccgaaaggc taatttctac tcttgtagat ctgatggtcc atgtctgtta              50

SEQ ID NO: 60           moltype = RNA   length = 22
FEATURE                 Location/Qualifiers
misc_feature            1..22
                        note = source = /note="Description of Artificial Sequence:
                        Synthetic oligonucleotide"
source                  1..22
                        mol_type = other RNA
                        organism = synthetic construct
SEQUENCE: 60
gccgaaaggc taatttctac tc                                            22

SEQ ID NO: 61           moltype = RNA   length = 50
FEATURE                 Location/Qualifiers
misc_feature            1..50
                        note = source = /note="Description of Artificial Sequence:
                        Synthetic oligonucleotide"
source                  1..50
                        mol_type = other RNA
                        organism = synthetic construct
SEQUENCE: 61
taatttctac tcttgtagat ctgatggtcc atgtctgtta gccgaaaggc              50

SEQ ID NO: 62           moltype = RNA   length = 38
FEATURE                 Location/Qualifiers
misc_feature            1..38
                        note = source = /note="Description of Artificial Sequence:
                        Synthetic oligonucleotide"
source                  1..38
                        mol_type = other RNA
                        organism = synthetic construct
SEQUENCE: 62
ttgtagatct gatggtccat gtctgttagc cgaaaggc                           38

SEQ ID NO: 63           moltype = DNA   length = 40
FEATURE                 Location/Qualifiers
modified_base           1
                        mod_base = OTHER
                        note = uracil
modified_base           4..6
                        mod_base = OTHER
                        note = uracil
modified_base           8
                        mod_base = OTHER
                        note = uracil
modified_base           11
                        mod_base = OTHER
                        note = uracil
modified_base           13..14
                        mod_base = OTHER
                        note = uracil
modified_base           16
                        mod_base = OTHER
                        note = uracil
modified_base           20
                        mod_base = OTHER
                        note = uracil
misc_feature            1..40
                        note = source = /note="Description of Artificial Sequence:
                        Synthetic oligonucleotide"
source                  1..40
                        mol_type = other DNA
                        organism = synthetic construct
SEQUENCE: 63
taatttctac tcttgtagat ctgatggtcc atgtctgtta                         40

SEQ ID NO: 64           moltype = DNA   length = 40
FEATURE                 Location/Qualifiers
modified_base           1
                        mod_base = OTHER
                        note = uracil
modified_base           4..5
                        mod_base = OTHER
                        note = uracil
```

```
modified_base        11
                     mod_base = OTHER
                     note = uracil
modified_base        13..14
                     mod_base = OTHER
                     note = uracil
modified_base        16
                     mod_base = OTHER
                     note = uracil
modified_base        20
                     mod_base = OTHER
                     note = uracil
misc_feature         1..40
                     note = source = /note="Description of Artificial Sequence:
                      Synthetic oligonucleotide"
source               1..40
                     mol_type = other DNA
                     organism = synthetic construct
SEQUENCE: 64
taattcccac tcttgtgggt ctgatggtcc atgtctgtta                                    40

SEQ ID NO: 65        moltype = RNA   length = 15
FEATURE              Location/Qualifiers
misc_feature         1..15
                     note = source = /note="Description of Artificial Sequence:
                      Synthetic oligonucleotide"
source               1..15
                     mol_type = other RNA
                     organism = synthetic construct
SEQUENCE: 65
taattcccac tcttg                                                               15

SEQ ID NO: 66        moltype = RNA   length = 14
FEATURE              Location/Qualifiers
misc_feature         1..14
                     note = source = /note="Description of Artificial Sequence:
                      Synthetic oligonucleotide"
source               1..14
                     mol_type = other RNA
                     organism = synthetic construct
SEQUENCE: 66
taattcccac tctc                                                                14

SEQ ID NO: 67        moltype = RNA   length = 19
FEATURE              Location/Qualifiers
misc_feature         1..19
                     note = source = /note="Description of Artificial Sequence:
                      Synthetic oligonucleotide"
source               1..19
                     mol_type = other RNA
                     organism = synthetic construct
SEQUENCE: 67
taattcccac tctcttgtg                                                           19

SEQ ID NO: 68        moltype = RNA   length = 15
FEATURE              Location/Qualifiers
misc_feature         1..15
                     note = source = /note="Description of Artificial Sequence:
                      Synthetic oligonucleotide"
source               1..15
                     mol_type = other RNA
                     organism = synthetic construct
SEQUENCE: 68
taattcccac tcctc                                                               15

SEQ ID NO: 69        moltype = RNA   length = 21
FEATURE              Location/Qualifiers
misc_feature         1..21
                     note = source = /note="Description of Artificial Sequence:
                      Synthetic oligonucleotide"
source               1..21
                     mol_type = other RNA
                     organism = synthetic construct
SEQUENCE: 69
taattcccac tcctcttgtt g                                                        21

SEQ ID NO: 70        moltype = RNA   length = 15
FEATURE              Location/Qualifiers
```

```
misc_feature           1..15
                       note = source = /note="Description of Artificial Sequence:
                        Synthetic oligonucleotide"
source                 1..15
                       mol_type = other RNA
                       organism = synthetic construct
SEQUENCE: 70
taattcccac tgctc                                                         15

SEQ ID NO: 71          moltype = RNA  length = 21
FEATURE                Location/Qualifiers
misc_feature           1..21
                       note = source = /note="Description of Artificial Sequence:
                        Synthetic oligonucleotide"
source                 1..21
                       mol_type = other RNA
                       organism = synthetic construct
SEQUENCE: 71
taattcccac tgctcttgct g                                                  21

SEQ ID NO: 72          moltype = RNA  length = 16
FEATURE                Location/Qualifiers
misc_feature           1..16
                       note = source = /note="Description of Artificial Sequence:
                        Synthetic oligonucleotide"
source                 1..16
                       mol_type = other RNA
                       organism = synthetic construct
SEQUENCE: 72
taattcccac tcgctc                                                        16

SEQ ID NO: 73          moltype = RNA  length = 23
FEATURE                Location/Qualifiers
misc_feature           1..23
                       note = source = /note="Description of Artificial Sequence:
                        Synthetic oligonucleotide"
source                 1..23
                       mol_type = other RNA
                       organism = synthetic construct
SEQUENCE: 73
taattcccac tcgctcttgc ttg                                                23

SEQ ID NO: 74          moltype = RNA  length = 16
FEATURE                Location/Qualifiers
misc_feature           1..16
                       note = source = /note="Description of Artificial Sequence:
                        Synthetic oligonucleotide"
source                 1..16
                       mol_type = other RNA
                       organism = synthetic construct
SEQUENCE: 74
taattcccac tcgctc                                                        16

SEQ ID NO: 75          moltype = RNA  length = 23
FEATURE                Location/Qualifiers
misc_feature           1..23
                       note = source = /note="Description of Artificial Sequence:
                        Synthetic oligonucleotide"
source                 1..23
                       mol_type = other RNA
                       organism = synthetic construct
SEQUENCE: 75
taattcccac tcgctcttgc gtg                                                23

SEQ ID NO: 76          moltype = RNA  length = 17
FEATURE                Location/Qualifiers
misc_feature           1..17
                       note = source = /note="Description of Artificial Sequence:
                        Synthetic oligonucleotide"
source                 1..17
                       mol_type = other RNA
                       organism = synthetic construct
SEQUENCE: 76
taattcccac tccgctc                                                       17

SEQ ID NO: 77          moltype = RNA  length = 25
FEATURE                Location/Qualifiers
```

|  |  |  |
|---|---|---|
| misc_feature | 1..25 | |
| | note = source = /note="Description of Artificial Sequence: Synthetic oligonucleotide" | |
| source | 1..25 | |
| | mol_type = other RNA | |
| | organism = synthetic construct | |

SEQUENCE: 77
taattcccac tccgctcttg cgttg    25

|  |  |  |
|---|---|---|
| SEQ ID NO: 78 | moltype = DNA length = 28 | |
| FEATURE | Location/Qualifiers | |
| modified_base | 1..2 | |
| | mod_base = OTHER | |
| | note = uracil | |
| modified_base | 4 | |
| | mod_base = OTHER | |
| | note = uracil | |
| modified_base | 8 | |
| | mod_base = OTHER | |
| | note = uracil | |
| misc_feature | 1..28 | |
| | note = source = /note="Description of Artificial Sequence: Synthetic oligonucleotide" | |
| source | 1..28 | |
| | mol_type = other DNA | |
| | organism = synthetic construct | |

SEQUENCE: 78
ttgtgggtct gatggtccat gtctgtta    28

|  |  |  |
|---|---|---|
| SEQ ID NO: 79 | moltype = DNA length = 25 | |
| FEATURE | Location/Qualifiers | |
| modified_base | 1 | |
| | mod_base = OTHER | |
| | note = uracil | |
| modified_base | 5 | |
| | mod_base = OTHER | |
| | note = uracil | |
| misc_feature | 1..25 | |
| | note = source = /note="Description of Artificial Sequence: Synthetic oligonucleotide" | |
| source | 1..25 | |
| | mol_type = other DNA | |
| | organism = synthetic construct | |

SEQUENCE: 79
tgggtctgat ggtccatgtc tgtta    25

|  |  |  |
|---|---|---|
| SEQ ID NO: 80 | moltype = DNA length = 30 | |
| FEATURE | Location/Qualifiers | |
| modified_base | 1..2 | |
| | mod_base = OTHER | |
| | note = uracil | |
| modified_base | 4 | |
| | mod_base = OTHER | |
| | note = uracil | |
| modified_base | 6 | |
| | mod_base = OTHER | |
| | note = uracil | |
| modified_base | 10 | |
| | mod_base = OTHER | |
| | note = uracil | |
| misc_feature | 1..30 | |
| | note = source = /note="Description of Artificial Sequence: Synthetic oligonucleotide" | |
| source | 1..30 | |
| | mol_type = other DNA | |
| | organism = synthetic construct | |

SEQUENCE: 80
ttgtgtgggt ctgatggtcc atgtctgtta    30

|  |  |  |
|---|---|---|
| SEQ ID NO: 81 | moltype = DNA length = 25 | |
| FEATURE | Location/Qualifiers | |
| modified_base | 1 | |
| | mod_base = OTHER | |
| | note = uracil | |
| modified_base | 5 | |
| | mod_base = OTHER | |
| | note = uracil | |

```
misc_feature            1..25
                        note = source = /note="Description of Artificial Sequence:
                         Synthetic oligonucleotide"
source                  1..25
                        mol_type = other DNA
                        organism = synthetic construct
SEQUENCE: 81
tgggtctgat ggtccatgtc tgtta                                                 25

SEQ ID NO: 82           moltype = DNA  length = 31
FEATURE                 Location/Qualifiers
modified_base           1..2
                        mod_base = OTHER
                        note = uracil
modified_base           4..5
                        mod_base = OTHER
                        note = uracil
modified_base           7
                        mod_base = OTHER
                        note = uracil
modified_base           11
                        mod_base = OTHER
                        note = uracil
misc_feature            1..31
                        note = source = /note="Description of Artificial Sequence:
                         Synthetic oligonucleotide"
source                  1..31
                        mol_type = other DNA
                        organism = synthetic construct
SEQUENCE: 82
ttgttgtggg tctgatggtc catgtctgtt a                                          31

SEQ ID NO: 83           moltype = DNA  length = 25
FEATURE                 Location/Qualifiers
modified_base           1
                        mod_base = OTHER
                        note = uracil
modified_base           5
                        mod_base = OTHER
                        note = uracil
misc_feature            1..25
                        note = source = /note="Description of Artificial Sequence:
                         Synthetic oligonucleotide"
source                  1..25
                        mol_type = other DNA
                        organism = synthetic construct
SEQUENCE: 83
tgggtctgat ggtccatgtc tgtta                                                 25

SEQ ID NO: 84           moltype = DNA  length = 31
FEATURE                 Location/Qualifiers
modified_base           1..2
                        mod_base = OTHER
                        note = uracil
modified_base           5
                        mod_base = OTHER
                        note = uracil
modified_base           7
                        mod_base = OTHER
                        note = uracil
modified_base           11
                        mod_base = OTHER
                        note = uracil
misc_feature            1..31
                        note = source = /note="Description of Artificial Sequence:
                         Synthetic oligonucleotide"
source                  1..31
                        mol_type = other DNA
                        organism = synthetic construct
SEQUENCE: 84
ttgctgtggg tctgatggtc catgtctgtt a                                          31

SEQ ID NO: 85           moltype = DNA  length = 25
FEATURE                 Location/Qualifiers
modified_base           1
                        mod_base = OTHER
                        note = uracil
```

```
modified_base           5
                        mod_base = OTHER
                        note = uracil
misc_feature            1..25
                        note = source = /note="Description of Artificial Sequence:
                         Synthetic oligonucleotide"
source                  1..25
                        mol_type = other DNA
                        organism = synthetic construct
SEQUENCE: 85
tgggtctgat ggtccatgtc tgtta                                               25

SEQ ID NO: 86           moltype = DNA  length = 32
FEATURE                 Location/Qualifiers
modified_base           1..2
                        mod_base = OTHER
                        note = uracil
modified_base           5..6
                        mod_base = OTHER
                        note = uracil
modified_base           8
                        mod_base = OTHER
                        note = uracil
modified_base           12
                        mod_base = OTHER
                        note = uracil
misc_feature            1..32
                        note = source = /note="Description of Artificial Sequence:
                         Synthetic oligonucleotide"
source                  1..32
                        mol_type = other DNA
                        organism = synthetic construct
SEQUENCE: 86
ttgcttgtgg gtctgatggt ccatgtctgt ta                                       32

SEQ ID NO: 87           moltype = DNA  length = 25
FEATURE                 Location/Qualifiers
modified_base           1
                        mod_base = OTHER
                        note = uracil
modified_base           5
                        mod_base = OTHER
                        note = uracil
misc_feature            1..25
                        note = source = /note="Description of Artificial Sequence:
                         Synthetic oligonucleotide"
source                  1..25
                        mol_type = other DNA
                        organism = synthetic construct
SEQUENCE: 87
tgggtctgat ggtccatgtc tgtta                                               25

SEQ ID NO: 88           moltype = DNA  length = 32
FEATURE                 Location/Qualifiers
modified_base           1..2
                        mod_base = OTHER
                        note = uracil
modified_base           6
                        mod_base = OTHER
                        note = uracil
modified_base           8
                        mod_base = OTHER
                        note = uracil
modified_base           12
                        mod_base = OTHER
                        note = uracil
misc_feature            1..32
                        note = source = /note="Description of Artificial Sequence:
                         Synthetic oligonucleotide"
source                  1..32
                        mol_type = other DNA
                        organism = synthetic construct
SEQUENCE: 88
ttgcgtgtgg gtctgatggt ccatgtctgt ta                                       32
```

```
SEQ ID NO: 89              moltype = DNA  length = 25
FEATURE                    Location/Qualifiers
modified_base              1
                           mod_base = OTHER
                           note = uracil
modified_base              5
                           mod_base = OTHER
                           note = uracil
misc_feature               1..25
                           note = source = /note="Description of Artificial Sequence:
                           Synthetic oligonucleotide"
source                     1..25
                           mol_type = other DNA
                           organism = synthetic construct
SEQUENCE: 89
tgggtctgat ggtccatgtc tgtta                                              25

SEQ ID NO: 90              moltype = DNA  length = 33
FEATURE                    Location/Qualifiers
modified_base              1..2
                           mod_base = OTHER
                           note = uracil
modified_base              6..7
                           mod_base = OTHER
                           note = uracil
modified_base              9
                           mod_base = OTHER
                           note = uracil
modified_base              13
                           mod_base = OTHER
                           note = uracil
misc_feature               1..33
                           note = source = /note="Description of Artificial Sequence:
                           Synthetic oligonucleotide"
source                     1..33
                           mol_type = other DNA
                           organism = synthetic construct
SEQUENCE: 90
ttgcgttgtg ggtctgatgg tccatgtctg tta                                     33

SEQ ID NO: 91              moltype = DNA  length = 25
FEATURE                    Location/Qualifiers
modified_base              1
                           mod_base = OTHER
                           note = uracil
modified_base              5
                           mod_base = OTHER
                           note = uracil
misc_feature               1..25
                           note = source = /note="Description of Artificial Sequence:
                           Synthetic oligonucleotide"
source                     1..25
                           mol_type = other DNA
                           organism = synthetic construct
SEQUENCE: 91
tgggtctgat ggtccatgtc tgtta                                              25

SEQ ID NO: 92              moltype = DNA  length = 55
FEATURE                    Location/Qualifiers
misc_feature               1..55
                           note = source = /note="Description of Artificial Sequence:
                           Synthetic primer"
source                     1..55
                           mol_type = other DNA
                           organism = synthetic construct
SEQUENCE: 92
tcgtcggcag cgtcagatgt gtataagaga cagagtgttc agtctccgtg aacgt             55

SEQ ID NO: 93              moltype = DNA  length = 56
FEATURE                    Location/Qualifiers
misc_feature               1..56
                           note = source = /note="Description of Artificial Sequence:
                           Synthetic primer"
source                     1..56
                           mol_type = other DNA
                           organism = synthetic construct
SEQUENCE: 93
gtctcgtggg ctcggagatg tgtataagag acaggtcctt agcagcttcc tcctcc            56
```

```
SEQ ID NO: 94          moltype = DNA  length = 24
FEATURE                Location/Qualifiers
misc_feature           1..24
                       note = source = /note="Description of Artificial Sequence:
                        Synthetic primer"
source                 1..24
                       mol_type = other DNA
                       organism = synthetic construct
SEQUENCE: 94
caagcagaag acggcatacg agat                                              24

SEQ ID NO: 95          moltype = DNA  length = 29
FEATURE                Location/Qualifiers
misc_feature           1..29
                       note = source = /note="Description of Artificial Sequence:
                        Synthetic primer"
source                 1..29
                       mol_type = other DNA
                       organism = synthetic construct
SEQUENCE: 95
aatgatacgg cgaccaccga gatctacac                                         29

SEQ ID NO: 96          moltype = RNA  length = 10
FEATURE                Location/Qualifiers
misc_feature           1..10
                       note = source = /note="Description of Artificial Sequence:
                        Synthetic oligonucleotide"
source                 1..10
                       mol_type = other RNA
                       organism = synthetic construct
SEQUENCE: 96
taatttctac                                                              10

SEQ ID NO: 97          moltype = RNA  length = 11
FEATURE                Location/Qualifiers
misc_feature           1..11
                       note = source = /note="Description of Artificial Sequence:
                        Synthetic oligonucleotide"
source                 1..11
                       mol_type = other RNA
                       organism = synthetic construct
SEQUENCE: 97
taatttctac t                                                            11

SEQ ID NO: 98          moltype = RNA  length = 13
FEATURE                Location/Qualifiers
misc_feature           1..13
                       note = source = /note="Description of Artificial Sequence:
                        Synthetic oligonucleotide"
source                 1..13
                       mol_type = other RNA
                       organism = synthetic construct
SEQUENCE: 98
taatttctac tct                                                          13

SEQ ID NO: 99          moltype = RNA  length = 14
FEATURE                Location/Qualifiers
misc_feature           1..14
                       note = source = /note="Description of Artificial Sequence:
                        Synthetic oligonucleotide"
source                 1..14
                       mol_type = other RNA
                       organism = synthetic construct
SEQUENCE: 99
taatttctac tctt                                                         14

SEQ ID NO: 100         moltype = DNA  length = 41
FEATURE                Location/Qualifiers
modified_base          1
                       mod_base = OTHER
                       note = uracil
modified_base          4..6
                       mod_base = OTHER
                       note = uracil
modified_base          8
                       mod_base = OTHER
                       note = uracil
```

```
modified_base          11
                       mod_base = OTHER
                       note = uracil
modified_base          13..14
                       mod_base = OTHER
                       note = uracil
modified_base          16
                       mod_base = OTHER
                       note = uracil
modified_base          20
                       mod_base = OTHER
                       note = uracil
misc_feature           1..41
                       note = source = /note="Description of Artificial Sequence:
                        Synthetic oligonucleotide"
source                 1..41
                       mol_type = other DNA
                       organism = synthetic construct
SEQUENCE: 100
taatttctac tcttgtagat ctggtgaagt tggttcggga g                              41

SEQ ID NO: 101         moltype = DNA  length = 29
FEATURE                Location/Qualifiers
modified_base          1..2
                       mod_base = OTHER
                       note = uracil
modified_base          4
                       mod_base = OTHER
                       note = uracil
modified_base          8
                       mod_base = OTHER
                       note = uracil
misc_feature           1..29
                       note = source = /note="Description of Artificial Sequence:
                        Synthetic oligonucleotide"
source                 1..29
                       mol_type = other DNA
                       organism = synthetic construct
SEQUENCE: 101
ttgtagatct ggtgaagttg gttcgggag                                           29

SEQ ID NO: 102         moltype = RNA  length = 11
FEATURE                Location/Qualifiers
misc_feature           1..11
                       note = source = /note="Description of Artificial Sequence:
                        Synthetic oligonucleotide"
source                 1..11
                       mol_type = other RNA
                       organism = synthetic construct
SEQUENCE: 102
ggaatttcta c                                                              11

SEQ ID NO: 103         moltype = DNA  length = 41
FEATURE                Location/Qualifiers
modified_base          1
                       mod_base = OTHER
                       note = uracil
modified_base          4..6
                       mod_base = OTHER
                       note = uracil
modified_base          8
                       mod_base = OTHER
                       note = uracil
modified_base          11
                       mod_base = OTHER
                       note = uracil
modified_base          13..14
                       mod_base = OTHER
                       note = uracil
modified_base          16
                       mod_base = OTHER
                       note = uracil
modified_base          20
                       mod_base = OTHER
                       note = uracil
misc_feature           1..41
                       note = source = /note="Description of Artificial Sequence:
                        Synthetic oligonucleotide"
```

```
source                  1..41
                        mol_type = other DNA
                        organism = synthetic construct
SEQUENCE: 103
taatttctac tcttgtagat tctgcaggga caataggagc c                           41

SEQ ID NO: 104          moltype = DNA  length = 29
FEATURE                 Location/Qualifiers
modified_base           1..2
                        mod_base = OTHER
                        note = uracil
modified_base           4
                        mod_base = OTHER
                        note = uracil
modified_base           8
                        mod_base = OTHER
                        note = uracil
misc_feature            1..29
                        note = source = /note="Description of Artificial Sequence:
                          Synthetic oligonucleotide"
source                  1..29
                        mol_type = other DNA
                        organism = synthetic construct
SEQUENCE: 104
ttgtagattc tgcagggaca ataggagcc                                         29

SEQ ID NO: 105          moltype = DNA  length = 41
FEATURE                 Location/Qualifiers
modified_base           1
                        mod_base = OTHER
                        note = uracil
modified_base           4..6
                        mod_base = OTHER
                        note = uracil
modified_base           8
                        mod_base = OTHER
                        note = uracil
modified_base           11
                        mod_base = OTHER
                        note = uracil
modified_base           13..14
                        mod_base = OTHER
                        note = uracil
modified_base           16
                        mod_base = OTHER
                        note = uracil
modified_base           20
                        mod_base = OTHER
                        note = uracil
misc_feature            1..41
                        note = source = /note="Description of Artificial Sequence:
                          Synthetic oligonucleotide"
source                  1..41
                        mol_type = other DNA
                        organism = synthetic construct
SEQUENCE: 105
taatttctac tcttgtagat gggtgcatac ctgtctggct g                           41

SEQ ID NO: 106          moltype = DNA  length = 29
FEATURE                 Location/Qualifiers
modified_base           1..2
                        mod_base = OTHER
                        note = uracil
modified_base           4
                        mod_base = OTHER
                        note = uracil
modified_base           8
                        mod_base = OTHER
                        note = uracil
misc_feature            1..29
                        note = source = /note="Description of Artificial Sequence:
                          Synthetic oligonucleotide"
source                  1..29
                        mol_type = other DNA
                        organism = synthetic construct
SEQUENCE: 106
ttgtagatgg gtgcatacct gtctggctg                                         29

SEQ ID NO: 107          moltype = RNA  length = 41
```

```
FEATURE                    Location/Qualifiers
misc_feature               1..41
                           note = source = /note="Description of Artificial Sequence:
                           Synthetic oligonucleotide"
source                     1..41
                           mol_type = other RNA
                           organism = synthetic construct
SEQUENCE: 107
taatttctac tcttgtagat tatgacctgt atggagggga g                                41

SEQ ID NO: 108             moltype = RNA   length = 29
FEATURE                    Location/Qualifiers
misc_feature               1..29
                           note = source = /note="Description of Artificial Sequence:
                           Synthetic oligonucleotide"
source                     1..29
                           mol_type = other RNA
                           organism = synthetic construct
SEQUENCE: 108
ttgtagatta tgacctgtat ggaggggag                                              29

SEQ ID NO: 109             moltype = DNA   length = 41
FEATURE                    Location/Qualifiers
modified_base              1
                           mod_base = OTHER
                           note = uracil
modified_base              4..6
                           mod_base = OTHER
                           note = uracil
modified_base              8
                           mod_base = OTHER
                           note = uracil
modified_base              11
                           mod_base = OTHER
                           note = uracil
modified_base              13..14
                           mod_base = OTHER
                           note = uracil
modified_base              16
                           mod_base = OTHER
                           note = uracil
modified_base              20
                           mod_base = OTHER
                           note = uracil
misc_feature               1..41
                           note = source = /note="Description of Artificial Sequence:
                           Synthetic oligonucleotide"
source                     1..41
                           mol_type = other DNA
                           organism = synthetic construct
SEQUENCE: 109
taatttctac tcttgtagat gcacgaagct ctccgatgtg t                                41

SEQ ID NO: 110             moltype = DNA   length = 29
FEATURE                    Location/Qualifiers
modified_base              1..2
                           mod_base = OTHER
                           note = uracil
modified_base              4
                           mod_base = OTHER
                           note = uracil
modified_base              8
                           mod_base = OTHER
                           note = uracil
misc_feature               1..29
                           note = source = /note="Description of Artificial Sequence:
                           Synthetic oligonucleotide"
source                     1..29
                           mol_type = other DNA
                           organism = synthetic construct
SEQUENCE: 110
ttgtagatgc acgaagctct ccgatgtgt                                              29

SEQ ID NO: 111             moltype = DNA   length = 41
FEATURE                    Location/Qualifiers
modified_base              1
                           mod_base = OTHER
                           note = uracil
```

```
modified_base          4..6
                       mod_base = OTHER
                       note = uracil
modified_base          8
                       mod_base = OTHER
                       note = uracil
modified_base          11
                       mod_base = OTHER
                       note = uracil
modified_base          13..14
                       mod_base = OTHER
                       note = uracil
modified_base          16
                       mod_base = OTHER
                       note = uracil
modified_base          20
                       mod_base = OTHER
                       note = uracil
misc_feature           1..41
                       note = source = /note="Description of Artificial Sequence:
                        Synthetic oligonucleotide"
source                 1..41
                       mol_type = other DNA
                       organism = synthetic construct
SEQUENCE: 111
taatttctac tcttgtagat gtgtaacata cctggaggac a                          41

SEQ ID NO: 112         moltype = DNA  length = 29
FEATURE                Location/Qualifiers
modified_base          1..2
                       mod_base = OTHER
                       note = uracil
modified_base          4
                       mod_base = OTHER
                       note = uracil
modified_base          8
                       mod_base = OTHER
                       note = uracil
misc_feature           1..29
                       note = source = /note="Description of Artificial Sequence:
                        Synthetic oligonucleotide"
source                 1..29
                       mol_type = other DNA
                       organism = synthetic construct
SEQUENCE: 112
ttgtagatgt gtaacatacc tggaggaca                                        29

SEQ ID NO: 113         moltype = DNA  length = 41
FEATURE                Location/Qualifiers
modified_base          1
                       mod_base = OTHER
                       note = uracil
modified_base          4..6
                       mod_base = OTHER
                       note = uracil
modified_base          8
                       mod_base = OTHER
                       note = uracil
modified_base          11
                       mod_base = OTHER
                       note = uracil
modified_base          13..14
                       mod_base = OTHER
                       note = uracil
modified_base          16
                       mod_base = OTHER
                       note = uracil
modified_base          20
                       mod_base = OTHER
                       note = uracil
misc_feature           1..41
                       note = source = /note="Description of Artificial Sequence:
                        Synthetic oligonucleotide"
source                 1..41
                       mol_type = other DNA
                       organism = synthetic construct
SEQUENCE: 113
taatttctac tcttgtagat gtcctccctc tagtggctga g                          41
```

```
SEQ ID NO: 114            moltype = DNA  length = 29
FEATURE                   Location/Qualifiers
modified_base             1..2
                          mod_base = OTHER
                          note = uracil
modified_base             4
                          mod_base = OTHER
                          note = uracil
modified_base             8
                          mod_base = OTHER
                          note = uracil
misc_feature              1..29
                          note = source = /note="Description of Artificial Sequence:
                           Synthetic oligonucleotide"
source                    1..29
                          mol_type = other DNA
                          organism = synthetic construct
SEQUENCE: 114
ttgtagatgt cctccctcta gtggctgag                                              29

SEQ ID NO: 115            moltype = DNA  length = 41
FEATURE                   Location/Qualifiers
modified_base             1
                          mod_base = OTHER
                          note = uracil
modified_base             4..6
                          mod_base = OTHER
                          note = uracil
modified_base             8
                          mod_base = OTHER
                          note = uracil
modified_base             11
                          mod_base = OTHER
                          note = uracil
modified_base             13..14
                          mod_base = OTHER
                          note = uracil
modified_base             16
                          mod_base = OTHER
                          note = uracil
modified_base             20
                          mod_base = OTHER
                          note = uracil
misc_feature              1..41
                          note = source = /note="Description of Artificial Sequence:
                           Synthetic oligonucleotide"
source                    1..41
                          mol_type = other DNA
                          organism = synthetic construct
SEQUENCE: 115
taatttctac tcttgtagat agcggcacaa ggctcagctg a                                41

SEQ ID NO: 116            moltype = DNA  length = 29
FEATURE                   Location/Qualifiers
modified_base             1..2
                          mod_base = OTHER
                          note = uracil
modified_base             4
                          mod_base = OTHER
                          note = uracil
modified_base             8
                          mod_base = OTHER
                          note = uracil
misc_feature              1..29
                          note = source = /note="Description of Artificial Sequence:
                           Synthetic oligonucleotide"
source                    1..29
                          mol_type = other DNA
                          organism = synthetic construct
SEQUENCE: 116
ttgtagatag cggcacaagg ctcagctga                                              29

SEQ ID NO: 117            moltype = DNA  length = 41
FEATURE                   Location/Qualifiers
modified_base             1
                          mod_base = OTHER
                          note = uracil
```

```
modified_base            4..6
                         mod_base = OTHER
                         note = uracil
modified_base            8
                         mod_base = OTHER
                         note = uracil
modified_base            11
                         mod_base = OTHER
                         note = uracil
modified_base            13..14
                         mod_base = OTHER
                         note = uracil
modified_base            16
                         mod_base = OTHER
                         note = uracil
modified_base            20
                         mod_base = OTHER
                         note = uracil
misc_feature             1..41
                         note = source = /note="Description of Artificial Sequence:
                          Synthetic oligonucleotide"
source                   1..41
                         mol_type = other DNA
                         organism = synthetic construct
SEQUENCE: 117
taatttctac tcttgtagat actttccatt ctctgctgga t                          41

SEQ ID NO: 118           moltype = DNA  length = 29
FEATURE                  Location/Qualifiers
modified_base            1..2
                         mod_base = OTHER
                         note = uracil
modified_base            4
                         mod_base = OTHER
                         note = uracil
modified_base            8
                         mod_base = OTHER
                         note = uracil
misc_feature             1..29
                         note = source = /note="Description of Artificial Sequence:
                          Synthetic oligonucleotide"
source                   1..29
                         mol_type = other DNA
                         organism = synthetic construct
SEQUENCE: 118
ttgtagatac tttccattct ctgctggat                                        29

SEQ ID NO: 119           moltype = DNA  length = 41
FEATURE                  Location/Qualifiers
modified_base            1
                         mod_base = OTHER
                         note = uracil
modified_base            4..6
                         mod_base = OTHER
                         note = uracil
modified_base            8
                         mod_base = OTHER
                         note = uracil
modified_base            11
                         mod_base = OTHER
                         note = uracil
modified_base            13..14
                         mod_base = OTHER
                         note = uracil
modified_base            16
                         mod_base = OTHER
                         note = uracil
modified_base            20
                         mod_base = OTHER
                         note = uracil
misc_feature             1..41
                         note = source = /note="Description of Artificial Sequence:
                          Synthetic oligonucleotide"
source                   1..41
                         mol_type = other DNA
                         organism = synthetic construct
SEQUENCE: 119
taatttctac tcttgtagat ccttccgctc acctccgcct g                          41
```

```
SEQ ID NO: 120            moltype = DNA   length = 29
FEATURE                   Location/Qualifiers
modified_base             1..2
                          mod_base = OTHER
                          note = uracil
modified_base             4
                          mod_base = OTHER
                          note = uracil
modified_base             8
                          mod_base = OTHER
                          note = uracil
misc_feature              1..29
                          note = source = /note="Description of Artificial Sequence:
                           Synthetic oligonucleotide"
source                    1..29
                          mol_type = other DNA
                          organism = synthetic construct
SEQUENCE: 120
ttgtagatcc ttccgctcac ctccgcctg                                              29

SEQ ID NO: 121            moltype = DNA   length = 41
FEATURE                   Location/Qualifiers
modified_base             1
                          mod_base = OTHER
                          note = uracil
modified_base             4..6
                          mod_base = OTHER
                          note = uracil
modified_base             8
                          mod_base = OTHER
                          note = uracil
modified_base             11
                          mod_base = OTHER
                          note = uracil
modified_base             13..14
                          mod_base = OTHER
                          note = uracil
modified_base             16
                          mod_base = OTHER
                          note = uracil
modified_base             20
                          mod_base = OTHER
                          note = uracil
misc_feature              1..41
                          note = source = /note="Description of Artificial Sequence:
                           Synthetic oligonucleotide"
source                    1..41
                          mol_type = other DNA
                          organism = synthetic construct
SEQUENCE: 121
taatttctac tcttgtagat ctcttcctcc tactcaccat c                                41

SEQ ID NO: 122            moltype = DNA   length = 29
FEATURE                   Location/Qualifiers
modified_base             1..2
                          mod_base = OTHER
                          note = uracil
modified_base             4
                          mod_base = OTHER
                          note = uracil
modified_base             8
                          mod_base = OTHER
                          note = uracil
misc_feature              1..29
                          note = source = /note="Description of Artificial Sequence:
                           Synthetic oligonucleotide"
source                    1..29
                          mol_type = other DNA
                          organism = synthetic construct
SEQUENCE: 122
ttgtagatct cttcctccta ctcaccatc                                              29

SEQ ID NO: 123            moltype = RNA   length = 41
FEATURE                   Location/Qualifiers
misc_feature              1..41
                          note = source = /note="Description of Artificial Sequence:
                           Synthetic oligonucleotide"
```

```
source                  1..41
                        mol_type = other RNA
                        organism = synthetic construct
SEQUENCE: 123
taatttctac tcttgtagat ctcttcctcc tactcaccat c                              41

SEQ ID NO: 124          moltype = RNA   length = 31
FEATURE                 Location/Qualifiers
misc_feature            1..31
                        note = source = /note="Description of Artificial Sequence:
                         Synthetic oligonucleotide"
source                  1..31
                        mol_type = other RNA
                        organism = synthetic construct
SEQUENCE: 124
tcttgtagat ctcttcctcc tactcaccat c                                         31

SEQ ID NO: 125          moltype = RNA   length = 30
FEATURE                 Location/Qualifiers
misc_feature            1..30
                        note = source = /note="Description of Artificial Sequence:
                         Synthetic oligonucleotide"
source                  1..30
                        mol_type = other RNA
                        organism = synthetic construct
SEQUENCE: 125
cttgtagatc tcttcctcct actcaccatc                                           30

SEQ ID NO: 126          moltype = RNA   length = 29
FEATURE                 Location/Qualifiers
misc_feature            1..29
                        note = source = /note="Description of Artificial Sequence:
                         Synthetic oligonucleotide"
source                  1..29
                        mol_type = other RNA
                        organism = synthetic construct
SEQUENCE: 126
ttgtagatct cttcctccta ctcaccatc                                            29

SEQ ID NO: 127          moltype = RNA   length = 28
FEATURE                 Location/Qualifiers
misc_feature            1..28
                        note = source = /note="Description of Artificial Sequence:
                         Synthetic oligonucleotide"
source                  1..28
                        mol_type = other RNA
                        organism = synthetic construct
SEQUENCE: 127
tgtagatctc ttcctcctac tcaccatc                                             28

SEQ ID NO: 128          moltype = RNA   length = 27
FEATURE                 Location/Qualifiers
misc_feature            1..27
                        note = source = /note="Description of Artificial Sequence:
                         Synthetic oligonucleotide"
source                  1..27
                        mol_type = other RNA
                        organism = synthetic construct
SEQUENCE: 128
gtagatctct tcctcctact caccatc                                              27

SEQ ID NO: 129          moltype = RNA   length = 41
FEATURE                 Location/Qualifiers
misc_feature            1..41
                        note = source = /note="Description of Artificial Sequence:
                         Synthetic oligonucleotide"
source                  1..41
                        mol_type = other RNA
                        organism = synthetic construct
SEQUENCE: 129
taatttctac tcttgtagat gcacgaagct ctccgatgtg t                              41

SEQ ID NO: 130          moltype = RNA   length = 31
FEATURE                 Location/Qualifiers
misc_feature            1..31
                        note = source = /note="Description of Artificial Sequence:
                         Synthetic oligonucleotide"
```

| | | |
|---|---|---|
| source | 1..31<br>mol_type = other RNA<br>organism = synthetic construct | |
| SEQUENCE: 130 | | |
| tcttgtagat gcacgaagct ctccgatgtg t | | 31 |
| | | |
| SEQ ID NO: 131<br>FEATURE<br>misc_feature | moltype = RNA  length = 30<br>Location/Qualifiers<br>1..30<br>note = source = /note="Description of Artificial Sequence:<br>Synthetic oligonucleotide" | |
| source | 1..30<br>mol_type = other RNA<br>organism = synthetic construct | |
| SEQUENCE: 131 | | |
| cttgtagatg cacgaagctc tccgatgtgt | | 30 |
| | | |
| SEQ ID NO: 132<br>FEATURE<br>misc_feature | moltype = RNA  length = 29<br>Location/Qualifiers<br>1..29<br>note = source = /note="Description of Artificial Sequence:<br>Synthetic oligonucleotide" | |
| source | 1..29<br>mol_type = other RNA<br>organism = synthetic construct | |
| SEQUENCE: 132 | | |
| ttgtagatgc acgaagctct ccgatgtgt | | 29 |
| | | |
| SEQ ID NO: 133<br>FEATURE<br>misc_feature | moltype = RNA  length = 28<br>Location/Qualifiers<br>1..28<br>note = source = /note="Description of Artificial Sequence:<br>Synthetic oligonucleotide" | |
| source | 1..28<br>mol_type = other RNA<br>organism = synthetic construct | |
| SEQUENCE: 133 | | |
| tgtagatgca cgaagctctc cgatgtgt | | 28 |
| | | |
| SEQ ID NO: 134<br>FEATURE<br>misc_feature | moltype = RNA  length = 27<br>Location/Qualifiers<br>1..27<br>note = source = /note="Description of Artificial Sequence:<br>Synthetic oligonucleotide" | |
| source | 1..27<br>mol_type = other RNA<br>organism = synthetic construct | |
| SEQUENCE: 134 | | |
| gtagatgcac gaagctctcc gatgtgt | | 27 |
| | | |
| SEQ ID NO: 135<br>FEATURE<br>misc_feature | moltype = RNA  length = 41<br>Location/Qualifiers<br>1..41<br>note = source = /note="Description of Artificial Sequence:<br>Synthetic oligonucleotide" | |
| source | 1..41<br>mol_type = other RNA<br>organism = synthetic construct | |
| SEQUENCE: 135 | | |
| taatttctac tcttgtagat gtcctccctc tagtggctga g | | 41 |
| | | |
| SEQ ID NO: 136<br>FEATURE<br>misc_feature | moltype = RNA  length = 31<br>Location/Qualifiers<br>1..31<br>note = source = /note="Description of Artificial Sequence:<br>Synthetic oligonucleotide" | |
| source | 1..31<br>mol_type = other RNA<br>organism = synthetic construct | |
| SEQUENCE: 136 | | |
| tcttgtagat gtcctccctc tagtggctga g | | 31 |
| | | |
| SEQ ID NO: 137<br>FEATURE<br>misc_feature | moltype = RNA  length = 30<br>Location/Qualifiers<br>1..30<br>note = source = /note="Description of Artificial Sequence:<br>Synthetic oligonucleotide" | |

```
                        -continued source                  1..30
                        mol_type = other RNA
                        organism = synthetic construct
SEQUENCE: 137
cttgtagatg tcctccctct agtggctgag                                    30

SEQ ID NO: 138          moltype = RNA   length = 29
FEATURE                 Location/Qualifiers
misc_feature            1..29
                        note = source = /note="Description of Artificial Sequence:
                        Synthetic oligonucleotide"
source                  1..29
                        mol_type = other RNA
                        organism = synthetic construct
SEQUENCE: 138
ttgtagatgt cctccctcta gtggctgag                                     29

SEQ ID NO: 139          moltype = RNA   length = 28
FEATURE                 Location/Qualifiers
misc_feature            1..28
                        note = source = /note="Description of Artificial Sequence:
                        Synthetic oligonucleotide"
source                  1..28
                        mol_type = other RNA
                        organism = synthetic construct
SEQUENCE: 139
tgtagatgtc ctccctctag tggctgag                                      28

SEQ ID NO: 140          moltype = RNA   length = 27
FEATURE                 Location/Qualifiers
misc_feature            1..27
                        note = source = /note="Description of Artificial Sequence:
                        Synthetic oligonucleotide"
source                  1..27
                        mol_type = other RNA
                        organism = synthetic construct
SEQUENCE: 140
gtagatgtcc tccctctagt ggctgag                                       27

SEQ ID NO: 141          moltype = DNA   length = 15
FEATURE                 Location/Qualifiers
misc_feature            1..15
                        note = source = /note="Description of Artificial Sequence:
                        Synthetic primer"
source                  1..15
                        mol_type = other DNA
                        organism = synthetic construct
SEQUENCE: 141
gtctcgtggg ctcgg                                                    15

SEQ ID NO: 142          moltype = DNA   length = 14
FEATURE                 Location/Qualifiers
misc_feature            1..14
                        note = source = /note="Description of Artificial Sequence:
                        Synthetic primer"
source                  1..14
                        mol_type = other DNA
                        organism = synthetic construct
SEQUENCE: 142
tcgtcggcag cgtc                                                     14

SEQ ID NO: 143          moltype = AA    length = 6
FEATURE                 Location/Qualifiers
REGION                  1..6
                        note = source = /note="Description of Artificial Sequence:
                        Synthetic 6xHis tag"
source                  1..6
                        mol_type = protein
                        organism = synthetic construct
SEQUENCE: 143
HHHHHH                                                              6

SEQ ID NO: 144          moltype =    length =
SEQUENCE: 144
000
```

```
SEQ ID NO: 145          moltype = RNA   length = 30
FEATURE                 Location/Qualifiers
misc_difference         11..30
                        note = n =a, u, g, c, unknown or other
misc_feature            1..30
                        note = source = /note="Description of Artificial Sequence:
                          Synthetic oligonucleotide"
source                  1..30
                        mol_type = other RNA
                        organism = synthetic construct
SEQUENCE: 145
tcttgtagat nnnnnnnnnn nnnnnnnnnn                                              30

SEQ ID NO: 146          moltype =    length =
SEQUENCE: 146
000

SEQ ID NO: 147          moltype =    length =
SEQUENCE: 147
000

SEQ ID NO: 148          moltype = RNA   length = 50
FEATURE                 Location/Qualifiers
misc_difference         31..50
                        note = n =a, u, g, c, unknown or other
misc_feature            1..50
                        note = source = /note="Description of Artificial Sequence:
                          Synthetic oligonucleotide"
source                  1..50
                        mol_type = other RNA
                        organism = synthetic construct
SEQUENCE: 148
gccgaaaggc taatttctac tcttgtagat nnnnnnnnnn nnnnnnnnnn                        50

SEQ ID NO: 149          moltype = RNA   length = 50
FEATURE                 Location/Qualifiers
misc_difference         21..40
                        note = n =a, u, g, c, unknown or other
misc_feature            1..50
                        note = source = /note="Description of Artificial Sequence:
                          Synthetic oligonucleotide"
source                  1..50
                        mol_type = other RNA
                        organism = synthetic construct
SEQUENCE: 149
taatttctac tcttgtagat nnnnnnnnnn nnnnnnnnnn gccgaaaggc                        50

SEQ ID NO: 150          moltype = RNA   length = 40
FEATURE                 Location/Qualifiers
misc_difference         21..40
                        note = n =a, u, g, c, unknown or other
misc_feature            1..40
                        note = source = /note="Description of Artificial Sequence:
                          Synthetic oligonucleotide"
source                  1..40
                        mol_type = other RNA
                        organism = synthetic construct
SEQUENCE: 150
taatttctac tcttgtagat nnnnnnnnnn nnnnnnnnnn                                   40

SEQ ID NO: 151          moltype = RNA   length = 40
FEATURE                 Location/Qualifiers
misc_difference         21..40
                        note = n =a, u, g, c, unknown or other
misc_feature            1..40
                        note = source = /note="Description of Artificial Sequence:
                          Synthetic oligonucleotide"
source                  1..40
                        mol_type = other RNA
                        organism = synthetic construct
SEQUENCE: 151
taattcccac tcttgtgggt nnnnnnnnnn nnnnnnnnnn                                   40

SEQ ID NO: 152          moltype = RNA   length = 44
FEATURE                 Location/Qualifiers
misc_difference         25..44
                        note = n =a, u, g, c, unknown or other
```

```
misc_feature               1..44
                           note = source = /note="Description of Artificial Sequence:
                            Synthetic oligonucleotide"
source                     1..44
                           mol_type = other RNA
                           organism = synthetic construct
SEQUENCE: 152
taattcccac tctcttgtgt gggtnnnnnn nnnnnnnnnn nnnn                      44

SEQ ID NO: 153             moltype = RNA  length = 46
FEATURE                    Location/Qualifiers
misc_difference            27..46
                           note = n =a, u, g, c, unknown or other
misc_feature               1..46
                           note = source = /note="Description of Artificial Sequence:
                            Synthetic oligonucleotide"
source                     1..46
                           mol_type = other RNA
                           organism = synthetic construct
SEQUENCE: 153
taattcccac tgctcttgct gtgggtnnnn nnnnnnnnnn nnnnnn                    46

SEQ ID NO: 154             moltype = RNA  length = 48
FEATURE                    Location/Qualifiers
misc_difference            29..48
                           note = n =a, u, g, c, unknown or other
misc_feature               1..48
                           note = source = /note="Description of Artificial Sequence:
                            Synthetic oligonucleotide"
source                     1..48
                           mol_type = other RNA
                           organism = synthetic construct
SEQUENCE: 154
taattcccac tcgctcttgc gtgtgggtnn nnnnnnnnnn nnnnnnnn                  48

SEQ ID NO: 155             moltype = RNA  length = 46
FEATURE                    Location/Qualifiers
misc_difference            27..46
                           note = n =a, u, g, c, unknown or other
misc_feature               1..46
                           note = source = /note="Description of Artificial Sequence:
                            Synthetic oligonucleotide"
source                     1..46
                           mol_type = other RNA
                           organism = synthetic construct
SEQUENCE: 155
taattcccac tcctcttgtt gtgggtnnnn nnnnnnnnnn nnnnnn                    46

SEQ ID NO: 156             moltype = RNA  length = 48
FEATURE                    Location/Qualifiers
misc_difference            29..48
                           note = n =a, u, g, c, unknown or other
misc_feature               1..48
                           note = source = /note="Description of Artificial Sequence:
                            Synthetic oligonucleotide"
source                     1..48
                           mol_type = other RNA
                           organism = synthetic construct
SEQUENCE: 156
taattcccac tcgctcttgc ttgtgggtnn nnnnnnnnnn nnnnnnnn                  48

SEQ ID NO: 157             moltype = RNA  length = 50
FEATURE                    Location/Qualifiers
misc_difference            31..50
                           note = n =a, u, g, c, unknown or other
misc_feature               1..50
                           note = source = /note="Description of Artificial Sequence:
                            Synthetic oligonucleotide"
source                     1..50
                           mol_type = other RNA
                           organism = synthetic construct
SEQUENCE: 157
taattcccac tccgctcttg cgttgtgggt nnnnnnnnnn nnnnnnnnnn                50

SEQ ID NO: 158             moltype =     length =
SEQUENCE: 158
000
```

```
SEQ ID NO: 159         moltype = RNA  length = 38
FEATURE                Location/Qualifiers
source                 1..38
                       mol_type = other RNA
                       organism = synthetic construct
misc_feature           1..38
                       note = Description of Artificial Sequence: Synthetic
                         oligonucleotide
misc_difference        9..28
                       note = n =a, u, g, c, unknown or other
SEQUENCE: 159
ttgtagatnn nnnnnnnnnn nnnnnnnngc cgaaaggc                              38
```